United States Patent
Feldman et al.

(10) Patent No.: US 11,535,865 B2
(45) Date of Patent: Dec. 27, 2022

(54) CO-PACKAGING TO MITIGATE INTERMOLECULAR RECOMBINATION

(71) Applicants: THE BROAD INSTITUTE, INC., Cambridge, MA (US); MASSACHUSETTS INSTITUTE OF TECHNOLOGY, Cambridge, MA (US)

(72) Inventors: David Feldman, Cambridge, MA (US); Avtar Singh, Cambridge, MA (US); Paul Blainey, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 203 days.

(21) Appl. No.: 16/269,138

(22) Filed: Feb. 6, 2019

(65) Prior Publication Data
US 2019/0241909 A1    Aug. 8, 2019

Related U.S. Application Data

(60) Provisional application No. 62/627,183, filed on Feb. 6, 2018.

(51) Int. Cl.
*C12N 15/86* (2006.01)
*C40B 40/08* (2006.01)

(52) U.S. Cl.
CPC .......... *C12N 15/86* (2013.01); *C12N 2310/20* (2017.05); *C40B 40/08* (2013.01)

(58) Field of Classification Search
None
See application file for complete search history.

(56) References Cited

U.S. PATENT DOCUMENTS

2019/0241909 A1*  8/2019  Feldman ............... C12N 15/86

OTHER PUBLICATIONS

Xie et al. BioRxiv Jan. 29, 2018, https://doi.org/10.1101/255638). (Year: 2018).*
Adamson, et al., "A Multiplexed Single-Cell CRISPR Screening Platform Enables Systematic Dissection of the Unfolded Protein Response", Cell, vol. 167, No. 7, Dec. 15, 2016, 42 pages.
Banasik, et al., "Integrase-defective lentiviral vectors: progress and applications", Gene Therapy (2010) 17, 150-157, 8 pages.
Hill, et al., "On the design of CRISPR-based Single-Cell Molecular Screens", Nature Methods, vol. 15, No. 4, Apr. 2018, 22 pages.
Hu, et al., "Retroviral Recombination and Reverse Transcription", Science 250, 1227-33 (1990).
Maricque, "A genome-integrated massively parallel reporter assay reveals DNA sequence determinants of cis-regulatory activity in neural cells", Nucleic Acids Research, 2017, vol. 45, No. 4 e16 doi: 10.1093/nar/gkw942, 11 pages.
Tran, et al., "Conserved determinants of lentiviral genome dimerization", Retrovirology, (2015) 12:83, 16 pages.
Xie, et al., "Frequent sgRNA-barcode recombination in single-cell perturbation assays", PLOS ONE, Jun. 6, 2018, e0198635, 7 pages.

* cited by examiner

*Primary Examiner* — Shanon A. Foley
*Assistant Examiner* — Myron G Hill
(74) *Attorney, Agent, or Firm* — F. Brent Nix, Esq.; Johnson, Marcou, Isaacs & Nix, LLC; Michael B. Scher, Esq.

(57) ABSTRACT

The subject matter disclosed herein is generally directed to methods and compositions for stable transduction of target cells with libraries of genetic elements. The invention reduces intermolecular recombination between library elements and integration of multiple genetic elements.

24 Claims, 2 Drawing Sheets
Specification includes a Sequence Listing.

CO-PACKAGING TO MITIGATE INTERMOLECULAR RECOMBINATION

CROSS-REFERENCE TO RELATED APPLICATIONS

This application claims the benefit of U.S. Provisional Application No. 62/627,183, filed Feb. 6, 2018. The entire contents of the above-identified application are hereby fully incorporated herein by reference.

STATEMENT REGARDING FEDERALLY SPONSORED RESEARCH

This invention was made with government support under Grant Nos. HG009283 and HG006193 granted by National Institutes of Health. The government has certain rights in the invention.

REFERENCE TO AN ELECTRONIC SEQUENCE LISTING

The contents of the electronic sequence listing ("BROD_2465WP_ST25.txt", 301 KB, created on Jan. 30, 2019) is herein incorporated by reference in its entirety.

TECHNICAL FIELD

The subject matter disclosed herein is generally directed to methods and compositions for stable transduction of target cells with libraries of genetic elements. The invention reduces intermolecular recombination between library elements and integration of multiple genetic elements.

BACKGROUND

Lentiviral vectors provide a convenient, scalable platform to deliver genetic perturbations to cells en masse and read out the identity of each perturbation by next-generation sequencing[1,2]. Certain screen modalities rely on the delivery of multiple sequences per lentiviral vector in order to probe gene interactions with combinations of perturbations or to encode the identity of each perturbation in an easily-detectable barcode sequence, such as in CRISPR-based single-cell gene expression screens[3-8]. However, these methods are highly susceptible to intermolecular recombination that scrambles engineered associations between the variable sequences. For screens where all variable elements are sequenced directly (e.g. targeted pairs of gene knockouts), recombination events can be detected and filtered out before statistical analysis[6, 9]. However, in situations where certain functional sequences are not read out, such as when a barcode stands in as a proxy for a genetic perturbation, recombination can lead to mislabeled data and has been noted to decrease the statistical power of genetic screens at a given number of cells analyzed[10, 11].

Intermolecular recombination can arise from the template-switching activity of the lentiviral reverse-transcriptase[16]. As the lentivirus capsid normally packages a dimer of RNA genomes, the effect persists even under dilute conditions where cells are infected by a single virion. The fraction of cells with recombined integrants depends on the distance between variable sequences and has been measured to exceed 30% for distances of >1 kb, which may occur when the sequences are separated by regulatory elements such as promoters, or used as 3' barcodes in an expressed transcript, where recombination events can lead to an effective scrambling of barcodes and perturbations, which may be referred to herein as barcode swapping[10-12].

SUMMARY

The invention provides improved lentiviral or retroviral systems with reduced intermolecular recombination between library elements and reduced integration of multiple genetic elements in a target cell.

In one aspect, the invention provides a non-naturally occurring lentiviral or retroviral system comprising a polynucleotide having at least a first engineered association and a second engineered association, wherein the system has reduced recombination activity, or template switching activity, or multiple integration activity.

In an embodiment, the engineered system comprises an inhibitor of recombination activity, or template switching activity, or multiple integration activity. In an embodiment, the inhibitor of template switching is a carrier polynucleotide. The carrier polynucleotide can be involved in or affect any aspect of lentiviral packaging, and functions to reduce recombination activity or template switching activity, or multiple integration. For example, in an embodiment of the invention, the carrier polynucleotide is packaged with or forms a heterodimer with the polynucleotide comprising the one or more engineered associations, but lacks sufficient homology such that recombination activity, template switching activity, or multiple integration activity is reduced or eliminated. In an embodiment of the invention, the reduction in recombination activity, template switching activity, or multiple integration activity can be 2×, 5×, 10×, 20×, 50×, 100×, 500×, 1000× or greater as compared to packaging without the carrier polynucleotide. In packaging reactions, carrier polynucleotides are usually in excess. In certain embodiments, the carrier polynucleotide to payload polynucleotide ratio in packaging is from 5:1 to 10:1 or from 10:1 to 20:1 or from 20:1 to 50:1, or from 50:1 to 100:1 or from 100:1 to 500:1, of from 500:1 to 1000:1 or greater.

In another embodiment, the inhibitor of recombination activity, or template switching activity, or multiple integration activity can be any carrier polynucleotide transfected into a packaging cell and present with the payload to be packaged, which carrier polynucleotide is not designed to be packaged. Such carriers include, without limitation, single and double stranded DNA, replicable and non-replicable plasmid type vectors, including prokaryotic and eukaryotic vectors. In a non-limiting example set forth herein, bacterial plasmid pUC19, which does not replicate in a packaging cell, is not transcribed, and is not designed to be packaged in a lentiviral particle, is demonstrate to inhibit recombination activity, template switching activity, or multiple integration activity.

In an embodiment, the inhibitor of recombination activity, or template switching activity, or multiple integration activity comprises a polynucleotide designed to hybridize with all or part of the 5' UTR, including but not limited to such regions as US-PBS complex or the dimer initiation site (DIS).

In an embodiment, recombination activity, template switching activity, or multiple integration activity is reduced by rearranging elements of the payload polynucleotide. This includes without limitation, deletion of 5' UTR elements and/or introduction of 5' UTR elements elsewhere in the sequence of the payload to be packaged. In an embodiment, introduction and/or relocation of the DIS provides lentivirus genomes (e,g., payloads) that package predominantly or completely as monomers.

In certain embodiments of the invention, recombination activity, template switching activity, or multiple integration activity is modulated by altering interaction of the payload with the capsid. In one embodiment, the lentivirus nucleocapsid (NC) protein is altered by mutating the zinc-finger region so as to disrupt NC-dependent dimerization.

In an embodiment of the invention, the system comprises a multiplicity of payload polynucleotides, each having at least a first engineered association and a second engineered association. The multiplicity of polynucleotides can be 2, 3, 4, 5, 6, 7, 8, 9, 10 or more and further any number of polynucleotides each having at least a first engineered association and a second engineered association.

In an embodiment of the invention, the first engineered association comprises a genetic perturbation. In an embodiment of the invention, both the first and the second engineered association each comprises a genetic perturbation. In an embodiment of the invention, the first engineered association comprises a genetic perturbation and the second engineered association comprises an identifier, such as but not limited to a unique molecular identifier. In an embodiment, the unique molecular identifier is a barcode.

In an embodiment of the invention, the carrier polynucleotide comprises or encodes non-recombinogenic RNA sequences or proteins that are capable of dimerizing with the polynucleotide having engineered associations. In certain embodiments, the RNA sequences or proteins disrupt recombination with the polynucleotide having engineered associations.

According to the invention the reduced recombination or template activity comprises reduced hairpin formation or dimerization through modification, knockdown or knockout of retroviral genomic RNA or retroviral protein involved in dimerization.

Further, in certain embodiments, the modification, knockdown or knockout of the retroviral genomic RNA retroviral protein comprises modification, knockdown or knockout of nucleocapsid (NC)-protein(s) or RNA for expression thereof or modification, knockdown or knockout of stem-loop I element (SLI) element or modification, knockdown or knockout of genomic RNA whereby U5:AUG pairing is prevented or modification, knockdown or knockout of a dimer initiation site (DIS).

In an embodiment of the invention, the polynucleotide sequence encoding one or more genetic perturbations encodes an over expressed gene, an RNAi based system, a zinc finger nuclease, a transcription activator-like effector nuclease (TALEN), a meganuclease, or a CRISPR-Cas system.

In another embodiment, the sequence encoding one or more genetic perturbations encodes a CRISPR-Cas9 system. In another embodiment, the sequence encoding one or more genetic perturbations encodes one or more guides.

In an aspect, the invention provides a method of preparing a lentiviral or retroviral system comprising a polynucleotide having at least a first engineered association and a second engineered association wherein the system has reduced recombination activity or template switching activity, or multiple integration activity. In an embodiment of the invention, the reduction can be 2×, 5×, 10×, 20×, 50×, 100×, 500×, 1000× or greater. In an embodiment, the method comprises packaging the polynucleotide with an inhibitor of template switching.

In an embodiment, the method comprises packaging the polynucleotide with a carrier polynucleotide. As set forth above, the carrier polynucleotide can be involved in or affect any aspect of lentiviral packaging and functions to reduce recombination activity or template switching activity, or multiple integration. In an embodiment of the invention, the method comprises packaging of a multiplicity of polynucleotides, each having at least a first engineered association and a second engineered association. The multiplicity of polynucleotides can be 2, 3, 4, 5, 6, 7, 8, 9, 10 or more and further any number of polynucleotides each having at least a first engineered association and a second engineered association.

In an embodiment of the invention, the method comprises genetic perturbation. In an embodiment of the invention, both the first and the second engineered association each comprises a genetic perturbation. In an embodiment of the invention the first engineered association comprises a genetic perturbation and the second engineered association comprises an identifier, such as but not limited to a unique molecular identifier. In an embodiment, the unique molecular identifier is a barcode. In an embodiment of the invention the method comprises use of non-recombinogenic RNA sequences or proteins that are capable of dimerizing with the polynucleotide having engineered associations.

According to the invention, the reduced recombination or template activity comprises reduced hairpin formation or dimerization through modification, knockdown or knockout of retroviral genomic RNA or retroviral protein involved in dimerization. Further, in certain embodiments, the modification, knockdown or knockout of the retroviral protein comprises modification, knockdown or knockout of nucleocapsid (NC)-protein(s) or RNA for expression thereof or modification, knockdown or knockout of stem-loop I element (SLI) element or modification, knockdown or knockout of genomic RNA whereby U5:AUG pairing is prevented or modification, knockdown or knockout of a dimer initiation site (DIS).

In an aspect, the invention provides a method of preparing a lentiviral or retroviral system comprising a polynucleotide having at least a first engineered association and a second engineered association wherein the system has reduced recombination activity or template switching activity, or multiple integration activity. In an embodiment of the invention, the reduction can be 2×, 5×, 10×, 20×, 50×, 100×, 500×, 1000× or greater. In an embodiment, the method comprises packaging the polynucleotide with an inhibitor of template switching.

In an embodiment, the method comprises packaging the polynucleotide with a carrier polynucleotide. As set forth above, the carrier polynucleotide can be involved in or affect any aspect of lentiviral packaging and function to reduce recombination activity or template switching activity, or multiple integration activity. In an embodiment of the invention, the method comprises packaging of a multiplicity of polynucleotides, each having at least a first engineered association and a second engineered association. The multiplicity of polynucleotides can be 2, 3, 4, 5, 6, 7, 8, 9, 10 or more and further any number of polynucleotides each having at least a first engineered association and a second engineered association.

In an embodiment of the invention, the method comprises a genetic perturbation. In an embodiment of the invention, both the first and the second engineered association each comprises a genetic perturbation. In an embodiment of the invention, the first engineered association comprises a genetic perturbation and the second engineered association comprises an identifier, such as but not limited to a unique molecular identifier. In an embodiment, the unique molecular identifier is a barcode.

In an embodiment of the invention the method comprises use of non-recombinogenic RNA sequences or proteins that are capable of dimerizing with the polynucleotide having engineered associations. According to the invention, the reduced recombination or template activity comprises reduced hairpin formation or dimerization through modification, knockdown or knockout of retroviral genomic RNA or retroviral protein involved in dimerization.

Further, in certain embodiments, the modification, knockdown or knockout of the retroviral protein comprises modification, knockdown or knockout of nucleocapsid (NC)-protein(s) or RNA for expression thereof or modification, knockdown or knockout of stem-loop I element (SLI) element or modification, knockdown or knockout of genomic RNA whereby U5:AUG pairing is prevented or modification, knockdown or knockout of a dimer initiation site (DIS).

Screening using the CRISPR technology and method and systems of the invention is particularly advantageous because of its simplicity, specificity and versatility. For example genome-wide GeCKO and SAM libraries target every gene in the mouse or human genes and knock-out or transcriptionally activate each gene. Alternatively, libraries may be pathway-focused and screened under specific conditions such as by positive or negative selection, to identify important genes in a pathway. In an embodiment, a population of cells may be transfected with a library to knock out or activate certain genes, transfectants of interest identified on the basis of phenotypic screens, and cell products of the transfection identified by a unique molecular identifier originally associated with each gene knocked out, knocked down or activated. In certain embodiments, phenotypic screens identify gene expression profiles which may then be associated with an original transfectant. Generally in such embodiments, genetic elements for knock out, knock down, or activation are each associated in the library with an identifier, which can be but is not limited to a unique molecular identifier such as a barcode.

Lentiviral packaged libraries include particles containing heterodimers and recombinant heterodimers. Packaged heterodimers occur, for example, when two or more library members are contained in one cell of a packaging cell line and is accompanied by recombination or template switching in of the heterodimer. For example, a targeting library may be constructed such that in each library member, a gene targeting sequence such as a guide sequence of a CRISPR system is separated to some degree from an identifier element such as a barcode, but the intervening sequence is the same, and promotes recombination between library members when dimerized. In certain embodiments, the sequence intervening sequence common to the library members corresponds to the direct repeat that binds to a CRISPR protein. Recombination produces mispairing of guide sequences with barcodes, hence degrades information obtainable from the screen. The lentiviral systems described herein minimize recombination, providing lentivirus packages that are effectively monomeric. By "effectively monomeric" is meant that a library member is packaged as a monomer or in a manner that reduces or eliminates recombination. In certain embodiments, a library member, which is a polynucleotide having at least a first engineered association and a second engineered association, is packaged with a nucleic acid that is not recombinogenic, referred to herein as a stuffer. In certain non-limiting embodiments, a stuffer nucleic acid lacks any substantial homology with the polynucleotide having the first and second engineered association. In certain embodiments, a nucleic acid is provided in a packaging cell that is not packaged but reduces heterodimers and recombination thereof. The nucleic acid can be any replicable vector that need not produce a packageable polynucleotide. In an embodiment of the invention, the vector is pUC19.

Certain evidence has suggested that lentiviral genome dimerization normally occurs after RNA is packaged and virus particles are released. For example, 70S RNA dimers could not be isolated from infected cells and viral particles harvested upon formation contained monomeric RNA which dimerized minutes or hours after particle release. Also, dimerization of the RNA in the particles was blocked if the virus was solubilized with detergent. (Canaani et al., 1973, Proc. Natl. Acad. Sci. USA 72:401-405). In certain models, NC protein contributes to dimerization. For example, in one model, the NC protein after release from the Gag polyprotein, binds to each RNA and unfolds double-stranded structures near the 5' ends, allowing interstrand contacts to form. In this regard, there are observations that prevention of gag polyprotein cleavage by protease inactivation or mutation of NC results in virus particles that contain monomeric RNA. (Oertle and Spahr, 1990; Stewart et al., 1990, J Virol 64:5076-92; Dupraz et al., 1990).

Certain key nucleotides involved in the RNA dimerization event make up a palindromic sequence between the PBS and the major splice donor, and RNA sequences on both sides of this palindrome can form a stem-loop structure with the palindrome in the hairpin loop. Deletion of this stem-loop motif completely abolished dimerization of the 1 HIV-1 RNA fragment in vitro. Skripkin et al., 1994, Proc Natl Acad Sci USA 91:4945-4949.

Further, duplication of the DIS/DLS region in viral RNA causes production of virus particles containing partially monomeric RNAs without modifying any viral proteins and yields particles comparable in certain aspects to wild-type particles. Sakuragi et al., 2002, J. Virol. 76:959-967. The results indicate that RNA dimerization is not required for viral RNA packaging, virion maturation, and reverse transcription.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which.

Figure 1:
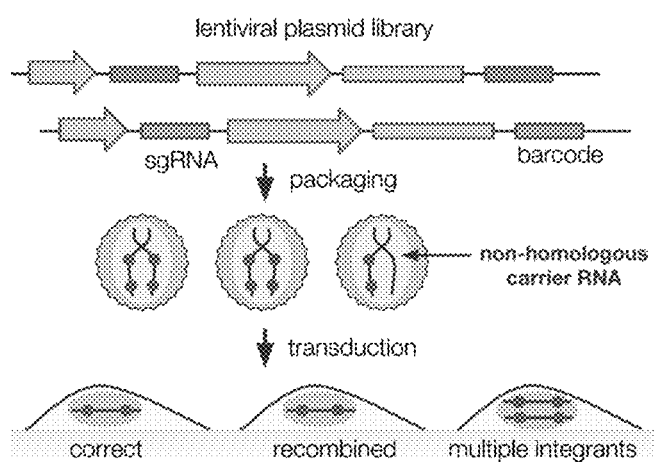
FIG. 1—Schematic of delivery of barcoded lentiviral plasmid library into target cells. Viral genomes containing sgRNAs and transcribed RNA barcodes, driven by U6 and EF1a promoters, are packaged into virions and integrated into target cells. Dimeric packaging of library plasmids may yield homodimeric or heterodimeric library associations or, in the case of cow packaging with a non-homologous carrier lentivirus (purple), a functionally monomeric virion. Virions with two different library elements have the capacity for recombination between sgRNAs and barcodes as well as potential for integration of multiple perturbations into the target cell, whereas co-packaging with a non-homologous vector limits these alternatives.
Figure 2:
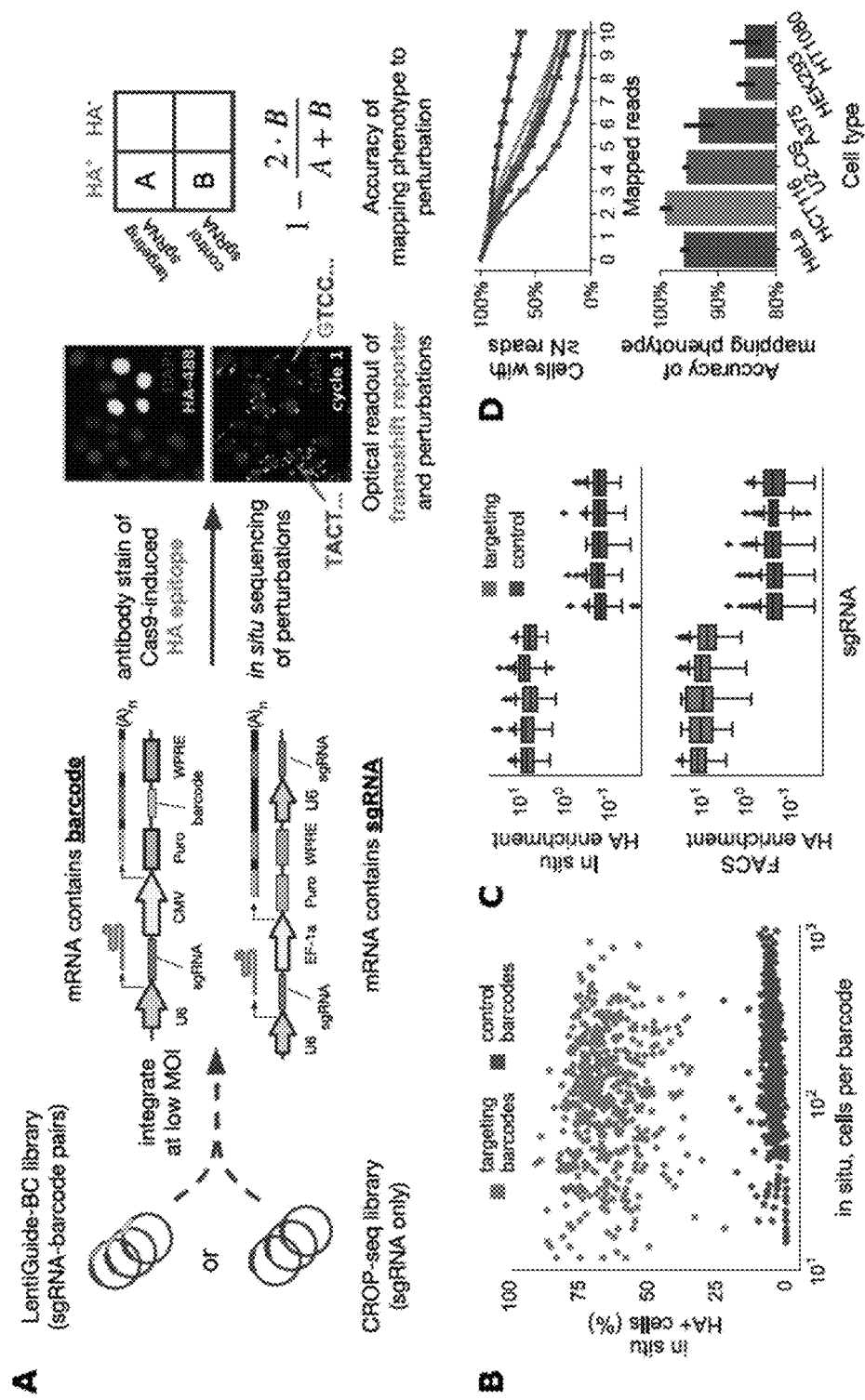
FIG. 2—An example method of constructing viral libraries using the methods described herein.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology $2^{nd}$ ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +1-10% or less, +/−5% or less, +/−1 % or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

As used herein, "engineered association" means a library member portion that comprises an engineered structural and/or functional part, including but not limited to a guide sequence for a CRISPR system, or a tag or identifier such as a unique molecular identifier (UMI) or barcode or other tracking element. The engineered structural or functional part is physically associated with the library member in that it is linked to nucleotides or other chemical parts of the library member. Two or more engineered associations are linked when they are comprised by a single polynucleotide or other monomeric molecule. A library polynucleotide comprising engineered associations may be referred to as a "payload" or "template."

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Retroviral systems, including lentivirus-based systems, can be pseudo-diploid, that is two viral genomes are packaged into each viral particle and are non-covalently linked. During viral genome replication, the reverse transcriptase can switch from one template to another when it synthesizes a DNA provirus from a dimeric RNA genome, and this process happens most frequently at homologous regions. The frequency of recombination may depend on the distance between two regions which has been estimated to be 2% every kilobase. Thus, when libraries of distinct vector sequence are packaged together, template switching could lead to recombination that randomly shuffles associations between sequences, such as associations between sequences encoding one or more genetic perturbations and unique molecular sequence, for example a unique molecular sequence that identifies the encoding perturbation.

Embodiments disclosed herein provide retroviral systems comprising modifications that mitigates those effects by reducing recombination or template switching activity. Further included are modified methods for retroviral vector packaging. The modified retroviral systems disclosed herein may be used for combinatorial screening of perturbations, including single cell screening.

Engineered Viral Systems

The present disclosure includes non-naturally engineered viral systems. In some examples, the non-naturally occurring engineered viral systems may be a lentiviral or retroviral system. The systems disclosed herein may comprise a first polynucleotide having at least a first and second engineered association. For ease of reference, the remaining disclosure will address systems with a first and second engineered association, but more than two engineered associations are also envisioned. One or more activities of the engineered systems may be reduced (e.g., as compared to a non-engineered counterpart system). Such activities may include recombination activity, or template switching activity, and multiple integration activity.

The engineered systems herein may comprise a multiplicity of polynucleotides. In certain embodiments, the retroviral system may comprise a multiplicity of first polynucleotides. The multiplicity of first polynucleotides may comprise different combinations of engineered associations. As used herein, the term "retroviral" is intended to encompass both retroviral and lentivirus-based systems. The first and second engineered association represent sequences that need to remain associated with one another throughout the life cycle of the polynucleotide. For example, the polynucleotide may be a vector and the first and second association encode elements that need to remain associated on the same polynucleotide for further downstream applications. In certain example embodiments, the first and engineered associations may be located 1 kb or greater apart on the polynucleotide sequence. In certain example embodiments, the engineered associations may be located 2 kb or greater apart on the polynucleotide sequence.

The retroviral system may comprise an inhibitor of recombination or template switching. In certain example embodiment, the retroviral system may further comprise a second polypeptide. The second polynucleotide may be a carrier polynucleotide comprising non-recombinogenic RNA sequences or sequences with limited homology to the first nucleotide or otherwise configured to impair or prevent homologous recombination with the first polynucleotide when packaged together within a viral particle. In another embodiment, the second polynucleotide may result in reduced hairpin formation or dimerization through modification, knockdown or knockout of retroviral genomic RNA or retroviral proteins involved in dimerization.

In certain example embodiments, the second polypeptide may be 2 kb to 10 kb in size. In certain example embodiments, the second polypeptide is 2.0 kb, 2.1 kb, 2.2 kb, 2.3 kb, 2.4 kb, 2.5 kb, 2.6 kb, 2.7 kb, 2.8 kb, 2.9 kb, 3.0 kb, 3.1 kb, 3.2 kb, 3.3 kb, 3.4 kb, 3.5 kb, 3.6 kb, 3.7 kb, 3.8 kb, 3.9 kb, 4.0 kb, 4.1 kb, 4.2 kb, 4.3 kb, 4.4 kb, 4.5 kb, 4.6 kb, 4.7 kb, 4.8 kb, 4.9 kb, 5.0 kb, 5.1 kb, 5.2 kb, 5.3 kb, 5.4 kb, 5.5 kb 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.1 kb, 7.2 kb, 7.3 kb, 7.4 kb, 7.5 kb, 7.6 kb, 7.7 kb, 7.8 kb, 7.9 kb, 8.0 kb, 8.1 kb, 8.2 kb, 8.3 kb, 8.4 kb, 8.5 kb, 8.6 kb, 8.7 kb, 8.8 kb, 8.9 kb, 9.0 kb, 9.1 kb, 9.2 kb, 9.3 kb, 9.4 kb, 9.5 kb, 9.6 kb, 9.7 kb, 9.8 kb, 9.9 kb, or 10.0 kb in size.

In certain example embodiments, the second polypeptide may be selected to have less than 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% complementarity to the first polynucleotide.

In certain example embodiments, the second polypeptide is a lentiviral vector. In certain example embodiments, the lentiviral vector has long terminal repeat to long terminal repeat distance (LTR-LTR distance) of 2.5 kb, 2.4 kb, 2.3 kb, 2.2 kb, 2.1 kb, 2.0 kb, 1.9 kb, 1.8 kb, 1.7 kb. 1.6 kb, 1.5 kb, 1.4 kb, 1.3 kb, 1.2 kb. 1.1 kb, or 1.0 kb.

In certain example embodiments, the lentiviral vector comprises one or more LTR mutations in one or both LTR regions that abrogate integration capability.

Other factors that may be considered in selecting or designing second polynucleotide include GC content, presence/absence of repeats, sequence signatures that affect DNA helix parameters, using supercoiled versus relaxed plasmids, nicked or un-nicked plasmids, methylated or non-methylated plasmids.

Retroviral Systems

The viral backbone of the retroviral system may be any retrovirus suitable for use in delivering expression constructs to cells. Example retroviral systems include moloney murine leukemia virus (MoMuLV), feline immunodeficiency virus (FIV), HIV-1 based packaging systems (HIV), and lentiviral based systems. In certain example embodiments, the retroviral system is based on Moloney murine leukemia virus (MoMuLV), Harvey murine sarcoma virus (HaMuSV), murine mammary tumor virus (MuMTV), gibbon ape leukemia virus (GaLV) human immunodeficiency virus (HIV) and Rous Sarcoma Virus (RSV). (see, e.g., Buchscher et al, J. Virol. 66:2731-2739 (1992); Johann et al, J. Virol. 66: 1635-1640 (1992); Sommnerfelt et al, Virol. 176:58-59 (1990); Wilson et al, J. Virol. 63:2374-2378 (1989); Miller et al, J. Virol. 65:2220-2224 (1991); PCT/US94/05700).

Vectors that are based on HIV may retain <5% of the parental genome, and <25% of the genome may be incorporated into packaging constructs, which minimizes the possibility of the generation of revertant replication-competent HIV. The vector region may include sequences form the 5' and 3' LTRs of a lentivirus. In some instances, the vector domain includes the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Where desired, the packaged viral barcoded library may be made up of self inactivating vectors that contain deletions of the regulatory elements in the downstream long-terminal-repeat sequence, eliminating transcription of the packaging signal that is required for vector mobilization. As such, the vector region may include an inactivated or self-inactivating 3' LTR. The 3' LTR, may be made self-inactivating by any convenient method. For example, the U3 element of the 3' LTR may contain a deletion of its enhancer sequence, such as the TATA box. Sp1 and NF-kappa B sites.

As a result of the self-inactivating 3' LTR, the provirus that is integrated into the host cell genome will comprise an inactivated 5' LTR. Optionally, the U3 sequence from the lentiviral 5' LTR may be replaced with a promoter sequence in the viral construct. This may increase the titer of virus recovered from the packaging cell line. An enhancer sequence may also be included. In certain aspects, the viral construct is a non-integrating lentiviral construct, where the construct does not integrate by virtue of having a defective (e.g., by site-specific mutation) or absent integrase gene. Integrate-detective lentiviral vectors are described, e.g., in Banasik and McCray (2010) Gene Therapy 17(2):150-157.

In certain example embodiments, a lentivirus based system is used. Lentiviruses are members of the retrovirus family. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al, J. Virol. 66:2731-2739 (1992); Johann et al, J. Virol. 66: 1635-1640 (1992); Sommnerfelt et al, Virol. 176:58-59 (1990); Wilson et al, J. Virol. 63:2374-2378 (1989); Miller et al, J. Virol. 65:2220-2224 (1991); PCT/US94/05700).

The embodiments disclosed herein may also be useful in non-retroviral based systems, that are pseudo-diploid or otherwise known to have the same recombination and template-switching limitations of lentivirus and retrovirus systems disclosed herein.

Carrier Polynucleotides

The invention provides inhibitors of recombination activity, template switching activity, or multiple integration activity. In some cases, the engineered systems described herein comprise an inhibitor of template switching. In an embodiment, the inhibitor of template switching is a carrier polynucleotide. The carrier polynucleotide can be involved in or affect any aspect of lentiviral packaging, and functions to reduce recombination activity or template switching activity, or multiple integration. For example, in an embodiment of the invention, the carrier polynucleotide is packaged with or forms a heterodimer with the polynucleotide comprising the one or more engineered associations, but lacks sufficient homology such that recombination activity, template switching activity, or multiple integration activity is reduced or eliminated. In an embodiment of the invention, the reduction in recombination activity, template switching activity, or multiple integration activity can be 2×, 5×, 10×, 20×, 50×, 100×, 500×, 1000× or greater as compared to packaging without the carrier polynucleotide. In packaging reactions, carrier polynucleotides are usually in excess. In certain embodiments, the carrier polynucleotide to payload polynucleotide ratio in packaging is from 5:1 to 10:1 or from 10:1 to 20:1 or from 20:1 to 50:1, or from 50:1 to 100:1 or from 100:1 to 500:1, of from 500:1 to 1000:1 or greater.

In another embodiment, the inhibitor of recombination activity, or template switching activity, or multiple integration activity can be any carrier polynucleotide transfected into a packaging cell and present with the payload to be packaged, which carrier polynucleotide is not designed to be packaged. Such carriers include, without limitation, single and double stranded DNA, replicable and non-replicable plasmid type vectors, including prokaryotic and eukaryotic vectors. In a non-limiting example set forth herein, bacterial plasmid pUC19, which does not replicate in a packaging cell, is not transcribed, and is not designed to be packaged in a lentiviral particle, is demonstrate to inhibit recombination activity, template switching activity, or multiple integration activity.

In some embodiments, the carrier polynucleotide comprises or encodes one or more non-recombinogenic RNA sequences. Alternatively or additionally, the carrier polynucleotide may encode proteins that capable of dimerizing with the polynucleotide having engineered association.

Reduced recombination or template activity herein may comprise reduced hairpin formation or dimerization through modification, knockdown or knockout of retroviral genomic RNA or retroviral protein involved in dimerization. In some examples, the retroviral genomic RNA or retroviral protein comprises nucleocapsid (NC)-protein(s) or RNA encoding thereof, stem-loop I element (SLI), genomic RNA in which U5:AUG pairing is prevented, a dimer initiation site (DIS), or any combination thereof.

In an embodiment, the inhibitor of recombination activity, or template switching activity, or multiple integration activity comprises a polynucleotide designed to hybridize with all or part of the 5' UTR, including but not limited to such regions as U5-PBS complex or the dimer initiation site (DIS). In an embodiment, the inhibitor polynucleotide can be RNA produced concurrently with the payload, or added to the payload prior to packaging. In an embodiment, the inhibitor polynucleotide can be synthetic. Tran et al., 2015, Retrovirology 12:83 reviews conserved determinants of lentiviral genome dimerization.

In an embodiment, recombination activity, template switching activity, or multiple integration activity is reduced by rearranging elements of the payload polynucleotide. This includes without limitation, deletion of 5' UTR elements and/or introduction of 5' UTR elements elsewhere in the sequence of the payload to be packaged. In an embodiment, introduction and/or relocation of the DIS provides lentivirus genomes (e,g., payloads) that package predominantly or completely as monomers. Sakuragi et al., 2002, J. Virol. 76:959-967 reports several HIV mutants comprising multiple and rearranged copies of viral E/DLS sequences. According to the invention, 5' UTR elements can be added and/or rearranged in payload genomes, taking care not to interrupt desired genetic elements (associations) provided therein.

In certain embodiments of the invention, recombination activity, template switching activity, or multiple integration activity is modulated by altering interaction of the payload with the capsid. In one embodiment, the lentivirus nucleocapsid (NC) protein is altered by mutating the zinc-finger region so as to disrupt NC-dependent dimerization. See, e.g., Tran et al., 2015, reviewing 5' UTR and NC features involved in dimerization.

Genetic Perturbations

In one example embodiment, the first polynucleotide may encode one or more genetic perturbations. The sequences encoding one or more genetic perturbations may comprise an over-expressed gene, siRNAs, microRNAs, regulatory RNAs, ribozymes, antisense RNAs, guide sequences, or a site-specific nuclease. The polynucleotides (e.g., polynucleotides with sequence encoding one or more genetic perturbations) may encode a site-specific nuclease such as, but not limited to, zinc-finger nuclease (ZFN), a transcription activator-like effector nuclease (TALENs) a CRISPR system, a component thereof, a portion thereof, or any combination thereof. Alternatively or additionally, the polynucleotides may encode one or more overexpressed genes, a RNAi based system, a component thereof, or a portion thereof. In some examples, the polynucleotides encode a CRISPR-Cas system or a component thereof. The CRISPR-Cas system may be a CRISPR-Cas9 system. In some cases, the polynucleotides encode one or more guide sequences.

Suitable site-specific nuclease systems are described in further detail below. The perturbation(s) may comprise single-order perturbations. The perturbation(s) may comprise combinatorial perturbations. The perturbations may include gene knock-outs, gene knock-ins, transpositions, inversions, and/or one or more nucleotide insertions, deletions, or substitutions.

In some cases, the polynucleotide comprises a first and a second engineered associations. The associations may comprise one or more genetic perturbations. For example, the first engineered association may comprise a first genetic perturbation and the second engineered association may comprise a second genetic perturbation.

TALENs

In certain embodiments, the sequence encoding the one or more genetic perturbation encodes a (modified) transcription activator-like effector nuclease (TALEN) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference. By means of further guidance, and without limitation, naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26. The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety. In certain embodiments, targeting is affected by a polynucleic acid binding TALEN fragment. In certain embodiments, the targeting domain comprises or consists of a catalytically inactive TALEN or nucleic acid binding fragment thereof.

Zn-Finger Nucleases

In certain embodiments, the sequence encoding one or more genetic perturbations comprises or consists of a (modified) zinc-finger nuclease (ZFN) system. The ZFN system uses artificial restriction enzymes generated by fusing a zinc finger DNA-binding domain to a DNA-cleavage domain that can be engineered to target desired DNA sequences. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference. By means of further guidance, and without limitation, artificial zinc-finger (ZF) technology involves arrays of ZF modules to target new DNA-binding sites in the genome. Each finger module in a ZF array targets three DNA bases. A customized array of individual zinc finger domains is assembled into a ZF protein (ZFP). ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. In certain embodiments, the targeting domain comprises or consists of a nucleic acid binding zinc finger nuclease or a nucleic acid binding fragment thereof. In certain embodiments, the nucleic acid binding (fragment of) a zinc finger nuclease is catalytically inactive.

Meganuclease

In certain embodiments, the sequences encoding one or more genetic perturbations comprises a (modified) meganuclease, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference. In certain embodiments, targeting is affected by a polynucleic acid binding meganuclease fragment. In certain embodiments, targeting is affected by a polynucleic acid binding catalytically inactive meganuclease (fragment). Accordingly in particular embodiments, the targeting domain comprises or consists of a nucleic acid binding meganuclease or a nucleic acid binding fragment thereof.

CRISPR-Cas Systems

In certain embodiments, the sequence encoding the one or more genetic perturbation encodes a (modified) CRISPR/Cas complex or system. General information on CRISPR/Cas Systems, components thereof, and delivery of such components, including methods, materials, delivery vehicles, vectors, particles, and making and using thereof, including as to amounts and formulations, as well as CRISPR/Cas-expressing eukaryotic cells, CRISPR/Cas expressing eukaryotes, such as a mouse, is described herein elsewhere. In certain embodiments, targeting is affected by an oligonucleic acid binding CRISPR protein fragment and/or a gRNA. In certain embodiments, targeting is affected by a nucleic acid binding catalytically inactive CRISPR protein (fragment). Accordingly in particular embodiments, the targeting domain comprises oligonucleic acid binding CRISPR protein or an oligonucleic acid binding fragment of a CRISPR protein and/or a gRNA.

As used herein, the term "Cas" generally refers to a (modified) effector protein of the CRISPR/Cas system or complex, and can be without limitation a (modified) Cas9, or other enzymes such as Cpf1, C2c1, C2c2, C2c3, group 29, or group 30 protein. The term "Cas" may be used herein interchangeably with the terms "CRISPR" protein, "CRISPR/Cas protein", "CRISPR effector", "CRISPR/Cas effector", "CRISPR enzyme", "CRISPR/Cas enzyme" and the like, unless otherwise apparent, such as by specific and exclusive reference to Cas9. It is to be understood that the term "CRISPR protein" may be used interchangeably with "CRISPR enzyme", irrespective of whether the CRISPR protein has altered, such as increased or decreased (or no) enzymatic activity, compared to the wild type CRISPR protein. Likewise, as used herein, in certain embodiments, where appropriate and which will be apparent to the skilled person, the term "nuclease" may refer to a modified nuclease wherein catalytic activity has been altered, such as having increased or decreased nuclease activity, or no nuclease activity at all, as well as nickase activity, as well as otherwise modified nuclease as defined herein elsewhere, unless otherwise apparent, such as by specific and exclusive reference to unmodified nuclease.

In some embodiments, the CRISPR effector protein is Cas9, Cpf1, C2c1, C2c2, or Cas13a, Cas13b, or Cas13c. In some embodiments, the CRISPR effector protein is a DNA-targeting CRISPR effector protein. In some embodiments, the CRISPR effector protein is a Type-II CRISPR effector protein such as Cas9. In some embodiments, the CRISPR effector protein is a Type-V CRISPR effector protein such as Cpf1 or C2c1. In some embodiments, the CRISPR effector protein is a RNA-targeting CRISPR effector protein. In some embodiments, the CRISPR effector protein is a Type-VI CRISPR effector protein such as Cas13a, Cas13b, or Cas13c.

In some embodiments, the CRISPR effector protein is a Cas9, for instance SaCas9, SpCas9, StCas9, CjCas9 and so forth—any ortholog is envisaged. In some embodiments, the CRISPR effector protein is a Cpf1, for instance AsCpf1, LbCpf1, FnCpf1 and so forth—any ortholog is envisaged. In certain embodiments, the targeting component as described herein according to the invention is a (endo)nuclease or a variant thereof having altered or modified activity (i.e. a modified nuclease, as described herein elsewhere). In certain embodiments, said nuclease is a targeted or site-specific or homing nuclease or a variant thereof having altered or modified activity. In certain embodiments, said nuclease or targeted/site-specific/homing nuclease is, comprises, consists essentially of, or consists of a (modified) CRISPR/Cas system or complex, a (modified) Cas protein, a (modified) zinc finger, a (modified) zinc finger nuclease (ZFN), a (modified) transcription factor-like effector (TALE), a (modified) transcription factor-like effector nuclease (TALEN), or a (modified) meganuclease. In certain embodiments, said (modified) nuclease or targeted/site-specific/homing nuclease is, comprises, consists essentially of, or consists of a (modified) RNA-guided nuclease.

In particular embodiments, more particularly where the nuclease is a CRISPR protein, the targeting domain further comprises a guide molecule which targets a selected nucleic acid. For instance, in the context of the CRISPR/Cas system, the guide RNA is capable of hybridizing with a selected nucleic acid sequence. As used herein, "hybridization" or "hybridizing" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PGR, or the cleavage of a polynucleotide by an enzyme. A sequence capable of hybridizing with a given sequence is referred to as the "complement" of the given sequence.

Guide Sequences

In certain example embodiments, one of the engineered associations may comprise one of the above Cas proteins. In another embodiment, one of the engineered associations may comprise a Cas protein and second engineered association may comprise a guide sequence. In yet another embodiment, the engineered associations may comprise two or more guide sequences. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiments, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such as deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3'phosphorothioate (MS), S-constrained ethyl(cEt), or 2'-O-methyl 3'thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., *J. Med. Chem.* 2005, 48:901-904; Bramsen et al., Front. Genet., 2012, 3:154; Deng et al., PNAS, 2015, 112:11870-11875; Sharma et al., *MedChemComm.*, 2014, 5:1454-1471; Hendel et al., Nat. Biotechnol. (2015) 33(9): 985-989; Li et al., *Nature Biomedical Engineering*, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., *Nature Biomedical Engineering*, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., *Nat. Biotechnol.* (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells genetically edited by a CRISPR system (see Lee et al., *eLife*, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine (5moU), inosine, 7-methyl-guanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sufonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of th guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complementary stretch (the "anti-repeat" being complementary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas proten (Chen et al. Cell. (2013); 155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes may have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, 02 concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB 1. Blue light stimulation induces an activating conformational change in cryptochrome-2, resulting in recruitment of its binding partner CIB1. This binding is fast and reversible, achieving saturation in <15 sec following pulsed stimulation and returning to baseline<15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The disclosure contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 $mW/cm^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans;4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., //www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another example inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc., as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100 .mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm$^2$ to about 100 W/cm$^2$. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm$^2$ (FDA recommendation), although energy densities of up to 750 mW/cm$^2$ have been used. In physiotherapy, ultrasound is typically used as an energy source in a range up to about 3 to 4 W/cm$^2$ (WHO recommendation). In other therapeutic applications, higher intensities of ultrasound may be employed, for example, HIFU at 100 W/cm up to 1 kW/cm$^2$ (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142). Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm$^{-2}$.

Even more preferably, the exposure to an ultrasound energy source is at a power density of from about 1 to about 15 Wcm$^{-2}$.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm$^{-2}$ to about 10 Wcm$^{-2}$ with a frequency ranging from about 0.015 to about 10 MHz (see WO 98/52609). However, alternatives are also possible, for example, exposure to an ultrasound energy source at an acoustic power density of above 100 Wcm$^{-2}$, but for reduced periods of time, for example, 1000 Wcm$^{-2}$ for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

In certain example embodiments, the system may comprise a first guide sequence and a second guide sequence such as used in paired nickase system or self-inactivating systems. Paired nickase systems are used, for example, to minimize off-target effects. Typically, guides are designed in pairs and used with a nickase to introduce two nicks, one on each strand, into a DNA duplex, each nick targeted to adjacent but different sequences of a genomic locus. In an embodiment, the guides are expressed from the same promoter. In and embodiment, the guides are in tandem. In such embodiments, the guides are designed to work together, encoded on a single polynucleotide and packaged together. By reducing or eliminating recombination or template switching activity, the invention improves the performance of multiplexed nickase systems comprising two or more guide pairs (i.e., targeting two or more genetic loci). In a self-inactivating (SIN) system two or more loci are targeted. One target comprises, for example, a genomic locus intended to be modified and the second target comprises a locus associated with a CRISPR system component whereby the function of the CRISPR system may be targeted. In certain SIN systems, it will be desired to maintain the linkage of a guide that targets the genomic locus with the guide that targets the CRISPR component. Example self-inactivating systems are disclosed in WO/2015/070083, WO/2015/089354, and WO/2015/089351. Example tandem guide systems are disclosed in WO/2014/204724, WO/2014/093622, and WO/2014/204725.

Unique Molecular Sequence

In certain example embodiments, one of the engineered association may a unique molecular identifier. The unique molecular identifier may be a random nucleotide sequence that uniquely identifies the polynucleotide and/or the other engineered associations encoded on the first polynucleotide.

In certain example embodiment, the unique molecular sequence may be a barcode. The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment. Although it is not necessary to understand the mechanism of an invention, it is believed that the barcode sequence provides a high-quality individual read of a barcode associated with a single cell, a viral vector, labeling ligand (e.g., an aptamer), protein, shRNA, sgRNA or cDNA such that multiple species can be sequenced together.

Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

In preferred embodiments, sequencing is performed using unique molecular identifiers (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. The UMI may also be used to determine the number of transcripts that gave rise to an amplified product, or in the case of target barcodes as described herein, the number of binding events. In preferred embodiments, the amplification is by PCR or multiple displacement amplification (MDA).

In certain embodiments, an UMI with a random sequence of between 4 and 20 base pairs is added to a template, which is amplified and sequenced. In preferred embodiments, the UMI is added to the 5' end of the template. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No:11, 163-166). Not being bound by a theory, the UMI's are designed such that assignment to the original can take place despite up to 4-7 errors during amplification or sequencing. Not being bound by a theory, an UMI may be used to discriminate between true barcode sequences.

Unique molecular identifiers can be used, for example, to normalize samples for variable amplification efficiency. For example, in various embodiments, featuring a solid or semisolid support (for example a hydrogel bead), to which nucleic acid barcodes (for example a plurality of barcodes sharing the same sequence) are attached, each of the barcodes may be further coupled to a unique molecular identifier, such that every barcode on the particular solid or semisolid support receives a distinct unique molecule identifier. A unique molecular identifier can then be, for example, transferred to a target molecule with the associated barcode, such that the target molecule receives not only a nucleic acid barcode, but also an identifier unique among the identifiers originating from that solid or semisolid support.

A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. Target molecule and/or target nucleic acids can be labeled with multiple nucleic acid barcodes in combinatorial fashion, such as a nucleic acid barcode concatemer. Typically, a nucleic acid barcode is used to identify a target molecule and/or target nucleic acid as being from a particular discrete volume, having a particular physical property (for example, affinity, length, sequence, etc.), or having been subject to certain treatment conditions. Target molecule and/or target nucleic acid can be associated with multiple nucleic acid barcodes to provide information about all of these features (and more). Each member of a given population of UMIs, on the other hand, is typically associated with (for example, covalently bound to or a component of the same molecule as) individual members of a particular set of identical, specific (for example, discreet volume-, physical property-, or treatment condition-specific) nucleic acid barcodes. Thus, for example, each member of a set of origin-specific nucleic acid barcodes, or other nucleic acid identifier or connector oligonucleotide, having identical or matched barcode sequences, may be associated with (for example, covalently bound to or a component of the same molecule as) a distinct or different UMI.

As disclosed herein, unique nucleic acid identifiers may be used to label the target molecules and/or target nucleic acids, for example origin-specific barcodes and the like. The nucleic acid identifiers, nucleic acid barcodes, can include a short sequence of nucleotides that can be used as an identifier for an associated molecule, location, or condition. In certain embodiments, the nucleic acid identifier further includes one or more unique molecular identifiers and/or barcode receiving adapters. A nucleic acid identifier can have a length of about, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt). In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 bp or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety.

One or more nucleic acid identifiers (for example a nucleic acid barcode) can be attached, or "tagged," to a target molecule. This attachment can be direct (for example, covalent or noncovalent binding of the nucleic acid identifier to the target molecule) or indirect (for example, via an additional molecule). Such indirect attachments may, for example, include a barcode bound to a specific-binding agent that recognizes a target molecule. In certain embodiments, a barcode is attached to protein G and the target molecule is an antibody or antibody fragment. Attachment of a barcode to target molecules (for example, proteins and other biomolecules) can be performed using standard methods well known in the art. For example, barcodes can be linked via cysteine residues (for example, C-terminal cysteine residues). In other examples, barcodes can be chemically introduced into polypeptides (for example, antibodies) via a variety of functional groups on the polypeptide using appropriate group-specific reagents (see for example www.drmr.com/abcon). In certain embodiments, barcode tagging can occur via a barcode receiving adapter associate with (for example, attached to) a target molecule, as described herein.

Target molecules can be optionally labeled with multiple barcodes in combinatorial fashion (for example, using multiple barcodes bound to one or more specific binding agents that specifically recognizing the target molecule), thus greatly expanding the number of unique identifiers possible within a particular barcode pool. In certain embodiments, barcodes are added to a growing barcode concatemer attached to a target molecule, for example, one at a time. In other embodiments, multiple barcodes are assembled prior to attachment to a target molecule. Compositions and methods for concatemerization of multiple barcodes are described, for example, in International Patent Publication No. WO 2014/047561, which is incorporated herein by reference in its entirety.

In some embodiments, a nucleic acid identifier (for example, a nucleic acid barcode) may be attached to sequences that allow for amplification and sequencing (for example, SBS3 and P5 elements for Illumina sequencing). In certain embodiments, a nucleic acid barcode can further include a hybridization site for a primer (for example, a single-stranded DNA primer) attached to the end of the barcode. For example, an origin-specific barcode may be a nucleic acid including a barcode and a hybridization site for a specific primer. In particular embodiments, a set of origin-specific barcodes includes a unique primer specific barcode made, for example, using a randomized oligo type NNNNNNNNNNNN.

A nucleic acid identifier can further include a unique molecular identifier and/or additional barcodes specific to, for example, a common support to which one or more of the nucleic acid identifiers are attached. Thus, a pool of target molecules can be added, for example, to a discrete volume containing multiple solid or semisolid supports (for example, beads) representing distinct treatment conditions (and/or, for example, one or more additional solid or semisolid support can be added to the discreet volume sequentially after introduction of the target molecule pool), such that the precise combination of conditions to which a given target molecule was exposed can be subsequently determined by sequencing the unique molecular identifiers associated with it.

Labeled target molecules and/or target nucleic acids associated origin-specific nucleic acid barcodes (optionally in combination with other nucleic acid barcodes as described herein) can be amplified by methods known in the art, such as polymerase chain reaction (PCR). For example, the nucleic acid barcode can contain universal primer recognition sequences that can be bound by a PCR primer for PCR amplification and subsequent high-throughput sequencing. In certain embodiments, the nucleic acid barcode includes or is linked to sequencing adapters (for example, universal primer recognition sequences) such that the barcode and sequencing adapter elements are both coupled to the target molecule. In particular examples, the sequence of the origin specific barcode is amplified, for example using PCR. In some embodiments, an origin-specific barcode further comprises a sequencing adaptor. In some embodiments, an origin-specific barcode further comprises universal priming sites. A nucleic acid barcode (or a concatemer thereof), a target nucleic acid molecule (for example, a DNA or RNA molecule), a nucleic acid encoding a target peptide or polypeptide, and/or a nucleic acid encoding a specific binding agent may be optionally sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others. In some embodiments, the sequence of labeled target molecules is determined by non-sequencing based methods. For example, variable length probes or primers can be used to distinguish barcodes (for example, origin-specific barcodes) labeling distinct target molecules by, for example, the length of the barcodes, the length of target nucleic acids, or the length of nucleic acids encoding target polypeptides. In other instances, barcodes can include sequences identifying, for example, the type of molecule for a particular target molecule (for example, polypeptide, nucleic acid, small molecule, or lipid). For example, in a pool of labeled target molecules containing multiple types of target molecules, polypeptide target molecules can receive one identifying sequence, while target nucleic acid molecules can receive a different identifying sequence. Such identifying sequences can be used to selectively amplify barcodes labeling particular types of target molecules, for example, by using PCR primers specific to identifying sequences specific to particular types of target molecules. For example, barcodes labeling polypeptide target molecules can be selectively amplified from a pool, thereby retrieving only the barcodes from the polypeptide subset of the target molecule pool.

A nucleic acid barcode can be sequenced, for example, after cleavage, to determine the presence, quantity, or other feature of the target molecule. In certain embodiments, a nucleic acid barcode can be further attached to a further nucleic acid barcode. For example, a nucleic acid barcode can be cleaved from a specific-binding agent after the specific-binding agent binds to a target molecule or a tag (for example, an encoded polypeptide identifier element cleaved from a target molecule), and then the nucleic acid barcode can be ligated to an origin-specific barcode. The resultant nucleic acid barcode concatemer can be pooled with other such concatemers and sequenced. The sequencing reads can be used to identify which target molecules were originally present in which discrete volumes.

Libraries and Cell Lines

The compositions of the present invention further include libraries comprising a multiplicity of the retroviral systems disclosed herein. A number of libraries may be used in accordance with the present invention, including but not limited to, normalized and non-normalized libraries for sense and antisense expression; libraries selected for specific chromosomes or regions of chromosomes (e.g. as comprised in YACs or BACs), which would be possible by inclusion of the f1 origin; and libraries derived from a tissue source; and genomic libraries.

In some cases, the compositions herein comprise a viral expression library. The viral expression library may comprise viral particles, wherein each viral particle comprises a polynucleotide having engineered associations comprising a sequence encoding one or more genetic perturbations and a unique molecular sequence clone, and one or more polypeptides that comprise non-recombinogenic RNA sequences, or proteins that are capable of dimerizing with the polynucleotide.

The libraries employed in embodiments of the subject methods can be produced using any convenient protocol. According to certain embodiments, preparing the libraries includes combining polynucleotide having a first engineered association and a second engineered association with a vector construct comprising a vector domain of vector sequence under conditions sufficient to produce transfection plasmids which, upon transfection of a packaging cell, result in the production of viral particles containing the polynucleotide as part of genomic nucleic acids encapsidated in viral protein shells. To prepare the product transfection plasmids used for transfection, a polynucleotide may be inserted into a vector nucleic acid, where any suitable protocol may be employed. Examples of suitable protocols include, but are not limited to: DNA ligase mediated joining, recombination enzyme mediate joining, Gateway® cloning technology (Life Technologies, Carlsbad, Calif.), and the like.

The resultant product transfection plasmids may then be used to transfect a suitable packaging cell line for production of library viral particles. The packaging cell line provides the viral proteins that are required in trans for the packaging of the viral genomic RNA into viral particles. The packaging cell line may be any cell line that is capable of expressing retroviral proteins, including HEK293, HeLa, D17, MDCK, BHK, NIH3T3, CHO, CrFK, and Cf2Th. In some embodiments, the construct is used together with a viral reporter construct which may comprise one or more reporter genes under the control of a constitutive or conditional promoter. The packaging cell line may stably express necessary viral proteins. Such a packaging cell line is described, for example, in U.S. Pat. No. 6,218,181. Alternatively, a packaging cell line may be transiently transfected with plasmids comprising nucleic acids that encode the necessary viral proteins. In another embodiment, a packaging cell line that does not stably express the necessary viral proteins is co-transfected with two or more plasmids. One of the plasmids comprises the viral construct comprising the polynucleotide. The other plasmid(s) comprises nucleic acids encoding the proteins necessary to allow the cells to produce functional virus that is able to infect the desired host cell. The packaging cell line may not express envelope gene products. In this case, the packaging cell line will package the viral genome into particles that lack an envelope protein. As the envelope protein is responsible, in part, for the host range of the viral particles, the viruses preferably are pseudotyped. A "pseudotyped" retrovirus is a retroviral particle having an envelope protein that is from a virus other than the virus from which the RNA genome is derived. The envelope protein may be from a different retrovirus or a non-retrovirus. One envelope protein is the vesicular stomatitis virus G (VSV-G) protein. Thus, the packaging cell line may be transfected with a plasmid that includes sequences encoding a membrane-associated protein, such as VSV-G, that will permit entry of the virus into a target cell. One of skill in the art can choose an appropriate pseudo type specific and/or more efficient for the target cell used. In addition to conferring a specific host range, a chosen pseudotype may permit the virus to be concentrated to a very high titer. Viruses alternatively can be pseudotyped with ecotropic envelope proteins that limit infection to a specific species.

The compositions of the present invention further include retrovirus particles derived from said first and second polynucleotides and other packaging vectors needed to form a complete viral particle. Such retrovirus particles are produced by the transfection of the polynucleotides and/or packaging vectors into retroviral cell packaging cell lines. Thus stably transfected cell lines comprising said sequences are also within the scope of the invention disclosed herein. The compositions of the invention further include provirus sequences derived from the retrovirus particles. The provirus sequences may be present in an integrated form within the genome of a recipient cell, or may be present in a free, circularized form. An integrated provirus is produced upon infection of a recipient cell, wherein the infection leads to the production an integration into the cell genome of the provirus nucleic acid sequence. The circularized provirus sequence may generally be produced upon excision of the integrated provirus from the recipient cell genome.

The compositions of the present invention still further include cells containing the retroviral systems disclosed herein, whether the packaging cell lines or recipient cell lines. Additionally, the present invention includes transgenic animals containing the retroviral systems disclosed herein, including preferably animals containing retroviral systems form which sequences (sense or antisense) are expressed in one or more cells.

Methods for Making Lentiviral System

In one aspect, the embodiments disclosed herein are directed to methods of preparing a lentiviral or retroviral system comprising a polynucleotide having engineered associations comprising a sequence encoding one or more genetic perturbations and a unique molecular sequence wherein the system has reduced recombination or template switching, activity. The methods may comprise packaging the polynucleotide with a modulator of one or more activities of the system. The modulator may be an inhibitor of recombination or template switching activity. For example, the modular may be an inhibitor of template switching. In one embodiment, polynucleotides encoding the one or more genetic perturbation and associated unique molecular sequence are cloned into a suitable lentiviral or retroviral vector ("targeting vector"). Suitable vectors include, for example; pBA571 (Addgene Cat #85968), pMJ114 (Addgene Cat #85995), pMJ179 (Addgene Cat #85996), pMJ1117 (Addgene Cat #85997). Carrier plasmids are likewise selected. The carrier plasmids do not include sequences encoding the one or more genetic perturbations or the unique molecular sequence. Instead carrier plasmids are selected to comprise non-recombinogenic sequences, or encode proteins that are capable of dimerizing with the polynucleotide of sequence. Example carrier polynucleotides include pr_H2b-BFB (encoding a hi stone subunit tagged with blue fluorescent protein) and pLX_TRC131_LacZ (control vector used in ORF screens). In certain embodiments, the carrier plasmid may comprise a lentiviral or retroviral plasmid that has been modified to be non-integrating. For example, a lentiviral vector may be made non-integrating by mutating the 5' long terminal repeat (LTR) and having a short LTR to LTR distance of 2.1 kb. Example proteins that are capable of dimerizing are disclosed in retroviral nucleoproteins (NC). The target vector and carrier may then be introduced along with standard lentiviral or retroviral packaging plasmids that encode remaining elements need for full viral particle production into a packaging cell lines to generate a viral clone library, each clone comprising a different target vector and one or more carrier vectors. The target vector may be diluted in a composition with one or more carrier vectors prior to introduction in the packaging cell line. In certain example embodiments, the target vector is diluted in a solution comprising one or more carrier vectors prior to introduction into the packaging cell line at a dilution of 1:10, 1:20, 1:30, 1:40, 1:50, 1:60, 1:70, 1:80, 1:90, 1:100, 1:200, 1:300, 1:400, 1:500, 1:600, 1:700, 1:800, 1:900, 1:1000, 1:2000, 1:3000, 1:4000, or 1:5000.

Also provided herein include a cell or cell line for the viral systems herein. The cell or cell line may be used for producing viral particles. In some cases, the compositions may comprise a cell or cell line for producing viral particles comprising a set of polynucleotide constructs such that the viral particles comprise polynucleotides having engineered associations comprising a sequence encoding one or more genetic perturbations and a unique molecular sequence clone, and one or more polypeptides that comprise non-recombinogenic RNA sequences, or proteins that are capable of dimerizing with the polynucleotide.

Genetic Screens

In some embodiments, the present disclosure includes methods for screening cells for genetic perturbations. The methods may comprise one or more of: (i) providing (e.g., culturing) a cell or population of cells in one or more discrete volumes; introducing the system described herein, such that each cell receives one or more polynucleotides each having at least one genetic perturbation and a unique identifier; detecting genomic, genetic, proteomic, epigenetic and/or phenotypic differences in single cells; and identifying the at least one genetic perturbation in each cell based on the unique identifier.

In one aspect, the present invention provides for a method of reconstructing a cellular network or circuit, comprising introducing at least 1, 2, 3, 4 or more single-order or combinatorial perturbations to a plurality of cells in a population of cells, wherein each cell in the plurality of the cells receives at least 1 perturbation; measuring comprising: detecting genomic, genetic, proteomic, epigenetic and/or phenotypic differences in single cells compared to one or more cells that did not receive any perturbation, and detecting the perturbation(s) in single cells; and determining measured differences relevant to the perturbations by applying a model accounting for co-variates to the measured differences, whereby intercellular and/or intracellular networks or circuits are inferred. The measuring in single cells may comprise single cell sequencing. The single cell sequencing may comprise cell barcodes, whereby the cell-of-origin of each RNA is recorded. The single cell sequencing may comprise unique molecular identifiers (UMI), whereby the capture rate of the measured signals, such as transcript copy number or probe binding events, in a single cell is determined. The model may comprise accounting for the capture rate of measured signals, whether the perturbation actually perturbed the cell (phenotypic impact), the presence of subpopulations of either different cells or cell states, and/or analysis of matched cells without any perturbation.

The single-order or combinatorial perturbations may comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 perturbations. The perturbation(s) may target genes in a pathway or intracellular network.

The measuring may comprise detecting the transcriptome of each of the single cells. The perturbation(s) may comprise one or more genetic perturbation(s). The perturbation(s) may comprise one or more epigenetic or epigenomic perturbation(s). At least one perturbation may be introduced with RNAi- or a CRISPR-Cas system. At least one perturbation may be introduced via a chemical agent, biological agent, an intracellular spatial relationship between two or more cells, an increase or decrease of temperature, addition or subtraction of energy, electromagnetic energy, or ultrasound.

The cell(s) may comprise a cell in a model non-human organism, a model non-human mammal that expresses a Cas protein, a mouse that expresses a Cas protein, a mouse that expresses Cpf1, a cell in vivo or a cell ex vivo or a cell in vitro. The cell(s) may also comprise a human cell.

The measuring or measured differences may comprise measuring or measured differences of DNA, RNA, protein or post translational modification; or measuring or measured differences of protein or post translational modification correlated to RNA and/or DNA level(s).

The perturbing or perturbation(s) may comprise(s) genetic perturbing. The perturbing or perturbation(s) may comprise(s) single-order perturbations. The perturbing or perturbation(s) may comprise(s) combinatorial perturbations. The perturbing or perturbation(s) may comprise gene knock-down, gene knock-out, gene activation, gene insertion, or regulatory element deletion. The perturbation may result in a change. The perturbing or perturbation(s) may comprise genome-wide perturbation. The perturbing or perturbation(s) may comprise performing CRISPR-Cas-based perturbation. The perturbing or perturbation(s) may comprise performing pooled single or combinatorial CRISPR-Cas-based perturbation with a genome-wide library of sgRNAs. The perturbations may be of a selected group of targets based on similar pathways or network of targets.

The perturbing or perturbation(s) may comprises performing pooled combinatorial CRISPR-Cas-based perturbation with a genome-wide library of sgRNAs. Each sgRNA may be associated with a unique perturbation barcode. Each sgRNA may be co-delivered with a reporter mRNA comprising the unique perturbation barcode (or sgRNA perturbation barcode).

The perturbing or perturbation(s) may comprise subjecting the cell to an increase or decrease in temperature. The perturbing or perturbation(s) may comprise subjecting the cell to a chemical agent. The perturbing or perturbation(s) may comprise subjecting the cell to a biological agent. The biological agent may be a toll like receptor agonist or cytokine. The perturbing or perturbation(s) may comprise subjecting the cell to a chemical agent, biological agent and/or temperature increase or decrease across a gradient.

The cell may be in a microfluidic system. The cell may be in a droplet. The population of cells may be sequenced by using microfluidics to partition each individual cell into a droplet containing a unique barcode, thus allowing a cell barcode to be introduced.

The perturbing or perturbation(s) may comprise transforming or transducing the cell or a population that includes and from which the cell is isolated with one or more genomic sequence-perturbation constructs that perturbs a genomic sequence in the cell. The sequence-perturbation construct may be a viral vector, preferably a lentivirus vector. The perturbing or perturbation(s) may comprise multiplex transformation or transduction with a plurality of genomic sequence-perturbation constructs.

In another aspect, or in alternative embodiments of aspects described herein, the present invention provides for a method wherein proteins or transcripts expressed in single cells are determined in response to a perturbation, wherein the proteins or transcripts are detected in the single cells by binding of more than one labeling ligand comprising an oligonucleotide tag, and wherein the oligonucleotide tag comprises a unique constituent identifier (UCI) specific for a target protein or transcript. The single cells may be fixed in discrete particles. The discrete particles may be washed and sorted, such that cell barcodes may be added, e.g. sgRNA perturbation barcodes as described above. The oligonucleotide tag and sgRNA perturbation barcode may comprise a universal ligation handle sequence, whereby a unique cell barcode may be generated by split-pool ligation. The labeling ligand may comprise an oligonucleotide label comprising a regulatory sequence configured for amplification by T7 polymerase. The labeling ligands may comprise oligonucleotide sequences configured to hybridize to a transcript specific region. Not being bound by a theory, both proteins and RNAs may be detected after perturbation. The oligonucleotide label may further comprise a photocleavable linker. The oligonucleotide label may further comprise a restriction enzyme site between the labeling ligand and unique constituent identifier (UCI). The ligation handle may comprise a restriction site for producing an overhang complementary with a first index sequence overhang, and wherein the method further comprises digestion with a restriction enzyme. The ligation handle may comprise a nucleotide sequence complementary with a ligation primer sequence and wherein the overhang complementary with a first index sequence overhang is produced by hybridization of the ligation primer to the ligation handle. The method may further comprise quantitating the relative amount of UCI sequence associated with a first cell to the amount of the same UCI sequence associated with a second cell, whereby the relative differences of a cellular constituent between cell(s) are determined. The labeling ligand may comprise an antibody or an antibody fragment. The antibody fragment may be a nanobody, Fab, Fab', (Fab')2, Fv, ScFv, diabody, triabody, tetrabody, Bis-scFv, minibody, Fab2, or Fab3 fragment. The labeling ligand may comprise an aptamer. The labeling ligand may be a nucleotide sequence complementary to a target sequence.

Single cell sequencing may comprise whole transcriptome amplification.

The method in aspects of the invention may comprise comparing an RNA profile of the perturbed cell with any mutations in the cell to also correlate phenotypic or transcriptome profile and genotypic profile.

In another aspect, or in alternative embodiments of aspects described herein, the present invention provides for a method comprising determining genetic interactions by causing a set of P genetic perturbations in single cells of the population of cells, wherein the method comprises: determining, based upon random sampling, a subset of $\pi$ genetic perturbations from the set of P genetic perturbations; performing said subset of $\pi$ genetic perturbations in a population of cells; performing single-cell molecular profiling of the population of genetically perturbed cells; inferring, from the results and based upon the random sampling, single-cell molecular profiles for the set of P genetic perturbations in cells. The method may further comprise: from the results, determining genetic interactions. The method may further comprise: confirming genetic interactions determined with additional genetic manipulations.

The set of P genetic perturbations or said subset of $\pi$ genetic perturbations may comprise single-order genetic perturbations. The set of P genetic perturbations or said subset of $\pi$ genetic perturbations may comprise combinatorial genetic perturbations. The genetic perturbation may comprise gene knock-down, gene knock-out, gene activation, gene insertion, or regulatory element deletion. The set of P genetic perturbations or said subset of $\pi$ genetic perturbations may comprise genome-wide perturbations. The set of P genetic perturbations or said subset of $\pi$ genetic perturbations may comprise k-order combinations of single genetic perturbations, wherein k is an integer ranging from 2 to 15, and wherein the method comprises determining k-order genetic interactions. The set of P genetic perturbations may comprise combinatorial genetic perturbations, such as k-order combinations of single-order genetic perturbations, wherein k is an integer ranging from 2 to 15, and wherein the method comprises determining j-order genetic interactions, with j<k.

The method in aspects of this invention may comprise performing RNAi- or CRISPR-Cas-based perturbation. The method may comprise an array-format or pool-format perturbation. The method may comprise pooled single or combinatorial CRISPR-Cas-based perturbation with a genome-wide library of sgRNAs. The method may comprise pooled combinatorial CRISPR-Cas-based perturbation with a genome-wide library of sgRNAs.

The random sampling may comprise matrix completion, tensor completion, compressed sensing, or kernel learning. The random sampling may comprise matrix completion, tensor completion, or compressed sensing, and wherein $\pi$ is of the order of log P.

The cell may comprise a eukaryotic cell. The eukaryotic cell may comprise a mammalian cell. The mammalian cell may comprise a human cell. The cell may be from a population comprising $10^2$ to $10^8$ cells and DNA or RNA or protein or post translational modification measurements or variables per cell comprise 50 or more.

The perturbation of the population of cells may be performed in vivo. The perturbation of the population of cells may be performed ex vivo and the population of cells may be adoptively transferred to a subject. The population of cells may comprise tumor cells. The method may comprise a lineage barcode associated with single cells, whereby the lineage or clonality of single cells may be determined.

The perturbing may be across a library of cells to thereby obtain RNA level and/or optionally protein level, whereby cell-to-cell circuit data at genomic or transcript or expression level is determined. The library of cells may comprise or is from a tissue sample. The tissue sample may comprise or is from a biopsy from a mammalian subject. The mammalian subject may comprise a human subject. The biopsy may be from a tumor. The method may further comprise reconstructing cell-to-cell circuits.

The method may comprise measuring open chromatin and may comprise fragmenting chromatin inside isolated intact nuclei from a cell, adding universal primers at cutting sites, and uniquely tagging DNA that originated from the cell.

The method may comprise measuring protein and RNA levels and may comprise CyTOF.

In another aspect, the present invention provides for a method of determining any combination of protein detection, RNA detection, open chromatin detection, protein-protein interactions, protein-RNA interactions, or protein-DNA interactions comprising any of the preceding methods.

In another aspect, the present invention provides for a method for screening compounds or agents capable of modifying a cellular network or circuit comprising performing any method as described herein, wherein perturbing further comprises exposing the cell to each compound or agent.

In another aspect, the present invention provides for a method of identifying a therapeutic, and to a therapeutic identified by the method described herein.

In another aspect, the present invention provides a method of reconstructing a cellular network or circuit, comprising introducing at least 1, 2, 3, 4 or more single-order or combinatorial perturbations to each cell in a population of cells; measuring genomic, genetic and/or phenotypic differences of each cell and coupling combinatorial perturbations with measured differences to infer intercellular and/or intracellular networks or circuits. The single-order or combinatorial perturbations can comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99 or massively parallel perturbations. The perturbation(s) can comprise one or more genetic perturbation. The perturbation(s) can comprise one or more epigenetic or epigenomic perturbation. The perturbation can be introduced with RNAi- or a CRISPR-Cas system. For example, reference is also made to Dahlman et al., Nature Biotechnology (2015) doi:10.1038/nbt.3390 Published online 5 Oct. 2015 to allow efficient orthogonal genetic and epigenetic manipulation. Dahlman et al., Nature Biotechnology (2015) doi:10.1038/nbt.3390 have developed a CRISPR-based method that uses catalytically active Cas9 and distinct single guide (sgRNA) constructs to knock out and activate different genes in the same cell. These sgRNAs, with 14- to 15-bp target sequences and MS2 binding loops, can activate gene expression using an active Streptococcus pyogenes Cas9 nuclease, without inducing double-stranded breaks. Dahlman et al., Nature Biotechnology (2015) doi: 10.1038/nbt.3390 use these 'dead RNAs' to perform orthogonal gene knockout and transcriptional activation in human cells.

The at least one perturbation can be introduced via a chemical agent, an intracellular spatial relationship between two or more cells, an increase or decrease of temperature, addition or subtraction of energy, electromagnetic energy, or ultrasound. The cell can comprise a cell in a model non-human organism, a model non-human mammal that expresses a Cas protein, a mouse that expresses a Cas protein, a cell in vivo or a cell ex vivo or a cell in vitro. The measuring or measured differences can comprise measuring or measured differences of DNA, RNA, protein or post translational modification; or measuring or measured differences of protein or post translational modification correlated to RNA and/or DNA level(s). The method can include sequencing, and prior to sequencing: perturbing and isolating a single cell with at least one labeling ligand specific for binding at one or more target RNA transcripts, or isolating a single cell with at least one labeling ligand specific for binding at one or more target RNA transcripts and perturbing the cell; and/or lysing the cell under conditions wherein the labeling ligand binds to the target RNA transcript(s).

The method in aspects of this invention may also include, prior to sequencing perturbing and isolating a single cell with at least one labeling ligand specific for binding at one or more target RNA transcripts, or isolating a single cell with at least one labeling ligand specific for binding at one or more target RNA transcripts and perturbing the cell; and lysing the cell under conditions wherein the labeling ligand binds to the target RNA transcript(s). The perturbing and isolating a single cell may be with at least one labeling ligand specific for binding at one or more target RNA transcripts. The isolating a single cell may be with at least one labeling ligand specific for binding at one or more target RNA transcripts and perturbing the cell.

The perturbing of the present invention may involve genetic perturbing, single-order genetic perturbations or combinatorial genetic perturbations. The perturbing may also involve gene knock-down, gene knock-out, gene activation, gene insertion or regulatory element deletion. The perturbation may be genome-wide perturbation. The perturbation may be performed by RNAi- or CRISPR-Cas-based perturbation, performed by pooled single or combinatorial CRISPR-Cas-based perturbation with a genome-wide library of sgRNAs or performing pooled combinatorial CRISPR-Cas-based perturbation with a genome-wide library of sgRNAs.

In addition to loss-of-function (LOF) mutations, embodiments disclosed herein may also be used to modulate transcription without modifying genomic sequences. For example, inactive Cas9 (dCas9) can be catalytically fused to transcriptional activation and repression domains. CRISPR activation (CRISPRa) and CRISPR inhibition (CRISPRi) can be achieved by direct fusion or recruitment of activation and repression domains, such as VP64 and KRAB, respectively. Methods for setting up GOF and LOF genetic screens are described in detail in Joung et al. Nat Protoc. 2017 April: 12(4): 828-863.

Methods and tools for genome-scale screening of perturbations in single cells using CRISPR-Cas9 have been described, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; and International publication serial number WO/2017/075294). The present invention is compatible with perturb-seq, such that lentiviral vectors targeting genes for perturbation may be identified and assigned to the proteomic and gene expression readouts of single cells based on transcripts encoding for guide sequence specific barcodes. The present invention can be used to prevent recombination during packaging lentiviral libraries that may shuffle associations between guide sequences and barcode transcripts, thus greatly improving phenotypic readouts associated with a perturbation.

Methods for Reducing Intermolecular Recombination

In some embodiments, the present disclosure provides methods for reducing intermolecular recombination with a lentiviral genome plasmid of interest in a library (e.g., lentiviral library). The methods may comprise mixing the lentiviral genome plasmid of interest with a lentiviral carrier plasmid, and packaging the mixture. The lentiviral carrier plasmid may comprise a non-integrating lentiviral vector, a non-recombinogenic lentiviral vector, or a combination thereof. The library herein may comprise a barcode library, a plurality of guide polynucleotides, a plurality of sgRNAs, or any combination thereof.

The lentiviral genome plasmid of interest and the lentiviral carrier plasmid may be mixed at a suitable ratio. The ratio of the lentiviral genome plasmid of interest to the lentiviral carrier plasmid may be at least 1:1, 2:1, 10:1, 20:1, 30:1, 40:1, 50:1, 60:1, 70:1, 60:1, 70:1, 80:1, 90:1, 100:1, 120:1, 150:1, or 200:1.

The invention is further described in the following examples, which do not limit the scope of the invention described in the claims.

EXAMPLES

Example 1

Lentiviral vectors provide a convenient, scalable platform to deliver genetic perturbations to cells en masse and read out the identity of each perturbation by next-generation sequencing[1, 2]. There is increasing interest in screening approaches reliant on the delivery of multiple library elements to each cell, for example, in CRISPR-based single-cell gene expression screens[3-8]. Such approaches facilitate the study of genetic interactions by probing cells with combinations of perturbations or convenient detection of perturbations by readout of a barcode sequence. However, the goal of accurately delivering a single integrated library variant per cell is complicated by aspects of lentiviral delivery.

Lentiviral virions normally contain two copies of the viral genome. During standard lentivirus production, transfection of packaging cells with multiple plasmids generates virions containing two distinct library elements, which can then lead to intermolecular recombination that shuffles variable library sequences ("barcode swapping"). Together with the inadvertent integration of multiple variants in individual target cells, this process has the effect of reducing the sensitivity of pooled screens. For screens where all library elements are read out (e.g. targeted pairs of gene knockouts), recombination events can be detected and filtered out before statistical analysis[6, 9]. However, in situations where functional library elements are not sequenced directly, but are rather inferred via a linked barcode, recombination or multiple integration can lead to mislabeled data and has been noted to decrease the statistical power of genetic screens at a given number of cells analyzed[10, 11].

Recombination can arise from the template-switching activity of the lentiviral reverse-transcriptase[12]. As the lentivirus capsid normally packages a dimer of RNA genomes, intermolecular recombination could in principle occur in target cells infected by a single virion. The fraction of target cells with recombined integrants depends on the distance between variable sequences and has been measured to exceed 30% for distances greater than 1 kb[13]. Such wide spacing of library elements is common when the elements are separated by regulatory sequences or when an element is used as a 3' barcode in an expressed transcript[10, 11, 13].

To quantify the frequencies of barcode swapping and multiple integration events, we performed clonal analysis of target cells transduced with a library of CRISPR sgRNA and transcribed barcode elements separated by >1.7 kb. Similar to other groups, Applicant found that standard lentiviral packaging results in substantial (>30%) barcode swapping between library elements. Applicant further observed that an unexpectedly high number of target cells had multiple library variants integrated into their genomes even when transduced at low multiplicity-of-infection (MOI). Here Applicant shows that by diluting the perturbation library plasmid with sufficient excess of carrier plasmid in the packaging step, Applicant was able to substantially reduce barcode swaps (<4%) and attenuate the rate of multiple integrations several-fold. Altogether, this co-packaging strategy constitutes a simple solution to improve data quality for genetic screens without constraining library vector design or necessitating individual ("arrayed") packaging of library element.

Results

In order to test the feasibility of barcoding a U6-driven sgRNA with a short sequence located in the 3' UTR of a Pol II-driven resistance transcript, Applicant individually cloned 8 lentiviral plasmids with different sgRNA-barcode pairs and transduced HeLa cells at an MOI<5%, pooling either before or after lentiviral packaging. After flow sorting and clonally expanding single cells, Applicant analyzed the sgRNA and barcode sequences present in each clone using next-generation sequencing (Methods). Applicant observed that pooled lentiviral packaging resulted in barcode swaps in 37% of clones with a single detected integration, whereas no swapping was detected between individually packaged lentiviral genome sequences (Table 1). Similar results were obtained when packaging a library of 400 barcodes (cloned as a pool) using the standard protocol. Applicant reports barcode swapping rates as the functional and measurable outcome of recombination. Overall, the results are consistent with observations by a number of groups and precautionary comments published in some of the first examples of pooled single-cell gene expression screens[10, 11, 14].

The standard pooled lentivirus packaging protocol calls for transfecting the packaging cell line with the lentiviral perturbation library and associated packaging plasmids needed to produce virus (Methods). The present clonal analysis of target cells transduced by virus produced in this manner revealed not only barcode swaps but also a higher occurrence of multiple integrants per cell than predicted by a Poisson model of independent integration events, even at MOI below 5%. The presence of multiple genomic integrants even at limiting virus dilutions could be explained by the ability of a single virion to integrate both packaged genomes, or non-independence of integration probability across target cells, possibly as a result of differences in cell state.

Hypothesizing that recombination and multiple integration events are driven by co-packaging of two RNA genomes per lentiviral capsid[13] and co-delivery of multiple genomes to individual target cells, Applicant tested dilution of the perturbation library plasmids in unrelated carrier plasmids as a means of mitigating both of these undesired effects. Three lentiviral plasmids were evaluated as carriers, including two integration-capable vectors (pR_H2B-BFP encoding a histone subunit tagged with blue fluorescent protein, and pLX_TRC313_LacZ, a control vector used in ORF screens). In addition, Applicant tested a non-integrating lentiviral vector with a mutated 5' long terminal repeat (LTR) and a short LTR-LTR distance of 2.1 kb in hopes of avoiding unnecessary genomic integrations[15]. All three carriers tested reduced recombination rates to 0-4%. Interestingly, Applicant found that while it was necessary to use the integrating carrier plasmids in 1.000-fold excess over the perturbation library, the non-integrating carrier plasmid reduced barcode swaps to the same extent at a dilution of only 1:10, perhaps due to enhanced expression of the shorter LTR-LTR transcript in the packaging cell line. Furthermore, co-packaging with a non-homologous lentiviral vector also limited instances of multiple distinct integrations, likely due to a reduction in the probability that two perturbation library variants enter the target cell.

Applicant also tested dilution in a non-lentiviral carrier plasmid, pUC19, hypothesizing that stringent dilution of the perturbation library could reduce the number of library, variants in each packaging cell to one or fewer and minimize the risk that heterodimeric virions are produced. This strategy was found to decrease the recombination rate to 6%. However, Applicant still observed 18% of cell clones with greater than one integrated library variant, consistent with the correlated infection hypothesis and indicating that lentiviral plasmids may be a better choice of carrier material.

A limitation of this dilution strategy is a 100-fold decrease in titer relative to lentivirus prepared with the non-diluted perturbation library, measured by counting the number of cell colonies surviving after antibiotic selection. To investigate the trade-off between titer and unwanted lentiviral effects, Applicant titrated the dilution ratio of one of the integrating lentiviral carrier plasmids (pLX_TRC313_LacZ) but found that 100-fold excess did not show the desired performance, with 25% of colonies showing barcode swaps or multiple integrants. Nevertheless, even with diminished viral titer, Applicant was able to transduce a library of 1,000 perturbations with 300-fold cell coverage.

Applicant also explored whether recombination events hypothetically occurring in the packaging cell line could be reduced by shortening packaging times. The time from transfection to harvesting viral supernatant was reduced from 48 h to 11 h, a decrease in barcode swapping was not observed, consistent with a model where most of the recombination occurs in the target cells.

ments monitored via transcribed barcodes)[16]. By addressing both recombination and multiple integration, co-packaged lentiviral libraries have the potential to improve the accuracy of perturbation barcoding and boost the sensitivity of screens that deliver library constructs with multiple variable elements.

Applicant chose to employ clonal analysis of the genomic integrants by next-generation sequencing to achieve sensitive and unbiased detection of perturbation library elements with single-cell resolution. As Applicant amplified each variable sequence in a separate PCR reaction, this approach is not subject to artifacts resulting from PCR-based recombination. Moreover, the readout does not depend on events subsequent to integration and antibiotic selection, such as detection of a fluorescent marker or perturbation of cellular phenotype that may be confounded by multiple integrations. However, clonal analysis is practically limited to the scale of 100-1000 clones per sequencing run, making it better suited for high-confidence measurements of undesired integration events than for systematic optimization across many test conditions.

Under the standard assumption of a zero-truncated Poisson distribution of lentiviral integrations, one would expect a multiple integration rate below 2.5% when transducing cells at an MOI below 5%. However, despite working in this range for our infections, the measured multiple integration

TABLE 1

Clonal analysis of lentiviral packaging strategies for barcoded perturbation libraries. Individual transduced cells were isolated by flow sorting and clonally expanded prior to genomic DNA extraction and examination of sgRNA and barcode identity by next-generation sequencing. Each clone was classified by the number of observed integrations, with single integrants further subdivided by whether the sgRNA matched the associated barcode. A recombination rate (rightmost column) was estimated by dividing the number of recombined single integrants by the total number of cells with a single integration. Standard packaging refers to transfection of the pooled perturbation library alone with packaging plasmids (pMD2.G and psPAX2); for arrayed packaging, each library element was individually co-transfected with packaging plasmids for production of a pure population of virions that was subsequently pooled. Carrier plasmids come in three varieties: non-lentiviral (pUC19), integrating lentiviral (pR_H2B-BFP and pLX_TRC313_LacZ) and non-integrating lentiviral (pR_LG). Finally, a quick harvest (11 hours) of the packaged lentivirus was also explored; for all other conditions, virus was packaged for 48 hours

| Packaging condition | # of barcodes | # of cell clones analyzed | Single integration, correct association | Single integration, barcode swap | Multiple integration | Estimated barcode swap rate | Relative titer |
|---|---|---|---|---|---|---|---|
| arrayed | 8 | 48 | 46 (95.8%) | 0 (0.0%) | 2 (4.2%) | 0% | 100% |
| standard | 8 | 61 | 34 (55.7%) | 20 (32.8%) | 7 (11.5%) | 37.0% | 100% |
| standard | 400 | 28 | 16 (57.1%) | 8 (28.6%) | 4 (14.3%) | 33.3% | 100% |
| 10x dilution in pR_LG | 400 | 68 | 67 (98.5%) | 1 (1.5%) | 0 (0.0%) | 1.5% | 1% |
| 1000x dilution in pR_H2B-BFP | 8 | 61 | 59 (96.7%) | 0 (0.0%) | 2 (3.3%) | 0% | 1% |
| 1000x dilution in pLX_TRC313_LacZ | 400 | 53 | 50 (94.3%) | 2 (3.8%) | 1 (1.9%) | 3.8% | 1% |
| 100x dilution in pLX_TRC313_Lacz | 400 | 16 | 12 (75.0%) | 1 (6.2%) | 3 (18.8%) | 7.7% | 3% |
| 1000x dilution in pUC19 | 8 | 45 | 35 (77.8%) | 2 (4.4%) | 8 (17.8%) | 5.4% | 1% |
| standard, quick harvest (11 h) | 8 | 51 | 28 (54.9%) | 17 (33.3%) | 6 (11.8%) | 37.8% | 3% |

In the context of genetic screens, lentiviral co-packaging can greatly reduce barcode swaps and decrease the background of multiple integrants without constraining library vector design or necessitating individual packaging of library elements. The latter approach was used by Adamson et al. to avoid recombination in a single-cell gene expression screen, but is limited in scalability[14]. Datlinger et al. developed a—specialized CROP-seq vector in which the sgRNA is itself transcribed by Pol II and captured in a 3' RNA-seq protocol, obviating the need for an additional barcode and eliminating concerns about recombination[5]. However, this approach requires locating the perturbation within the 3' LTR and is not generalizable to some types of screens (e.g. paired perturbation screens, or screens of regulatory elerate was greater than 10%, suggesting that, at least in our HeLa cell system, lentiviral integrations detected after antibiotic selection are correlated and do not follow a zero-truncated Poisson distribution as is commonly assumed[17]. It is likely that multiple integration background is a persistent noise source in genetic screens utilizing lentivirus, with an effect that depends on the particular system. A lack of statistical independence between integration events underscores the need to maintain high representation of library elements in transduced cells in order to average over technical and biological noise.

Decreased viral titer is a potential drawback to the dilute co-packaging approach. Here, Applicant opted to perform clonal analysis under stringent dilution conditions, which minimized recombination but exacerbated the viral titer issue. For example, using the integration-defective pR_LG 1:10 co-packaging condition, Applicant was able to generate 10,000 HeLa colonies per mL of viral supernatant. At this titer, 35 mL of viral supernatant would be sufficient for one replicate of a screen involving 1,000 perturbations with 300 initially infected cells per library element. The cost of tissue culture and transfection reagents to generate 35 mL of viral supernatant is currently orders of magnitude smaller than the cost of preparing and sequencing single-cell gene expression libraries covering 1,000 perturbations and does not thus pose a limit to the achievable scale of the screen. On the other hand, this titer may be prohibitive for a genome-wide CRISPR screen reading out enrichment of more than 50,000 sgRNAs by amplicon sequencing. Ultimately, any particular screen will exhibit an optimal trade-off between degradation of data quality by lentiviral recombination and loss of titer due to co-packaging with a carrier plasmid, and the user may select an appropriate level of dilution to balance these effects.

The ability to minimize both recombination and multiple integrations by diluting the transfer vector in another lentiviral plasmid supports the hypothesis that RNA dimerization during lentiviral packaging is involved in these undesired outcomes. In the case of dilution with excess lentiviral carrier plasmid, most library genomes are likely packaged with a non-homologous carrier genome such that the frequency of virions containing two library variants is substantially reduced. Meanwhile, limiting dilution with a non-lentiviral carrier plasmid may reduce the likelihood that two library variants are transfected into the same cell for packaging, hence preventing two different library RNA genomes from dimerizing. Both of these approaches mitigate the potential for template switching and recombination between two different library genomes in the target cells.

Alternative approaches to control recombination include directly inhibiting the template-switching activity of the viral reverse transcriptase in the transduced cells or biasing packaging to a single genome per virion by modifying the RNA sequence or proteins involved in dimerization[18]. Such efforts could potentially address both the effects of recombination and multiple genomic integrations without a corresponding loss in titer due to dilution.

Methods

Single cell clonal analysis of integrated sgRNAs and barcodes was performed by transducing a lentiviral library into a target cell population, selecting with antibiotic, sorting and expanding single cells, and separately PCR-amplifying and deep sequencing the sgRNA and barcode sequences from each expanded colony. All cell lines were transduced at an MOI<5%, determined by counting the fraction of cells surviving antibiotic selection.

Lentivirus was prepared following published methods[19]. All cell culture used Dulbecco's Modified Eagle's Medium supplemented with 10% FBS (GE Life Sciences SH30070.03T), 100 units/mL penicillin, and 100 µg/mL streptomycin. A 4:3:2 ratio by mass of packaging plasmids pMD2.G (Addgene 12259) and psPAX2 (Addgene 12260), and library transfer vector pLas (Supplementary Sequence 1, lentiviral backbone derived from Addgene 61427) was transfected into 293FT cells (Thermo Fisher R70007) using Lipofectamine 2000 (Invitrogen 11668019). Fresh media was exchanged 4 h after transfection. At 24 h post-transfection, 2 mM caffeine (Sigma-Aldrich C0750) was added, and at 48 h post-transfection lentiviral supernatant was filtered through 0.45 µm cellulose acetate filters (VWR 28145-481), frozen at −80° C., and thawed immediately before use. HeLa cells (a gift from Dr. Iain Cheeseman's lab) were infected by mixing lentiviral supernatant with 8 µg/mL polybrene (Sigma-Aldrich 107689-10G) and centrifuging at 1000 g for 2 h at 33° C. At 6 h post-infection, media was exchanged, and at 24 h post-infection cells were passaged into media containing 300 µg/mL zeocin (Thermo Fisher R25001) and selected for one week. Single cells were sorted into 96-well plates and clonally expanded. More than 90% of wells with cell growth contained single colonies, determined by visual inspection. These expanded clones were analyzed by extracting gDNA, separately amplifying sgRNA and barcode sequences by PCR, and deep sequencing the amplicons (Illumina Mini Seq).

Sequence data from each colony were analyzed by matching reads to known sgRNAs within an allowed edit distance of 2 bases and barcodes within an allowed edit distance of 1 base to accommodate errors in oligo synthesis (Supplementary Table 1). Sequences with fewer than 30 reads or a read fraction below 10% were discarded. Multiple integration events were defined by the presence of more than one sgRNA or more than one barcode sequence. Single integration with barcode swapping was defined as detection of one sgRNA and one barcode cognate to a different sgRNA. We report the frequency of observed barcode swapping events, which does not include multiple integration of the same library element, recombination between two identical library elements, or secondary recombination events that restore the original sgRNA-barcode pairing.

sgRNA vector sequences and vector details are provided below in Table 2. (Pred sgRNA identified as SEQ ID NOs: 1-945) (Required "match" sequences identified as SEQ ID NOs: 946-1573)

TABLE 2

| condition | date | plate | well | pattern | fraction | pred_sgRNA | solitary | matches_per_sample | match | count |
|---|---|---|---|---|---|---|---|---|---|---|
| pLas, individually packaged | 20170T1608 | | B09 | pL43 | 83.80% | AGAGCACTGCACTCCTTCA | FALSE | 2 | CCAGTTA | 3540 |
| pLas, individually packaged | 20170T1608 | | B09 | sgRNA9 | 2.70% | AGAGCACTGCACTCCTTCA | FALSE | 2 | AGAGCACTGCACTCCTTCA | 356 |
| pLas, individually packaged | 20170T1608 | | B12 | pL43 | 87.40% | AGAGCACTGCACTCCTTCA | FALSE | 2 | CCAGTTA | 3955 |

TABLE 2-continued

| condition | date | platewell | pattern | fraction | pred_sgRNA | solitary | matches_per_sample | match | count |
|---|---|---|---|---|---|---|---|---|---|
| pLas, individually packaged | 20170T1608 | B12 | sgRNA | 96.00% | AGAGCACTGCACTCCTTCA | FALSE | 2 | AGAGCACTGCACTCCTTCA | 924 |
| pLas, individually packaged | 20170T1608 | C09 | pL43 | 95.70% | AGTAGTCCGGGATATCAGCG | FALSE | 2 | CCTCTTC | 3707 |
| pLas, individually packaged | 20170T1608 | C09 | sgRNA | 95.80% | AGTAGTCCGGGATATCAGCG | FALSE | 2 | AGTAGTCCGGGATATCAGCG | 1451 |
| pLas, individually packaged | 20170T1608 | C10 | pL43 | 95.70% | ATACAACTGCTTGCAACAGG | FALSE | 2 | ATTCCGA | 4431 |
| pLas, individually packaged | 20170T1608 | C10 | sgRNA | 93.60% | ATACAACTGCTTGCAACAGG | FALSE | 2 | ATACAACTGCTTGCAACAGG | 904 |
| pLas, individually packaged | 20170T1608 | C12 | pL43 | 94.40% | TCCACCGGCGAAAGAGATCC | FALSE | 2 | CAATCGG | 4541 |
| pLas, individually packaged | 20170T1608 | C12 | sgRNA | 94.40% | TCCACCGGCGAAAGAGATCC | FALSE | 2 | TCCACCGGCGAAAGAGATCC | 34 |
| pLas, individually packaged | 20170T1608 | D09 | pL43 | 96.00% | CGCCGCCCCCGGACGCGACC | FALSE | 2 | CATGCGT | 4873 |
| pLas, individually packaged | 20170T1608 | D09 | sgRNA | 94.90% | CGCCGCCCCCGGACGCGACC | FALSE | 2 | CGCCGCCCCCGGACGCGACC | 806 |
| pLas, individually packaged | 20170T1608 | D11 | pL43 | 10.60% | TCATATTACGAGTCAGTAGG | TRUE | 3 | AGAGAGA | 493 |
| pLas, individually packaged | 20170T1608 | D11 | pL43 | 85.30% | AGAGCACTGCACTCCTTCA | FALSE | 3 | CCAGTTA | 3980 |
| pLas, individually packaged | 20170T1608 | D11 | sgRNA | 87.60% | AGAGCACTGCACTCCTTCA | FALSE | 3 | AGAGCACTGCACTCCTTCA | 212 |
| pLas, individually packaged | 20170T1608 | D12 | pL43 | 94.80% | TCATATTACGAGTCAGTAGG | FALSE | 2 | AGAGAGA | 4567 |
| pLas, individually packaged | 20170T1608 | D12 | sgRNA | 94.60% | TCATATTACGAGTCAGTAGG | FALSE | 2 | TCATATTACGAGTCAGTAGG | 1346 |
| pLas, individually packaged | 20170T1608 | E10 | pL43 | 95.10% | CCAGTACAAACCTACCTACG | FALSE | 2 | AAGAGGA | 4585 |
| pLas, individually packaged | 20170T1608 | E10 | sgRNA | 95.70% | CCAGTACAAACCTACCTACG | FALSE | 2 | CCAGTACAAACCTACCTACG | 425 |
| pLas, individually packaged | 20170T1608 | E11 | pL43 | 94.70% | AGAGCACTGCACTCCTTCA | FALSE | 2 | CCAGTTA | 4781 |
| pLas, individually packaged | 20170T1608 | E11 | sgRNA | 95.50% | AGAGCACTGCACTCCTTCA | FALSE | 2 | AGAGCACTGCACTCCTTCA | 233 |

TABLE 2-continued

| condition | date | platewell | pattern | fraction | pred_sgRNA | solitary | matches_per_sample | match | count |
|---|---|---|---|---|---|---|---|---|---|
| pLas, individually packaged | 20170T1 608 | E12 | pL43 | 94.20% | AGAGCACTGCACTCCTTCA | FALSE | 2 | CCAGTTA | 4257 |
| pLas, individually packaged | 20170T1 608 | E12 | sgRNA | 95.80% | AGAGCACTGCACTCCTTCA | FALSE | 2 | AGAGCACTGCACTCCTTCA | 1084 |
| pLas, individually packaged | 20170T1 608 | F10 | pL43 | 94.70% | AGAGCACTGCACTCCTTCA | FALSE | 2 | CCAGTTA | 3828 |
| pLas, individually packaged | 20170T1 608 | F10 | sgRNA | 93.30% | AGAGCACTGCACTCCTTCA | FALSE | 2 | AGAGCACTGCACTCCTTCA | 532 |
| pLas, individually packaged | 20170T1 608 | F11 | pL43 | 47.30% | CCTGCAACGGGACTAGTTGG | FALSE | 4 | CGTCATA | 2137 |
| pLas, individually packaged | 20170T1 608 | F11 | pL43 | 48.40% | ATACAACTGCTTGCAACAGG | FALSE | 4 | ATTCCGA | 2184 |
| pLas, individually packaged | 20170T1 608 | F11 | sgRNA | 46.70% | ATACAACTGCTTGCAACAGG | FALSE | 4 | ATACAACTGCTTGCAACAGG | 314 |
| pLas, individually packaged | 20170T1 608 | F11 | sgRNA | 46.80% | CCTGCAACGGGACTAGTTGG | FALSE | 4 | CCTGCAACGGGACTAGTTGG | 315 |
| pLas, individually packaged | 20170T1 608 | F12 | pL43 | 95.60% | CGCCGCCCCCGGACGCGACC | FALSE | 2 | CATGCGT | 4409 |
| pLas, individually packaged | 20170T1 608 | F12 | sgRNA | 95.30% | CGCCGCCCCCGGACGCGACC | FALSE | 2 | CGCCGCCCCCGGACGCGACC | 843 |
| pLas, individually packaged | 20170T1 608 | G09 | pL43 | 79.80% | AGAGCACTGCACTCCTTCA | FALSE | 2 | CCAGTTA | 2743 |
| pLas, individually packaged | 20170T1 608 | G09 | sgRNA | 94.10% | AGAGCACTGCACTCCTTCA | FALSE | 2 | AGAGCACTGCACTCCTTCA | 434 |
| pLas, individually packaged | 20170T1 608 | G12 | pL43 | 90.80% | CCAGTACAAACCTACCTACG | FALSE | 2 | AAGAGGA | 4450 |
| pLas, individually packaged | 20170T1 608 | G12 | sgRNA | 94.60% | CCAGTACAAACCTACCTACG | FALSE | 2 | CCAGTACAAACCTACCTACG | 945 |
| pLas, individually packaged | 20170T1 608 | H09 | pL43 | 95.20% | CGCCGCCCCCGGACGCGACC | FALSE | 2 | CATGCGT | 4742 |
| pLas, individually packaged | 20170T1 608 | H09 | sgRNA | 95.90% | CGCCGCCCCCGGACGCGACC | FALSE | 2 | CGCCGCCCCCGGACGCGACC | 1368 |
| pLas, individually packaged | 20170T1 608 | H10 | pL43 | 95.60% | CGCCGCCCCCGGACGCGACC | FALSE | 2 | CATGCGT | 4531 |
| pLas, individually packaged | 20170T1 608 | H10 | sgRNA | 95.60% | CGCCGCCCCCGGACGCGACC | FALSE | 2 | CGCCGCCCCCGGACGCGACC | 900 |

TABLE 2-continued

| condition | date | platewell | pattern | fraction | pred_sgRNA | solitary | matches_per_sample | match | count |
|---|---|---|---|---|---|---|---|---|---|
| pLas, individually packaged | 20170T1608 | H11 | pL43 | 86.10% | TCCACCGGCGAAAGAGATCC | FALSE | 2 | CAATCGG | 3570 |
| pLas, individually packaged | 20170T1608 | H11 | sgRNA | 94.80% | TCCACCGGCGAAAGAGATCC | FALSE | 2 | TCCACCGGCGAAAGAGATCC | 2455 |
| pLas, individually packaged | 20170T1608 | H12 | pL43 | 80.90% | ATACAACTGCTTGCAACAGG | FALSE | 2 | ATTCCGA | 3032 |
| pLas, individually packaged | 20170T1608 | H12 | sgRNA | 87.80% | ATACAACTGCTTGCAACAGG | FALSE | 2 | ATACAACTGCTTGCAACAGG | 1155 |
| pLas, individually packaged | 20170T2608 | B01 | pL43 | 43.50% | AGAGCACTGCACTCCTTCA | FALSE | 4 | CCAGTTA | 1799 |
| pLas, individually packaged | 20170T2608 | B01 | pL43 | 53.90% | TCATATTACGAGTCAGTAGG | FALSE | 4 | AGAGAGA | 2225 |
| pLas, individually packaged | 20170T2608 | B01 | sgRNA | 46.70% | AGAGCACTGCACTCCTTCA | FALSE | 4 | AGAGCACTGCACTCCTTCA | 293 |
| pLas, individually packaged | 20170T2608 | B01 | sgRNA | 48.70% | TCATATTACGAGTCAGTAGG | FALSE | 4 | TCATATTACGAGTCAGTAGG | 306 |
| pLas, individually packaged | 20170T2608 | B02 | pL43 | 96.60% | CGCCGCCCCCGGACGCGACC | FALSE | 2 | CATGCGT | 4180 |
| pLas, individually packaged | 20170T2608 | B02 | sgRNA | 95.10% | CGCCGCCCCCGGACGCGACC | FALSE | 2 | CGCCGCCCCCGGACGCGACC | 874 |
| pLas, individually packaged | 20170T2608 | B03 | pL43 | 96.90% | CCTGCAACGGGACTAGTTGG | FALSE | 2 | CGTCATA | 4136 |
| pLas, individually packaged | 20170T2608 | B03 | sgRNA | 95.80% | CCTGCAACGGGACTAGTTGG | FALSE | 2 | CCTGCAACGGGACTAGTTGG | 877 |
| pLas, individually packaged | 20170T2608 | B04 | pL43 | 96.00% | AGTAGTCCGGGATATCAGCG | FALSE | 2 | CCTCTTC | 3368 |
| pLas, individually packaged | 20170T2608 | B04 | sgRNA | 93.70% | AGTAGTCCGGGATATCAGCG | FALSE | 2 | AGTAGTCCGGGATATCAGCG | 388 |
| pLas, individually packaged | 20170T2608 | C01 | pL43 | 96.50% | AGTAGTCCGGGATATCAGCG | FALSE | 2 | CCTCTTC | 3512 |
| pLas, individually packaged | 20170T2608 | C01 | sgRNA | 96.50% | AGTAGTCCGGGATATCAGCG | FALSE | 2 | AGTAGTCCGGGATATCAGCG | 599 |
| pLas, individually packaged | 20170T2608 | C02 | pL43 | 94.50% | CCTGCAACGGGACTAGTTGG | FALSE | 2 | CGTCATA | 3691 |
| pLas, individually packaged | 20170T2608 | C02 | sgRNA | 95.50% | CCTGCAACGGGACTAGTTGG | FALSE | 2 | CCTGCAACGGGACTAGTTGG | 764 |

TABLE 2-continued

| condition | date | plate | well | pat-tern | frac-tion | pred_sgRNA | soli-tary | matches_per_sample | match | count |
|---|---|---|---|---|---|---|---|---|---|---|
| pLas, individually packaged | 20170T2 | 608 | C03 | pL43 | 96.90% | ATACAACTGCTT GCAACAGG | FALSE | 2 | ATTCCGA | 4307 |
| pLas, individually packaged | 20170T2 | 608 | C03 | sgRNA | 93.80% | ATACAACTGCTT GCAACAGG | FALSE | 2 | ATACAACTGCTT GCAACAGG | 405 |
| pLas, individually packaged | 20170T2 | 608 | C04 | pL43 | 97.20% | CGCCGCCCCCG GACGCGACC | FALSE | 2 | CATGCGT | 4177 |
| pLas, individually packaged | 20170T2 | 608 | C04 | sgRNA | 96.30% | CGCCGCCCCCG GACGCGACC | FALSE | 2 | CGCCGCCCCCGG ACGCGACC | 235 |
| pLas, individually packaged | 20170T2 | 608 | D01 | pL43 | 97.00% | TCATATTACGAG TCAGTAGG | FALSE | 2 | AGAGAGA | 3954 |
| pLas, individually packaged | 20170T2 | 608 | D01 | sgRNA | 95.90% | TCATATTACGAG TCAGTAGG | FALSE | 2 | TCATATTACGAGT CAGTAGG | 352 |
| pLas, individually packaged | 20170T2 | 608 | D02 | pL43 | 94.30% | TCATATTACGAG TCAGTAGG | FALSE | 2 | AGAGAGA | 3606 |
| pLas, individually packaged | 20170T2 | 608 | D02 | sgRNA | 96.00% | TCATATTACGAG TCAGTAGG | FALSE | 2 | TCATATTACGAGT CAGTAGG | 1285 |
| pLas, individually packaged | 20170T2 | 608 | D03 | pL43 | 95.50% | CCTGCAACGGG ACTAGTTGG | FALSE | 2 | CGTCATA | 3714 |
| pLas, individually packaged | 20170T2 | 608 | D03 | sgRNA | 94.80% | CCTGCAACGGG ACTAGTTGG | FALSE | 2 | CCTGCAACGGGA CTAGTTGG | 1102 |
| pLas, individually packaged | 20170T2 | 608 | D04 | pL43 | 94.70% | CCAGTACAAAC CTACCTACG | FALSE | 2 | AAGAGGA | 3834 |
| pLas, individually packaged | 20170T2 | 608 | D04 | sgRNA | 94.00% | CCAGTACAAAC CTACCTACG | FALSE | 2 | CCAGTACAAACC TACCTACG | 299 |
| pLas, individually packaged | 20170T2 | 608 | E01 | pL43 | 97.00% | AGTAGTCCGGG ATATCAGCG | FALSE | 2 | CCTCTTC | 3354 |
| pLas, individually packaged | 20170T2 | 608 | E01 | sgRNA | 93.60% | AGTAGTCCGGG ATATCAGCG | FALSE | 2 | AGTAGTCCGGGA TATCAGCG | 497 |
| pLas, individually packaged | 20170T2 | 608 | E02 | pL43 | 96.10% | AGAGCACTGCA CTCCTTCA | FALSE | 2 | CCAGTTA | 3865 |
| pLas, individually packaged | 20170T2 | 608 | E02 | sgRNA | 94.60% | AGAGCACTGCA CTCCTTCA | FALSE | 2 | AGAGCACTGCAC TCCTTCA | 881 |
| pLas, individually packaged | 20170T2 | 608 | E03 | pL43 | 97.00% | TCATATTACGAG TCAGTAGG | FALSE | 2 | AGAGAGA | 3574 |
| pLas, individually packaged | 20170T2 | 608 | E03 | sgRNA | 95.00% | TCATATTACGAG TCAGTAGG | FALSE | 2 | TCATATTACGAGT CAGTAGG | 498 |

TABLE 2-continued

| condition | date | platewell | pattern | fraction | pred_sgRNA | solitary | matches_per_sample | match | count |
|---|---|---|---|---|---|---|---|---|---|
| pLas, individually packaged | 20170T2 608 | E04 | pL43 | 96.50% | AGAGCACTGCACTCCTTCA | FALSE | 2 | CCAGTTA | 4290 |
| pLas, individually packaged | 20170T2 608 | E04 | sgRNA | 95.30% | AGAGCACTGCACTCCTTCA | FALSE | 2 | AGAGCACTGCACTCCTTCA | 505 |
| pLas, individually packaged | 20170T2 608 | F01 | pL43 | 96.60% | TCCACCGGCGAAAGAGATCC | FALSE | 2 | CAATCGG | 4255 |
| pLas, individually packaged | 20170T2 608 | F01 | sgRNA | 94.60% | TCCACCGGCGAAAGAGATCC | FALSE | 2 | TCCACCGGCGAAAGAGATCC | 905 |
| pLas, individually packaged | 20170T2 608 | F02 | pL43 | 97.30% | ATACAACTGCTTGCAACAGG | FALSE | 2 | ATTCCGA | 4292 |
| pLas, individually packaged | 20170T2 608 | F02 | sgRNA | 96.50% | ATACAACTGCTTGCAACAGG | FALSE | 2 | ATACAACTGCTTGCAACAGG | 625 |
| pLas, individually packaged | 20170T2 608 | F03 | pL43 | 97.40% | CCTGCAACGGGACTAGTTGG | FALSE | 2 | CGTCATA | 4249 |
| pLas, individually packaged | 20170T2 608 | F03 | sgRNA | 93.70% | CCTGCAACGGGACTAGTTGG | FALSE | 2 | CCTGCAACGGGACTAGTTGG | 328 |
| pLas, individually packaged | 20170T2 608 | F04 | pL43 | 96.90% | ATACAACTGCTTGCAACAGG | FALSE | 2 | ATTCCGA | 3725 |
| pLas, individually packaged | 20170T2 608 | F04 | sgRNA | 95.10% | ATACAACTGCTTGCAACAGG | FALSE | 2 | ATACAACTGCTTGCAACAGG | 254 |
| pLas, individually packaged | 20170T2 608 | G01 | pL43 | 97.20% | ATACAACTGCTTGCAACAGG | FALSE | 2 | ATTCCGA | 4241 |
| pLas, individually packaged | 20170T2 608 | G01 | sgRNA | 95.10% | ATACAACTGCTTGCAACAGG | FALSE | 2 | ATACAACTGCTTGCAACAGG | 1193 |
| pLas, individually packaged | 20170T2 608 | G02 | pL43 | 97.60% | CCTGCAACGGGACTAGTTGG | FALSE | 2 | CGTCATA | 4452 |
| pLas, individually packaged | 20170T2 608 | G02 | sgRNA | 94.60% | CCTGCAACGGGACTAGTTGG | FALSE | 2 | CCTGCAACGGGACTAGTTGG | 712 |
| pLas, individually packaged | 20170T2 608 | G03 | pL43 | 97.50% | TCATATTACGAGTCAGTAGG | FALSE | 2 | AGAGAGA | 4061 |
| pLas, individually packaged | 20170T2 608 | G03 | sgRNA | 95.40% | TCATATTACGAGTCAGTAGG | FALSE | 2 | TCATATTACGAGTCAGTAGG | 536 |
| pLas, individually packaged | 20170T2 608 | G04 | pL43 | 96.90% | CGCCGCCCCCGGACGCGACC | FALSE | 2 | CATGCGT | 3959 |
| pLas, individually packaged | 20170T2 608 | G04 | sgRNA | 96.20% | CGCCGCCCCCGGACGCGACC | FALSE | 2 | CGCCGCCCCCGGACGCGACC | 179 |

TABLE 2-continued

| condition | date | platewell | pattern | fraction | pred_sgRNA | solitary | matches_per_sample | match | count |
|---|---|---|---|---|---|---|---|---|---|
| pLas, individually packaged | 20170T2 608 | H01 | pL43 | 97.20% | AGAGCACTGCACTCCTTCA | FALSE | 2 | CCAGTTA | 4232 |
| pLas, individually packaged | 20170T2 608 | H01 | sgRNA | 95.20% | AGAGCACTGCACTCCTTCA | FALSE | 2 | AGAGCACTGCACTCCTTCA | 1226 |
| pLas, individually packaged | 20170T2 608 | H02 | pL43 | 96.30% | AGTAGTCCGGGATATCAGCG | FALSE | 2 | CCTCTTC | 3553 |
| pLas, individually packaged | 20170T2 608 | H02 | sgRNA | 95.80% | AGTAGTCCGGGATATCAGCG | FALSE | 2 | AGTAGTCCGGGATATCAGCG | 1508 |
| pLas, individually packaged | 20170T2 608 | H03 | pL43 | 97.40% | CCAGTACAAACCTACCTACG | FALSE | 2 | AAGAGGA | 4423 |
| pLas, individually packaged | 20170T2 608 | H03 | sgRNA | 96.60% | CCAGTACAAACCTACCTACG | FALSE | 2 | CCAGTACAAACCTACCTACG | 1501 |
| pLas, individually packaged | 20170T2 608 | H04 | pL43 | 97.70% | CCTGCAACGGGACTAGTTGG | FALSE | 2 | CGTCATA | 4444 |
| pLas, individually packaged | 20170T2 608 | H04 | sgRNA | 96.40% | CCTGCAACGGGACTAGTTGG | FALSE | 2 | CCTGCAACGGGACTAGTTGG | 862 |
| pLas, standard_8 | 20170T3 608 | A01 | pL43 | 38.30% | AGTAGTCCGGGATATCAGCG | FALSE | 5 | CCTCTTC | 916 |
| pLas, standard_8 | 20170T3 608 | A01 | pL43 | 51.20% | ATACAACTGCTTGCAACAGG | FALSE | 5 | ATTCCGA | 1222 |
| pLas, standard_8 | 20170T3 608 | A01 | sgRNA | 14.30% | AGAGCACTGCACTCCTTCA | TRUE | 5 | AGAGCACTGCACTCCTTCA | 314 |
| pLas, standard_8 | 20170T3 608 | A01 | sgRNA | 29.50% | AGTAGTCCGGGATATCAGCG | FALSE | 5 | AGTAGTCCGGGATATCAGCG | 648 |
| pLas, standard_8 | 20170T3 608 | A01 | sgRNA | 49.80% | ATACAACTGCTTGCAACAGG | FALSE | 5 | ATACAACTGCTTGCAACAGG | 1094 |
| pLas, standard_8 | 20170T3 608 | A02 | pL43 | 97.10% | ATACAACTGCTTGCAACAGG | FALSE | 2 | ATTCCGA | 4458 |
| pLas, standard_8 | 20170T3 608 | A02 | sgRNA | 95.20% | ATACAACTGCTTGCAACAGG | FALSE | 2 | ATACAACTGCTTGCAACAGG | 1199 |
| pLas, standard_8 | 20170T3 608 | A03 | pL43 | 96.70% | CCTGCAACGGGACTAGTTGG | FALSE | 2 | CGTCATA | 3846 |
| pLas, standard_8 | 20170T3 608 | A03 | sgRNA | 96.00% | CCTGCAACGGGACTAGTTGG | FALSE | 2 | CCTGCAACGGGACTAGTTGG | 3791 |
| pLas, standard_8 | 20170T3 608 | A04 | pL43 | 12.90% | AGAGCACTGCACTCCTTCA | TRUE | 3 | AGGCTCT | 202 |
| pLas, standard_8 | 20170T3 608 | A04 | pL43 | 75.50% | AGAGCACTGCACTCCTTCA | TRUE | 3 | CCAGTTA | 1184 |
| pLas, standard_8 | 20170T3 608 | A04 | sgRNA | 95.50% | TCATATTACGAGTCAGTAGG | TRUE | 3 | TCATATTACGAGTCAGTAGG | 3631 |
| pLas, standard_8 | 20170T3 608 | A05 | pL43 | 94.30% | CGCCGCCCCCGGACGCGACC | FALSE | 2 | CATGCGT | 3658 |
| pLas, standard_8 | 20170T3 608 | A05 | sgRNA | 92.60% | CGCCGCCCCCGGACGCGACC | FALSE | 2 | CGCCGCCCCCGGACGCGACC | 312 |

TABLE 2-continued

| condition | date | platewell | pat-tern | frac-tion | pred_sgRNA | soli-tary | matches_per_sample | match | count |
|---|---|---|---|---|---|---|---|---|---|
| pLas, standard_8 | 20170T3608 | A06 | pL43 | 22.20% | CCTGCAACGGGACTAGTTGG | TRUE | 5 | CGTCATA | 1003 |
| pLas, standard_8 | 20170T3608 | A06 | pL43 | 23.50% | ATACAACTGCTTGCAACAGG | FALSE | 5 | ATTCCGA | 1062 |
| pLas, standard_8 | 20170T3608 | A06 | pL43 | 51.50% | TCCACCGGCGAAAGAGATCC | FALSE | 5 | CAATCGG | 2328 |
| pLas, standard_8 | 20170T3608 | A06 | sgRNA | 37.00% | ATACAACTGCTTGCAACAGG | FALSE | 5 | ATACAACTGCTTGCAACAGG | 125 |
| pLas, standard_8 | 20170T3608 | A06 | sgRNA | 57.40% | TCCACCGGCGAAAGAGATCC | FALSE | 5 | TCCACCGGCGAAAGAGATCC | 194 |
| pLas, standard_8 | 20170T3608 | A07 | pL43 | 97.60% | CCTGCAACGGGACTAGTTGG | TRUE | 2 | CGTCATA | 3824 |
| pLas, standard_8 | 20170T3608 | A07 | sgRNA | 95.00% | AGTAGTCCGGGATATCAGCG | TRUE | 2 | AGTAGTCCGGGATATCAGCG | 1558 |
| pLas, standard_8 | 20170T3608 | A08 | pL43 | 91.30% | ATACAACTGCTTGCAACAGG | FALSE | 2 | ATTCCGA | 2460 |
| pLas, standard_8 | 20170T3608 | A08 | sgRNA | 91.30% | ATACAACTGCTTGCAACAGG | FALSE | 2 | ATACAACTGCTTGCAACAGG | 2853 |
| pLas, standard_8 | 20170T3608 | B01 | pL43 | 91.50% | AGTAGTCCGGGATATCAGCG | FALSE | 2 | CCTCTTC | 2732 |
| pLas, standard_8 | 20170T3608 | B01 | sgRNA | 95.70% | AGTAGTCCGGGATATCAGCG | FALSE | 2 | AGTAGTCCGGGATATCAGCG | 3419 |
| pLas, standard_8 | 20170T3608 | B02 | pL43 | 97.30% | CCAGTACAAACCTACCTACG | FALSE | 2 | AAGAGGA | 4877 |
| pLas, standard_8 | 20170T3608 | B02 | sgRNA | 96.20% | CCAGTACAAACCTACCTACG | FALSE | 2 | CCAGTACAAACCTACCTACG | 403 |
| pLas, standard_8 | 20170T3608 | B03 | pL43 | 67.90% | TCCACCGGCGAAAGAGATCC | TRUE | 2 | CAATCGG | 1752 |
| pLas, standard_8 | 20170T3608 | B03 | sgRNA | 93.20% | ATACAACTGCTTGCAACAGG | TRUE | 2 | ATACAACTGCTTGCAACAGG | 743 |
| pLas, standard_8 | 20170T3608 | B04 | pL43 | 96.50% | ATACAACTGCTTGCAACAGG | FALSE | 2 | ATTCCGA | 4275 |
| pLas, standard_8 | 20170T3608 | B04 | sgRNA | 95.10% | ATACAACTGCTTGCAACAGG | FALSE | 2 | ATACAACTGCTTGCAACAGG | 447 |
| pLas, standard_8 | 20170T3608 | B05 | pL43 | 97.00% | AGTAGTCCGGGATATCAGCG | FALSE | 2 | CCTCTTC | 3946 |
| pLas, standard_8 | 20170T3608 | B05 | sgRNA | 96.40% | AGTAGTCCGGGATATCAGCG | FALSE | 2 | AGTAGTCCGGGATATCAGCG | 986 |
| pLas, standard_8 | 20170T3608 | B06 | pL43 | 96.50% | AGTAGTCCGGGATATCAGCG | TRUE | 2 | CCTCTTC | 3955 |
| pLas, standard_8 | 20170T3608 | B06 | sgRNA | 95.30% | ATACAACTGCTTGCAACAGG | TRUE | 2 | ATACAACTGCTTGCAACAGG | 1075 |
| pLas, standard_8 | 20170T3608 | B07 | pL43 | 96.50% | CGCCGCCCCGGACGCGACC | FALSE | 2 | CATGCGT | 4415 |
| pLas, standard_8 | 20170T3608 | B07 | sgRNA | 96.70% | CGCCGCCCCGGACGCGACC | FALSE | 2 | CGCCGCCCCGGACGCGACC | 652 |
| pLas, standard_8 | 20170T3608 | B08 | pL43 | 45.70% | AGTAGTCCGGGATATCAGCG | FALSE | 4 | CCTCTTC | 1938 |

TABLE 2-continued

| condition | date | platewell | pattern | fraction | pred_sgRNA | solitary | matches_per_sample | match | count |
|---|---|---|---|---|---|---|---|---|---|
| pLas, standard_8 | 20170T3608 | B08 | pL43 | 51.40% | AGAGCACTGCACTCCTTCA | FALSE | 4 | CCAGTTA | 2177 |
| pLas, standard_8 | 20170T3608 | B08 | sgRNA | 47.90% | AGAGCACTGCACTCCTTCA | FALSE | 4 | AGAGCACTGCACTCCTTCA | 512 |
| pLas, standard_8 | 20170T3608 | B08 | sgRNA | 47.90% | AGTAGTCCGGGATATCAGCG | FALSE | 4 | AGTAGTCCGGGATATCAGCG | 513 |
| pLas, standard_8 | 20170T3608 | C01 | pL43 | 97.10% | ATACAACTGCTTGCAACAGG | FALSE | 2 | ATTCCGA | 5003 |
| pLas, standard_8 | 20170T3608 | C01 | sgRNA | 96.40% | ATACAACTGCTTGCAACAGG | FALSE | 2 | ATACAACTGCTTGCAACAGG | 782 |
| pLas, standard_8 | 20170T3608 | C02 | pL43 | 95.60% | CCAGTACAAACCTACCTACG | TRUE | 2 | AAGAGGA | 4832 |
| pLas, standard_8 | 20170T3608 | C02 | sgRNA | 95.90% | CCTGCAACGGGACTAGTTGG | TRUE | 2 | CCTGCAACGGGACTAGTTGG | 1433 |
| pLas, standard_8 | 20170T3608 | C03 | pL43 | 96.80% | CCTGCAACGGGACTAGTTGG | TRUE | 2 | CGTCATA | 5059 |
| pLas, standard_8 | 20170T3608 | C03 | sgRNA | 95.40% | AGTAGTCCGGGATATCAGCG | TRUE | 2 | AGTAGTCCGGGATATCAGCG | 638 |
| pLas, standard_8 | 20170T3608 | C04 | pL43 | 97.20% | CCTGCAACGGGACTAGTTGG | TRUE | 2 | CGTCATA | 4324 |
| pLas, standard_8 | 20170T3608 | C04 | sgRNA | 95.30% | TCATATTACGAGTCAGTAGG | TRUE | 2 | TCATATTACGAGTCAGTAGG | 323 |
| pLas, standard_8 | 20170T3608 | C05 | pL43 | 97.10% | TCCACCGGCGAAAGAGATCC | FALSE | 2 | CAATCGG | 4711 |
| pLas, standard_8 | 20170T3608 | C05 | sgRNA | 94.40% | TCCACCGGCGAAAGAGATCC | FALSE | 2 | TCCACCGGCGAAAGAGATCC | 1218 |
| pLas, standard_8 | 20170T3608 | C06 | pL43 | 94.60% | TCATATTACGAGTCAGTAGG | FALSE | 2 | AGAGAGA | 4576 |
| pLas, standard_8 | 20170T3608 | C06 | sgRNA | 96.30% | TCATATTACGAGTCAGTAGG | FALSE | 2 | TCATATTACGAGTCAGTAGG | 949 |
| pLas, standard_8 | 20170T3608 | C07 | pL43 | 93.00% | CCAGTACAAACCTACCTACG | FALSE | 2 | AAGAGGA | 3743 |
| pLas, standard_8 | 20170T3608 | C07 | sgRNA | 95.20% | CCAGTACAAACCTACCTACG | FALSE | 2 | CCAGTACAAACCTACCTACG | 758 |
| pLas, standard_8 | 20170T3608 | C08 | pL43 | 95.40% | CCAGTACAAACCTACCTACG | TRUE | 2 | AAGAGGA | 4504 |
| pLas, standard_8 | 20170T3608 | C08 | sgRNA | 95.40% | CCTGCAACGGGACTAGTTGG | TRUE | 2 | CCTGCAACGGGACTAGTTGG | 577 |
| pLas, standard_8 | 20170T3608 | D01 | pL43 | 96.00% | CCTGCAACGGGACTAGTTGG | FALSE | 2 | CGTCATA | 4673 |
| pLas, standard_8 | 20170T3608 | D01 | sgRNA | 94.90% | CCTGCAACGGGACTAGTTGG | FALSE | 2 | CCTGCAACGGGACTAGTTGG | 691 |
| pLas, standard_8 | 20170T3608 | D02 | pL43 | 96.20% | AGAGCACTGCACTCCTTCA | FALSE | 2 | CCAGTTA | 5213 |
| pLas, standard_8 | 20170T3608 | D02 | sgRNA | 96.10% | AGAGCACTGCACTCCTTCA | FALSE | 2 | AGAGCACTGCACTCCTTCA | 724 |
| pLas, standard_8 | 20170T3608 | D03 | pL43 | 59.90% | TCATATTACGAGTCAGTAGG | FALSE | 2 | AGAGAGA | 1526 |

TABLE 2-continued

| condition | date | platewell | pattern | fraction | pred_sgRNA | solitary | matches_per_sample | match | count |
|---|---|---|---|---|---|---|---|---|---|
| pLas, standard_8 | 20170T3608 | D03 | sgRNA | 94.70% | TCATATTACGAGTCAGTAGG | FALSE | 2 | TCATATTACGAGTCAGTAGG | 622 |
| pLas, standard_8 | 20170T3608 | D04 | pL43 | 95.00% | TCCACCGGCGAAAGAGATCC | FALSE | 2 | CAATCGG | 4568 |
| pLas, standard_8 | 20170T3608 | D04 | sgRNA | 95.20% | TCCACCGGCGAAAGAGATCC | FALSE | 2 | TCCACCGGCGAAAGAGATCC | 239 |
| pLas, standard_8 | 20170T3608 | D05 | pL43 | 96.50% | CGCCGCCCCGGACGCGACC | FALSE | 2 | CATGCGT | 4945 |
| pLas, standard_8 | 20170T3608 | D05 | sgRNA | 96.90% | CGCCGCCCCGGACGCGACC | FALSE | 2 | CGCCGCCCCGGACGCGACC | 409 |
| pLas, standard_8 | 20170T3608 | D06 | pL43 | 96.50% | ATACAACTGCTTGCAACAGG | FALSE | 2 | ATTCCGA | 4165 |
| pLas, standard_8 | 20170T3608 | D06 | sgRNA | 94.60% | ATACAACTGCTTGCAACAGG | FALSE | 2 | ATACAACTGCTTGCAACAGG | 591 |
| pLas, standard_8 | 20170T3608 | D07 | pL43 | 96.80% | CCAGTACAAACCTACCTACG | FALSE | 2 | AAGAGGA | 4170 |
| pLas, standard_8 | 20170T3608 | D07 | sgRNA | 96.80% | CCAGTACAAACCTACCTACG | FALSE | 2 | CCAGTACAAACCTACCTACG | 605 |
| pLas, standard_8 | 20170T3608 | D08 | pL43 | 48.30% | CCTGCAACGGGACTAGTTGG | FALSE | 4 | CGTCATA | 2156 |
| pLas, standard_8 | 20170T3608 | D08 | pL43 | 48.90% | TCATATTACGAGTCAGTAGG | FALSE | 4 | AGAGAGA | 2180 |
| pLas, standard_8 | 20170T3608 | D08 | sgRNA | 45.20% | TCATATTACGAGTCAGTAGG | FALSE | 4 | TCATATTACGAGTCAGTAGG | 150 |
| pLas, standard_8 | 20170T3608 | D08 | sgRNA | 49.40% | CCTGCAACGGGACTAGTTGG | FALSE | 4 | CCTGCAACGGGACTAGTTGG | 164 |
| pLas, standard_8 | 20170T3608 | E01 | pL43 | 93.70% | AGAGCACTGCACTCCTTCA | FALSE | 2 | CCAGTTA | 3427 |
| pLas, standard_8 | 20170T3608 | E01 | sgRNA | 94.20% | AGAGCACTGCACTCCTTCA | FALSE | 2 | AGAGCACTGCACTCCTTCA | 1096 |
| pLas, standard_8 | 20170T3608 | E02 | pL43 | 44.00% | AGAGCACTGCACTCCTTCA | FALSE | 4 | CCAGTTA | 1441 |
| pLas, standard_8 | 20170T3608 | E02 | pL43 | 52.70% | ATACAACTGCTTGCAACAGG | FALSE | 4 | ATTCCGA | 1726 |
| pLas, standard_8 | 20170T3608 | E02 | sgRNA | 45.10% | ATACAACTGCTTGCAACAGG | FALSE | 4 | ATACAACTGCTTGCAACAGG | 208 |
| pLas, standard_8 | 20170T3608 | E02 | sgRNA | 48.60% | AGAGCACTGCACTCCTTCA | FALSE | 4 | AGAGCACTGCACTCCTTCA | 224 |
| pLas, standard_8 | 20170T3608 | E03 | pL43 | 97.40% | CCTGCAACGGGACTAGTTGG | FALSE | 2 | CGTCATA | 3657 |
| pLas, standard_8 | 20170T3608 | E03 | sgRNA | 95.50% | CCTGCAACGGGACTAGTTGG | FALSE | 2 | CCTGCAACGGGACTAGTTGG | 385 |
| pLas, standard_8 | 20170T3608 | E04 | pL43 | 97.20% | TCATATTACGAGTCAGTAGG | FALSE | 2 | AGAGAGA | 3853 |
| pLas, standard_8 | 20170T3608 | E04 | sgRNA | 95.10% | TCATATTACGAGTCAGTAGG | FALSE | 2 | TCATATTACGAGTCAGTAGG | 254 |
| pLas, standard_8 | 20170T3608 | E05 | pL43 | 96.60% | CGCCGCCCCGGACGCGACC | FALSE | 2 | CATGCGT | 3585 |

TABLE 2-continued

| condition | date | plate | well | pattern | fraction | pred_sgRNA | solitary | matches_per_sample | match | count |
|---|---|---|---|---|---|---|---|---|---|---|
| pLas, standard_8 | 20170T3 | 608 | E05 | sgRNA | 97.30% | CGCCGCCCCCG GACGCGACC | FALSE | 2 | CGCCGCCCCGG ACGCGACC | 655 |
| pLas, standard_8 | 20170T3 | 608 | E06 | pL43 | 97.60% | TCATATTACGAG TCAGTAGG | TRUE | 2 | AGAGAGA | 3875 |
| pLas, standard_8 | 20170T3 | 608 | E06 | sgRNA | 92.90% | ATACAACTGCTT GCAACAGG | TRUE | 2 | ATACAACTGCTT GCAACAGG | 262 |
| pLas, standard_8 | 20170T3 | 608 | E07 | pL43 | 97.10% | ATACAACTGCTT GCAACAGG | TRUE | 2 | ATTCCGA | 3665 |
| pLas, standard_8 | 20170T3 | 608 | E07 | sgRNA | 94.50% | AGAGCACTGCA CTCCTTCA | TRUE | 2 | AGAGCACTGCAC TCCTTCA | 241 |
| pLas, standard_8 | 20170T3 | 608 | E08 | pL43 | 95.40% | AGAGCACTGCA CTCCTTCA | FALSE | 2 | CCAGTTA | 3312 |
| pLas, standard_8 | 20170T3 | 608 | E08 | sgRNA | 95.40% | AGAGCACTGCA CTCCTTCA | FALSE | 2 | AGAGCACTGCAC TCCTTCA | 248 |
| pLas, standard_8 | 20170T3 | 608 | F01 | pL43 | 97.10% | CCAGTACAAAC CTACCTACG | TRUE | 2 | AAGAGGA | 4357 |
| pLas, standard_8 | 20170T3 | 608 | F01 | sgRNA | 94.70% | AGAGCACTGCA CTCCTTCA | TRUE | 2 | AGAGCACTGCAC TCCTTCA | 1724 |
| pLas, standard_8 | 20170T3 | 608 | F03 | pL43 | 97.00% | ATACAACTGCTT GCAACAGG | FALSE | 2 | ATTCCGA | 4167 |
| pLas, standard_8 | 20170T3 | 608 | F03 | sgRNA | 95.40% | ATACAACTGCTT GCAACAGG | FALSE | 2 | ATACAACTGCTT GCAACAGG | 740 |
| pLas, standard_8 | 20170T3 | 608 | F04 | pL43 | 96.70% | AGAGCACTGCA CTCCTTCA | TRUE | 2 | CCAGTTA | 4419 |
| pLas, standard_8 | 20170T3 | 608 | F04 | sgRNA | 96.20% | CCTGCAACGGG ACTAGTTGG | TRUE | 2 | CCTGCAACGGGA CTAGTTGG | 332 |
| pLas, standard_8 | 20170T3 | 608 | F05 | pL43 | 96.70% | AGAGCACTGCA CTCCTTCA | TRUE | 2 | CCAGTTA | 4215 |
| pLas, standard_8 | 20170T3 | 608 | F05 | sgRNA | 96.20% | CCTGCAACGGG ACTAGTTGG | TRUE | 2 | CCTGCAACGGGA CTAGTTGG | 833 |
| pLas, standard_8 | 20170T3 | 608 | F06 | pL43 | 96.80% | CGCCGCCCCCG GACGCGACC | TRUE | 2 | CATGCGT | 3523 |
| pLas, standard_8 | 20170T3 | 608 | F06 | sgRNA | 95.50% | CCTGCAACGGG ACTAGTTGG | TRUE | 2 | CCTGCAACGGGA CTAGTTGG | 231 |
| pLas, standard_8 | 20170T3 | 608 | F07 | pL43 | 95.90% | AGAGCACTGCA CTCCTTCA | FALSE | 2 | CCAGTTA | 3831 |
| pLas, standard_8 | 20170T3 | 608 | F07 | sgRNA | 96.00% | AGAGCACTGCA CTCCTTCA | FALSE | 2 | AGAGCACTGCAC TCCTTCA | 697 |
| pLas, standard_8 | 20170T3 | 608 | F08 | pL43 | 96.50% | AGAGCACTGCA CTCCTTCA | FALSE | 2 | CCAGTTA | 3858 |
| pLas, standard_8 | 20170T3 | 608 | F08 | sgRNA | 94.60% | AGAGCACTGCA CTCCTTCA | FALSE | 2 | AGAGCACTGCAC TCCTTCA | 1214 |
| pLas, standard_8 | 20170T3 | 608 | G01 | pL43 | 96.80% | TCATATTACGAG TCAGTAGG | FALSE | 2 | AGAGAGA | 4622 |
| pLas, standard_8 | 20170T3 | 608 | G01 | sgRNA | 94.10% | TCATATTACGAG TCAGTAGG | FALSE | 2 | TCATATTACGAGT CAGTAGG | 1423 |
| pLas, standard_8 | 20170T3 | 608 | G02 | pL43 | 46.40% | CCAGTACAAAC CTACCTACG | FALSE | 3 | AAGAGGA | 2320 |

TABLE 2-continued

| condition | date | platewell | pattern | fraction | pred_sgRNA | solitary | matches_per_sample | match | count |
|---|---|---|---|---|---|---|---|---|---|
| pLas, standard_8 | 20170T3608 | G02 | pL43 | 51.00% | TCATATTACGAGTCAGTAGG | TRUE | 3 | AGAGAGA | 2550 |
| pLas, standard_8 | 20170T3608 | G02 | sgRNA | 95.50% | CCAGTACAAACCTACCTACG | FALSE | 3 | CCAGTACAAACCTACCTACG | 612 |
| pLas, standard_8 | 20170T3608 | G05 | pL43 | 96.60% | CCTGCAACGGGACTAGTTGG | FALSE | 2 | CGTCATA | 3919 |
| pLas, standard_8 | 20170T3608 | G05 | sgRNA | 95.80% | CCTGCAACGGGACTAGTTGG | FALSE | 2 | CCTGCAACGGGACTAGTTGG | 2747 |
| pLas, standard_8 | 20170T3608 | G06 | pL43 | 95.30% | ATACAACTGCTTGCAACAGG | TRUE | 2 | ATTCCGA | 4219 |
| pLas, standard_8 | 20170T3608 | G06 | sgRNA | 94.70% | AGAGCACTGCACTCCTTCA | TRUE | 2 | AGAGCACTGCACTCCTTCA | 1060 |
| pLas, standard_8 | 20170T3608 | G07 | pL43 | 96.90% | TCATATTACGAGTCAGTAGG | FALSE | 2 | AGAGAGA | 4940 |
| pLas, standard_8 | 20170T3608 | G07 | sgRNA | 94.90% | TCATATTACGAGTCAGTAGG | FALSE | 2 | TCATATTACGAGTCAGTAGG | 991 |
| pLas, standard_8 | 20170T3608 | G08 | pL43 | 97.50% | TCATATTACGAGTCAGTAGG | FALSE | 2 | AGAGAGA | 4771 |
| pLas, standard_8 | 20170T3608 | G08 | sgRNA | 95.50% | TCATATTACGAGTCAGTAGG | FALSE | 2 | TCATATTACGAGTCAGTAGG | 1030 |
| pLas, standard_8 | 20170T3608 | H01 | pL43 | 97.10% | CCTGCAACGGGACTAGTTGG | TRUE | 2 | CGTCATA | 4412 |
| pLas, standard_8 | 20170T3608 | H01 | sgRNA | 95.00% | ATACAACTGCTTGCAACAGG | TRUE | 2 | ATACAACTGCTTGCAACAGG | 830 |
| pLas, standard_8 | 20170T3608 | H02 | pL43 | 96.60% | ATACAACTGCTTGCAACAGG | TRUE | 2 | ATTCCGA | 4004 |
| pLas, standard_8 | 20170T3608 | H02 | sgRNA | 95.00% | AGAGCACTGCACTCCTTCA | TRUE | 2 | AGAGCACTGCACTCCTTCA | 1371 |
| pLas, standard_8 | 20170T3608 | H03 | pL43 | 96.90% | TCCACCGGCGAAAGAGATCC | TRUE | 2 | CAATCGG | 3486 |
| pLas, standard_8 | 20170T3608 | H03 | sgRNA | 92.90% | ATACAACTGCTTGCAACAGG | TRUE | 2 | ATACAACTGCTTGCAACAGG | 39 |
| pLas, standard_8 | 20170T3608 | H04 | pL43 | 97.80% | ATACAACTGCTTGCAACAGG | FALSE | 2 | ATTCCGA | 4240 |
| pLas, standard_8 | 20170T3608 | H04 | sgRNA | 94.60% | ATACAACTGCTTGCAACAGG | FALSE | 2 | ATACAACTGCTTGCAACAGG | 227 |
| pLas, standard_8 | 20170T3608 | H05 | pL43 | 97.30% | TCATATTACGAGTCAGTAGG | TRUE | 2 | AGAGAGA | 4390 |
| pLas, standard_8 | 20170T3608 | H05 | sgRNA | 95.90% | CCTGCAACGGGACTAGTTGG | TRUE | 2 | CCTGCAACGGGACTAGTTGG | 375 |
| pLas, standard_8 | 20170T3608 | H06 | pL43 | 30.90% | AGAGCACTGCACTCCTTCA | TRUE | 3 | AGGCTCT | 715 |
| pLas, standard_8 | 20170T3608 | H06 | pL43 | 62.70% | ATACAACTGCTTGCAACAGG | FALSE | 3 | ATTCCGA | 1451 |
| pLas, standard_8 | 20170T3608 | H06 | sgRNA | 95.00% | ATACAACTGCTTGCAACAGG | FALSE | 3 | ATACAACTGCTTGCAACAGG | 3966 |
| pLas, standard_8 | 20170T3608 | H07 | pL43 | 97.30% | ATACAACTGCTTGCAACAGG | FALSE | 2 | ATTCCGA | 4431 |

TABLE 2-continued

| condition | date | plate | well | pat-tern | frac-tion | pred_sgRNA | soli-tary | matches_per_sample | match | count |
|---|---|---|---|---|---|---|---|---|---|---|
| pLas, standard_8 | 20170T3 | 608 | H07 | sgRNA | 95.00% | ATACAACTGCTTGCAACAGG | FALSE | 2 | ATACAACTGCTTGCAACAGG | 707 |
| pLas, standard_8 | 20170T3 | 608 | H08 | pL43 | 97.60% | AGAGCACTGCACTCCTTCA | TRUE | 2 | CCAGTTA | 4408 |
| pLas, standard_8 | 20170T3 | 608 | H08 | sgRNA | 94.20% | ATACAACTGCTTGCAACAGG | TRUE | 2 | ATACAACTGCTTGCAACAGG | 1007 |
| pLas + pR_H2B-BFP (1:1000) | 20170T4 | 608 | A05 | pL43 | 97.50% | AGAGCACTGCACTCCTTCA | FALSE | 2 | CCAGTTA | 4557 |
| pLas + pR_H2B-BFP (1:1000) | 20170T4 | 608 | A05 | sgRNA | 94.40% | AGAGCACTGCACTCCTTCA | FALSE | 2 | AGAGCACTGCACTCCTTCA | 1303 |
| pLas + pR_H2B-BFP (1:1000) | 20170T4 | 608 | A06 | pL43 | 97.40% | CGCCGCCCCGGACGCGACC | FALSE | 2 | CATGCGT | 4231 |
| pLas + pR_H2B-BFP (1:1000) | 20170T4 | 608 | A06 | sgRNA | 96.40% | CGCCGCCCCGGACGCGACC | FALSE | 2 | CGCCGCCCCGGACGCGACC | 1004 |
| pLas + pR_H2B-BFP (1:1000) | 20170T4 | 608 | A07 | pL43 | 97.00% | AGAGCACTGCACTCCTTCA | FALSE | 2 | CCAGTTA | 4116 |
| pLas + pR_H2B-BFP (1:1000) | 20170T4 | 608 | A07 | sgRNA | 94.60% | AGAGCACTGCACTCCTTCA | FALSE | 2 | AGAGCACTGCACTCCTTCA | 823 |
| pLas + pR_H2B-BFP (1:1000) | 20170T4 | 608 | A08 | pL43 | 97.60% | TCATATTACGAGTCAGTAGG | FALSE | 2 | AGAGAGA | 3955 |
| pLas + pR_H2B-BFP (1:1000) | 20170T4 | 608 | A08 | sgRNA | 90.90% | TCATATTACGAGTCAGTAGG | FALSE | 2 | TCATATTACGAGTCAGTAGG | 765 |
| pLas + pR_H2B-BFP (1:1000) | 20170T4 | 608 | A09 | pL43 | 93.70% | CCAGTACAAACCTACCTACG | FALSE | 2 | AAGAGGA | 3001 |
| pLas + pR_H2B-BFP (1:1000) | 20170T4 | 608 | A09 | sgRNA | 95.60% | CCAGTACAAACCTACCTACG | FALSE | 2 | CCAGTACAAACCTACCTACG | 5907 |
| pLas + pR_H2B-BFP (1:1000) | 20170T4 | 608 | A10 | pL43 | 96.70% | AGAGCACTGCACTCCTTCA | FALSE | 2 | CCAGTTA | 4527 |
| pLas + pR_H2B-BFP (1:1000) | 20170T4 | 608 | A10 | sgRNA | 95.00% | AGAGCACTGCACTCCTTCA | FALSE | 2 | AGAGCACTGCACTCCTTCA | 906 |
| pLas + pR_H2B-BFP (1:1000) | 20170T4 | 608 | A11 | pL43 | 97.40% | CCTGCAACGGGACTAGTTGG | FALSE | 2 | CGTCATA | 4269 |
| pLas + pR_H2B-BFP (1:1000) | 20170T4 | 608 | A11 | sgRNA | 96.30% | CCTGCAACGGGACTAGTTGG | FALSE | 2 | CCTGCAACGGGACTAGTTGG | 1234 |
| pLas + pR_H2B-BFP (1:1000) | 20170T4 | 608 | A12 | pL43 | 92.50% | CCTGCAACGGGACTAGTTGG | FALSE | 2 | CGTCATA | 3147 |
| pLas + pR_H2B-BFP (1:1000) | 20170T4 | 608 | A12 | sgRNA | 94.80% | CCTGCAACGGGACTAGTTGG | FALSE | 2 | CCTGCAACGGGACTAGTTGG | 3223 |

TABLE 2-continued

| condition | date | plate | well | pattern | fraction | pred_sgRNA | solitary | matches_per_sample | match | count |
|---|---|---|---|---|---|---|---|---|---|---|
| pLas + pR_H2B-BFP (1:1000) | 20170T4 | 608 | B05 | pL43 | 97.20% | TCATATTACGAGTCAGTAGG | FALSE | 2 | AGAGAGA | 3990 |
| pLas + pR_H2B-BFP (1:1000) | 20170T4 | 608 | B05 | sgRNA | 95.70% | TCATATTACGAGTCAGTAGG | FALSE | 2 | TCATATTACGAGTCAGTAGG | 902 |
| pLas + pR_H2B-BFP (1:1000) | 20170T4 | 608 | B06 | pL43 | 95.80% | TCCACCGGCGAAAGAGATCC | FALSE | 2 | CAATCGG | 3985 |
| pLas + pR_H2B-BFP (1:1000) | 20170T4 | 608 | B06 | sgRNA | 94.60% | TCCACCGGCGAAAGAGATCC | FALSE | 2 | TCCACCGGCGAAAGAGATCC | 821 |
| pLas + pR_H2B-BFP (1:1000) | 20170T4 | 608 | B07 | pL43 | 94.00% | AGTAGTCCGGGATATCAGCG | FALSE | 2 | CCTCTTC | 3237 |
| pLas + pR_H2B-BFP (1:1000) | 20170T4 | 608 | B07 | sgRNA | 95.40% | AGTAGTCCGGGATATCAGCG | FALSE | 2 | AGTAGTCCGGGATATCAGCG | 2166 |
| pLas + pR_H2B-BFP (1:1000) | 20170T4 | 608 | B08 | pL43 | 96.20% | CCAGTACAAACCTACCTACG | FALSE | 2 | AAGAGGA | 4316 |
| pLas + pR_H2B-BFP (1:1000) | 20170T4 | 608 | B08 | sgRNA | 94.40% | CCAGTACAAACCTACCTACG | FALSE | 2 | CCAGTACAAACCTACCTACG | 1056 |
| pLas + pR_H2B-BFP (1:1000) | 20170T4 | 608 | B09 | pL43 | 68.70% | CCTGCAACGGGACTAGTTGG | FALSE | 2 | CGTCATA | 2349 |
| pLas + pR_H2B-BFP (1:1000) | 20170T4 | 608 | B09 | sgRNA | 94.90% | CCTGCAACGGGACTAGTTGG | FALSE | 2 | CCTGCAACGGGACTAGTTGG | 1363 |
| pLas + pR_H2B-BFP (1:1000) | 20170T4 | 608 | B10 | pL43 | 90.00% | TCATATTACGAGTCAGTAGG | FALSE | 2 | AGAGAGA | 3146 |
| pLas + pR_H2B-BFP (1:1000) | 20170T4 | 608 | B10 | sgRNA | 94.90% | TCATATTACGAGTCAGTAGG | FALSE | 2 | TCATATTACGAGTCAGTAGG | 259 |
| pLas + pR_H2B-BFP (1:1000) | 20170T4 | 608 | B11 | pL43 | 90.00% | AGAGCACTGCACTCCTTCA | FALSE | 2 | CCAGTTA | 3920 |
| pLas + pR_H2B-BFP (1:1000) | 20170T4 | 608 | B11 | sgRNA | 95.10% | AGAGCACTGCACTCCTTCA | FALSE | 2 | AGAGCACTGCACTCCTTCA | 409 |
| pLas + pR_H2B-BFP (1:1000) | 20170T4 | 608 | B12 | pL43 | 79.40% | CGCCGCCCCGGACGCGACC | FALSE | 2 | CATGCGT | 3303 |
| pLas + pR_H2B-BFP (1:1000) | 20170T4 | 608 | B12 | sgRNA | 93.20% | CGCCGCCCCGGACGCGACC | FALSE | 2 | CGCCGCCCCGGACGCGACC | 547 |
| pLas + pR_H2B-BFP (1:1000) | 20170T4 | 608 | C05 | pL43 | 96.40% | AGAGCACTGCACTCCTTCA | FALSE | 2 | CCAGTTA | 3254 |
| pLas + pR_H2B-BFP (1:1000) | 20170T4 | 608 | C05 | sgRNA | 94.70% | AGAGCACTGCACTCCTTCA | FALSE | 2 | AGAGCACTGCACTCCTTCA | 1888 |

TABLE 2-continued

| condition | date | platewell | pattern | fraction | pred_sgRNA | solitary | matches_per_sample | match | count |
|---|---|---|---|---|---|---|---|---|---|
| pLas + pR_H2B-BFP (1:1000) | 20170T4 608 | C06 | pL43 | 96.40% | AGTAGTCCGGG ATATCAGCG | FALSE | 2 | CCTCTTC | 3564 |
| pLas + pR_H2B-BFP (1:1000) | 20170T4 608 | C06 | sgRNA | 96.70% | AGTAGTCCGGG ATATCAGCG | FALSE | 2 | AGTAGTCCGGGA TATCAGCG | 231 |
| pLas + pR_H2B-BFP (1:1000) | 20170T4 608 | C07 | pL43 | 96.30% | AGAGCACTGCA CTCCTTCA | FALSE | 2 | CCAGTTA | 4010 |
| pLas + pR_H2B-BFP (1:1000) | 20170T4 608 | C07 | sgRNA | 95.30% | AGAGCACTGCA CTCCTTCA | FALSE | 2 | AGAGCACTGCAC TCCTTCA | 1061 |
| pLas + pR_H2B-BFP (1:1000) | 20170T4 608 | C08 | pL43 | 93.40% | ATACAACTGCTT GCAACAGG | FALSE | 2 | ATTCCGA | 3041 |
| pLas + pR_H2B-BFP (1:1000) | 20170T4 608 | C08 | sgRNA | 94.70% | ATACAACTGCTT GCAACAGG | FALSE | 2 | ATACAACTGCTT GCAACAGG | 537 |
| pLas + pR_H2B-BFP (1:1000) | 20170T4 608 | C09 | pL43 | 94.60% | AGAGCACTGCA CTCCTTCA | FALSE | 2 | CCAGTTA | 3373 |
| pLas + pR_H2B-BFP (1:1000) | 20170T4 608 | C09 | sgRNA | 94.70% | AGAGCACTGCA CTCCTTCA | FALSE | 2 | AGAGCACTGCAC TCCTTCA | 1522 |
| pLas + pR_H2B-BFP (1:1000) | 20170T4 608 | C10 | pL43 | 94.70% | TCCACCGGCGA AAGAGATCC | FALSE | 2 | CAATCGG | 3893 |
| pLas + pR_H2B-BFP (1:1000) | 20170T4 608 | C10 | sgRNA | 92.90% | TCCACCGGCGA AAGAGATCC | FALSE | 2 | TCCACCGGCGAA AGAGATCC | 1347 |
| pLas + pR_H2B-BFP (1:1000) | 20170T4 608 | C11 | pL43 | 83.40% | AGTAGTCCGGG ATATCAGCG | FALSE | 2 | CCTCTTC | 2594 |
| pLas + pR_H2B-BFP (1:1000) | 20170T4 608 | C11 | sgRNA | 95.80% | AGTAGTCCGGG ATATCAGCG | FALSE | 2 | AGTAGTCCGGGA TATCAGCG | 1086 |
| pLas + pR_H2B-BFP (1:1000) | 20170T4 608 | C12 | pL43 | 92.90% | TCATATTACGAG TCAGTAGG | FALSE | 2 | AGAGAGA | 3721 |
| pLas + pR_H2B-BFP (1:1000) | 20170T4 608 | C12 | sgRNA | 95.90% | TCATATTACGAG TCAGTAGG | FALSE | 2 | TCATATTACGAGT CAGTAGG | 635 |
| pLas + pR_H2B-BFP (1:1000) | 20170T4 608 | D05 | pL43 | 96.20% | AGAGCACTGCA CTCCTTCA | FALSE | 2 | CCAGTTA | 3267 |
| pLas + pR_H2B-BFP (1:1000) | 20170T4 608 | D05 | sgRNA | 93.90% | AGAGCACTGCA CTCCTTCA | FALSE | 2 | AGAGCACTGCAC TCCTTCA | 962 |
| pLas + pR_H2B-BFP (1:1000) | 20170T4 608 | D06 | pL43 | 96.80% | CCAGTACAAAC CTACCTACG | FALSE | 2 | AAGAGGA | 4031 |
| pLas + pR_H2B-BFP (1:1000) | 20170T4 608 | D06 | sgRNA | 96.20% | CCAGTACAAAC CTACCTACG | FALSE | 2 | CCAGTACAAACC TACCTACG | 410 |

TABLE 2-continued

| condition | date | platewell | pattern | fraction | pred_sgRNA | solitary | matches_per_sample | match | count |
|---|---|---|---|---|---|---|---|---|---|
| pLas + pR_H2B-BFP (1:1000) | 20170T4608 | D07 | pL43 | 97.00% | CCAGTACAAACCTACCTACG | FALSE | 2 | AAGAGGA | 3789 |
| pLas + pR_H2B-BFP (1:1000) | 20170T4608 | D07 | sgRNA | 96.70% | CCAGTACAAACCTACCTACG | FALSE | 2 | CCAGTACAAACCTACCTACG | 232 |
| pLas + pR_H2B-BFP (1:1000) | 20170T4608 | D08 | pL43 | 94.40% | AGAGCACTGCACTCCTTCA | FALSE | 2 | CCAGTTA | 3480 |
| pLas + pR_H2B-BFP (1:1000) | 20170T4608 | D08 | sgRNA | 94.80% | AGAGCACTGCACTCCTTCA | FALSE | 2 | AGAGCACTGCACTCCTTCA | 921 |
| pLas + pR_H2B-BFP (1:1000) | 20170T4608 | D09 | pL43 | 95.90% | ATACAACTGCTTGCAACAGG | FALSE | 2 | ATTCCGA | 3652 |
| pLas + pR_H2B-BFP (1:1000) | 20170T4608 | D09 | sgRNA | 95.10% | ATACAACTGCTTGCAACAGG | FALSE | 2 | ATACAACTGCTTGCAACAGG | 501 |
| pLas + pR_H2B-BFP (1:1000) | 20170T4608 | D10 | pL43 | 85.60% | AGAGCACTGCACTCCTTCA | FALSE | 2 | CCAGTTA | 2837 |
| pLas + pR_H2B-BFP (1:1000) | 20170T4608 | D10 | sgRNA | 94.20% | AGAGCACTGCACTCCTTCA | FALSE | 2 | AGAGCACTGCACTCCTTCA | 3426 |
| pLas + pR_H2B-BFP (1:1000) | 20170T4608 | D11 | pL43 | 11.50% | TCCACCGGCGAAAGAGATCC | TRUE | 6 | CAATCGG | 259 |
| pLas + pR_H2B-BFP (1:1000) | 20170T4608 | D11 | pL43 | 12.70% | AGAGCACTGCACTCCTTCA | FALSE | 6 | AGGCTCT | 285 |
| pLas + pR_H2B-BFP (1:1000) | 20170T4608 | D11 | pL43 | 17.10% | AGAGCACTGCACTCCTTCA | FALSE | 6 | CCAGTTA | 385 |
| pLas + pR_H2B-BFP (1:1000) | 20170T4608 | D11 | pL43 | 19.90% | CCAGTACAAACCTACCTACG | TRUE | 6 | AAGAGGA | 447 |
| pLas + pR_H2B-BFP (1:1000) | 20170T4608 | D11 | pL43 | 27.90% | TCATATTACGAGTCAGTAGG | TRUE | 6 | AGAGAGA | 628 |
| pLas + pR_H2B-BFP (1:1000) | 20170T4608 | D11 | sgRNA | 94.40% | AGAGCACTGCACTCCTTCA | FALSE | 6 | AGAGCACTGCACTCCTTCA | 4967 |
| pLas + pR_H2B-BFP (1:1000) | 20170T4608 | D12 | pL43 | 91.10% | CGCCGCCCCGGACGCGACC | FALSE | 2 | CATGCGT | 3688 |
| pLas + pR_H2B-BFP (1:1000) | 20170T4608 | D12 | sgRNA | 96.30% | CGCCGCCCCGGACGCGACC | FALSE | 2 | CGCCGCCCCGGACGCGACC | 678 |
| pLas + pR_H2B-BFP (1:1000) | 20170T4608 | E05 | pL43 | 96.60% | AGTAGTCCGGGATATCAGCG | FALSE | 2 | CCTCTTC | 3289 |
| pLas + pR_H2B-BFP (1:1000) | 20170T4608 | E05 | sgRNA | 95.60% | AGTAGTCCGGGATATCAGCG | FALSE | 2 | AGTAGTCCGGGATATCAGCG | 1545 |

TABLE 2-continued

| condition | date | platewell | pattern | fraction | pred_sgRNA | solitary | matches_per_sample | match | count |
|---|---|---|---|---|---|---|---|---|---|
| pLas + pR_H2B-BFP (1:1000) | 20170T4 608 | E06 | pL43 | 97.10% | ATACAACTGCTTGCAACAGG | FALSE | 2 | ATTCCGA | 4055 |
| pLas + pR_H2B-BFP (1:1000) | 20170T4 608 | E06 | sgRNA | 95.30% | ATACAACTGCTTGCAACAGG | FALSE | 2 | ATACAACTGCTTGCAACAGG | 763 |
| pLas + pR_H2B-BFP (1:1000) | 20170T4 608 | E07 | pL43 | 97.00% | TCCACCGGCGAAAGAGATCC | FALSE | 2 | CAATCGG | 4106 |
| pLas + pR_H2B-BFP (1:1000) | 20170T4 608 | E07 | sgRNA | 93.70% | TCCACCGGCGAAAGAGATCC | FALSE | 2 | TCCACCGGCGAAAGAGATCC | 298 |
| pLas + pR_H2B-BFP (1:1000) | 20170T4 608 | E08 | pL43 | 95.50% | TCATATTACGAGTCAGTAGG | FALSE | 2 | AGAGAGA | 4002 |
| pLas + pR_H2B-BFP (1:1000) | 20170T4 608 | E08 | sgRNA | 98.30% | TCATATTACGAGTCAGTAGG | FALSE | 2 | TCATATTACGAGTCAGTAGG | 116 |
| pLas + pR_H2B-BFP (1:1000) | 20170T4 608 | E09 | pL43 | 89.30% | TCATATTACGAGTCAGTAGG | FALSE | 2 | AGAGAGA | 2769 |
| pLas + pR_H2B-BFP (1:1000) | 20170T4 608 | E09 | sgRNA | 95.10% | TCATATTACGAGTCAGTAGG | FALSE | 2 | TCATATTACGAGTCAGTAGG | 741 |
| pLas + pR_H2B-BFP (1:1000) | 20170T4 608 | E10 | pL43 | 88.50% | CCTGCAACGGGACTAGTTGG | FALSE | 2 | CGTCATA | 3852 |
| pLas + pR_H2B-BFP (1:1000) | 20170T4 608 | E10 | sgRNA | 96.00% | CCTGCAACGGGACTAGTTGG | FALSE | 2 | CCTGCAACGGGACTAGTTGG | 819 |
| pLas + pR_H2B-BFP (1:1000) | 20170T4 608 | E11 | pL43 | 89.60% | AGTAGTCCGGGATATCAGCG | FALSE | 2 | CCTCTTC | 3194 |
| pLas + pR_H2B-BFP (1:1000) | 20170T4 608 | E11 | sgRNA | 97.00% | AGTAGTCCGGGATATCAGCG | FALSE | 2 | AGTAGTCCGGGATATCAGCG | 292 |
| pLas + pR_H2B-BFP (1:1000) | 20170T4 608 | E12 | pL43 | 87.20% | ATACAACTGCTTGCAACAGG | FALSE | 2 | ATTCCGA | 3306 |
| pLas + pR_H2B-BFP (1:1000) | 20170T4 608 | E12 | sgRNA | 88.00% | ATACAACTGCTTGCAACAGG | FALSE | 2 | ATACAACTGCTTGCAACAGG | 176 |
| pLas + pR_H2B-BFP (1:1000) | 20170T4 608 | F05 | pL43 | 94.40% | CCTGCAACGGGACTAGTTGG | FALSE | 2 | CGTCATA | 2604 |
| pLas + pR_H2B-BFP (1:1000) | 20170T4 608 | F05 | sgRNA | 95.80% | CCTGCAACGGGACTAGTTGG | FALSE | 2 | CCTGCAACGGGACTAGTTGG | 3619 |
| pLas + pR_H2B-BFP (1:1000) | 20170T4 608 | F06 | pL43 | 97.10% | TCATATTACGAGTCAGTAGG | FALSE | 2 | AGAGAGA | 3573 |
| pLas + pR_H2B-BFP (1:1000) | 20170T4 608 | F06 | sgRNA | 95.10% | TCATATTACGAGTCAGTAGG | FALSE | 2 | TCATATTACGAGTCAGTAGG | 252 |

TABLE 2-continued

| condition | date | platewell | pattern | fraction | pred_sgRNA | solitary | matches_per_sample | match | count |
|---|---|---|---|---|---|---|---|---|---|
| pLas + pR_H2B-BFP (1:1000) | 20170T4 608 | F07 | pL43 | 96.50% | CCAGTACAAACCTACCTACG | FALSE | 2 | AAGAGGA | 3298 |
| pLas + pR_H2B-BFP (1:1000) | 20170T4 608 | F07 | sgRNA | 96.70% | CCAGTACAAACCTACCTACG | FALSE | 2 | CCAGTACAAACCTACCTACG | 177 |
| pLas + pR_H2B-BFP (1:1000) | 20170T4 608 | F08 | pL43 | 97.10% | CCTGCAACGGGACTAGTTGG | FALSE | 2 | CGTCATA | 3554 |
| pLas + pR_H2B-BFP (1:1000) | 20170T4 608 | F08 | sgRNA | 95.90% | CCTGCAACGGGACTAGTTGG | FALSE | 2 | CCTGCAACGGGACTAGTTGG | 279 |
| pLas + pR_H2B-BFP (1:1000) | 20170T4 608 | F09 | pL43 | 11.80% | TCCACCGGCGAAAGAGATCC | FALSE | 8 | CAATCGG | 220 |
| pLas + pR_H2B-BFP (1:1000) | 20170T4 608 | F09 | pL43 | 13.20% | AGAGCACTGCACTCCTTCA | FALSE | 8 | CCAGTTA | 245 |
| pLas + pR_H2B-BFP (1:1000) | 20170T4 608 | F09 | pL43 | 16.50% | TCATATTACGAGTCAGTAGG | TRUE | 8 | AGAGAGA | 306 |
| pLas + pR_H2B-BFP (1:1000) | 20170T4 608 | F09 | pL43 | 18.00% | CCAGTACAAACCTACCTACG | FALSE | 8 | AAGAGGA | 334 |
| pLas + pR_H2B-BFP (1:1000) | 20170T4 608 | F09 | pL43 | 23.90% | AGAGCACTGCACTCCTTCA | FALSE | 8 | AGGCTCT | 443 |
| pLas + pR_H2B-BFP (1:1000) | 20170T4 608 | F09 | sgRNA | 15.40% | TCCACCGGCGAAAGAGATCC | FALSE | 8 | TCCACCGGCGAAAGAGATCC | 46 |
| pLas + pR_H2B-BFP (1:1000) | 20170T4 608 | F09 | sgRNA | 21.10% | AGAGCACTGCACTCCTTCA | FALSE | 8 | AGAGCACTGCACTCCTTCA | 63 |
| pLas + pR_H2B-BFP (1:1000) | 20170T4 608 | F09 | sgRNA | 60.70% | CCAGTACAAACCTACCTACG | FALSE | 8 | CCAGTACAAACCTACCTACG | 181 |
| pLas + pR_H2B-BFP (1:1000) | 20170T4 608 | F11 | pL43 | 93.80% | CCTGCAACGGGACTAGTTGG | FALSE | 2 | CGTCATA | 3904 |
| pLas + pR_H2B-BFP (1:1000) | 20170T4 608 | F11 | sgRNA | 95.40% | CCTGCAACGGGACTAGTTGG | FALSE | 2 | CCTGCAACGGGACTAGTTGG | 922 |
| pLas + pR_H2B-BFP (1:1000) | 20170T4 608 | F12 | pL43 | 90.60% | CCAGTACAAACCTACCTACG | FALSE | 2 | AAGAGGA | 3835 |
| pLas + pR_H2B-BFP (1:1000) | 20170T4 608 | F12 | sgRNA | 95.80% | CCAGTACAAACCTACCTACG | FALSE | 2 | CCAGTACAAACCTACCTACG | 752 |
| pLas + pR_H2B-BFP (1:1000) | 20170T4 608 | G05 | pL43 | 96.50% | CGCCGCCCCCGGACGCGACC | FALSE | 2 | CATGCGT | 3920 |
| pLas + pR_H2B-BFP (1:1000) | 20170T4 608 | G05 | sgRNA | 94.20% | CGCCGCCCCCGGACGCGACC | FALSE | 2 | CGCCGCCCCCGGACGCGACC | 799 |

TABLE 2-continued

| condition | date | platewell | pattern | fraction | pred_sgRNA | solitary | matches_per_sample | match | count |
|---|---|---|---|---|---|---|---|---|---|
| pLas + pR_H2B-BFP (1:1000) | 20170T4 608 | G06 | pL43 | 96.80% | CGCCGCCCCCG GACGCGACC | FALSE | 2 | CATGCGT | 4425 |
| pLas + pR_H2B-BFP (1:1000) | 20170T4 608 | G06 | sgRNA | 95.30% | CGCCGCCCCCG GACGCGACC | FALSE | 2 | CGCCGCCCCGG ACGCGACC | 1567 |
| pLas + pR_H2B-BFP (1:1000) | 20170T4 608 | G07 | pL43 | 95.20% | AGAGCACTGCA CTCCTTCA | FALSE | 2 | CCAGTTA | 3330 |
| pLas + pR_H2B-BFP (1:1000) | 20170T4 608 | G07 | sgRNA | 93.40% | AGAGCACTGCA CTCCTTCA | FALSE | 2 | AGAGCACTGCAC TCCTTCA | 2697 |
| pLas + pR_H2B-BFP (1:1000) | 20170T4 608 | G08 | pL43 | 95.90% | TCATATTACGAG TCAGTAGG | FALSE | 2 | AGAGAGA | 3450 |
| pLas + pR_H2B-BFP (1:1000) | 20170T4 608 | G08 | sgRNA | 95.50% | TCATATTACGAG TCAGTAGG | FALSE | 2 | TCATATTACGAGT CAGTAGG | 191 |
| pLas + pR_H2B-BFP (1:1000) | 20170T4 608 | G09 | pL43 | 95.30% | AGTAGTCCGGG ATATCAGCG | FALSE | 2 | CCTCTTC | 3053 |
| pLas + pR_H2B-BFP (1:1000) | 20170T4 608 | G09 | sgRNA | 96.70% | AGTAGTCCGGG ATATCAGCG | FALSE | 2 | AGTAGTCCGGGA TATCAGCG | 436 |
| pLas + pR_H2B-BFP (1:1000) | 20170T4 608 | G10 | pL43 | 92.40% | TCATATTACGAG TCAGTAGG | FALSE | 2 | AGAGAGA | 3573 |
| pLas + pR_H2B-BFP (1:1000) | 20170T4 608 | G10 | sgRNA | 93.90% | TCATATTACGAG TCAGTAGG | FALSE | 2 | TCATATTACGAGT CAGTAGG | 371 |
| pLas + pR_H2B-BFP (1:1000) | 20170T4 608 | G11 | pL43 | 94.00% | CCAGTACAAAC CTACCTACG | FALSE | 2 | AAGAGGA | 3619 |
| pLas + pR_H2B-BFP (1:1000) | 20170T4 608 | G11 | sgRNA | 96.00% | CCAGTACAAAC CTACCTACG | FALSE | 2 | CCAGTACAAACC TACCTACG | 917 |
| pLas + pR_H2B-BFP (1:1000) | 20170T4 608 | G12 | pL43 | 94.80% | TCATATTACGAG TCAGTAGG | FALSE | 2 | AGAGAGA | 4109 |
| pLas + pR_H2B-BFP (1:1000) | 20170T4 608 | G12 | sgRNA | 95.60% | TCATATTACGAG TCAGTAGG | FALSE | 2 | TCATATTACGAGT CAGTAGG | 562 |
| pLas + pR_H2B-BFP (1:1000) | 20170T4 608 | H06 | pL43 | 97.00% | AGAGCACTGCA CTCCTTCA | FALSE | 2 | CCAGTTA | 4164 |
| pLas + pR_H2B-BFP (1:1000) | 20170T4 608 | H06 | sgRNA | 94.00% | AGAGCACTGCA CTCCTTCA | FALSE | 2 | AGAGCACTGCAC TCCTTCA | 1025 |
| pLas + pR_H2B-BFP (1:1000) | 20170T4 608 | H07 | pL43 | 97.10% | CCTGCAACGGG ACTAGTTGG | FALSE | 2 | CGTCATA | 4657 |
| pLas + pR_H2B-BFP (1:1000) | 20170T4 608 | H07 | sgRNA | 95.50% | CCTGCAACGGG ACTAGTTGG | FALSE | 2 | CCTGCAACGGGA CTAGTTGG | 1003 |

TABLE 2-continued

| condition | date | platewell | pattern | fraction | pred_sgRNA | solitary | matches_per_sample | match | count |
|---|---|---|---|---|---|---|---|---|---|
| pLas + pR_H2B-BFP (1:1000) | 20170T4608 | H08 | pL43 | 97.80% | TCATATTACGAGTCAGTAGG | FALSE | 2 | AGAGAGA | 4015 |
| pLas + pR_H2B-BFP (1:1000) | 20170T4608 | H08 | sgRNA | 95.20% | TCATATTACGAGTCAGTAGG | FALSE | 2 | TCATATTACGAGTCAGTAGG | 460 |
| pLas + pR_H2B-BFP (1:1000) | 20170T4608 | H09 | pL43 | 96.00% | AGTAGTCCGGGATATCAGCG | FALSE | 2 | CCTCTTC | 3802 |
| pLas + pR_H2B-BFP (1:1000) | 20170T4608 | H09 | sgRNA | 95.10% | AGTAGTCCGGGATATCAGCG | FALSE | 2 | AGTAGTCCGGGATATCAGCG | 818 |
| pLas + pR_H2B-BFP (1:1000) | 20170T4608 | H11 | pL43 | 95.90% | CCAGTACAAACCTACCTACG | FALSE | 2 | AAGAGGA | 3996 |
| pLas + pR_H2B-BFP (1:1000) | 20170T4608 | H11 | sgRNA | 95.10% | CCAGTACAAACCTACCTACG | FALSE | 2 | CCAGTACAAACCTACCTACG | 855 |
| pLas + pR_H2B-BFP (1:1000) | 20170T4608 | H12 | pL43 | 74.40% | CGCCGCCCCCGGACGCGACC | FALSE | 2 | CATGCGT | 2767 |
| pLas + pR_H2B-BFP (1:1000) | 20170T4608 | H12 | sgRNA | 94.40% | CGCCGCCCCCGGACGCGACC | FALSE | 2 | CGCCGCCCCCGGACGCGACC | 772 |
| pLas + pUC19 (1:1000) | 20170T3608 | A09 | pL43 | 84.80% | AGTAGTCCGGGATATCAGCG | FALSE | 2 | CCTCTTC | 2367 |
| pLas + pUC19 (1:1000) | 20170T3608 | A09 | sgRNA | 95.00% | AGTAGTCCGGGATATCAGCG | FALSE | 2 | AGTAGTCCGGGATATCAGCG | 2635 |
| pLas + pUC19 (1:1000) | 20170T3608 | A10 | pL43 | 93.20% | AGTAGTCCGGGATATCAGCG | TRUE | 2 | CCTCTTC | 3551 |
| pLas + pUC19 (1:1000) | 20170T3608 | A10 | sgRNA | 95.30% | CCAGTACAAACCTACCTACG | TRUE | 2 | CCAGTACAAACCTACCTACG | 1346 |
| pLas + pUC19 (1:1000) | 20170T3608 | A11 | pL43 | 95.10% | AGTAGTCCGGGATATCAGCG | FALSE | 2 | CCTCTTC | 3567 |
| pLas + pUC19 (1:1000) | 20170T3608 | A11 | sgRNA | 95.10% | AGTAGTCCGGGATATCAGCG | FALSE | 2 | AGTAGTCCGGGATATCAGCG | 1483 |
| pLas + pUC19 (1:1000) | 20170T3608 | A12 | pL43 | 96.50% | AGAGCACTGCACTCCTTCA | FALSE | 2 | CCAGTTA | 4125 |
| pLas + pUC19 (1:1000) | 20170T3608 | A12 | sgRNA | 95.30% | AGAGCACTGCACTCCTTCA | FALSE | 2 | AGAGCACTGCACTCCTTCA | 1775 |
| pLas + pUC19 (1:1000) | 20170T3608 | B09 | pL43 | 74.90% | TCATATTACGAGTCAGTAGG | FALSE | 2 | AGAGAGA | 2884 |
| pLas + pUC19 (1:1000) | 20170T3608 | B09 | sgRNA | 95.40% | TCATATTACGAGTCAGTAGG | FALSE | 2 | TCATATTACGAGTCAGTAGG | 1102 |
| pLas + pUC19 (1:1000) | 20170T3608 | B10 | pL43 | 13.90% | AGAGCACTGCACTCCTTCA | TRUE | 4 | CCAGTTA | 353 |
| pLas + pUC19 (1:1000) | 20170T3608 | B10 | pL43 | 20.20% | TCATATTACGAGTCAGTAGG | TRUE | 4 | AGAGAGA | 512 |
| pLas + pUC19 (1:1000) | 20170T3608 | B10 | pL43 | 30.80% | CCAGTACAAACCTACCTACG | TRUE | 4 | AAGAGGA | 781 |
| pLas + pUC19 (1:1000) | 20170T3608 | B10 | sgRNA | 89.30% | CGCCGCCCCCGGACGCGACC | TRUE | 4 | CGCCGCCCCCGGACGCGACC | 134 |

TABLE 2-continued

| condition | date | platewell | pattern | fraction | pred_sgRNA | solitary | matches_per_sample | match | count |
|---|---|---|---|---|---|---|---|---|---|
| pLas + pUC19 (1:1000) | 20170T3 608 | B11 | pL43 | 92.00% | TCATATTACGAG TCAGTAGG | FALSE | 2 | AGAGAGA | 4607 |
| pLas + pUC19 (1:1000) | 20170T3 608 | B11 | sgRNA | 94.90% | TCATATTACGAG TCAGTAGG | FALSE | 2 | TCATATTACGAGT CAGTAGG | 632 |
| pLas + pUC19 (1:1000) | 20170T3 608 | B12 | pL43 | 10.30% | TCATATTACGAG TCAGTAGG | TRUE | 4 | AGAGAGA | 343 |
| pLas + pUC19 (1:1000) | 20170T3 608 | B12 | pL43 | 16.50% | CCAGTACAAAC CTACCTACG | TRUE | 4 | AAGAGGA | 549 |
| pLas + pUC19 (1:1000) | 20170T3 608 | B12 | pL43 | 45.00% | AGTAGTCCGGG ATATCAGCG | FALSE | 4 | CCTCTTC | 1500 |
| pLas + pUC19 (1:1000) | 20170T3 608 | B12 | sgRNA | 95.80% | AGTAGTCCGGG ATATCAGCG | FALSE | 4 | AGTAGTCCGGGA TATCAGCG | 3532 |
| pLas + pUC19 (1:1000) | 20170T3 608 | C09 | pL43 | 93.70% | TCATATTACGAG TCAGTAGG | FALSE | 2 | AGAGAGA | 3994 |
| pLas + pUC19 (1:1000) | 20170T3 608 | C09 | sgRNA | 95.60% | TCATATTACGAG TCAGTAGG | FALSE | 2 | TCATATTACGAGT CAGTAGG | 1916 |
| pLas + pUC19 (1:1000) | 20170T3 608 | C10 | pL43 | 15.70% | AGAGCACTGCA CTCCTTCA | TRUE | 3 | AGGCTCT | 453 |
| pLas + pUC19 (1:1000) | 20170T3 608 | C10 | pL43 | 57.60% | TCCACCGGCGA AAGAGATCC | FALSE | 3 | CAATCGG | 1658 |
| pLas + pUC19 (1:1000) | 20170T3 608 | C10 | sgRNA | 94.60% | TCCACCGGCGA AAGAGATCC | FALSE | 3 | TCCACCGGCGAA AGAGATCC | 1320 |
| pLas + pUC19 (1:1000) | 20170T3 608 | C11 | pL43 | 71.90% | AGAGCACTGCA CTCCTTCA | FALSE | 2 | CCAGTTA | 2500 |
| pLas + pUC19 (1:1000) | 20170T3 608 | C11 | sgRNA | 95.30% | AGAGCACTGCA CTCCTTCA | FALSE | 2 | AGAGCACTGCAC TCCTTCA | 61 |
| pLas + pUC19 (1:1000) | 20170T3 608 | C12 | pL43 | 10.80% | TCCACCGGCGA AAGAGATCC | TRUE | 5 | CAATCGG | 302 |
| pLas + pUC19 (1:1000) | 20170T3 608 | C12 | pL43 | 16.20% | TCATATTACGAG TCAGTAGG | TRUE | 5 | AGAGAGA | 456 |
| pLas + pUC19 (1:1000) | 20170T3 608 | C12 | pL43 | 17.10% | CCAGTACAAAC CTACCTACG | TRUE | 5 | AAGAGGA | 480 |
| pLas + pUC19 (1:1000) | 20170T3 608 | C12 | pL43 | 40.00% | AGAGCACTGCA CTCCTTCA | FALSE | 5 | CCAGTTA | 1123 |
| pLas + pUC19 (1:1000) | 20170T3 608 | C12 | sgRNA | 94.90% | AGAGCACTGCA CTCCTTCA | FALSE | 5 | AGAGCACTGCAC TCCTTCA | 1643 |
| pLas + pUC19 (1:1000) | 20170T3 608 | D09 | pL43 | 11.80% | CCAGTACAAAC CTACCTACG | TRUE | 3 | AAGAGGA | 338 |
| pLas + pUC19 (1:1000) | 20170T3 608 | D09 | pL43 | 57.60% | TCATATTACGAG TCAGTAGG | FALSE | 3 | AGAGAGA | 1647 |
| pLas + pUC19 (1:1000) | 20170T3 608 | D09 | sgRNA | 91.00% | TCATATTACGAG TCAGTAGG | FALSE | 3 | TCATATTACGAGT CAGTAGG | 783 |
| pLas + pUC19 (1:1000) | 20170T3 608 | D10 | pL43 | 94.70% | CGCCGCCCCCG GACGCGACC | FALSE | 2 | CATGCGT | 4961 |
| pLas + pUC19 (1:1000) | 20170T3 608 | D10 | sgRNA | 95.70% | CGCCGCCCCCG GACGCGACC | FALSE | 2 | CGCCGCCCCGG ACGCGACC | 991 |
| pLas + pUC19 (1:1000) | 20170T3 608 | D11 | pL43 | 94.80% | AGTAGTCCGGG ATATCAGCG | FALSE | 2 | CCTCTTC | 4155 |

TABLE 2-continued

| condition | date | plate | well | pattern | fraction | pred_sgRNA | solitary | matches_per_sample | match | count |
|---|---|---|---|---|---|---|---|---|---|---|
| pLas + pUC19 (1:1000) | 20170608 | T3 | D11 | sgRNA | 95.70% | AGTAGTCCGGGAATATCAGCG | FALSE | 2 | AGTAGTCCGGGATATCAGCG | 933 |
| pLas + pUC19 (1:1000) | 20170608 | T3 | D12 | pL43 | 76.80% | TCATATTACGAGTCAGTAGG | TRUE | 2 | AGAGAGA | 2695 |
| pLas + pUC19 (1:1000) | 20170608 | T3 | D12 | sgRNA | 94.90% | CCAGTACAAACCTACCTACG | TRUE | 2 | CCAGTACAAACCTACCTACG | 1313 |
| pLas + pUC19 (1:1000) | 20170608 | T3 | E09 | pL43 | 91.10% | TCATATTACGAGTCAGTAGG | FALSE | 2 | AGAGAGA | 3176 |
| pLas + pUC19 (1:1000) | 20170608 | T3 | E09 | sgRNA | 96.10% | TCATATTACGAGTCAGTAGG | FALSE | 2 | TCATATTACGAGTCAGTAGG | 928 |
| pLas + pUC19 (1:1000) | 20170608 | T3 | E10 | pL43 | 10.50% | AGAGCACTGCACTCCTTCA | TRUE | 7 | AGGCTCT | 288 |
| pLas + pUC19 (1:1000) | 20170608 | T3 | E10 | pL43 | 12.50% | AGAGCACTGCACTCCTTCA | TRUE | 7 | CCAGTTA | 343 |
| pLas + pUC19 (1:1000) | 20170608 | T3 | E10 | pL43 | 13.60% | TCCACCGGCGAAAGAGATCC | TRUE | 7 | ACTGGCT | 371 |
| pLas + pUC19 (1:1000) | 20170608 | T3 | E10 | pL43 | 13.70% | TCATATTACGAGTCAGTAGG | TRUE | 7 | AGAGAGA | 375 |
| pLas + pUC19 (1:1000) | 20170608 | T3 | E10 | pL43 | 13.80% | TCCACCGGCGAAAGAGATCC | TRUE | 7 | CAATCGG | 376 |
| pLas + pUC19 (1:1000) | 20170608 | T3 | E10 | pL43 | 19.30% | CCAGTACAAACCTACCTACG | TRUE | 7 | AAGAGGA | 529 |
| pLas + pUC19 (1:1000) | 20170608 | T3 | E10 | sgRNA | 85.30% | CCTGCAACGGGACTAGTTGG | TRUE | 7 | CCTGCAACGGGACTAGTTGG | 320 |
| pLas + pUC19 (1:1000) | 20170608 | T3 | E11 | pL43 | 94.90% | CCAGTACAAACCTACCTACG | FALSE | 2 | AAGAGGA | 3540 |
| pLas + pUC19 (1:1000) | 20170608 | T3 | E11 | sgRNA | 95.40% | CCAGTACAAACCTACCTACG | FALSE | 2 | CCAGTACAAACCTACCTACG | 722 |
| pLas + pUC19 (1:1000) | 20170608 | T3 | E12 | pL43 | 93.00% | CGCCGCCCCGGACGCGACC | FALSE | 2 | CATGCGT | 3594 |
| pLas + pUC19 (1:1000) | 20170608 | T3 | E12 | sgRNA | 93.80% | CGCCGCCCCGGACGCGACC | FALSE | 2 | CGCCGCCCCGGACGCGACC | 61 |
| pLas + pUC19 (1:1000) | 20170608 | T3 | F09 | pL43 | 95.60% | CGCCGCCCCGGACGCGACC | FALSE | 2 | CATGCGT | 3644 |
| pLas + pUC19 (1:1000) | 20170608 | T3 | F09 | sgRNA | 94.50% | CGCCGCCCCGGACGCGACC | FALSE | 2 | CGCCGCCCCGGACGCGACC | 242 |
| pLas + pUC19 (1:1000) | 20170608 | T3 | F10 | pL43 | 95.40% | CCTGCAACGGGACTAGTTGG | FALSE | 2 | CGTCATA | 4252 |
| pLas + pUC19 (1:1000) | 20170608 | T3 | F10 | sgRNA | 94.30% | CCTGCAACGGGACTAGTTGG | FALSE | 2 | CCTGCAACGGGACTAGTTGG | 644 |
| pLas + pUC19 (1:1000) | 20170608 | T3 | F11 | pL43 | 12.20% | AGAGCACTGCACTCCTTCA | TRUE | 3 | AGGCTCT | 360 |
| pLas + pUC19 (1:1000) | 20170608 | T3 | F11 | pL43 | 72.70% | CCTGCAACGGGACTAGTTGG | FALSE | 3 | CGTCATA | 2141 |
| pLas + pUC19 (1:1000) | 20170608 | T3 | F11 | sgRNA | 94.50% | CCTGCAACGGGACTAGTTGG | FALSE | 3 | CTGCAACGGGACTAGTTGG | 2120 |
| pLas + pUC19 (1:1000) | 20170608 | T3 | F12 | pL43 | 16.30% | AGAGCACTGCACTCCTTCA | TRUE | 3 | AGGCTCT | 460 |

TABLE 2-continued

| condition | date | plate | well | pattern | fraction | pred_sgRNA | solitary | matches_per_sample | match | count |
|---|---|---|---|---|---|---|---|---|---|---|
| pLas + pUC19 (1:1000) | 20170T3 | 608 | F12 | pL43 | 67.60% | CCTGCAACGGGACTAGTTGG | FALSE | 3 | CGTCATA | 1906 |
| pLas + pUC19 (1:1000) | 20170T3 | 608 | F12 | sgRNA | 95.50% | CCTGCAACGGGACTAGTTGG | FALSE | 3 | CCTGCAACGGGACTAGTTGG | 708 |
| pLas + pUC19 (1:1000) | 20170T3 | 608 | G09 | pL43 | 13.20% | AGAGCACTGCACTCCTTCA | FALSE | 6 | CCAGTTA | 331 |
| pLas + pUC19 (1:1000) | 20170T3 | 608 | G09 | pL43 | 16.10% | CCAGTACAAACCTACCTACG | TRUE | 6 | AAGAGGA | 404 |
| pLas + pUC19 (1:1000) | 20170T3 | 608 | G09 | pL43 | 21.70% | TCCACCGGCGAAAGAGATCC | FALSE | 6 | CAATCGG | 546 |
| pLas + pUC19 (1:1000) | 20170T3 | 608 | G09 | pL43 | 24.30% | TCATATTACGAGTCAGTAGG | TRUE | 6 | AGAGAGA | 612 |
| pLas + pUC19 (1:1000) | 20170T3 | 608 | G09 | sgRNA | 34.80% | AGAGCACTGCACTCCTTCA | FALSE | 6 | AGAGCACTGCACTCCTTCA | 32 |
| pLas + pUC19 (1:1000) | 20170T3 | 608 | G09 | sgRNA | 58.70% | TCCACCGGCGAAAGAGATCC | FALSE | 6 | TCCACCGGCGAAAGAGATCC | 54 |
| pLas + pUC19 (1:1000) | 20170T3 | 608 | G10 | pL43 | 91.70% | ATACAACTGCTTGCAACAGG | FALSE | 2 | ATTCCGA | 4180 |
| pLas + pUC19 (1:1000) | 20170T3 | 608 | G10 | sgRNA | 93.80% | ATACAACTGCTTGCAACAGG | FALSE | 2 | ATACAACTGCTTGCAACAGG | 1091 |
| pLas + pUC19 (1:1000) | 20170T3 | 608 | G11 | pL43 | 18.10% | TCCACCGGCGAAAGAGATCC | TRUE | 4 | CAATCGG | 434 |
| pLas + pUC19 (1:1000) | 20170T3 | 608 | G11 | pL43 | 23.10% | CCAGTACAAACCTACCTACG | TRUE | 4 | AAGAGGA | 553 |
| pLas + pUC19 (1:1000) | 20170T3 | 608 | G11 | pL43 | 29.40% | AGAGCACTGCACTCCTTCA | FALSE | 4 | CCAGTTA | 703 |
| pLas + pUC19 (1:1000) | 20170T3 | 608 | G11 | sgRNA | 93.70% | AGAGCACTGCACTCCTTCA | FALSE | 4 | AGAGCACTGCACTCCTTCA | 6346 |
| pLas + pUC19 (1:1000) | 20170T3 | 608 | G12 | pL43 | 92.20% | AGAGCACTGCACTCCTTCA | FALSE | 2 | CCAGTTA | 4422 |
| pLas + pUC19 (1:1000) | 20170T3 | 608 | G12 | sgRNA | 95.40% | AGAGCACTGCACTCCTTCA | FALSE | 2 | AGAGCACTGCACTCCTTCA | 1195 |
| pLas + pUC19 (1:1000) | 20170T3 | 608 | H09 | pL43 | 95.70% | AGAGCACTGCACTCCTTCA | FALSE | 2 | CCAGTTA | 4388 |
| pLas + pUC19 (1:1000) | 20170T3 | 608 | H09 | sgRNA | 95.90% | AGAGCACTGCACTCCTTCA | FALSE | 2 | AGAGCACTGCACTCCTTCA | 845 |
| pLas + pUC19 (1:1000) | 20170T3 | 608 | H10 | pL43 | 94.30% | AGTAGTCCGGGATATCAGCG | FALSE | 2 | CCTCTTC | 3658 |
| pLas + pUC19 (1:1000) | 20170T3 | 608 | H10 | sgRNA | 96.40% | AGTAGTCCGGGATATCAGCG | FALSE | 2 | AGTAGTCCGGGATATCAGCG | 1427 |
| pLas + pUC19 (1:1000) | 20170T3 | 608 | H11 | pL43 | 95.10% | TCATATTACGAGTCAGTAGG | FALSE | 2 | AGAGAGA | 4519 |
| pLas + pUC19 (1:1000) | 20170T3 | 608 | H11 | sgRNA | 95.80% | TCATATTACGAGTCAGTAGG | FALSE | 2 | TCATATTACGAGTCAGTAGG | 364 |
| pLas + pUC19 (1:1000) | 20170T3 | 608 | H12 | pL43 | 93.60% | CGCCGCCCCCGGACGCGACC | FALSE | 2 | CATGCGT | 4552 |
| pLas + pUC19 (1:1000) | 20170T3 | 608 | H12 | sgRNA | 94.40% | CGCCGCCCCCGGACGCGACC | FALSE | 2 | CGCCGCCCCCGGACGCGACC | 167 |

TABLE 2-continued

| condition | date | platewell | pattern | fraction | pred_sgRNA | solitary | matches_per_sample | match | count |
|---|---|---|---|---|---|---|---|---|---|
| pLas + pUC19 (1:1000) | 20170T4 608 | A01 | pL43 | 96.20% | AGAGCACTGCACTCCTTCA | FALSE | 2 | CCAGTTA | 4068 |
| pLas + pUC19 (1:1000) | 20170T4 608 | A01 | sgRNA | 95.00% | AGAGCACTGCACTCCTTCA | FALSE | 2 | AGAGCACTGCACTCCTTCA | 1106 |
| pLas + pUC19 (1:1000) | 20170T4 608 | A02 | pL43 | 94.70% | AGTAGTCCGGGATATCAGCG | FALSE | 2 | CCTCTTC | 3081 |
| pLas + pUC19 (1:1000) | 20170T4 608 | A02 | sgRNA | 94.80% | AGTAGTCCGGGATATCAGCG | FALSE | 2 | AGTAGTCCGGGATATCAGCG | 311 |
| pLas + pUC19 (1:1000) | 20170T4 608 | A03 | pL43 | 91.20% | CCAGTACAAACCTACCTACG | FALSE | 2 | AAGAGGA | 2564 |
| pLas + pUC19 (1:1000) | 20170T4 608 | A03 | sgRNA | 96.10% | CCAGTACAAACCTACCTACG | FALSE | 2 | CCAGTACAAACCTACCTACG | 123 |
| pLas + pUC19 (1:1000) | 20170T4 608 | A04 | pL43 | 94.10% | ATACAACTGCTTGCAACAGG | FALSE | 2 | ATTCCGA | 3348 |
| pLas + pUC19 (1:1000) | 20170T4 608 | A04 | sgRNA | 94.70% | ATACAACTGCTTGCAACAGG | FALSE | 2 | ATACAACTGCTTGCAACAGG | 1009 |
| pLas + pUC19 (1:1000) | 20170T4 608 | B01 | pL43 | 96.40% | CGCCGCCCCCGGACGCGACC | FALSE | 2 | CATGCGT | 4085 |
| pLas + pUC19 (1:1000) | 20170T4 608 | B01 | sgRNA | 95.30% | CGCCGCCCCCGGACGCGACC | FALSE | 2 | CGCCGCCCCCGGACGCGACC | 946 |
| pLas + pUC19 (1:1000) | 20170T4 608 | B02 | pL43 | 93.10% | CGCCGCCCCCGGACGCGACC | FALSE | 2 | CATGCGT | 3533 |
| pLas + pUC19 (1:1000) | 20170T4 608 | B02 | sgRNA | 95.90% | CGCCGCCCCCGGACGCGACC | FALSE | 2 | CGCCGCCCCCGGACGCGACC | 1965 |
| pLas + pUC19 (1:1000) | 20170T4 608 | B03 | pL43 | 93.90% | AGTAGTCCGGGATATCAGCG | FALSE | 2 | CCTCTTC | 3112 |
| pLas + pUC19 (1:1000) | 20170T4 608 | B03 | sgRNA | 95.60% | AGTAGTCCGGGATATCAGCG | FALSE | 2 | AGTAGTCCGGGATATCAGCG | 1585 |
| pLas + pUC19 (1:1000) | 20170T4 608 | B04 | pL43 | 95.10% | CGCCGCCCCCGGACGCGACC | FALSE | 2 | CATGCGT | 3625 |
| pLas + pUC19 (1:1000) | 20170T4 608 | B04 | sgRNA | 96.10% | CGCCGCCCCCGGACGCGACC | FALSE | 2 | CGCCGCCCCCGGACGCGACC | 374 |
| pLas + pUC19 (1:1000) | 20170T4 608 | C01 | pL43 | 95.10% | AGAGCACTGCACTCCTTCA | FALSE | 2 | CCAGTTA | 3670 |
| pLas + pUC19 (1:1000) | 20170T4 608 | C01 | sgRNA | 93.70% | AGAGCACTGCACTCCTTCA | FALSE | 2 | AGAGCACTGCACTCCTTCA | 848 |
| pLas + pUC19 (1:1000) | 20170T4 608 | C02 | pL43 | 85.10% | CGCCGCCCCCGGACGCGACC | FALSE | 2 | CATGCGT | 2940 |
| pLas + pUC19 (1:1000) | 20170T4 608 | C02 | sgRNA | 94.80% | CGCCGCCCCCGGACGCGACC | FALSE | 2 | CGCCGCCCCCGGACGCGACC | 454 |
| pLas + pUC19 (1:1000) | 20170T4 608 | C03 | pL43 | 90.50% | CCTGCAACGGGACTAGTTGG | FALSE | 2 | CGTCATA | 3055 |
| pLas + pUC19 (1:1000) | 20170T4 608 | C03 | sgRNA | 95.50% | CCTGCAACGGGACTAGTTGG | FALSE | 2 | CCTGCAACGGGACTAGTTGG | 1330 |
| pLas + pUC19 (1:1000) | 20170T4 608 | C04 | pL43 | 92.00% | AGAGCACTGCACTCCTTCA | FALSE | 2 | CCAGTTA | 2854 |
| pLas + pUC19 (1:1000) | 20170T4 608 | C04 | sgRNA | 93.70% | AGAGCACTGCACTCCTTCA | FALSE | 2 | AGAGCACTGCACTCCTTCA | 593 |

TABLE 2-continued

| condition | date | platewell | pattern | fraction | pred_sgRNA | solitary | matches_per_sample | match | count |
|---|---|---|---|---|---|---|---|---|---|
| pLas + pUC19 (1:1000) | 20170T4608 | D01 | pL43 | 96.50% | CCTGCAACGGGACTAGTTGG | FALSE | 2 | CGTCATA | 3679 |
| pLas + pUC19 (1:1000) | 20170T4608 | D01 | sgRNA | 95.80% | CCTGCAACGGGACTAGTTGG | FALSE | 2 | CCTGCAACGGGACTAGTTGG | 692 |
| pLas, 11h packaging | 20170T2608 | B05 | pL43 | 96.80% | CCTGCAACGGGACTAGTTGG | TRUE | 2 | CGTCATA | 3770 |
| pLas, 11h packaging | 20170T2608 | B05 | sgRNA | 95.30% | AGAGCACTGCACTCCTTCA | TRUE | 2 | AGAGCACTGCACTCCTTCA | 1369 |
| pLas, 11h packaging | 20170T2608 | B06 | pL43 | 83.60% | CCTGCAACGGGACTAGTTGG | FALSE | 2 | CGTCATA | 2362 |
| pLas, 11h packaging | 20170T2608 | B06 | sgRNA | 95.70% | CCTGCAACGGGACTAGTTGG | FALSE | 2 | CCTGCAACGGGACTAGTTGG | 1597 |
| pLas, 11h packaging | 20170T2608 | B07 | pL43 | 96.30% | TCATATTACGAGTCAGTAGG | TRUE | 2 | AGAGAGA | 3817 |
| pLas, 11h packaging | 20170T2608 | B07 | sgRNA | 94.40% | ATACAACTGCTTGCAACAGG | TRUE | 2 | ATACAACTGCTTGCAACAGG | 1232 |
| pLas, 11h packaging | 20170T2608 | B08 | pL43 | 96.90% | CGCCGCCCCCGGACGCGACC | FALSE | 2 | CATGCGT | 4509 |
| pLas, 11h packaging | 20170T2608 | B08 | sgRNA | 95.90% | CGCCGCCCCCGGACGCGACC | FALSE | 2 | CGCCGCCCCCGGACGCGACC | 649 |
| pLas, 11h packaging | 20170T2608 | B09 | pL43 | 87.80% | CGCCGCCCCCGGACGCGACC | FALSE | 2 | CATGCGT | 3644 |
| pLas, 11h packaging | 20170T2608 | B09 | sgRNA | 96.10% | CGCCGCCCCCGGACGCGACC | FALSE | 2 | CGCCGCCCCCGGACGCGACC | 416 |
| pLas, 11h packaging | 20170T2608 | B10 | pL43 | 46.40% | CCAGTACAAACCTACCTACG | FALSE | 4 | AAGAGGA | 1539 |
| pLas, 11h packaging | 20170T2608 | B10 | pL43 | 47.30% | TCATATTACGAGTCAGTAGG | FALSE | 4 | AGAGAGA | 1570 |
| pLas, 11h packaging | 20170T2608 | B10 | sgRNA | 40.90% | TCATATTACGAGTCAGTAGG | FALSE | 4 | TCATATTACGAGTCAGTAGG | 74 |
| pLas, 11h packaging | 20170T2608 | B10 | sgRNA | 51.90% | CCAGTACAAACCTACCTACG | FALSE | 4 | CCAGTACAAACCTACCTACG | 94 |
| pLas, 11h packaging | 20170T2608 | B11 | pL43 | 75.30% | CGCCGCCCCCGGACGCGACC | FALSE | 2 | CATGCGT | 3109 |
| pLas, 11h packaging | 20170T2608 | B11 | sgRNA | 95.80% | CGCCGCCCCCGGACGCGACC | FALSE | 2 | CGCCGCCCCCGGACGCGACC | 684 |
| pLas, 11h packaging | 20170T2608 | B12 | pL43 | 69.70% | CCTGCAACGGGACTAGTTGG | FALSE | 2 | CGTCATA | 2542 |
| pLas, 11h packaging | 20170T2608 | B12 | sgRNA | 95.00% | CCTGCAACGGGACTAGTTGG | FALSE | 2 | CCTGCAACGGGACTAGTTGG | 1034 |
| pLas, 11h packaging | 20170T2608 | C05 | pL43 | 97.50% | TCCACCGGCGAAAGAGATCC | TRUE | 2 | CAATCGG | 3989 |
| pLas, 11h packaging | 20170T2608 | C05 | sgRNA | 94.70% | AGTAGTCCGGGATATCAGCG | TRUE | 2 | AGTAGTCCGGGATATCAGCG | 1079 |
| pLas, 11h packaging | 20170T2608 | C06 | pL43 | 95.80% | ATACAACTGCTTGCAACAGG | TRUE | 2 | ATTCCGA | 4057 |
| pLas, 11h packaging | 20170T2608 | C06 | sgRNA | 94.40% | AGTAGTCCGGGATATCAGCG | TRUE | 2 | AGTAGTCCGGGATATCAGCG | 725 |

TABLE 2-continued

| condition | date | platewell | pattern | fraction | pred_sgRNA | solitary | matches_per_sample | match | count |
|---|---|---|---|---|---|---|---|---|---|
| pLas, 11h packaging | 20170T2608 | C07 | pL43 | 94.70% | AGTAGTCCGGGATATCAGCG | TRUE | 2 | CCTCTTC | 3449 |
| pLas, 11h packaging | 20170T2608 | C07 | sgRNA | 94.00% | ATACAACTGCTTGCAACAGG | TRUE | 2 | ATACAACTGCTTGCAACAGG | 676 |
| pLas, 11h packaging | 20170T2608 | C08 | pL43 | 96.50% | TCCACCGGCGAAAGAGATCC | TRUE | 2 | CAATCGG | 4264 |
| pLas, 11h packaging | 20170T2608 | C08 | sgRNA | 95.70% | CCTGCAACGGGACTAGTTGG | TRUE | 2 | CCTGCAACGGGACTAGTTGG | 737 |
| pLas, 11h packaging | 20170T2608 | C09 | pL43 | 96.00% | TCCACCGGCGAAAGAGATCC | FALSE | 2 | CAATCGG | 4160 |
| pLas, 11h packaging | 20170T2608 | C09 | sgRNA | 93.90% | TCCACCGGCGAAAGAGATCC | FALSE | 2 | TCCACCGGCGAAAGAGATCC | 726 |
| pLas, 11h packaging | 20170T2608 | C10 | pL43 | 12.20% | AGTAGTCCGGGATATCAGCG | TRUE | 6 | CCTCTTC | 426 |
| pLas, 11h packaging | 20170T2608 | C10 | pL43 | 33.00% | AGAGCACTGCACTCCTTCA | FALSE | 6 | AGGCTCT | 1152 |
| pLas, 11h packaging | 20170T2608 | C10 | pL43 | 46.60% | TCCACCGGCGAAAGAGATCC | FALSE | 6 | CAATCGG | 1625 |
| pLas, 11h packaging | 20170T2608 | C10 | sgRNA | 22.00% | CGCCGCCCCGGACGCGACC | TRUE | 6 | CGCCGCCCCGGACGCGACC | 172 |
| pLas, 11h packaging | 20170T2608 | C10 | sgRNA | 31.50% | AGAGCACTGCACTCCTTCA | FALSE | 6 | AGAGCACTGCACTCCTTCA | 246 |
| pLas, 11h packaging | 20170T2608 | C10 | sgRNA | 38.40% | TCCACCGGCGAAAGAGATCC | FALSE | 6 | TCCACCGGCGAAAGAGATCC | 300 |
| pLas, 11h packaging | 20170T2608 | C11 | pL43 | 43.80% | AGTAGTCCGGGATATCAGCG | TRUE | 4 | CCTCTTC | 1695 |
| pLas, 11h packaging | 20170T2608 | C11 | pL43 | 52.20% | ATACAACTGCTTGCAACAGG | FALSE | 4 | ATTCCGA | 2019 |
| pLas, 11h packaging | 20170T2608 | C11 | sgRNA | 32.20% | ATACAACTGCTTGCAACAGG | FALSE | 4 | ATACAACTGCTTGCAACAGG | 284 |
| pLas, 11h packaging | 20170T2608 | C11 | sgRNA | 63.80% | CGCCGCCCCGGACGCGACC | TRUE | 4 | CGCCGCCCCGGACGCGACC | 563 |
| pLas, 11h packaging | 20170T2608 | C12 | pL43 | 11.10% | TCCACCGGCGAAAGAGATCC | TRUE | 4 | CAATCGG | 322 |
| pLas, 11h packaging | 20170T2608 | C12 | pL43 | 17.90% | CCAGTACAAACCTACCTACG | TRUE | 4 | AAGAGGA | 518 |
| pLas, 11h packaging | 20170T2608 | C12 | pL43 | 38.60% | ATACAACTGCTTGCAACAGG | FALSE | 4 | ATTCCGA | 1115 |
| pLas, 11h packaging | 20170T2608 | C12 | sgRNA | 93.70% | ATACAACTGCTTGCAACAGG | FALSE | 4 | ATACAACTGCTTGCAACAGG | 417 |
| pLas, 11h packaging | 20170T2608 | D05 | pL43 | 97.20% | AGAGCACTGCACTCCTTCA | TRUE | 2 | CCAGTTA | 4097 |
| pLas, 11h packaging | 20170T2608 | D05 | sgRNA | 94.30% | ATACAACTGCTTGCAACAGG | TRUE | 2 | ATACAACTGCTTGCAACAGG | 834 |
| pLas, 11h packaging | 20170T2608 | D07 | pL43 | 97.60% | TCATATTACGAGTCAGTAGG | FALSE | 2 | AGAGAGA | 4546 |
| pLas, 11h packaging | 20170T2608 | D07 | sgRNA | 93.20% | TCATATTACGAGTCAGTAGG | FALSE | 2 | TCATATTACGAGTCAGTAGG | 205 |

TABLE 2-continued

| condition | date | platewell | pattern | fraction | pred_sgRNA | solitary | matches_per_sample | match | count |
|---|---|---|---|---|---|---|---|---|---|
| pLas, 11h packaging | 20170T2608 | D08 | pL43 | 92.00% | AGAGCACTGCACTCCTTCA | TRUE | 2 | CCAGTTA | 2574 |
| pLas, 11h packaging | 20170T2608 | D08 | sgRNA | 93.80% | CCAGTACAAACCTACCTACG | TRUE | 2 | CCAGTACAAACCTACCTACG | 456 |
| pLas, 11h packaging | 20170T2608 | D09 | pL43 | 96.80% | TCATATTACGAGTCAGTAGG | FALSE | 2 | AGAGAGA | 4523 |
| pLas, 11h packaging | 20170T2608 | D09 | sgRNA | 94.70% | TCATATTACGAGTCAGTAGG | FALSE | 2 | TCATATTACGAGTCAGTAGG | 304 |
| pLas, 11h packaging | 20170T2608 | D10 | pL43 | 95.60% | CGCCGCCCCCGGACGCGACC | TRUE | 2 | CATGCGT | 4801 |
| pLas, 11h packaging | 20170T2608 | D10 | sgRNA | 92.70% | ATACAACTGCTTGCAACAGG | TRUE | 2 | ATACAACTGCTTGCAACAGG | 190 |
| pLas, 11h packaging | 20170T2608 | D11 | pL43 | 85.10% | CCAGTACAAACCTACCTACG | FALSE | 2 | AAGAGGA | 3220 |
| pLas, 11h packaging | 20170T2608 | D11 | sgRNA | 95.50% | CCAGTACAAACCTACCTACG | FALSE | 2 | CCAGTACAAACCTACCTACG | 778 |
| pLas, 11h packaging | 20170T2608 | D12 | pL43 | 94.90% | ATACAACTGCTTGCAACAGG | FALSE | 2 | ATTCCGA | 4344 |
| pLas, 11h packaging | 20170T2608 | D12 | sgRNA | 96.50% | ATACAACTGCTTGCAACAGG | FALSE | 2 | ATACAACTGCTTGCAACAGG | 495 |
| pLas, 11h packaging | 20170T2608 | E06 | pL43 | 97.40% | TCATATTACGAGTCAGTAGG | FALSE | 2 | AGAGAGA | 4683 |
| pLas, 11h packaging | 20170T2608 | E06 | sgRNA | 96.70% | TCATATTACGAGTCAGTAGG | FALSE | 2 | TCATATTACGAGTCAGTAGG | 468 |
| pLas, 11h packaging | 20170T2608 | E07 | pL43 | 95.50% | TCATATTACGAGTCAGTAGG | FALSE | 2 | AGAGAGA | 3586 |
| pLas, 11h packaging | 20170T2608 | E07 | sgRNA | 93.60% | TCATATTACGAGTCAGTAGG | FALSE | 2 | TCATATTACGAGTCAGTAGG | 775 |
| pLas, 11h packaging | 20170T2608 | E09 | pL43 | 95.60% | ATACAACTGCTTGCAACAGG | TRUE | 2 | ATTCCGA | 4076 |
| pLas, 11h packaging | 20170T2608 | E09 | sgRNA | 96.30% | AGTAGTCCGGGATATCAGCG | TRUE | 2 | AGTAGTCCGGGATATCAGCG | 441 |
| pLas, 11h packaging | 20170T2608 | E10 | pL43 | 94.00% | CGCCGCCCCCGGACGCGACC | FALSE | 2 | CATGCGT | 4581 |
| pLas, 11h packaging | 20170T2608 | E10 | sgRNA | 94.90% | CGCCGCCCCCGGACGCGACC | FALSE | 2 | CGCCGCCCCCGGACGCGACC | 542 |
| pLas, 11h packaging | 20170T2608 | E11 | pL43 | 63.80% | AGAGCACTGCACTCCTTCA | FALSE | 2 | CCAGTTA | 1983 |
| pLas, 11h packaging | 20170T2608 | E11 | sgRNA | 94.60% | AGAGCACTGCACTCCTTCA | FALSE | 2 | AGAGCACTGCACTCCTTCA | 913 |
| pLas, 11h packaging | 20170T2608 | E12 | pL43 | 91.40% | CGCCGCCCCCGGACGCGACC | TRUE | 2 | CATGCGT | 3833 |
| pLas, 11h packaging | 20170T2608 | E12 | sgRNA | 96.00% | TCATATTACGAGTCAGTAGG | TRUE | 2 | TCATATTACGAGTCAGTAGG | 868 |
| pLas, 11h packaging | 20170T2608 | F05 | pL43 | 97.00% | CCTGCAACGGGACTAGTTGG | FALSE | 2 | CGTCATA | 4286 |
| pLas, 11h packaging | 20170T2608 | F05 | sgRNA | 96.30% | CCTGCAACGGGACTAGTTGG | FALSE | 2 | CCTGCAACGGGACTAGTTGG | 209 |

TABLE 2-continued

| condition | date | platewell | pattern | fraction | pred_sgRNA | solitary | matches_per_sample | match | count |
|---|---|---|---|---|---|---|---|---|---|
| pLas, 11h packaging | 20170T2608 | F06 | pL43 | 96.60% | CGCCGCCCCCGGACGCGACC | TRUE | 2 | CATGCGT | 3706 |
| pLas, 11h packaging | 20170T2608 | F06 | sgRNA | 95.70% | CCTGCAACGGGACTAGTTGG | TRUE | 2 | CCTGCAACGGGACTAGTTGG | 309 |
| pLas, 11h packaging | 20170T2608 | F07 | pL43 | 96.80% | AGAGCACTGCACTCCTTCA | TRUE | 2 | CCAGTTA | 4093 |
| pLas, 11h packaging | 20170T2608 | F07 | sgRNA | 94.50% | AGTAGTCCGGGATATCAGCG | TRUE | 2 | AGTAGTCCGGGATATCAGCG | 361 |
| pLas, 11h packaging | 20170T2608 | F08 | pL43 | 97.40% | CCTGCAACGGGACTAGTTGG | FALSE | 2 | CGTCATA | 3440 |
| pLas, 11h packaging | 20170T2608 | F08 | sgRNA | 94.20% | CCTGCAACGGGACTAGTTGG | FALSE | 2 | CCTGCAACGGGACTAGTTGG | 98 |
| pLas, 11h packaging | 20170T2608 | F10 | pL43 | 94.60% | CCTGCAACGGGACTAGTTGG | FALSE | 2 | CGTCATA | 4602 |
| pLas, 11h packaging | 20170T2608 | F10 | sgRNA | 95.40% | CCTGCAACGGGACTAGTTGG | FALSE | 2 | CCTGCAACGGGACTAGTTGG | 518 |
| pLas, 11h packaging | 20170T2608 | F11 | pL43 | 15.50% | AGAGCACTGCACTCCTTCA | FALSE | 4 | AGGCTCT | 626 |
| pLas, 11h packaging | 20170T2608 | F11 | pL43 | 80.40% | TCCACCGGCGAAAGAGATCC | TRUE | 4 | CAATCGG | 3245 |
| pLas, 11h packaging | 20170T2608 | F11 | sgRNA | 10.20% | AGAGCACTGCACTCCTTCA | FALSE | 4 | AGAGCACTGCACTCCTTCA | 79 |
| pLas, 11h packaging | 20170T2608 | F11 | sgRNA | 85.50% | TCATATTACGAGTCAGTAGG | TRUE | 4 | TCATATTACGAGTCAGTAGG | 664 |
| pLas, 11h packaging | 20170T2608 | F12 | pL43 | 95.60% | AGAGCACTGCACTCCTTCA | FALSE | 2 | CCAGTTA | 4146 |
| pLas, 11h packaging | 20170T2608 | F12 | sgRNA | 95.30% | AGAGCACTGCACTCCTTCA | FALSE | 2 | AGAGCACTGCACTCCTTCA | 486 |
| pLas, 11h packaging | 20170T2608 | G05 | pL43 | 97.20% | CGCCGCCCCCGGACGCGACC | FALSE | 2 | CATGCGT | 3720 |
| pLas, 11h packaging | 20170T2608 | G05 | sgRNA | 95.10% | CGCCGCCCCCGGACGCGACC | FALSE | 2 | CGCCGCCCCGGACGCGACC | 509 |
| pLas, 11h packaging | 20170T2608 | G06 | pL43 | 97.30% | CCTGCAACGGGACTAGTTGG | TRUE | 2 | CGTCATA | 3869 |
| pLas, 11h packaging | 20170T2608 | G06 | sgRNA | 95.80% | ATACAACTGCTTGCAACAGG | TRUE | 2 | ATACAACTGCTTGCAACAGG | 159 |
| pLas, 11h packaging | 20170T2608 | G07 | pL43 | 85.90% | CCTGCAACGGGACTAGTTGG | FALSE | 2 | CGTCATA | 1831 |
| pLas, 11h packaging | 20170T2608 | G07 | sgRNA | 95.00% | CCTGCAACGGGACTAGTTGG | FALSE | 2 | CCTGCAACGGGACTAGTTGG | 4525 |
| pLas, 11h packaging | 20170T2608 | G08 | pL43 | 95.30% | CCAGTACAAACCTACCTACG | FALSE | 2 | AAGAGGA | 3386 |
| pLas, 11h packaging | 20170T2608 | G08 | sgRNA | 94.70% | CCAGTACAAACCTACCTACG | FALSE | 2 | CCAGTACAAACCTACCTACG | 160 |
| pLas, 11h packaging | 20170T2608 | G09 | pL43 | 95.20% | CCTGCAACGGGACTAGTTGG | FALSE | 2 | CGTCATA | 4430 |
| pLas, 11h packaging | 20170T2608 | G09 | sgRNA | 96.00% | CCTGCAACGGGACTAGTTGG | FALSE | 2 | CCTGCAACGGGACTAGTTGG | 427 |

TABLE 2-continued

| condition | date | platewell | pattern | fraction | pred_sgRNA | solitary | matches_per_sample | match | count |
|---|---|---|---|---|---|---|---|---|---|
| pLas, 11h packaging | 20170T2608 | G10 | pL43 | 92.50% | AGAGCACTGCACTCCTTCA | TRUE | 2 | CCAGTTA | 4090 |
| pLas, 11h packaging | 20170T2608 | G10 | sgRNA | 95.80% | AGTAGTCCGGGATATCAGCG | TRUE | 2 | AGTAGTCCGGGATATCAGCG | 915 |
| pLas, 11h packaging | 20170T2608 | G11 | pL43 | 95.90% | TCATATTACGAGTCAGTAGG | FALSE | 2 | AGAGAGA | 3667 |
| pLas, 11h packaging | 20170T2608 | G11 | sgRNA | 94.80% | TCATATTACGAGTCAGTAGG | FALSE | 2 | TCATATTACGAGTCAGTAGG | 307 |
| pLas, 11h packaging | 20170T2608 | G12 | pL43 | 92.40% | AGAGCACTGCACTCCTTCA | FALSE | 2 | CCAGTTA | 4131 |
| pLas, 11h packaging | 20170T2608 | G12 | sgRNA | 95.70% | AGAGCACTGCACTCCTTCA | FALSE | 2 | AGAGCACTGCACTCCTTCA | 132 |
| pLas, 11h packaging | 20170T2608 | H05 | pL43 | 96.00% | AGTAGTCCGGGATATCAGCG | TRUE | 2 | CCTCTTC | 3216 |
| pLas, 11h packaging | 20170T2608 | H05 | sgRNA | 95.40% | CCTGCAACGGGACTAGTTGG | TRUE | 2 | CCTGCAACGGGACTAGTTGG | 1403 |
| pLas, 11h packaging | 20170T2608 | H06 | pL43 | 97.10% | TCATATTACGAGTCAGTAGG | FALSE | 2 | AGAGAGA | 4069 |
| pLas, 11h packaging | 20170T2608 | H06 | sgRNA | 95.00% | TCATATTACGAGTCAGTAGG | FALSE | 2 | TCATATTACGAGTCAGTAGG | 892 |
| pLas, 11h packaging | 20170T2608 | H07 | pL43 | 97.10% | AGAGCACTGCACTCCTTCA | FALSE | 2 | CCAGTTA | 4126 |
| pLas, 11h packaging | 20170T2608 | H07 | sgRNA | 94.50% | AGAGCACTGCACTCCTTCA | FALSE | 2 | AGAGCACTGCACTCCTTCA | 1827 |
| pLas, 11h packaging | 20170T2608 | H08 | pL43 | 97.00% | TCATATTACGAGTCAGTAGG | FALSE | 2 | AGAGAGA | 4237 |
| pLas, 11h packaging | 20170T2608 | H08 | sgRNA | 95.80% | TCATATTACGAGTCAGTAGG | FALSE | 2 | TCATATTACGAGTCAGTAGG | 1067 |
| pLas, 11h packaging | 20170T2608 | H09 | pL43 | 19.00% | TCATATTACGAGTCAGTAGG | TRUE | 3 | AGAGAGA | 337 |
| pLas, 11h packaging | 20170T2608 | H09 | pL43 | 35.90% | CCAGTACAAACCTACCTACG | TRUE | 3 | AAGAGGA | 636 |
| pLas, 11h packaging | 20170T2608 | H09 | sgRNA | 94.10% | AGAGCACTGCACTCCTTCA | TRUE | 3 | AGAGCACTGCACTCCTTCA | 9185 |
| pLas, 11h packaging | 20170T2608 | H11 | pL43 | 17.30% | AGAGCACTGCACTCCTTCA | TRUE | 5 | CCAGTTA | 426 |
| pLas, 11h packaging | 20170T2608 | H11 | pL43 | 18.50% | TCATATTACGAGTCAGTAGG | TRUE | 5 | AGAGAGA | 456 |
| pLas, 11h packaging | 20170T2608 | H11 | pL43 | 20.30% | TCCACCGGCGAAAGAGATCC | TRUE | 5 | CAATCGG | 502 |
| pLas, 11h packaging | 20170T2608 | H11 | pL43 | 21.10% | CCAGTACAAACCTACCTACG | TRUE | 5 | AAGAGGA | 522 |
| pLas, 11h packaging | 20170T2608 | H11 | sgRNA | 95.40% | CGCCGCCCCGGACGCGACC | TRUE | 5 | CGCCGCCCCGGACGCGACC | 3088 |
| pLas, 11h packaging | 20170T2608 | H12 | pL43 | 90.50% | AGAGCACTGCACTCCTTCA | FALSE | 2 | CCAGTTA | 3677 |
| pLas, 11h packaging | 20170T2608 | H12 | sgRNA | 95.20% | AGAGCACTGCACTCCTTCA | FALSE | 2 | AGAGCACTGCACTCCTTCA | 598 |

TABLE 2-continued

| condition | date | plate | well | pattern | fraction | pred_sgRNA | solitary | matches_per_sample | match | count |
|---|---|---|---|---|---|---|---|---|---|---|
| pLas + pR_LG (1:10) | 20170T1 | 924 | A01 | pL42_pool1 | 97.00% | CAAGGAGGACGGCAACATCC | FALSE | 2 | CTATATATGACC | 4947 |
| pLas + pR_LG (1:10) | 20170T1 | 924 | A01 | sgRNA | 89.50% | CAAGGAGGACGGCAACATCC | FALSE | 2 | CAAGGAGGACGGCAACATCC | 3492 |
| pLas + pR_LG (1:10) | 20170T1 | 924 | A02 | pL42_pool1 | 97.20% | GCCGTGCCGTAGCTATCCGG | FALSE | 2 | GACATGCGTAGC | 5560 |
| pLas + pR_LG (1:10) | 20170T1 | 924 | A02 | sgRNA | 89.80% | GCCGTGCCGTAGCTATCCGG | FALSE | 2 | GCCGTGCCGTAGCTATCCGG | 3437 |
| pLas + pR_LG (1:10) | 20170T1 | 924 | A03 | pL42_pool1 | 96.20% | TGTACTCCAGCTTGTGCCCC | FALSE | 2 | AGCTCTGACACA | 5246 |
| pLas + pR_LG (1:10) | 20170T1 | 924 | A03 | sgRNA | 89.70% | TGTACTCCAGCTTGTGCCCC | FALSE | 2 | TGTACTCCAGCTTGTGCCCC | 4470 |
| pLas + pR_LG (1:10) | 20170T1 | 924 | A04 | pL42_pool1 | 96.30% | AAGGAGGACGGCAACATCCT | FALSE | 2 | TCCAAAGAGACA | 5671 |
| pLas + pR_LG (1:10) | 20170T1 | 924 | A04 | sgRNA | 90.00% | AAGGAGGACGGCAACATCCT | FALSE | 2 | AAGGAGGACGGCAACATCCT | 4800 |
| pLas + pR_LG (1:10) | 20170T1 | 924 | A05 | pL42_pool1 | 97.20% | CAAGGAGGACGGCAACATCC | FALSE | 2 | CTATATATGACC | 5430 |
| pLas + pR_LG (1:10) | 20170T1 | 924 | A05 | sgRNA | 91.50% | CAAGGAGGACGGCAACATCC | FALSE | 2 | CAAGGAGGACGGCAACATCC | 5875 |
| pLas + pR_LG (1:10) | 20170T1 | 924 | A06 | pL42_pool1 | 96.90% | GCCGTGCCGTAGCTATCCGG | FALSE | 2 | AGATGATAACGG | 5589 |
| pLas + pR_LG (1:10) | 20170T1 | 924 | A06 | sgRNA | 89.20% | GCCGTGCCGTAGCTATCCGG | FALSE | 2 | GCCGTGCCGTAGCTATCCGG | 5212 |
| pLas + pR_LG (1:10) | 20170T1 | 924 | A07 | pL42_pool1 | 96.50% | AAGGAGGACGGCAACATCCT | FALSE | 2 | TCCAAAGAGACA | 5717 |
| pLas + pR_LG (1:10) | 20170T1 | 924 | A07 | sgRNA | 89.70% | AAGGAGGACGGCAACATCCT | FALSE | 2 | AAGGAGGACGGCAACATCCT | 5701 |
| pLas + pR_LG (1:10) | 20170T1 | 924 | A08 | pL42_pool1 | 96.40% | GTCCGTTCGACAATTTCACA | FALSE | 2 | AGATGGGTTCCG | 5163 |
| pLas + pR_LG (1:10) | 20170T1 | 924 | A08 | sgRNA | 86.70% | GTCCGTTCGACAATTTCACA | FALSE | 2 | GTCCGTTCGACAATTTCACA | 4141 |
| pLas + pR_LG (1:10) | 20170T1 | 924 | A09 | pL42_pool1 | 96.40% | GTACAGCTAAGTTAAACTCG | FALSE | 2 | AGCACGGAGACA | 5313 |
| pLas + pR_LG (1:10) | 20170T1 | 924 | A09 | sgRNA | 88.80% | GTACAGCTAAGTTAAACTCG | FALSE | 2 | GTACAGCTAAGTTAAACTCG | 3082 |
| pLas + pR_LG (1:10) | 20170T1 | 924 | A10 | pL42_pool1 | 96.80% | AAGGAGGACGGCAACATCCT | FALSE | 2 | GAATCCGCTCGC | 5743 |
| pLas + pR_LG (1:10) | 20170T1 | 924 | A10 | sgRNA | 90.60% | AAGGAGGACGGCAACATCCT | FALSE | 2 | AAGGAGGACGGCAACATCCT | 4341 |
| pLas + pR_LG (1:10) | 20170T1 | 924 | A11 | pL42_pool1 | 96.30% | GTCCGTTCGACAATTTCACA | FALSE | 2 | GACAAGTACACT | 5168 |
| pLas + pR_LG (1:10) | 20170T1 | 924 | A11 | sgRNA | 88.20% | GTCCGTTCGACAATTTCACA | FALSE | 2 | GTCCGTTCGACAATTTCACA | 4120 |
| pLas + pR_LG (1:10) | 20170T1 | 924 | B01 | pL42_pool1 | 97.10% | GTCCGTTCGACAATTTCACA | FALSE | 2 | CTCAATTTACAG | 5092 |
| pLas + pR_LG (1:10) | 20170T1 | 924 | B01 | sgRNA | 87.20% | GTCCGTTCGACAATTTCACA | FALSE | 2 | GTCCGTTCGACAATTTCACA | 2546 |

TABLE 2-continued

| condition | date | platewell | pat-tern | frac-tion | pred_sgRNA | soli-tary | matches_per_sam-ple | match | count |
|---|---|---|---|---|---|---|---|---|---|
| pLas + pR_LG (1:10) | 20170T1 924 | B02 | pL42_pool1 | 96.90% | AAGGAGGACGGCAACATCCT | FALSE | 2 | CTAGTGTCCACA | 5442 |
| pLas + pR_LG (1:10) | 20170T1 924 | B02 | sgRNA | 91.80% | AAGGAGGACGGCAACATCCT | FALSE | 2 | AAGGAGGACGGCAACATCCT | 3877 |
| pLas + pR_LG (1:10) | 20170T1 924 | B03 | pL42_pool1 | 97.00% | GCCGTGCCGTAGCTATCCGG | FALSE | 2 | GACAACGAGAAC | 5605 |
| pLas + pR_LG (1:10) | 20170T1 924 | B03 | sgRNA | 90.70% | GCCGTGCCGTAGCTATCCGG | FALSE | 2 | GCCGTGCCGTAGCTATCCGG | 4741 |
| pLas + pR_LG (1:10) | 20170T1 924 | B04 | pL42_pool1 | 96.90% | GGACGCTAAACCAACGGTGC | FALSE | 2 | AGAGACTTCACA | 5232 |
| pLas + pR_LG (1:10) | 20170T1 924 | B04 | sgRNA | 90.00% | GGACGCTAAACCAACGGTGC | FALSE | 2 | GGACGCTAAACCAACGGTGC | 4847 |
| pLas + pR_LG (1:10) | 20170T1 924 | B05 | pL42_pool1 | 96.90% | GTCCGTTCGACAATTTCACA | FALSE | 2 | AGATGGGTTCCG | 5302 |
| pLas + pR_LG (1:10) | 20170T1 924 | B05 | sgRNA | 88.00% | GTCCGTTCGACAATTTCACA | FALSE | 2 | GTCCGTTCGACAATTTCACA | 3966 |
| pLas + pR_LG (1:10) | 20170T1 924 | B06 | pL42_pool1 | 97.40% | GGACGCTAAACCAACGGTGC | FALSE | 2 | GACAGGCTACCT | 5500 |
| pLas + pR_LG (1:10) | 20170T1 924 | B06 | sgRNA | 91.60% | GGACGCTAAACCAACGGTGC | FALSE | 2 | GGACGCTAAACCAACGGTGC | 4698 |
| pLas + pR_LG (1:10) | 20170T1 924 | B07 | pL42_pool1 | 96.30% | AAGGAGGACGGCAACATCCT | FALSE | 2 | GAATGAACCACG | 6121 |
| pLas + pR_LG (1:10) | 20170T1 924 | B07 | sgRNA | 91.90% | AAGGAGGACGGCAACATCCT | FALSE | 2 | AAGGAGGACGGCAACATCCT | 5193 |
| pLas + pR_LG (1:10) | 20170T1 924 | B08 | pL42_pool1 | 97.40% | CAACATCCTGGGGCACAAGC | FALSE | 2 | GAACGCGAAAGC | 5179 |
| pLas + pR_LG (1:10) | 20170T1 924 | B08 | sgRNA | 90.70% | CAACATCCTGGGGCACAAGC | FALSE | 2 | CAACATCCTGGGGCACAAGC | 4939 |
| pLas + pR_LG (1:10) | 20170T1 924 | B09 | pL42_pool1 | 97.00% | GTCCGTTCGACAATTTCACA | FALSE | 2 | GACAAGTACACT | 5307 |
| pLas + pR_LG (1:10) | 20170T1 924 | B09 | sgRNA | 88.30% | GTCCGTTCGACAATTTCACA | FALSE | 2 | GTCCGTTCGACAATTTCACA | 4370 |
| pLas + pR_LG (1:10) | 20170T1 924 | B10 | pL42_pool1 | 95.90% | GCCGTGCCGTAGCTATCCGG | FALSE | 2 | CTCACTGACACT | 5921 |
| pLas + pR_LG (1:10) | 20170T1 924 | B10 | sgRNA | 90.20% | GCCGTGCCGTAGCTATCCGG | FALSE | 2 | GCCGTGCCGTAGCTATCCGG | 4136 |
| pLas + pR_LG (1:10) | 20170T1 924 | B11 | pL42_pool1 | 97.20% | GCCGTGCCGTAGCTATCCGG | FALSE | 2 | GACATGCGTAGC | 5359 |
| pLas + pR_LG (1:10) | 20170T1 924 | B11 | sgRNA | 89.30% | GCCGTGCCGTAGCTATCCGG | FALSE | 2 | GCCGTGCCGTAGCTATCCGG | 3745 |
| pLas + pR_LG (1:10) | 20170T1 924 | C01 | pL42_pool1 | 97.00% | AAGGAGGACGGCAACATCCT | FALSE | 2 | TCCAAAGAGACA | 5345 |
| pLas + pR_LG (1:10) | 20170T1 924 | C01 | sgRNA | 89.30% | AAGGAGGACGGCAACATCCT | FALSE | 2 | AAGGAGGACGGCAACATCCT | 5246 |
| pLas + pR_LG (1:10) | 20170T1 924 | C02 | pL42_pool1 | 97.80% | GCTGCTTGCGATACCAATAG | FALSE | 2 | AGCAGCCCTAGC | 5419 |
| pLas + pR_LG (1:10) | 20170T1 924 | C02 | sgRNA | 89.90% | GCTGCTTGCGATACCAATAG | FALSE | 2 | GCTGCTTGCGATACCAATAG | 4883 |

TABLE 2-continued

| condition | date | platewell | pattern | fraction | pred_sgRNA | solitary | matches_per_sample | match | count |
|---|---|---|---|---|---|---|---|---|---|
| pLas + pR_LG (1:10) | 20170924 | T1 C03 | pL42_pool1 | 96.20% | GCCGTGCCGTAGCTATCCGG | FALSE | 2 | CTCACTGACACT | 5307 |
| pLas + pR_LG (1:10) | 20170924 | T1 C03 | sgRNA | 89.60% | GCCGTGCCGTAGCTATCCGG | FALSE | 2 | GCCGTGCCGTAGCTATCCGG | 5020 |
| pLas + pR_LG (1:10) | 20170924 | T1 C04 | pL42_pool1 | 96.90% | CAACATCCTGGGGCACAAGC | FALSE | 2 | AGAGCAGAAAGG | 5495 |
| pLas + pR_LG (1:10) | 20170924 | T1 C04 | sgRNA | 88.30% | CAACATCCTGGGGCACAAGC | FALSE | 2 | CAACATCCTGGGGCACAAGC | 4555 |
| pLas + pR_LG (1:10) | 20170924 | T1 C05 | pL42_pool1 | 97.10% | GCCGTGCCGTAGCTATCCGG | FALSE | 2 | AGATGATAACGG | 5613 |
| pLas + pR_LG (1:10) | 20170924 | T1 C05 | sgRNA | 88.20% | GCCGTGCCGTAGCTATCCGG | FALSE | 2 | GCCGTGCCGTAGCTATCCGG | 4590 |
| pLas + pR_LG (1:10) | 20170924 | T1 C06 | pL42_pool1 | 97.10% | GGACGCTAAACCAACGGTGC | FALSE | 2 | TCCAGAGCACCT | 6229 |
| pLas + pR_LG (1:10) | 20170924 | T1 C06 | sgRNA | 89.80% | GGACGCTAAACCAACGGTGC | FALSE | 2 | GGACGCTAAACCAACGGTGC | 4789 |
| pLas + pR_LG (1:10) | 20170924 | T1 C07 | pL42_pool1 | 96.50% | AGGAGGACGGCAACATCCTG | FALSE | 2 | AGCGACCTTACA | 5522 |
| pLas + pR_LG (1:10) | 20170924 | T1 C07 | sgRNA | 90.50% | AGGAGGACGGCAACATCCTG | FALSE | 2 | AGGAGGACGGCAACATCCTG | 5621 |
| pLas + pR_LG (1:10) | 20170924 | T1 C08 | pL42_pool1 | 96.70% | GCTGCTTGCGATACCAATAG | FALSE | 2 | AGCAGTGTACCT | 5399 |
| pLas + pR_LG (1:10) | 20170924 | T1 C08 | sgRNA | 87.90% | GCTGCTTGCGATACCAATAG | FALSE | 2 | GCTGCTTGCGATACCAATAG | 3869 |
| pLas + pR_LG (1:10) | 20170924 | T1 C09 | pL42_pool1 | 96.60% | GCCGTGCCGTAGCTATCCGG | FALSE | 2 | AGATGATAACGG | 5137 |
| pLas + pR_LG (1:10) | 20170924 | T1 C09 | sgRNA | 89.50% | GCCGTGCCGTAGCTATCCGG | FALSE | 2 | GCCGTGCCGTAGCTATCCGG | 3866 |
| pLas + pR_LG (1:10) | 20170924 | T1 C10 | pL42_pool1 | 97.30% | TGTACTCCAGCTTGTGCCCC | FALSE | 2 | AGCTAGCCTAGG | 6254 |
| pLas + pR_LG (1:10) | 20170924 | T1 C10 | sgRNA | 89.90% | TGTACTCCAGCTTGTGCCCC | FALSE | 2 | TGTACTCCAGCTTGTGCCCC | 4656 |
| pLas + pR_LG (1:10) | 20170924 | T1 C11 | pL42_pool1 | 97.20% | TGTACTCCAGCTTGTGCCCC | FALSE | 2 | AGCTAGCCTAGG | 5845 |
| pLas + pR_LG (1:10) | 20170924 | T1 C11 | sgRNA | 89.60% | TGTACTCCAGCTTGTGCCCC | FALSE | 2 | TGTACTCCAGCTTGTGCCCC | 4302 |
| pLas + pR_LG (1:10) | 20170924 | T1 C12 | pL42_pool1 | 96.80% | GTCCGTTCGACAATTTCACA | FALSE | 2 | AGATGGGTTCCG | 5299 |
| pLas + pR_LG (1:10) | 20170924 | T1 C12 | sgRNA | 86.90% | GTCCGTTCGACAATTTCACA | FALSE | 2 | GTCCGTTCGACAATTTCACA | 3506 |
| pLas + pR_LG (1:10) | 20170924 | T1 D01 | pL42_pool1 | 96.30% | GGACGCTAAACCAACGGTGC | FALSE | 2 | AGATCGACCACC | 5164 |
| pLas + pR_LG (1:10) | 20170924 | T1 D01 | sgRNA | 90.90% | GGACGCTAAACCAACGGTGC | FALSE | 2 | GGACGCTAAACCAACGGTGC | 4652 |
| pLas + pR_LG (1:10) | 20170924 | T1 D02 | pL42_pool1 | 95.90% | CAAGGAGGACGGCAACATCC | FALSE | 2 | CTATATATGACC | 519 |
| pLas + pR_LG (1:10) | 20170924 | T1 D02 | sgRNA | 94.10% | CAAGGAGGACGGCAACATCC | FALSE | 2 | CAAGGAGGACGGCAACATCC | 5149 |

TABLE 2-continued

| condition | date | platewell | pattern | fraction | pred_sgRNA | solitary | matches_per_sample | match | count |
|---|---|---|---|---|---|---|---|---|---|
| pLas + pR_LG (1:10) | 20170 924 | T1 D03 | pL42_pool1 | 97.10% | GTCCGTTCGACAATTTCACA | FALSE | 2 | CTCAATTTACAG | 5103 |
| pLas + pR_LG (1:10) | 20170 924 | T1 D03 | sgRNA | 88.70% | GTCCGTTCGACAATTTCACA | FALSE | 2 | GTCCGTTCGACAATTTCACA | 4837 |
| pLas + pR_LG (1:10) | 20170 924 | T1 D04 | pL42_pool1 | 97.30% | TGTACTCCAGCTTGTGCCCC | FALSE | 2 | AGCGCCGTCATT | 5431 |
| pLas + pR_LG (1:10) | 20170 924 | T1 D04 | sgRNA | 90.80% | TGTACTCCAGCTTGTGCCCC | FALSE | 2 | TGTACTCCAGCTTGTGCCCC | 5191 |
| pLas + pR_LG (1:10) | 20170 924 | T1 D05 | pL42_pool1 | 96.90% | GCTGCTTGCGATACCAATAG | FALSE | 2 | GAAGTGGGCAAC | 5282 |
| pLas + pR_LG (1:10) | 20170 924 | T1 D05 | sgRNA | 90.70% | GCTGCTTGCGATACCAATAG | FALSE | 2 | GCTGCTTGCGATACCAATAG | 4882 |
| pLas + pR_LG (1:10) | 20170 924 | T1 D06 | pL42_pool1 | 97.40% | TGTACTCCAGCTTGTGCCCC | FALSE | 2 | GAACTAGCCACT | 6051 |
| pLas + pR_LG (1:10) | 20170 924 | T1 D06 | sgRNA | 90.70% | TGTACTCCAGCTTGTGCCCC | FALSE | 2 | TGTACTCCAGCTTGTGCCCC | 4812 |
| pLas + pR_LG (1:10) | 20170 924 | T1 D07 | pL42_pool1 | 97.90% | TGTACTCCAGCTTGTGCCCC | FALSE | 2 | AGCTAGCCTAGG | 6191 |
| pLas + pR_LG (1:10) | 20170 924 | T1 D07 | sgRNA | 90.60% | TGTACTCCAGCTTGTGCCCC | FALSE | 2 | TGTACTCCAGCTTGTGCCCC | 4713 |
| pLas + pR_LG (1:10) | 20170 924 | T1 D08 | pL42_pool1 | 95.60% | GGACGCTAAACCAACGGTGC | FALSE | 2 | AGATCGACCACC | 5062 |
| pLas + pR_LG (1:10) | 20170 924 | T1 D08 | sgRNA | 91.10% | GGACGCTAAACCAACGGTGC | FALSE | 2 | GGACGCTAAACCAACGGTGC | 4437 |
| pLas + pR_LG (1:10) | 20170 924 | T1 D10 | pL42_pool1 | 97.00% | GTACAGCTAAGTTAAACTCG | FALSE | 2 | AGCACGGAGACA | 4601 |
| pLas + pR_LG (1:10) | 20170 924 | T1 D10 | sgRNA | 91.70% | GTACAGCTAAGTTAAACTCG | FALSE | 2 | GTACAGCTAAGTTAAACTCG | 4341 |
| pLas + pR_LG (1:10) | 20170 924 | T1 D11 | pL42_pool1 | 97.40% | GTCCGTTCGACAATTTCACA | FALSE | 2 | GACAAGTACACT | 5112 |
| pLas + pR_LG (1:10) | 20170 924 | T1 D11 | sgRNA | 88.80% | GTCCGTTCGACAATTTCACA | FALSE | 2 | GTCCGTTCGACAATTTCACA | 3948 |
| pLas + pR_LG (1:10) | 20170 924 | T1 D12 | pL42_pool1 | 97.40% | GCCGTGCCGTAGCTATCCGG | FALSE | 2 | AGATGATAACGG | 5286 |
| pLas + pR_LG (1:10) | 20170 924 | T1 D12 | sgRNA | 91.20% | GCCGTGCCGTAGCTATCCGG | FALSE | 2 | GCCGTGCCGTAGCTATCCGG | 3873 |
| pLas + pR_LG (1:10) | 20170 924 | T1 E01 | pL42_pool1 | 97.50% | GCCGTGCCGTAGCTATCCGG | FALSE | 2 | AGATGATAACGG | 5806 |
| pLas + pR_LG (1:10) | 20170 924 | T1 E01 | sgRNA | 88.40% | GCCGTGCCGTAGCTATCCGG | FALSE | 2 | GCCGTGCCGTAGCTATCCGG | 4418 |
| pLas + pR_LG (1:10) | 20170 924 | T1 E02 | pL42_pool1 | 96.70% | CAAGGAGGACGGCAACATCC | FALSE | 2 | CTATATATGACC | 4937 |
| pLas + pR_LG (1:10) | 20170 924 | T1 E02 | sgRNA | 92.60% | CAAGGAGGACGGCAACATCC | FALSE | 2 | CAAGGAGGACGGCAACATCC | 4515 |
| pLas + pR_LG (1:10) | 20170 924 | T1 E03 | pL42_pool1 | 96.30% | GCCGTGCCGTAGCTATCCGG | FALSE | 2 | CTCACTGACACT | 5638 |
| pLas + pR_LG (1:10) | 20170 924 | T1 E03 | sgRNA | 90.40% | GCCGTGCCGTAGCTATCCGG | FALSE | 2 | GCCGTGCCGTAGCTATCCGG | 4364 |

TABLE 2-continued

| condition | date | platewell | pattern | fraction | pred_sgRNA | solitary | matches_per_sample | match | count |
|---|---|---|---|---|---|---|---|---|---|
| pLas + pR_LG (1:10) | 20170T1 924 | E04 | pL42_pool1 | 96.90% | GTCCGTTCGACAATTTCACA | FALSE | 2 | CTCAATTTACAG | 5383 |
| pLas + pR_LG (1:10) | 20170T1 924 | E04 | sgRNA | 87.50% | GTCCGTTCGACAATTTCACA | FALSE | 2 | GTCCGTTCGACAATTTCACA | 4141 |
| pLas + pR_LG (1:10) | 20170T1 924 | E05 | pL42_pool1 | 97.30% | GGACGCTAAACCAACGGTGC | FALSE | 2 | GACAGGCTACCT | 5329 |
| pLas + pR_LG (1:10) | 20170T1 924 | E05 | sgRNA | 88.30% | GGACGCTAAACCAACGGTGC | FALSE | 2 | GGACGCTAAACCAACGGTGC | 4383 |
| pLas + pR_LG (1:10) | 20170T1 924 | E06 | pL42_pool1 | 97.40% | GTCCGTTCGACAATTTCACA | FALSE | 2 | AGATGGGTTCCG | 5458 |
| pLas + pR_LG (1:10) | 20170T1 924 | E06 | sgRNA | 88.70% | GTCCGTTCGACAATTTCACA | FALSE | 2 | GTCCGTTCGACAATTTCACA | 4981 |
| pLas + pR_LG (1:10) | 20170T1 924 | E07 | pL42_pool1 | 97.00% | GTCCGTTCGACAATTTCACA | FALSE | 2 | GACAAGTACACT | 5252 |
| pLas + pR_LG (1:10) | 20170T1 924 | E07 | sgRNA | 88.20% | GTCCGTTCGACAATTTCACA | FALSE | 2 | GTCCGTTCGACAATTTCACA | 4925 |
| pLas + pR_LG (1:10) | 20170T1 924 | E08 | pL42_pool1 | 96.60% | GTACAGCTAAGTTAAACTCG | FALSE | 2 | AGCACGGAGACA | 5176 |
| pLas + pR_LG (1:10) | 20170T1 924 | E08 | sgRNA | 91.50% | GTACAGCTAAGTTAAACTCG | FALSE | 2 | GTACAGCTAAGTTAAACTCG | 4568 |
| pLas + pR_LG (1:10) | 20170T1 924 | E09 | pL42_pool1 | 97.00% | GTCCGTTCGACAATTTCACA | FALSE | 2 | AGATGGGTTCCG | 5147 |
| pLas + pR_LG (1:10) | 20170T1 924 | E09 | sgRNA | 87.80% | GTCCGTTCGACAATTTCACA | FALSE | 2 | GTCCGTTCGACAATTTCACA | 3963 |
| pLas + pR_LG (1:10) | 20170T1 924 | E10 | pL42_pool1 | 97.10% | GTCCGTTCGACAATTTCACA | FALSE | 2 | AGATGGGTTCCG | 4793 |
| pLas + pR_LG (1:10) | 20170T1 924 | E10 | sgRNA | 88.00% | GTCCGTTCGACAATTTCACA | FALSE | 2 | GTCCGTTCGACAATTTCACA | 4321 |
| pLas + pR_LG (1:10) | 20170T1 924 | E11 | pL42_pool1 | 97.50% | CAAGGAGGACGGCAACATCC | FALSE | 2 | GAACTCAGGACA | 4387 |
| pLas + pR_LG (1:10) | 20170T1 924 | E11 | sgRNA | 91.10% | CAAGGAGGACGGCAACATCC | FALSE | 2 | CAAGGAGGACGGCAACATCC | 4034 |
| pLas + pR_LG (1:10) | 20170T1 924 | F01 | pL42_pool1 | 97.20% | CAAGGAGGACGGCAACATCC | FALSE | 2 | CTATATATGACC | 5619 |
| pLas + pR_LG (1:10) | 20170T1 924 | F01 | sgRNA | 89.10% | CAAGGAGGACGGCAACATCC | FALSE | 2 | CAAGGAGGACGGCAACATCC | 2595 |
| pLas + pR_LG (1:10) | 20170T1 924 | F02 | pL42_pool1 | 96.80% | CAAGGAGGACGGCAACATCC | FALSE | 2 | GAACTCAGGACA | 5330 |
| pLas + pR_LG (1:10) | 20170T1 924 | F02 | sgRNA | 92.50% | CAAGGAGGACGGCAACATCC | FALSE | 2 | CAAGGAGGACGGCAACATCC | 3447 |
| pLas + pR_LG (1:10) | 20170T1 924 | F03 | pL42_pool1 | 97.00% | CAACATCCTGGGGCACAAGC | FALSE | 2 | AGATTCATGACG | 5301 |
| pLas + pR_LG (1:10) | 20170T1 924 | F03 | sgRNA | 89.20% | CAACATCCTGGGGCACAAGC | FALSE | 2 | CAACATCCTGGGGCACAAGC | 4453 |
| pLas + pR_LG (1:10) | 20170T1 924 | F04 | pL42_pool1 | 97.60% | TGTACTCCAGCTTGTGCCCC | FALSE | 2 | AGCGCCGTCATT | 5303 |
| pLas + pR_LG (1:10) | 20170T1 924 | F04 | sgRNA | 89.70% | TGTACTCCAGCTTGTGCCCC | FALSE | 2 | TGTACTCCAGCTTGTGCCCC | 4379 |

TABLE 2-continued

| condition | date | platewell | pat-tern | frac-tion | pred_sgRNA | soli-tary | matches_per_sample | match | count |
|---|---|---|---|---|---|---|---|---|---|
| pLas + pR_LG (1:10) | 20170T1924 | F05 | pL42_pool1 | 96.70% | GTCCGTTCGACAATTTCACA | FALSE | 2 | AGCAACTTCACT | 5379 |
| pLas + pR_LG (1:10) | 20170T1924 | F05 | sgRNA | 86.80% | GTCCGTTCGACAATTTCACA | FALSE | 2 | GTCCGTTCGACAATTTCACA | 4602 |
| pLas + pR_LG (1:10) | 20170T1924 | F06 | pL42_pool1 | 97.10% | GTCCGTTCGACAATTTCACA | FALSE | 2 | AGATGGGTTCCG | 5479 |
| pLas + pR_LG (1:10) | 20170T1924 | F06 | sgRNA | 88.40% | GTCCGTTCGACAATTTCACA | FALSE | 2 | GTCCGTTCGACAATTTCACA | 4357 |
| pLas + pR_LG (1:10) | 20170T1924 | F07 | pL42_pool1 | 97.20% | GCTGCTTGCGATACCAATAG | TRUE | 2 | AGAGCTGCTACG | 5788 |
| pLas + pR_LG (1:10) | 20170T1924 | F07 | sgRNA | 88.60% | GCCGTGCCGTAGCTATCCGG | TRUE | 2 | GCCGTGCCGTAGCTATCCGG | 4696 |
| pLas + pR_LG (1:10) | 20170T1924 | F08 | pL42_pool1 | 96.70% | AAGGAGGACGGCAACATCCT | FALSE | 2 | TCCAAAGAGACA | 5231 |
| pLas + pR_LG (1:10) | 20170T1924 | F08 | sgRNA | 90.40% | AAGGAGGACGGCAACATCCT | FALSE | 2 | AAGGAGGACGGCAACATCCT | 4692 |
| pLas + pR_LG (1:10) | 20170T1924 | F09 | pL42_pool1 | 97.00% | CAAGGAGGACGGCAACATCC | FALSE | 2 | AGCCACCAGTAT | 5024 |
| pLas + pR_LG (1:10) | 20170T1924 | F09 | sgRNA | 91.50% | CAAGGAGGACGGCAACATCC | FALSE | 2 | CAAGGAGGACGGCAACATCC | 3869 |
| pLas + pR_LG (1:10) | 20170T1924 | F10 | pL42_pool1 | 95.90% | GGACGCTAAACCAACGGTGC | FALSE | 2 | TCCAGAGCACCT | 5167 |
| pLas + pR_LG (1:10) | 20170T1924 | F10 | sgRNA | 89.70% | GGACGCTAAACCAACGGTGC | FALSE | 2 | GGACGCTAAACCAACGGTGC | 4575 |
| pLas + pR_LG (1:10) | 20170T1924 | F11 | pL42_pool1 | 97.00% | GCTGCTTGCGATACCAATAG | FALSE | 2 | AGCAGTGTACCT | 5144 |
| pLas + pR_LG (1:10) | 20170T1924 | F11 | sgRNA | 89.10% | GCTGCTTGCGATACCAATAG | FALSE | 2 | GCTGCTTGCGATACCAATAG | 4141 |
| pLas + pR_LG (1:10) | 20170T1924 | F12 | pL42_pool1 | 96.40% | GTACAGCTAAGTTAAACTCG | FALSE | 2 | GAATTAGTGACC | 5578 |
| pLas + pR_LG (1:10) | 20170T1924 | F12 | sgRNA | 88.80% | GTACAGCTAAGTTAAACTCG | FALSE | 2 | GTACAGCTAAGTTAAACTCG | 3825 |
| pLas + pLX_TRC313_LacZ (1:1000) | 20170T2924 | A01 | pL42_pool1 | 97.40% | TGTACTCCAGCTTGTGCCCC | FALSE | 2 | AGCGCCGTCATT | 5888 |
| pLas + pLX_TRC313_LacZ (1:1000) | 20170T2924 | A01 | sgRNA | 90.00% | TGTACTCCAGCTTGTGCCCC | FALSE | 2 | TGTACTCCAGCTTGTGCCCC | 4612 |
| pLas + pLX_TRC313_LacZ (1:1000) | 20170T2924 | A02 | pL42_pool1 | 98.10% | TGTACTCCAGCTTGTGCCCC | FALSE | 2 | AGCTAGCCTAGG | 6329 |
| pLas + pLX_TRC313_LacZ (1:1000) | 20170T2924 | A02 | sgRNA | 91.60% | TGTACTCCAGCTTGTGCCCC | FALSE | 2 | TGTACTCCAGCTTGTGCCCC | 3870 |
| pLas + pLX_TRC313_LacZ (1:1000) | 20170T2924 | A05 | pL42_pool1 | 96.60% | TGTACTCCAGCTTGTGCCCC | FALSE | 2 | AGCTCTGACACA | 6816 |
| pLas + pLX_TRC313_LacZ (1:1000) | 20170T2924 | A05 | sgRNA | 90.10% | TGTACTCCAGCTTGTGCCCC | FALSE | 2 | TGTACTCCAGCTTGTGCCCC | 3081 |

TABLE 2-continued

| condition | date | platewell | pattern | fraction | pred_sgRNA | solitary | matches_per_sample | match | count |
|---|---|---|---|---|---|---|---|---|---|
| pLas + pLX_TRC313_LacZ (1:1000) | 20170T2 924 | A06 | pL42_pool1 | 96.70% | TGTACTCCAGCTTGTGCCCC | FALSE | 2 | CATGATCCCACA | 5634 |
| pLas + pLX_TRC313_LacZ (1:1000) | 20170T2 924 | A06 | sgRNA | 91.10% | TGTACTCCAGCTTGTGCCCC | FALSE | 2 | TGTACTCCAGCTTGTGCCCC | 3763 |
| pLas + pLX_TRC313_LacZ (1:1000) | 20170T2 924 | A07 | pL42_pool1 | 96.10% | GCCGTGCCGTAGCTATCCGG | FALSE | 2 | CTCACTGACACT | 5778 |
| pLas + pLX_TRC313_LacZ (1:1000) | 20170T2 924 | A07 | sgRNA | 89.40% | GCCGTGCCGTAGCTATCCGG | FALSE | 2 | GCCGTGCCGTAGCTATCCGG | 3233 |
| pLas + pLX_TRC313_LacZ (1:1000) | 20170T2 924 | A08 | pL42_pool1 | 96.40% | AAGGAGGACGGCAACATCCT | FALSE | 2 | GAATGAACCACG | 5705 |
| pLas + pLX_TRC313_LacZ (1:1000) | 20170T2 924 | A08 | sgRNA | 91.70% | AAGGAGGACGGCAACATCCT | FALSE | 2 | AAGGAGGACGGCAACATCCT | 2902 |
| pLas + pLX_TRC313_LacZ (1:1000) | 20170T2 924 | A09 | pL42_pool1 | 97.40% | CAAGGAGGACGGCAACATCC | FALSE | 2 | CTATATATGACC | 4537 |
| pLas + pLX_TRC313_LacZ (1:1000) | 20170T2 924 | A09 | sgRNA | 92.00% | CAAGGAGGACGGCAACATCC | FALSE | 2 | CAAGGAGGACGGCAACATCC | 2869 |
| pLas + pLX_TRC313_LacZ (1:1000) | 20170T2 924 | A10 | pL42_pool1 | 97.00% | TGTACTCCAGCTTGTGCCCC | FALSE | 2 | GAACTAGCCACT | 6008 |
| pLas + pLX_TRC313_LacZ (1:1000) | 20170T2 924 | A10 | sgRNA | 90.70% | TGTACTCCAGCTTGTGCCCC | FALSE | 2 | TGTACTCCAGCTTGTGCCCC | 3110 |
| pLas + pLX_TRC313_LacZ (1:1000) | 20170T2 924 | A11 | pL42_pool1 | 97.10% | GTCCGTTCGACAATTTCACA | FALSE | 2 | GACAAGTACACT | 5570 |
| pLas + pLX_TRC313_LacZ (1:1000) | 20170T2 924 | A11 | sgRNA | 86.90% | GTCCGTTCGACAATTTCACA | FALSE | 2 | GTCCGTTCGACAATTTCACA | 3042 |
| pLas + pLX_TRC313_LacZ (1:1000) | 20170T2 924 | A12 | pL42_pool1 | 97.70% | GCTGCTTGCGATACCAATAG | FALSE | 2 | AGCAGCCCTAGC | 5860 |
| pLas + pLX_TRC313_LacZ (1:1000) | 20170T2 924 | A12 | sgRNA | 89.60% | GCTGCTTGCGATACCAATAG | FALSE | 2 | GCTGCTTGCGATACCAATAG | 2508 |
| pLas + pLX_TRC313_LacZ (1:1000) | 20170T2 924 | B01 | pL42_pool1 | 96.20% | AGGAGGACGGCAACATCCTG | FALSE | 2 | AGCGACCTTACA | 5516 |
| pLas + pLX_TRC313_LacZ (1:1000) | 20170T2 924 | B01 | sgRNA | 91.00% | AGGAGGACGGCAACATCCTG | FALSE | 2 | AGGAGGACGGCAACATCCTG | 3684 |
| pLas + pLX_TRC313_LacZ (1:1000) | 20170T2 924 | B02 | pL42_pool1 | 96.20% | CAAGGAGGACGGCAACATCC | FALSE | 2 | GAACTCAGGACA | 6017 |
| pLas + pLX_TRC313_LacZ (1:1000) | 20170T2 924 | B02 | sgRNA | 92.90% | CAAGGAGGACGGCAACATCC | FALSE | 2 | CAAGGAGGACGGCAACATCC | 3527 |

TABLE 2-continued

| condition | date | platewell | pattern | fraction | pred_sgRNA | solitary | matches_per_sample | match | count |
|---|---|---|---|---|---|---|---|---|---|
| pLas + pLX_TRC313_ LacZ (1:1000) | 20170T2 924 | B03 | pL42_ pool1 | 97.30% | GTCCGTTCGACA ATTTCACA | FALSE | 2 | GACAAGTACACT | 5069 |
| pLas + pLX_TRC313_ LacZ (1:1000) | 20170T2 924 | B03 | sgRNA | 88.00% | GTCCGTTCGACA ATTTCACA | FALSE | 2 | GTCCGTTCGACA ATTTCACA | 3034 |
| pLas + pLX_TRC313_ LacZ (1:1000) | 20170T2 924 | B04 | pL42_ pool1 | 96.60% | AGGAGGACGGC AACATCCTG | FALSE | 2 | AGCGACCTTACA | 5231 |
| pLas + pLX_TRC313_ LacZ (1:1000) | 20170T2 924 | B04 | sgRNA | 90.20% | AGGAGGACGGC AACATCCTG | FALSE | 2 | AGGAGGACGGCA ACATCCTG | 3211 |
| pLas + pLX_TRC313_ LacZ (1:1000) | 20170T2 924 | B05 | pL42_ pool1 | 97.30% | GCCGTGCCGTA GCTATCCGG | FALSE | 2 | GACATGCGTAGC | 5816 |
| pLas + pLX_TRC313_ LacZ (1:1000) | 20170T2 924 | B05 | sgRNA | 89.70% | GCCGTGCCGTA GCTATCCGG | FALSE | 2 | GCCGTGCCGTAG CTATCCGG | 3329 |
| pLas + pLX_TRC313_ LacZ (1:1000) | 20170T2 924 | B06 | pL42_ pool1 | 95.70% | GGACGCTAAAC CAACGGTGC | FALSE | 2 | AGATCGACCACC | 5445 |
| pLas + pLX_TRC313_ LacZ (1:1000) | 20170T2 924 | B06 | sgRNA | 90.40% | GGACGCTAAAC CAACGGTGC | FALSE | 2 | GGACGCTAAACC AACGGTGC | 2914 |
| pLas + pLX_TRC313_ LacZ (1:1000) | 20170T2 924 | B07 | pL42_ pool1 | 96.30% | AAGGAGGACGG CAACATCCT | FALSE | 2 | GAATGAACCACG | 5476 |
| pLas + pLX_TRC313_ LacZ (1:1000) | 20170T2 924 | B07 | sgRNA | 90.40% | AAGGAGGACGG CAACATCCT | FALSE | 2 | AAGGAGGACGGC AACATCCT | 3405 |
| pLas + pLX_TRC313_ LacZ (1:1000) | 20170T2 924 | B08 | pL42_ pool1 | 96.70% | TGTACTCCAGCT TGTGCCCC | FALSE | 2 | AGCTCTGACACA | 5351 |
| pLas + pLX_TRC313_ LacZ (1:1000) | 20170T2 924 | B08 | sgRNA | 90.90% | TGTACTCCAGCT TGTGCCCC | FALSE | 2 | TGTACTCCAGCTT GTGCCCC | 3306 |
| pLas + pLX_TRC313_ LacZ (1:1000) | 20170T2 924 | B09 | pL42_ pool1 | 97.40% | GTACAGCTAAG TTAAACTCG | FALSE | 2 | TCCATCAATACG | 5332 |
| pLas + pLX_TRC313_ LacZ (1:1000) | 20170T2 924 | B09 | sgRNA | 90.30% | GTACAGCTAAG TTAAACTCG | FALSE | 2 | GTACAGCTAAGT TAAACTCG | 3539 |
| pLas + pLX_TRC313_ LacZ (1:1000) | 20170T2 924 | B10 | pL42_ pool1 | 96.80% | GGACGCTAAAC CAACGGTGC | FALSE | 2 | GACAGGCTACCT | 5495 |
| pLas + pLX_TRC313_ LacZ (1:1000) | 20170T2 924 | B10 | sgRNA | 90.90% | GGACGCTAAAC CAACGGTGC | FALSE | 2 | GGACGCTAAACC AACGGTGC | 3426 |
| pLas + pLX_TRC313_ LacZ (1:1000) | 20170T2 924 | B11 | pL42_ pool1 | 96.20% | GCCGTGCCGTA GCTATCCGG | FALSE | 2 | CTCACTGACACT | 5434 |
| pLas + pLX_TRC313_ LacZ (1:1000) | 20170T2 924 | B11 | sgRNA | 90.00% | GCCGTGCCGTA GCTATCCGG | FALSE | 2 | GCCGTGCCGTAG CTATCCGG | 2941 |

TABLE 2-continued

| condition | date | platewell | pattern | fraction | pred_sgRNA | solitary | matches_per_sample | match | count |
|---|---|---|---|---|---|---|---|---|---|
| pLas + pLX_TRC313_ LacZ (1:1000) | 20170T2 924 | B12 | pL42_ pool1 | 96.30% | AGGAGGACGGC AACATCCTG | FALSE | 2 | AGCGACCTTACA | 5569 |
| pLas + pLX_TRC313_ LacZ (1:1000) | 20170T2 924 | B12 | sgRNA | 91.10% | AGGAGGACGGC AACATCCTG | FALSE | 2 | AGGAGGACGGCA ACATCCTG | 2966 |
| pLas + pLX_TRC313_ LacZ (1:1000) | 20170T2 924 | C01 | pL42_ pool1 | 97.70% | GTACAGCTAAG TTAAACTCG | FALSE | 2 | CTAGATGTTAGC | 6135 |
| pLas + pLX_TRC313_ LacZ (1:1000) | 20170T2 924 | C01 | sgRNA | 88.80% | GTACAGCTAAG TTAAACTCG | FALSE | 2 | GTACAGCTAAGT TAAACTCG | 3119 |
| pLas + pLX_TRC313_ LacZ (1:1000) | 20170T2 924 | C02 | pL42_ pool1 | 97.10% | TGTACTCCAGCT TGTGCCCC | FALSE | 2 | AGCGCCGTCATT | 5592 |
| pLas + pLX_TRC313_ LacZ (1:1000) | 20170T2 924 | C02 | sgRNA | 90.60% | TGTACTCCAGCT TGTGCCCC | FALSE | 2 | TGTACTCCAGCTT GTGCCCC | 3382 |
| pLas + pLX_TRC313_ LacZ (1:1000) | 20170T2 924 | C03 | pL42_ pool1 | 96.90% | GCCGTGCCGTA GCTATCCGG | FALSE | 2 | GACAACGAGAAC | 5672 |
| pLas + pLX_TRC313_ LacZ (1:1000) | 20170T2 924 | C03 | sgRNA | 90.70% | GCCGTGCCGTA GCTATCCGG | FALSE | 2 | GCCGTGCCGTAG CTATCCGG | 3822 |
| pLas + pLX_TRC313_ LacZ (1:1000) | 20170T2 924 | C04 | pL42_ pool1 | 97.20% | AGGAGGACGGC AACATCCTG | FALSE | 2 | GAATGGACAGCG | 5859 |
| pLas + pLX_TRC313_ LacZ (1:1000) | 20170T2 924 | C04 | sgRNA | 91.00% | AGGAGGACGGC AACATCCTG | FALSE | 2 | AGGAGGACGGCA ACATCCTG | 3447 |
| pLas + pLX_TRC313_ LacZ (1:1000) | 20170T2 924 | C05 | pL42_ pool1 | 97.30% | CAACATCCTGG GGCACAAGC | FALSE | 2 | GAACGCGAAAGC | 5788 |
| pLas + pLX_TRC313_ LacZ (1:1000) | 20170T2 924 | C05 | sgRNA | 89.70% | CAACATCCTGG GGCACAAGC | FALSE | 2 | CAACATCCTGGG GCACAAGC | 3877 |
| pLas + pLX_TRC313_ LacZ (1:1000) | 20170T2 924 | C06 | pL42_ pool1 | 96.90% | GTCCGTTCGACA ATTTCACA | FALSE | 2 | GACAAGTACACT | 6389 |
| pLas + pLX_TRC313_ LacZ (1:1000) | 20170T2 924 | C06 | sgRNA | 87.60% | GTCCGTTCGACA ATTTCACA | FALSE | 2 | GTCCGTTCGACA ATTTCACA | 3539 |
| pLas + pLX_TRC313_ LacZ (1:1000) | 20170T2 924 | C09 | pL42_ pool1 | 96.10% | GCCGTGCCGTA GCTATCCGG | FALSE | 2 | CTCACTGACACT | 5733 |
| pLas + pLX_TRC313_ LacZ (1:1000) | 20170T2 924 | C09 | sgRNA | 90.70% | GCCGTGCCGTA GCTATCCGG | FALSE | 2 | GCCGTGCCGTAG CTATCCGG | 3107 |
| pLas + pLX_TRC313_ LacZ (1:1000) | 20170T2 924 | C11 | pL42_ pool1 | 96.50% | AAGGAGGACGG CAACATCCT | FALSE | 2 | TCCAAAGAGACA | 5408 |
| pLas + pLX_TRC313_ LacZ (1:1000) | 20170T2 924 | C11 | sgRNA | 91.40% | AAGGAGGACGG CAACATCCT | FALSE | 2 | AAGGAGGACGGC AACATCCT | 3554 |

TABLE 2-continued

| condition | date | platewell | pattern | fraction | pred_sgRNA | solitary | matches_per_sample | match | count |
|---|---|---|---|---|---|---|---|---|---|
| pLas + pLX_TRC313_ LacZ (1:1000) | 20170T2 924 | C12 | pL42_ pool1 | 96.40% | GGACGCTAAAC CAACGGTGC | FALSE | 2 | TCCAGAGCACCT | 6109 |
| pLas + pLX_TRC313_ LacZ (1:1000) | 20170T2 924 | C12 | sgRNA | 89.80% | GGACGCTAAAC CAACGGTGC | FALSE | 2 | GGACGCTAAACC AACGGTGC | 3255 |
| pLas + pLX_TRC313_ LacZ (1:1000) | 20170T2 924 | D01 | pL42_ pool1 | 96.90% | GGACGCTAAAC CAACGGTGC | FALSE | 2 | AGAGACTTCACA | 5626 |
| pLas + pLX_TRC313_ LacZ (1:1000) | 20170T2 924 | D01 | sgRNA | 88.60% | GGACGCTAAAC CAACGGTGC | FALSE | 2 | GGACGCTAAACC AACGGTGC | 2686 |
| pLas + pLX_TRC313_ LacZ (1:1000) | 20170T2 924 | D02 | pL42_ pool1 | 96.80% | GGACGCTAAAC CAACGGTGC | FALSE | 2 | TCCAGAGCACCT | 6040 |
| pLas + pLX_TRC313_ LacZ (1:1000) | 20170T2 924 | D02 | sgRNA | 91.20% | GGACGCTAAAC CAACGGTGC | FALSE | 2 | GGACGCTAAACC AACGGTGC | 3286 |
| pLas + pLX_TRC313_ LacZ (1:1000) | 20170T2 924 | D03 | pL42_ pool1 | 97.10% | GCTGCTTGCGAT ACCAATAG | TRUE | 2 | GAAGTGGGCAAC | 5323 |
| pLas + pLX_TRC313_ LacZ (1:1000) | 20170T2 924 | D03 | sgRNA | 90.30% | TGTACTCCAGCT TGTGCCCC | TRUE | 2 | TGTACTCCAGCTT GTGCCCC | 3042 |
| pLas + pLX_TRC313_ LacZ (1:1000) | 20170T2 924 | D04 | pL42_ pool1 | 96.30% | TGTACTCCAGCT TGTGCCCC | FALSE | 2 | AGCTCTGACACA | 5512 |
| pLas + pLX_TRC313_ LacZ (1:1000) | 20170T2 924 | D04 | sgRNA | 89.40% | TGTACTCCAGCT TGTGCCCC | FALSE | 2 | TGTACTCCAGCTT GTGCCCC | 2991 |
| pLas + pLX_TRC313_ LacZ (1:1000) | 20170T2 924 | D05 | pL42_ pool1 | 96.20% | GCCGTGCCGTA GCTATCCGG | FALSE | 2 | CTCACTGACACT | 5837 |
| pLas + pLX_TRC313_ LacZ (1:1000) | 20170T2 924 | D05 | sgRNA | 89.70% | GCCGTGCCGTA GCTATCCGG | FALSE | 2 | GCCGTGCCGTAG CTATCCGG | 3416 |
| pLas + pLX_TRC313_ LacZ (1:1000) | 20170T2 924 | D06 | pL42_ pool1 | 98.00% | TGTACTCCAGCT TGTGCCCC | FALSE | 2 | AGCTAGCCTAGG | 6296 |
| pLas + pLX_TRC313_ LacZ (1:1000) | 20170T2 924 | D06 | sgRNA | 90.50% | TGTACTCCAGCT TGTGCCCC | FALSE | 2 | TGTACTCCAGCTT GTGCCCC | 3879 |
| pLas + pLX_TRC313_ LacZ (1:1000) | 20170T2 924 | D07 | pL42_ pool1 | 96.80% | AAGGAGGACGG CAACATCCT | FALSE | 2 | CTAGTGTCCACA | 5837 |
| pLas + pLX_TRC313_ LacZ (1:1000) | 20170T2 924 | D07 | sgRNA | 91.60% | AAGGAGGACGG CAACATCCT | FALSE | 2 | AAGGAGGACGGC AACATCCT | 3677 |
| pLas + pLX_TRC313_ LacZ (1:1000) | 20170T2 924 | D08 | pL42_ pool1 | 97.10% | CAAGGAGGACG GCAACATCC | FALSE | 2 | AGCCAGTCAATC | 6163 |
| pLas + pLX_TRC313_ LacZ (1:1000) | 20170T2 924 | D08 | sgRNA | 90.60% | CAAGGAGGACG GCAACATCC | FALSE | 2 | CAAGGAGGACGG CAACATCC | 3415 |

TABLE 2-continued

| condition | date | platewell | pattern | fraction | pred_sgRNA | solitary | matches_per_sample | match | count |
|---|---|---|---|---|---|---|---|---|---|
| pLas + pLX_TRC313_ LacZ (1:1000) | 20170T2 924 | D09 | pL42_ pool1 | 97.50% | GCCGTGCCGTA GCTATCCGG | TRUE | 2 | GACATGCGTAGC | 5736 |
| pLas + pLX_TRC313_ LacZ (1:1000) | 20170T2 924 | D09 | sgRNA | 88.00% | GTCCGTTCGACA ATTTCACA | TRUE | 2 | GTCCGTTCGACA ATTTCACA | 3192 |
| pLas + pLX_TRC313_ LacZ (1:1000) | 20170T2 924 | D10 | pL42_ pool1 | 45.70% | GCCGTGCCGTA GCTATCCGG | FALSE | 4 | AGATGATAACGG | 2661 |
| pLas + pLX_TRC313_ LacZ (1:1000) | 20170T2 924 | D10 | pL42_ pool1 | 51.10% | GTCCGTTCGACA ATTTCACA | FALSE | 4 | AGCAACTTCACT | 2976 |
| pLas + pLX_TRC313_ LacZ (1:1000) | 20170T2 924 | D10 | sgRNA | 43.30% | GCCGTGCCGTA GCTATCCGG | FALSE | 4 | GCCGTGCCGTAG CTATCCGG | 1374 |
| pLas + pLX_TRC313_ LacZ (1:1000) | 20170T2 924 | D10 | sgRNA | 44.70% | GTCCGTTCGACA ATTTCACA | FALSE | 4 | GTCCGTTCGACA ATTTCACA | 1416 |
| pLas + pLX_TRC313_ LacZ (1:1000) | 20170T2 924 | D11 | pL42_ pool1 | 96.60% | GTCCGTTCGACA ATTTCACA | FALSE | 2 | AGCAACTTCACT | 5158 |
| pLas + pLX_TRC313_ LacZ (1:1000) | 20170T2 924 | D11 | sgRNA | 86.80% | GTCCGTTCGACA ATTTCACA | FALSE | 2 | GTCCGTTCGACA ATTTCACA | 2929 |
| pLas + pLX_TRC313_ LacZ (1:1000) | 20170T2 924 | D12 | pL42_ pool1 | 97.30% | GCTGCTTGCGAT ACCAATAG | FALSE | 2 | AGCAGCCCTAGC | 5908 |
| pLas + pLX_TRC313_ LacZ (1:1000) | 20170T2 924 | D12 | sgRNA | 89.00% | GCTGCTTGCGAT ACCAATAG | FALSE | 2 | GCTGCTTGCGAT ACCAATAG | 3297 |
| pLas + pLX_TRC313_ LacZ (1:1000) | 20170T2 924 | E01 | pL42_ pool1 | 97.50% | CAAGGAGGACG GCAACATCC | FALSE | 2 | GAACTCAGGACA | 6341 |
| pLas + pLX_TRC313_ LacZ (1:1000) | 20170T2 924 | E01 | sgRNA | 90.10% | CAAGGAGGACG GCAACATCC | FALSE | 2 | CAAGGAGGACGG CAACATCC | 3297 |
| pLas + pLX_TRC313_ LacZ (1:1000) | 20170T2 924 | E02 | pL42_ pool1 | 96.60% | CAAGGAGGACG GCAACATCC | FALSE | 2 | CTATATATGACC | 5665 |
| pLas + pLX_TRC313_ LacZ (1:1000) | 20170T2 924 | E02 | sgRNA | 92.20% | CAAGGAGGACG GCAACATCC | FALSE | 2 | CAAGGAGGACGG CAACATCC | 3177 |
| pLas + pLX_TRC313_ LacZ (1:1000) | 20170T2 924 | E03 | pL42_ pool1 | 96.00% | GTCCGTTCGACA ATTTCACA | FALSE | 2 | CTCAATTTACAG | 5694 |
| pLas + pLX_TRC313_ LacZ (1:1000) | 20170T2 924 | E03 | sgRNA | 86.90% | GTCCGTTCGACA ATTTCACA | FALSE | 2 | GTCCGTTCGACA ATTTCACA | 2666 |
| pLas + pLX_TRC313_ LacZ (1:1000) | 20170T2 924 | E04 | pL42_ pool1 | 96.20% | GGACGCTAAAC CAACGGTGC | FALSE | 2 | TCCAGAGCACCT | 5711 |
| pLas + pLX_TRC313_ LacZ (1:1000) | 20170T2 924 | E04 | sgRNA | 88.20% | GGACGCTAAAC CAACGGTGC | FALSE | 2 | GGACGCTAAACC AACGGTGC | 3074 |

TABLE 2-continued

| condition | date | platewell | pattern | fraction | pred_sgRNA | solitary | matches_per_sample | match | count |
|---|---|---|---|---|---|---|---|---|---|
| pLas + pLX_TRC313_LacZ (1:1000) | 20170T2924 | E05 | pL42_pool1 | 96.10% | GGACGCTAAACCAACGGTGC | FALSE | 2 | AGAGACTTCACA | 6920 |
| pLas + pLX_TRC313_LacZ (1:1000) | 20170T2924 | E05 | sgRNA | 88.80% | GGACGCTAAACCAACGGTGC | FALSE | 2 | GGACGCTAAACCAACGGTGC | 3316 |
| pLas + pLX_TRC313_LacZ (1:1000) | 20170T2924 | E06 | pL42_pool1 | 96.50% | CAAGGAGGACGGCAACATCC | FALSE | 2 | AGCCACCAGTAT | 5948 |
| pLas + pLX_TRC313_LacZ (1:1000) | 20170T2924 | E06 | sgRNA | 90.70% | CAAGGAGGACGGCAACATCC | FALSE | 2 | CAAGGAGGACGGCAACATCC | 3701 |
| pLas + pLX_TRC313_LacZ (1:1000) | 20170T2924 | E07 | pL42_pool1 | 96.90% | CAACATCCTGGGGCACAAGC | FALSE | 2 | GAACGCGAAAGC | 6218 |
| pLas + pLX_TRC313_LacZ (1:1000) | 20170T2924 | E07 | sgRNA | 88.20% | CAACATCCTGGGGCACAAGC | FALSE | 2 | CAACATCCTGGGGCACAAGC | 3216 |
| pLas + pLX_TRC313_LacZ (1:1000) | 20170T2924 | E09 | pL42_pool1 | 97.30% | TGTACTCCAGCTTGTGCCCC | FALSE | 2 | AGCTAGCCTAGG | 6260 |
| pLas + pLX_TRC313_LacZ (1:1000) | 20170T2924 | E09 | sgRNA | 89.40% | TGTACTCCAGCTTGTGCCCC | FALSE | 2 | TGTACTCCAGCTTGTGCCCC | 2857 |
| pLas + pLX TRC313 LacZ (1:1000) | 20170T2924 | E10 | pL42_pool1 | 95.60% | AGGAGGACGGCAACATCCTG | FALSE | 2 | AGCGACCTTACA | 5526 |
| pLas + pLX TRC313 LacZ (1:1000) | 20170T2924 | E10 | sgRNA | 90.80% | AGGAGGACGGCAACATCCTG | FALSE | 2 | AGGAGGACGGCAACATCCTG | 3033 |
| pLas + pLX TRC313 LacZ (1:1000) | 20170T2924 | E11 | pL42_pool1 | 97.20% | AAGGAGGACGGCAACATCCT | FALSE | 2 | GAATCCGCTCGC | 5387 |
| pLas + pLX TRC313 LacZ (1:1000) | 20170T2924 | E11 | sgRNA | 91.20% | AAGGAGGACGGCAACATCCT | FALSE | 2 | AAGGAGGACGGCAACATCCT | 2772 |
| pLas, standard_400 | 20170T2924 | F01 | pL42_pool1 | 97.50% | GCCGTGCCGTAGCTATCCGG | FALSE | 2 | AGATGATAACGG | 6077 |
| pLas, standard_400 | 20170T2924 | F01 | sgRNA | 88.50% | GCCGTGCCGTAGCTATCCGG | FALSE | 2 | GCCGTGCCGTAGCTATCCGG | 3723 |
| pLas, standard_400 | 20170T2924 | F02 | pL42_pool1 | 97.50% | CAAGGAGGACGGCAACATCC | FALSE | 2 | AGCCACCAGTAT | 5535 |
| pLas, standard_400 | 20170T2924 | F02 | sgRNA | 91.70% | CAAGGAGGACGGCAACATCC | FALSE | 2 | CAAGGAGGACGGCAACATCC | 3850 |
| pLas, standard_400 | 20170T2924 | F04 | pL42_pool1 | 96.80% | GTACAGCTAAGTTAAACTCG | TRUE | 2 | TCCATCAATACG | 5844 |
| pLas, standard_400 | 20170T2924 | F04 | sgRNA | 90.30% | CAAGGAGGACGGCAACATCC | TRUE | 2 | CAAGGAGGACGGCAACATCC | 3878 |
| pLas, standard_400 | 20170T2924 | F05 | pL42_pool1 | 96.90% | GTCCGTTCGACAATTTCACA | FALSE | 2 | AGATGGGTTCCG | 5399 |
| pLas, standard_400 | 20170T2924 | F05 | sgRNA | 86.50% | GTCCGTTCGACAATTTCACA | FALSE | 2 | GTCCGTTCGACAATTTCACA | 3780 |

TABLE 2-continued

| condition | date | plate | well | pattern | pat-fraction | pred_sgRNA | solitary | matches_per_sample | match | count |
|---|---|---|---|---|---|---|---|---|---|---|
| pLas, standard_400 | 20170T2924 | | F06 | pL42_pool1 | 96.20% | GCCGTGCCGTAGCTATCCGG | FALSE | 2 | CTCACTGACACT | 6156 |
| pLas, standard_400 | 20170T2924 | | F06 | sgRNA | 90.90% | GCCGTGCCGTAGCTATCCGG | FALSE | 2 | GCCGTGCCGTAGCTATCCGG | 3688 |
| pLas, standard_400 | 20170T2924 | | F07 | pL42_pool1 | 97.00% | GTCCGTTCGACAATTTCACA | FALSE | 2 | AGATGGGTTCCG | 6019 |
| pLas, standard_400 | 20170T2924 | | F07 | sgRNA | 88.60% | GTCCGTTCGACAATTTCACA | FALSE | 2 | GTCCGTTCGACAATTTCACA | 3235 |
| pLas, standard_400 | 20170T2924 | | G01 | pL42_pool1 | 46.40% | GTCCGTTCGACAATTTCACA | FALSE | 4 | AGCAACTTCACT | 2689 |
| pLas, standard_400 | 20170T2924 | | G01 | pL42_pool1 | 50.90% | TGTACTCCAGCTTGTGCCCC | TRUE | 4 | AGCTAGCCTAGG | 2953 |
| pLas, standard_400 | 20170T2924 | | G01 | sgRNA | 40.80% | GTCCGTTCGACAATTTCACA | FALSE | 4 | GTCCGTTCGACAATTTCACA | 1683 |
| pLas, standard_400 | 20170T2924 | | G01 | sgRNA | 41.40% | CAAGGAGGACGGCAACATCC | TRUE | 4 | CAAGGAGGACGGCAACATCC | 1711 |
| pLas, standard_400 | 20170T2924 | | G02 | pL42_pool1 | 97.00% | GTCCGTTCGACAATTTCACA | FALSE | 2 | GACAAGTACACT | 5757 |
| pLas, standard_400 | 20170T2924 | | G02 | sgRNA | 87.80% | GTCCGTTCGACAATTTCACA | FALSE | 2 | GTCCGTTCGACAATTTCACA | 3507 |
| pLas, standard_400 | 20170T2924 | | G03 | pL42_pool1 | 96.80% | GTCCGTTCGACAATTTCACA | TRUE | 2 | AGATGGGTTCCG | 5176 |
| pLas, standard_400 | 20170T2924 | | G03 | sgRNA | 90.90% | AAGGAGGACGGCAACATCCT | TRUE | 2 | AAGGAGGACGGCAACATCCT | 3746 |
| pLas, standard_400 | 20170T2924 | | G04 | pL42_pool1 | 97.00% | CAAGGAGGACGGCAACATCC | TRUE | 2 | AGCCAGTCAATC | 8030 |
| pLas, standard_400 | 20170T2924 | | G04 | sgRNA | 86.70% | GTCCGTTCGACAATTTCACA | TRUE | 2 | GTCCGTTCGACAATTTCACA | 3434 |
| pLas, standard_400 | 20170T2924 | | G05 | pL42_pool1 | 96.80% | GTCCGTTCGACAATTTCACA | TRUE | 2 | AGCAACTTCACT | 5624 |
| pLas, standard_400 | 20170T2924 | | G05 | sgRNA | 90.20% | CAACATCCTGGGGCACAAGC | TRUE | 2 | CAACATCCTGGGGCACAAGC | 4140 |
| pLas, standard_400 | 20170T2924 | | G06 | pL42_pool1 | 44.90% | GGACGCTAAACCAACGGTGC | FALSE | 4 | GACAGGCTACCT | 2487 |
| pLas, standard_400 | 20170T2924 | | G06 | pL42_pool1 | 52.20% | AGGAGGACGGCAACATCCTG | FALSE | 4 | GAATGGACAGCG | 2895 |
| pLas, standard_400 | 20170T2924 | | G06 | sgRNA | 44.80% | GGACGCTAAACCAACGGTGC | FALSE | 4 | GGACGCTAAACCAACGGTGC | 1766 |
| pLas, standard_400 | 20170T2924 | | G06 | sgRNA | 46.10% | AGGAGGACGGCAACATCCTG | FALSE | 4 | AGGAGGACGGCAACATCCTG | 1817 |
| pLas, standard_400 | 20170T2924 | | G07 | pL42_pool1 | 97.30% | TGTACTCCAGCTTGTGCCCC | TRUE | 2 | AGCGCCGTCATT | 5570 |
| pLas, standard_400 | 20170T2924 | | G07 | sgRNA | 89.90% | AAGGAGGACGGCAACATCCT | TRUE | 2 | AAGGAGGACGGCAACATCCT | 3693 |
| pLas, standard_400 | 20170T2924 | | G08 | pL42_pool1 | 96.60% | TGTACTCCAGCTTGTGCCCC | TRUE | 2 | AGCGCCGTCATT | 5248 |
| pLas, standard_400 | 20170T2924 | | G08 | sgRNA | 91.60% | AAGGAGGACGGCAACATCCT | TRUE | 2 | AAGGAGGACGGCAACATCCT | 3721 |

TABLE 2-continued

| condition | date | platewell | pattern | fraction | pred_sgRNA | solitary | matches_per_sample | match | count |
|---|---|---|---|---|---|---|---|---|---|
| pLas, standard_400 | 20170T2924 | G09 | pL42_pool1 | 47.40% | AAGGAGGACGGCAACATCCT | TRUE | 4 | GAATGAACCACG | 2772 |
| pLas, standard_400 | 20170T2924 | G09 | pL42_pool1 | 49.50% | CAACATCCTGGGGCACAAGC | FALSE | 4 | GAACGCGAAAGC | 2895 |
| pLas, standard_400 | 20170T2924 | G09 | sgRNA43 | 30% | CAACATCCTGGGGCACAAGC | FALSE | 4 | CAACATCCTGGGGCACAAGC | 1706 |
| pLas, standard_400 | 20170T2924 | G09 | sgRNA44 | 60% | GCCGTGCCGTAGCTATCCGG | TRUE | 4 | GCCGTGCCGTAGCTATCCGG | 1760 |
| pLas, standard_400 | 20170T2924 | G10 | pL42_pool1 | 96.50% | CAAGGAGGACGGCAACATCC | FALSE | 2 | AGCCAGTCAATC | 6342 |
| pLas, standard_400 | 20170T2924 | G10 | sgRNA91 | 60% | CAAGGAGGACGGCAACATCC | FALSE | 2 | CAAGGAGGACGGCAACATCC | 3814 |
| pLas, standard_400 | 20170T2924 | G11 | pL42_pool1 | 97.20% | AGGAGGACGGCAACATCCTG | FALSE | 2 | AGCGGTATAACT | 5601 |
| pLas, standard_400 | 20170T2924 | G11 | sgRNA90 | 60% | AGGAGGACGGCAACATCCTG | FALSE | 2 | AGGAGGACGGCAACATCCTG | 3625 |
| pLas, standard_400 | 20170T2924 | G12 | pL42_pool1 | 97.00% | GTACAGCTAAGTTAAACTCG | FALSE | 2 | TCCATCAATACG | 6172 |
| pLas, standard_400 | 20170T2924 | G12 | sgRNA90 | 50% | GTACAGCTAAGTTAAACTCG | FALSE | 2 | GTACAGCTAAGTTAAACTCG | 4107 |
| pLas, standard_400 | 20170T2924 | H02 | pL42_pool1 | 96.60% | CAACATCCTGGGGCACAAGC | FALSE | 2 | AGCTTTCTGACT | 6904 |
| pLas, standard_400 | 20170T2924 | H02 | sgRNA89 | 70% | CAACATCCTGGGGCACAAGC | FALSE | 2 | CAACATCCTGGGGCACAAGC | 4167 |
| pLas, standard_400 | 20170T2924 | H04 | pL42_pool1 | 97.10% | CAACATCCTGGGGCACAAGC | FALSE | 2 | GAACGCGAAAGC | 6597 |
| pLas, standard_400 | 20170T2924 | H04 | sgRNA88 | 90% | CAACATCCTGGGGCACAAGC | FALSE | 2 | CAACATCCTGGGGCACAAGC | 4441 |
| pLas, standard_400 | 20170T2924 | H05 | pL42_pool1 | 96.90% | AGGAGGACGGCAACATCCTG | FALSE | 2 | AGCGGTATAACT | 5605 |
| pLas, standard_400 | 20170T2924 | H05 | sgRNA91 | 70% | AGGAGGACGGCAACATCCTG | FALSE | 2 | AGGAGGACGGCAACATCCTG | 5041 |
| pLas, standard_400 | 20170T2924 | H06 | pL42_pool1 | 97.20% | GCTGCTTGCGATACCAATAG | TRUE | 2 | AGAGCTGCTACG | 6005 |
| pLas, standard_400 | 20170T2924 | H06 | sgRNA90 | 60% | AAGGAGGACGGCAACATCCT | TRUE | 2 | AAGGAGGACGGCAACATCCT | 4160 |
| pLas, standard_400 | 20170T2924 | H07 | pL42_pool1 | 97.00% | CAAGGAGGACGGCAACATCC | TRUE | 2 | AGCCAGTCAATC | 6670 |
| pLas, standard_400 | 20170T2924 | H07 | sgRNA91 | 40% | TGTACTCCAGCTTGTGCCCC | TRUE | 2 | TGTACTCCAGCTTGTGCCCC | 3692 |
| pLas, standard_400 | 20170T2924 | H08 | pL42_pool1 | 47.30% | AAGGAGGACGGCAACATCCT | TRUE | 4 | GAATGAACCACG | 2843 |
| pLas, standard_400 | 20170T2924 | H08 | pL42_pool1 | 49.30% | CAACATCCTGGGGCACAAGC | FALSE | 4 | GAACGCGAAAGC | 2960 |
| pLas, standard_400 | 20170T2924 | H08 | sgRNA42 | 30% | CAACATCCTGGGGCACAAGC | FALSE | 4 | CAACATCCTGGGGCACAAGC | 1458 |
| pLas, standard_400 | 20170T2924 | H08 | sgRNA46 | 70% | GCCGTGCCGTAGCTATCCGG | TRUE | 4 | GCCGTGCCGTAGCTATCCGG | 1607 |

TABLE 2-continued

| condition | date | platewell | pat-tern | frac-tion | pred_sgRNA | soli-tary | matches_per_sam-ple | match | count |
|---|---|---|---|---|---|---|---|---|---|
| pLas, standard_400 | 20170T2 924 | H09 | pL42_pool1 | 97.10% | AGGAGGACGGCAACATCCTG | FALSE | 2 | AGCGGTATAACT | 6040 |
| pLas, standard_400 | 20170T2 924 | H09 | sgRNA | 91.30% | AGGAGGACGGCAACATCCTG | FALSE | 2 | AGGAGGACGGCAACATCCTG | 4335 |
| pLas, standard_400 | 20170T2 924 | H10 | pL42_pool1 | 96.40% | GTACAGCTAAGTTAAACTCG | FALSE | 2 | TCCATCAATACG | 6012 |
| pLas, standard_400 | 20170T2 924 | H10 | sgRNA | 91.80% | GTACAGCTAAGTTAAACTCG | FALSE | 2 | GTACAGCTAAGTTAAACTCG | 4678 |
| pLas, standard_400 | 20170T2 924 | H11 | pL42_pool1 | 97.20% | GGACGCTAAACCAACGGTGC | FALSE | 2 | GACAGGCTACCT | 2525 |
| pLas, standard_400 | 20170T2 924 | H11 | sgRNA | 90.50% | GGACGCTAAACCAACGGTGC | FALSE | 2 | GGACGCTAAACCAACGGTGC | 4621 |
| pLas, standard_400 | 20170T2 924 | H12 | pL42_pool1 | 96.60% | GGACGCTAAACCAACGGTGC | FALSE | 2 | AGAGACTTCACA | 6601 |
| pLas, standard_400 | 20170T2 924 | H12 | sgRNA | 90.60% | GGACGCTAAACCAACGGTGC | FALSE | 2 | GGACGCTAAACCAACGGTGC | 5162 |
| pLas + pLX_TRC313_LacZ (1:100) | 20170T1 924 | G01 | pL42_pool1 | 96.40% | AGGAGGACGGCAACATCCTG | FALSE | 2 | GATATCGTGACC | 5913 |
| pLas + pLX_TRC313_LacZ (1:100) | 20170T1 924 | G01 | sgRNA | 89.90% | AGGAGGACGGCAACATCCTG | FALSE | 2 | AGGAGGACGGCAACATCCTG | 1376 |
| pLas + pLX_TRC313_LacZ (1:100) | 20170T1 924 | G02 | pL42_pool1 | 97.00% | CAACATCCTGGGGCACAAGC | FALSE | 2 | CAACGCCCAAGG | 5458 |
| pLas + pLX_TRC313_LacZ (1:100) | 20170T1 924 | G02 | sgRNA | 91.20% | CAACATCCTGGGGCACAAGC | FALSE | 2 | CAACATCCTGGGGCACAAGC | 4271 |
| pLas + pLX_TRC313_LacZ (1:100) | 20170T1 924 | G03 | pL42_pool1 | 46.10% | AAGGAGGACGGCAACATCCT | FALSE | 4 | TAGGAAGTTAGG | 2373 |
| pLas + pLX_TRC313_LacZ (1:100) | 20170T1 924 | G03 | pL42_pool1 | 50.90% | TGTACTCCAGCTTGTGCCCC | FALSE | 4 | TTCGCCGAAAGC | 2622 |
| pLas + pLX_TRC313_LacZ (1:100) | 20170T1 924 | G03 | sgRNA | 43.60% | TGTACTCCAGCTTGTGCCCC | FALSE | 4 | TGTACTCCAGCTTGTGCCCC | 2285 |
| pLas + pLX_TRC313_LacZ (1:100) | 20170T1 924 | G03 | sgRNA | 47.10% | AAGGAGGACGGCAACATCCT | FALSE | 4 | AAGGAGGACGGCAACATCCT | 2470 |
| pLas + pLX_TRC313_LacZ (1:100) | 20170T1 924 | G04 | pL42_pool1 | 97.80% | CAAGGAGGACGGCAACATCC | FALSE | 2 | AGGCTATTAATG | 5677 |
| pLas + pLX_TRC313_LacZ (1:100) | 20170T1 924 | G04 | sgRNA | 90.80% | CAAGGAGGACGGCAACATCC | FALSE | 2 | CAAGGAGGACGGCAACATCC | 4803 |
| pLas + pLX_TRC313_LacZ (1:100) | 20170T1 924 | G05 | pL42_pool1 | 97.20% | GCTGCTTGCGATACCAATAG | FALSE | 2 | ATCAGTGGCAGC | 5807 |
| pLas + pLX_TRC313_LacZ (1:100) | 20170T1 924 | G05 | sgRNA | 89.20% | GCTGCTTGCGATACCAATAG | FALSE | 2 | GCTGCTTGCGATACCAATAG | 4589 |

TABLE 2-continued

| condition | date | platewell | pat-tern | frac-tion | pred_sgRNA | soli-tary | matches_per_sample | match | count |
|---|---|---|---|---|---|---|---|---|---|
| pLas + pLX_TRC313_LacZ (1:100) | 20170T1924 | G06 | pL42_pool1 | 96.90% | CAACATCCTGGGGCACAAGC | TRUE | 2 | TGTTAATGCAGG | 7332 |
| pLas + pLX_TRC313_LacZ (1:100) | 20170T1924 | G06 | sgRNA | 90.50% | GGACGCTAAACCAACGGTGC | TRUE | 2 | GGACGCTAAACCAACGGTGC | 4568 |
| pLas + pLX_TRC313_LacZ (1:100) | 20170T1924 | G07 | pL42_pool1 | 96.80% | CAACATCCTGGGGCACAAGC | FALSE | 2 | TCTATTTGACGG | 5698 |
| pLas + pLX_TRC313_LacZ (1:100) | 20170T1924 | G07 | sgRNA | 89.70% | CAACATCCTGGGGCACAAGC | FALSE | 2 | CAACATCCTGGGGCACAAGC | 3855 |
| pLas + pLX_TRC313_LacZ (1:100) | 20170T1924 | G08 | pL42_pool1 | 95.60% | CAACATCCTGGGGCACAAGC | FALSE | 2 | CCGTAACGAACA | 5272 |
| pLas + pLX_TRC313_LacZ (1:100) | 20170T1924 | G08 | sgRNA | 89.80% | CAACATCCTGGGGCACAAGC | FALSE | 2 | CAACATCCTGGGGCACAAGC | 3373 |
| pLas + pLX_TRC313_LacZ (1:100) | 20170T1924 | G09 | pL42_pool1 | 97.20% | GGACGCTAAACCAACGGTGC | FALSE | 2 | AGTTTGCAGCCA | 5286 |
| pLas + pLX_TRC313_LacZ (1:100) | 20170T1924 | G09 | sgRNA | 90.80% | GGACGCTAAACCAACGGTGC | FALSE | 2 | GGACGCTAAACCAACGGTGC | 3837 |
| pLas + pLX_TRC313_LacZ (1:100) | 20170T1924 | G10 | pL42_pool1 | 95.30% | GGACGCTAAACCAACGGTGC | FALSE | 2 | TCGAAATGACAC | 5229 |
| pLas + pLX_TRC313_LacZ (1:100) | 20170T1924 | G10 | sgRNA | 90.70% | GGACGCTAAACCAACGGTGC | FALSE | 2 | GGACGCTAAACCAACGGTGC | 4325 |
| pLas + pLX_TRC313_LacZ (1:100) | 20170T1924 | G11 | pL42_pool1 | 96.80% | AGGAGGACGGCAACATCCTG | FALSE | 2 | TCAGTGAATACG | 4733 |
| pLas + pLX_TRC313_LacZ (1:100) | 20170T1924 | G11 | sgRNA | 90.90% | AGGAGGACGGCAACATCCTG | FALSE | 2 | AGGAGGACGGCAACATCCTG | 3508 |
| pLas + pLX_TRC313_LacZ (1:100) | 20170T1924 | G12 | pL42_pool1 | 96.50% | GCCGTGCCGTAGCTATCCGG | FALSE | 2 | CGCAAAGGATT | 5455 |
| pLas + pLX_TRC313_LacZ (1:100) | 20170T1924 | G12 | sgRNA | 89.20% | GCCGTGCCGTAGCTATCCGG | FALSE | 2 | GCCGTGCCGTAGCTATCCGG | 2269 |
| pLas + pLX_TRC313_LacZ (1:100) | 20170T1924 | H01 | pL42_pool1 | 97.10% | GCTGCTTGCGATACCAATAG | FALSE | 2 | ATCAGTGGCAGC | 5905 |
| pLas + pLX_TRC313_LacZ (1:100) | 20170T1924 | H01 | sgRNA | 88.90% | GCTGCTTGCGATACCAATAG | FALSE | 2 | GCTGCTTGCGATACCAATAG | 1305 |
| pLas + pLX_TRC313_LacZ (1:100) | 20170T1924 | H02 | pL42_pool1 | 47.60% | GCTGCTTGCGATACCAATAG | TRUE | 4 | AACGATGGGACT | 2653 |
| pLas + pLX_TRC313_LacZ (1:100) | 20170T1924 | H02 | pL42_pool1 | 49.00% | AGGAGGACGGCAACATCCTG | FALSE | 4 | TCATTCAGAGCG | 2735 |

TABLE 2-continued

| condition | date | platewell | pattern | fraction | pred_sgRNA | solitary | matches_per_sample | match | count |
|---|---|---|---|---|---|---|---|---|---|
| pLas + pLX_TRC313_LacZ (1:100) | 20170T1 924 | H02 | sgRNA4 | 4.80% | AAGGAGGACGGCAACATCCT | TRUE | 4 | AAGGAGGACGGCAACATCCT | 1222 |
| pLas + pLX_TRC313_LacZ (1:100) | 20170T1 924 | H02 | sgRNA4 | 4.90% | AGGAGGACGGCAACATCCTG | FALSE | 4 | AGGAGGACGGCAACATCCTG | 1224 |
| pLas + pLX_TRC313_LacZ (1:100) | 20170T1 924 | H03 | pL42_95_pool1 | 5.50% | CAACATCCTGGGGCACAAGC | FALSE | 2 | TCTTCACAACCG | 5074 |
| pLas + pLX_TRC313_LacZ (1:100) | 20170T1 924 | H03 | sgRNA9 | 0.00% | CAACATCCTGGGGCACAAGC | FALSE | 2 | CAACATCCTGGGGCACAAGC | 4002 |
| pLas + pLX_TRC313_LacZ (1:100) | 20170T1 924 | H04 | pL42_48_pool1 | 8.50% | GTACAGCTAAGTTAAACTCG | TRUE | 3 | CGTGTGATGATA | 3104 |
| pLas + pLX_TRC313_LacZ (1:100) | 20170T1 924 | H04 | pL42_48_pool1 | 8.60% | AAGGAGGACGGCAACATCCT | FALSE | 3 | ATTGCTATTCGG | 3108 |
| pLas + pLX_TRC313_LacZ (1:100) | 20170T1 924 | H04 | sgRNA9 | 0.60% | AAGGAGGACGGCAACATCCT | FALSE | 3 | AAGGAGGACGGCAACATCCT | 3883 |

```
SEQ ID NO: 1574
LOCUS pLas 7963 bp ds-DNA circular
01-FEB-2018
DEFINITION .
FEATURES
Location/Qualifiers
feature        3591 . . . 4166        /label = "WPRE"
feature         292 . . .  336        /label = "HIV-1_psi_pack"
feature           1 . . .  181        /label = "HIV-1_5_LTR"
promoter       1854 . . . 3111        /label = "EF-1a"
misc_feature   1756 . . . 1841        /label = "scaffold_Dang_2015"
misc_feature   3118 . . . 3492        /label = "ZeoR "
regulatory      846 . . . 1079        /label = "RRE"
primer         1657 . . . 1676        /label = "LKO1_5_primer"
feature        4302 . . . 4482        /label = "HIV-1_5_LTR"
feature        4249 . . . 4301        /label = "delta_U3"
variation      2242 . . . 2242        /label = "C in all sequences"
feature        4232 . . . 4253        /label = "U3PPT"
misc_feature   3516 . . . 3527        /label = "barcode"
misc_feature   1736 . . . 1755        /label = "sgRNA"
feature        4232 . . . 4247        /label = "cPPT"
misc_feature    241 . . .  280        /label = "DIS_1"
promoter       1495 . . . 1734        /label = "hU6_promoter"
ORIGIN 1 gggtctctct ggttagacca gatctgagcc tgggagctct ctggctaact agggaaccca
  61 ctgcttaagc ctcaataaag cttgccttga gtgcttcaag tagtgtgtgc ccgtctgttg
 121 tgtgactctg gtaactagag atccctcaga ccctttagt cagtgtggaa aatctctagc
 181 agtggcgccc gaacagggac ttgaaagcga aagggaaacc agaggagctc tctcgacgca
 241 ggactcggct tgctgaagcg cgcacggcaa gaggcgaggg gcggcgactg gtgagtacgc
 301 caaaaatttt gactagcgga ggctagaagg agagagatgg gtgcgagagc gtcagtatta
 361 agcggggga  aattagatcg cgatgggaaa aaattcggtt aaggccaggg ggaaagaaaa
 421 aatataaatt aaaacatata gtatgggcaa gcagggagct agaacgattc gcagttaatc
```

```
 481 ctggcctgtt agaaacatca gaaggctgta gacaaatact gggacagcta caaccatccc 541 ttcagacagg atcagaagaa cttagatcat tatataatac agtagcaacc ctctattgtg 601 tgcatcaaag gatagagata aaagacacca aggaagcttt agacaagata gaggaagagc 661 aaaacaaaag taagaccacc gcacagcaag cggccgctga tcttcagacc tggaggagga 721 gatatgaggg acaattggag aagtgaatta tataaatata aagtagtaaa aattgaacca 781 ttaggagtag cacccaccaa ggcaaagaga agagtggtgc agagagaaaa aagagcagtg 841 ggaataggag ctttgttcct tgggttcttg ggagcagcag gaagcactat gggcgcagcg 901 tcaatgacgc tgacggtaca ggccagacaa ttattgtctg gtatagtgca gcagcagaac 961 aatttgctga gggctattga ggcgcaacag catctgttgc aactcacagt ctggggcatc 1021 aagcagctcc aggcaagaat cctggctgtg gaaagatacc taaaggatca acagctcctg 1081 gggatttggg gttgctctgg aaaactcatt tgcaccactg ctgtgccttg gaatgctagt 1141 tggagtaata aatctctgga acagatttgg aatcacacga cctggatgga gtgggacaga 1201 gaaattaaca attacacaag cttaatacac tccttaattg aagaatcgca aaaccagcaa 1261 gaaaagaatg aacaagaatt attggaatta gataaatggg caagtttgtg gaattggttt 1321 aacataacaa attggctgtg gtatataaaa ttattcataa tgatagtagg aggcttggta 1381 ggtttaagaa tagttttgc tgtactttct atagtgaata gagttaggca gggatattca 1441 ccattatcgt ttcagaccca cctcccaacc ccgaggggac ccagagaggg cctatttccc 1501 atgattcctt catatttgca tatacgatac aaggctgtta gagagataat tagaattaat 1561 ttgactgtaa acacaaagat attagtacaa aatacgtgac gtagaaagta ataatttctt 1621 gggtagtttg cagttttaaa attatgtttt aaaatggact atcatatgct taccgtaact 1681 tgaaagtatt tcgatttctt ggctttatat atcttGTGGA AAGGACGAAA CACCgnnnnn 1741 nnnnnnnnn nnnnngtttC agagctaTGC TGGAAACAGC Atagcaagtt Gaaataaggc 1801 tagtccgtta tcaacttgaa aaagtggcac cgagtcggtg cTTTTTTgga tcctgcaaag 1861 atggataaag ttttaaacag agaggaatct ttgcagctaa tggaccttct aggtcttgaa 1921 aggagtggga attggctccg gtgcccgtca gtgggcagag cgcacatcgc ccacagtccc 1981 cgagaagttg gggggagggg tcggcaattg atccggtgcc tagagaaggt ggcgcggggt 2041 aaactgggaa agtgatgtcg tgtactggct ccgcctttt cccgagggtg ggggagaacc 2101 gtatataagt gcagtagtcg ccgtgaacgt tctttttcgc aacgggtttg ccgccagaac 2161 acaggtaagt gccgtgtgtg ttcccgcgg gcctggcctc tttacgggtt atggcccttg 2221 cgtgccttga attacttcca ctggctgcag tacgtgattc ttgatcccga gcttcgggtt 2281 ggaagtgggt gggagagttc gaggccttgc gcttaaggag ccccttcgcc tcgtgcttga 2341 gttgaggcct ggcctgggcg ctgggccgc cgcgtgcgaa tctggtggca ccttcgcgcc 2401 tgtctcgctg ctttcgataa gtctctagcc atttaaaatt tttgatgacc tgctgcgacg 2461 cttttttct ggcaagatag tcttgtaaat gcgggccaag atctgcacac tggtatttcg 2521 gtttttgggg ccgcgggcgg cgacgggcc cgtgcgtccc agcgcacatg ttcggcgagg 2581 cggggcctgc gagcgcggcc accgagaatc ggacgggggt agtctcaagc tggccggcct 2641 gctctggtgc ctggcctcgc gccgccgtgt atcgccccgc cctgggcggc aaggctggcc 2701 cggtcggcac cagttgcgtg agcggaaaga tggccgcttc ccggccctgc tgcagggagc 2761 tcaaaatgga ggacgcggcg ctcgggagag cgggcgggtg agtcacccac acaaaggaaa 2821 agggccttc cgtcctcagc cgtcgcttca tgtgactcca cggagtaccg ggcgccgtcc 2881 aggcacctcg attagttctc gagcttttgg agtacgtcgt ctttaggttg gggggagggg
```

-continued

```
2941 ttttatgcga tggagtttcc ccacactgag tgggtggaga ctgaagttag gccagcttgg
3001 cacttgatgt aattctccst ggaatttgcc ctttttgagt ttggatcttg gttcattctc
3061 aagcctcaga cagtggttca aagttttttt cttccatttc aggtgtcgtg atgtacaATG
3121 GCCAAGTTGA CCAGTGCCGT TCCGGTGCTC ACCGCGCGCG ACGTCGCCGG AGCGGTCGAG
3181 TTCTGGACCG ACCGGCTCGG GTTCTCCCGG GACTTCGTGG AGGACGACTT CGCCGGTGTG
3241 GTCCGGGACG ACGTGACCCT GTTCATCAGC GCGGTCCAGG ACCAGGTGGT GCCGGACAAC
3301 ACCCTGGCCT GGGTGTGGGT GCGCGGCCTG GACGAGCTGT ACGCCGAGTG GTCGGAGGTC
3361 GTGTCCACGA ACTTCCGGGA CGCCTCCGGG CCGGCCATGA CCGAGATCGG CGAGCAGCCG
3421 TGGGGCGGG AGTTCGCCCT GCGCGACCCG GCCGGCAACT GCGTGCACTT CGTGGCCGAG
3481 GAGCAGGACT GAgCTAGCtg ttcaatcaac attccNNNNN NNNNNNNact ggctattcat
3541 tcgcCCTTTG GGTAAGCACA CGTCGAATTC GATATCAAGC TTATCGGTAA tcaacctctg
3601 gattacaaaa tttgtgaaag attgactggt attcttaact atgttgctcc ttttacgcta
3661 tgtggatacg ctgctttaat gcctttgtat catgctattg cttcccgtat ggctttcatt
3721 ttctcctcct tgtataaatc ctggttgctg tctctttatg aggagttgtg gcccgttgtc
3781 aggcaacgtg gcgtggtgtg cactgtgttt gctgacgcaa ccccactgg ttggggcatt
3841 gccaccacct gtcagctcct ttccgggact ttcgctttcc cctccctat tgccacggcg
3901 gaactcatcg ccgcctgcct tgcccgctgc tggacagggg ctcggctgtt gggcactgac
3961 aattccgtgg tgttgtcggg gaaatcatcg tcctttcctt ggctgctcgc ctgtgttgcc
4021 acctggattc tgcgcgggac gtccttctgc tacgtcccct cggccctcaa tccagcggac
4081 cttccttccc gcggcctgct gccggctctg cggcctcttc cgcgtcttcg ccttcgccct
4141 cagacgagtc ggatctccct ttgggccgcc tccccgcgtc gactttaaga ccaatgactt
4201 acaaggcagc tgtagatctt agccactttt taaaagaaaa ggggggactg gaagggctaa
4261 ttcactccca acgaagacaa gatctgcttt tgcttgtac tgggtctctc tggttagacc
4321 agatctgagc ctgggagctc tctggctaac tagggaaccc actgcttaag cctcaataaa
4381 gcttgccttg agtgcttcaa gtagtgtgtg cccgtctgtt gtgtgactct ggtaactaga
4441 gatccctcag accctttag tcagtgtgga aaatctctag cagtacgtat agtagttcat
4501 gtcatcttat tattcagtat ttataacttg caaagaaatg aatatcagag agtgagagga
4561 acttgtttat tgcagcttat aatggttaca aataaagcaa tagcatcaca aatttcacaa
4621 ataaagcatt ttttttcactg cattctagtt gtggtttgtc caaactcatc aatgtatctt
4681 atcatgtctg gctctagcta tcccgcccct aactccgccc atccgcccc taactccgcc
4741 cagttccgcc cattctccgc cccatggctg actaatttt tttatttatg cagaggccga
4801 ggccgcctcg gcctctgagc tattccagaa gtagtgagga ggcttttttg gaggcctagg
4861 gacgtaccca attcgcccta tagtgagtcg tattacgcgc gctcactggc cgtcgtttta
4921 caacgtcgtg actgggaaaa ccctggcgtt acccaactta atcgccttgc agcacatccc
4981 cctttcgcca gctggcgtaa tagcgaagag gcccgcaccg atcgcccttc ccaacagttg
5041 cgcagcctga atggcgaatg ggacgcgccc tgtagcggcg cattaagcgc ggcgggtgtg
5101 gtggttacgc gcagcgtgac cgctacactt gccagcgccc tagcgcccgc tcctttcgct
5161 ttcttccctt cctttctcgc cacgttcgcc ggctttcccc gtcaagctct aaatcggggg
5221 ctcccttag ggttccgatt tagtgcttta cggcacctcg accccaaaaa acttgattag
5281 ggtgatggtt cacgtagtgg gccatcgccc tgatagacgg ttttcgccc tttgacgttg
```

-continued

```
5341 gagtccacgt tctttaatag tggactcttg ttccaaactg gaacaacact caaccctatc 5401 tcggtctatt cttttgattt ataagggatt ttgccgattt cggcctattg gttaaaaaat 5461 gagctgattt aacaaaaatt taacgcgaat tttaacaaaa tattaacgct tacaatttag 5521 gtggcacttt tcggggaaat gtgcgcggaa cccctatttg tttattttc taaatacatt 5581 caaatatgta tccgctcatg agacaataac cctgataaat gcttcaataa tattgaaaaa 5641 ggaagagtat gagtattcaa catttccgtg tcgcccttat tcccttttt gcggcatttt 5701 gccttcctgt ttttgctcac ccagaaacgc tggtgaaagt aaaagatgct gaagatcagt 5761 tgggtgcacg agtgggttac atcgaactgg atctcaacag cggtaagatc cttgagagtt 5821 ttcgccccga agaacgtttt ccaatgatga gcacttttaa agttctgcta tgtggcgcgg 5881 tattatcccg tattgacgcc gggcaagagc aactcggtcg ccgcatacac tattctcaga 5941 atgacttggt tgagtactca ccagtcacag aaaagcatct tacggatggc atgacagtaa 6001 gagaattatg cagtgctgcc ataaccatga gtgataacac tgcggccaac ttacttctga 6061 caacgatcgg aggaccgaag gagctaaccg cttttttgca caacatgggg gatcatgtaa 6121 ctcgccttga tcgttgggaa ccggagctga atgaagccat accaaacgac gagcgtgaca 6181 ccacgatgcc tgtagcaatg gcaacaacgt tgcgcaaact attaactggc gaactactta 6241 ctctagcttc ccggcaacaa ttaatagact ggatggaggc ggataaagtt gcaggaccac 6301 ttctgcgctc ggcccttccg gctggctggt ttattgctga taaatctgga gccggtgagc 6361 gtgggtctcg cggtatcatt gcagcactgg ggccagatgg taagccctcc cgtatcgtag 6421 ttatctacac gacggggagt caggcaacta tggatgaacg aaatagacag atcgctgaga 6481 taggtgcctc actgattaag cattggtaac tgtcagacca agtttactca tatatacttt 6541 agattgattt aaaacttcat ttttaattta aaaggatcta ggtgaagatc ctttttgata 6601 atctcatgac caaaatccct taacgtgagt tttcgttcca ctgagcgtca gaccccgtag 6661 aaaagatcaa aggatcttct tgagatcctt ttttctgcg cgtaatctgc tgcttgcaaa 6721 caaaaaaacc accgctacca gcggtggttt gtttgccgga tcaagagcta ccaactcttt 6781 ttccgaaggt aactggcttc agcagagcgc agataccaaa tactgttctt ctagtgtagc 6841 cgtagttagg ccaccacttc aagaactctg tagcaccgcc tacatacctc gctctgctaa 6901 tcctgttacc agtggctgct gccagtggcg ataagtcgtg tcttaccggg ttggactcaa 6961 gacgatagtt accggataag gcgcagcggt cgggctgaac ggggggttcg tgcacacagc 7021 ccagcttgga gcgaacgacc tacaccgaac tgagatacct acagcgtgag ctatgagaaa 7081 gcgccacgct tcccgaaggg agaaaggcgg acaggtatcc ggtaagcggc agggtcggaa 7141 caggagagcg cacgagggag cttccagggg gaaacgcctg gtatctttat agtcctgtcg 7201 ggtttcgcca cctctgactt gagcgtcgat ttttgtgatg ctcgtcaggg ggcggagcc 7261 tatggaaaaa cgccagcaac gcggcctttt tacggttcct ggccttttgc tggccttttg 7321 ctcacatgtt ctttcctgcg ttatcccctg attctgtgga taaccgtatt accgcctttg 7381 agtgagctga taccgctcgc cgcagccgaa cgaccgagcg cagcgagtca gtgagcgagg 7441 aagcggaaga gcgcccaata cgcaaaccgc ctctccccgc gcgttggccg attcattaat 7501 gcagctggca cgacaggttt cccgactgga aagcgggcag tgagcgcaac gcaattaatg 7561 tgagttagct cactcattag gcaccccagg ctttacactt tatgcttccg gctcgtatgt 7621 tgtgtggaat tgtgagcgga taacaatttc acacaggaaa cagctatgac catgattacg 7681 ccaagcgcgc aattaaccct cactaaaggg aacaaaagct ggagctgcaa gcttaatgta 7741 gtcttatgca atactcttgt agtcttgcaa catggtaacg atgagttagc aacatgcctt
```

```
7801 acaaggagag aaaaagcacc gtgcatgccg attggtggaa gtaaggtggt acgatcgtgc 7861 cttattagga aggcaacaga cgggtctgac atggattgga cgaaccactg aattgccgca 7921 ttgcagagat attgtattta agtgcctagc tcgatacata aac
//
```

REFERENCES

1. Wang, T., Wei, J. J., Sabatini, D. M. & Lander, E. S. Genetic Screens in Human Cells Using the CRISPR-Cas9 System. Science (80-.). 343, 80-84 (2014).
2. Shalem, O. et al. Genome-Scale CRISPR-Cas9 Knockout Screening in Human Cells. Science (80-.). 343, 84-87 (2014).
3. Dixit, A. et al. Perturb-Seq: Dissecting Molecular Circuits with Scalable Single-Cell RNA Profiling of Pooled Genetic Screens. Cell 167, 1853-1866.e17 (2016).
4. Jaitin, D. A. et al. Dissecting Immune Circuits by Linking CRISPR-Pooled Screens with Single-Cell RNA-Seq. Cell 167, 1883-1896.e15 (2016).
5. Datlinger, P. et al. Pooled CRISPR screening with single-cell transcriptome readout. Nat. Methods 14, 297-301 (2017).
6. Han, K. et al. Synergistic drug combinations for cancer identified in a CRISPR screen for pairwise genetic interactions. Nat. Biotechnol. 35, 463-474 (2017).
7. Vidigal, J. A. & Ventura, A. Rapid and efficient one-step generation of paired gRNA CRISPR-Cas9 libraries. Nat. Commun. 6, 8083 (2015).
8. Zhu, S. et al. Genome-scale deletion screening of human long non-coding RNAs using a paired-guide RNA CRISPR-Cas9 library. Nat. Biotechnol. 34, 1279-1286 (2016).
9. Shen, J. P. et al. Combinatorial CRISPR-Cas9 screens for de novo mapping of genetic interactions. Nat. Methods 14, 573-576 (2017).
10. Hill, A. J. et al. On the design of CRISPR-based single cell molecular screens. bioRxiv 254334 (2018). doi: 10.1101/254334.
11. Xie, S., Cooley, A., Armendariz, D., Zhou, P. & Hon, G. Frequent sgRNA-barcode Recombination in Single-cell Perturbation Assays. bioRxiv 255638 (2018). doi:10.1101/255638.
12. Hu, W. S. & Temin, H. M. Retroviral recombination and reverse transcription. Science 250, 1227-33 (1990).
13. Sack, L. M., Davoli, T., Xu, Q., Li, M. Z. & Elledge, S. J. Sources of Error in Mammalian Genetic Screens. G3 (Bethesda). 6, 2781-90 (2016).
14. Adamson, B. et al. A Multiplexed Single-Cell CRISPR Screening Platform Enables Systematic Dissection of the Unfolded Protein Response. Cell 167, 1867-1882.e21 (2016).
15. Nightingale, S. J. et al. Transient Gene Expression by Nonintegrating Lentiviral Vectors. Mol. Ther. 13, 1121-1132 (2006).
16. Maricque, B. B., Dougherty, J. D. & Cohen, B. A. A genome-integrated massively parallel reporter assay reveals DNA sequence determinants of cis-regulatory activity in neural cells. Nucleic Acids Res. 45, gkw942 (2016).
17. Chen, S. et al. Genome-wide CRISPR screen in a mouse model of tumor growth and metastasis. Cell 160, 1246-60 (2015).
18. Paillart, J.-C., Shehu-Xhilaga, M., Marquet, R. & Mak, J. Dimerization of retroviral RNA genomes: an inseparable pair. Nat. Rev. Microbiol. 2, 461-472 (2004).
19. Joung, J. et al. Genome-scale CRISPR-Cas9 knockout and transcriptional activation screening. Nat. Protoc. 12, 828-863 (2017).

Example 2

An example method of constructing libraries of genetic elements. Provide A provides an example method of libraries comprising two engineered associations. The lentiviral vector shown under "mRNA contains barcode" (panel A) is an example of a vector with two elements (sgRNA and barcode) that will normally undergo swapping unless the co-packaging protocol is used. The associations did not undergo swapping because the libraries were constructed using the co-packaging methods described herein. The scatter plot (panel B) shows the accuracy of mapping over 1000 barcodes to two categories. The mapped barcodes did not have recombination, indicating the accuracy was improved by the co-packaging protocol disclosed herein.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A non-naturally occurring engineered lentiviral or retroviral system comprising a pooled set of payload polynucleotides, each having or encoding at least a genetic perturbation in association with a barcode that identifies the genetic perturbation(s), a multiplicity of carrier polynucleotides that are heterologous to the payload polynucleotides and do not have or encode at least a genetic perturbation in association with a barcode that identifies the genetic perturbation(s), and one or more packaging polynucleotides, wherein the system comprises a 5:1 weight ratio or greater mixture of the carrier polynucleotides to the pooled set of the payload polynucleotides, wherein a multiplicity of packaging cells transfected with the system are capable of producing a viral expression library comprising viral particles, wherein each one of the pooled set of the payload polynucleotides is comprised in at least one of the viral particles, and wherein the packaging cells are sufficiently capable of packaging no more than one payload polynucleotide per viral particle such that target cells transduced with the viral expression library have reduced recombination activity, or template switching activity, or multiple integration activity as compared to counterpart packaging cells transfected with a mixture comprising the pooled set of the payload polynucleotides in the absence of the 5:1 weight ratio or greater of the carrier polynucleotides to the pooled set of the payload polynucleotides.

2. The engineered system of claim 1, wherein the system comprises a weight ratio of the carrier polynucleotides to the payload polynucleotides of 5:1 or greater, 10:1 or greater, 20:1 or greater, 30:1 or greater, 40:1 or greater, 50:1 or greater, 60:1 or greater, 70:1 or greater, 80:1 or greater, 90:1 or greater, 100:1 or greater, 200:1 or greater, 300:1 or greater, 400:1 or greater, 500:1 or greater, 600:1 or greater, 700:1 or greater, 800:1 or greater, 900:1 or greater, 1000:1 or greater, 2000:1 or greater, 3000:1 or greater, 4000:1 or greater, or 5000:1 or greater.

3. The engineered system of claim 1, wherein each carrier polynucleotide comprises or encodes non-recombinogenic RNA sequences or proteins that are capable of dimerizing with the payload polynucleotides, and wherein the packaging cells are capable of packaging each payload polynucleotide as a dimer with one or more of said carrier polynucleotides, non-recombinogenic RNA sequences, or proteins, such that target cells transduced with the viral expression library.

4. The engineered system of claim 1, wherein each carrier polynucleotide comprises single and/or double stranded DNA; recombinant and/or non-recombinant plasmid type vectors; replicable and/or non-replicable plasmid type vectors; integrating and/or non-integrating plasmid type vectors; viral and/or non-viral plasmid type vectors; lentiviral or non-lentiviral plasmid type vectors; and/or retroviral and/or non-retroviral plasmid type vectors.

5. The engineered system of claim 4, wherein the carrier polynucleotide comprises a plasmid selected from the group consisting of pUC19, pr_H2b-BFB, pLX_TRC131_LacZ, and pR_LG.

6. The engineered system of claim 1, wherein the genetic perturbation(s) is/are an over expressed gene, RNAi based system, a zinc finger nuclease, a transcription activator-like effector nuclease (TALEN), a meganuclease, or a CRISPR-Cas system, a component thereof, or a portion thereof.

7. The engineered system of claim 6, wherein the payload polynucleotides encode a CRISPR-Cas system or a component thereof.

8. The engineered system of claim 7, wherein the CRISPR-Cas system is a CRISPR-Cas9 system.

9. The engineered system of claim 8, wherein the payload polynucleotides encode one or more guide sequences.

10. A method of screening cells for at least a genetic perturbation comprising:
    providing a target cell or population of target cells in one or more discrete volumes;

introducing a viral expression library comprising viral particles, wherein the viral expression library is produced by a multiplicity of packaging cells transfected with the system of claim 1, such that each target cell receives one of the set of the payload polynucleotides each having or encoding at least a genetic perturbation in association with a barcode that identifies the genetic perturbation(s);

detecting genomic, genetic, proteomic, epigenetic and/or phenotypic differences in single cells; and identifying the at least a genetic perturbation in each cell based on the associated barcode that identifies the genetic perturbation(s).

11. A method of preparing one or more packaging cells capable of producing a viral expression library the method comprising transfecting one or more packaging cells with a system comprising a pooled set of payload polynucleotides, each payload polynucleotide comprising or encoding at least a genetic perturbation in association with a barcode that identifies the genetic perturbation(s), a multiplicity of carrier polynucleotides that are heterologous to the payload polynucleotides and do not have or encode at least a genetic perturbation in association with a barcode that identifies the genetic perturbation(s), and one or more packaging polynucleotides, wherein the system comprises a 5:1 weight ratio or greater mixture of the carrier polynucleotides to the pooled set of the payload polynucleotides, wherein the packaging cells are capable of producing a viral expression library comprising viral particles, wherein each one of the pooled set of the payload polynucleotides is comprised in at least one of the viral particles of the viral expression library, wherein the packaging cells are sufficiently capable of packaging no more than one payload polynucleotide per viral particle such that target cells transduced with the viral expression library have reduced recombination activity, or template switching activity, or multiple integration activity, as compared to counterpart packaging cells transfected with a mixture comprising the payload polynucleotides in the absence of the 5:1 weight ratio or greater of the carrier polynucleotides to the pooled set of the payload polynucleotides.

12. The method of claim 11, wherein the carrier polynucleotide comprises or encodes non-recombinogenic RNA sequences or proteins that are capable of dimerizing with the payload polynucleotides, and wherein the packaging cells are capable of packaging each payload polynucleotide as a dimer with one or more of said carrier polynucleotides, non-recombinogenic RNA sequences, or proteins, such that target cells transduced with the viral expression library.

13. The method of claim 11, wherein the payload polynucleotides encode an RNAi based system, a zinc finger nuclease, a transcription activator-like effector nuclease (TALEN), a meganuclease, or a CRISPR-Cas system, or a component thereof.

14. A viral expression library comprising viral particles obtained by transfecting the non-naturally occurring engineered lentiviral or retroviral system of claim 1 into a multiplicity of packaging cells.

15. A packaging cell or packaging cells for producing a viral expression library comprising viral particles, wherein one or more packaging cells comprise a system comprising a pooled set of payload polynucleotides, each payload polynucleotide comprising or encoding at least a genetic perturbation associated with a barcode that identifies the genetic perturbation(s), a multiplicity of the carrier polynucleotides that are heterologous to the payload polynucleotide and do not comprise or encode at least a genetic perturbation associated with a barcode that identifies the genetic perturbation(s), and one or more packaging polynucleotides, wherein the system comprises a 5:1 weight ratio or greater mixture of the carrier polynucleotides to the pooled set of the payload polynucleotides, wherein the packaging cells are capable of producing a viral expression library comprising viral particles, wherein each one of the pooled set of the payload polynucleotides is comprised in at least one of the viral particles of the viral expression library, and wherein the packaging cells are sufficiently capable of packaging no more than one payload polynucleotide per viral particle such that target cells transduced with the viral expression library have reduced recombination activity, or template switching activity, or multiple integration activity, as compared to counterpart packaging cells transfected with a mixture comprising the payload polynucleotides in the absence of the 5:1 weight ratio or greater of the carrier polynucleotides to the pooled set of the payload polynucleotides.

16. A method of reducing intermolecular recombination with a lentiviral genome plasmid of interest in a pooled library, wherein the lentiviral genome plasmid of interest encodes at least a genetic perturbation associated with a barcode that identifies the genetic perturbation(s), the method comprising transfecting one or more packaging cells with a system comprising the pooled library of lentiviral genome plasmids, a multiplicity of viral carrier plasmids, wherein the lentiviral carrier plasmids are heterologous to the lentiviral genome plasmids and do not encode at least a genetic perturbation associated with a barcode that identifies the genetic perturbation(s), and one or more lentiviral packaging plasmids, wherein the system comprises a 5:1 weight ratio or greater of the lentiviral carrier plasmids to the lentiviral genome plasmids, wherein the packaging cells are capable of producing a lentiviral expression library comprising lentiviral particles, wherein each lentiviral genome plasmid of interest is comprised in at least one of the lentiviral particles, and wherein the packaging cells are sufficiently capable of packaging no more than lentiviral genome plasmid per lentiviral particle such that target cells transduced with the lentiviral expression library have reduced recombination activity, or template switching activity, or multiple integration activity, as compared to counterpart packaging cells transfected with a mixture comprising the library of the lentiviral genome plasmids in the absence of the 5:1 weight ratio or greater of the lentiviral carrier plasmids to the lentiviral genome plasmids.

17. The method of claim 16, wherein the lentiviral carrier plasmid comprises a non-integrating lentiviral vector.

18. The method of claim 17, wherein the lentiviral carrier plasmid comprises a non-recombinogenic lentiviral vector.

19. The method of claim 16, wherein the weight ratio of the lentiviral carrier plasmid to the lentiviral genome plasmid is at least 10:1.

20. The method of claim 16, wherein the weight ratio of the lentiviral carrier plasmid to the lentiviral genome plasmid is at least 50:1.

21. The method of claim 16, wherein the weight ratio of the lentiviral carrier plasmid to the lentiviral genome plasmid is at least 100:1.

22. The method of claim 16, wherein the library comprises a barcode library.

23. The method of claim 16, wherein the library comprises a plurality of guide polynucleotides.

24. The method of claim 16, wherein the library comprises a plurality of sgRNAs.

* * * * *

SEQUENCE LISTING

<160> NUMBER OF SEQ ID NOS: 1574

<210> SEQ ID NO 1
<211> LENGTH: 19
<212> TYPE: DNA

```
<213> ORGANISM: Artificial Sequence
<220> FEATURE:
<223> OTHER INFORMATION: Synthetic

<400> SEQUENCE: 1
agagcactgc actccttca                                              19

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
agagcactgc actccttca                                              19

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
agagcactgc actccttca                                              19

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
agagcactgc actccttca                                              19

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
agtagtccgg gatatcagcg                                             20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
agtagtccgg gatatcagcg                                             20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
atacaactgc ttgcaacagg                                             20
```

```
<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
atacaactgc ttgcaacagg                                                    20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tccaccggcg aaagagatcc                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
tccaccggcg aaagagatcc                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
cgccgccccc ggacgcgacc                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
cgccgccccc ggacgcgacc                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
tcatattacg agtcagtagg                                                    20

<210> SEQ ID NO 14
<211> LENGTH: 19
<212> TYPE: DNA
<213> ORGANISM: Artificial Sequence
<220> FEATURE:
```

<223> OTHER INFORMATION: Synthetic

<400> SEQUENCE: 14
agagcactgc actccttca                                            19

<210> SEQ ID NO 15
<211> LENGTH: 19
<212> TYPE: DNA
<213> ORGANISM: Artificial Sequence
<220> FEATURE:
<223> OTHER INFORMATION: Synthetic

<400> SEQUENCE: 15
agagcactgc actccttca                                            19

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
tcatattacg agtcagtagg                                           20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
tcatattacg agtcagtagg                                           20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
ccagtacaaa cctacctacg                                           20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ccagtacaaa cctacctacg                                           20

<210> SEQ ID NO 20
<211> LENGTH: 19
<212> TYPE: DNA
<213> ORGANISM: Artificial Sequence
<220> FEATURE:
<223> OTHER INFORMATION: Synthetic

<400> SEQUENCE: 20
agagcactgc actccttca                                            19

```
<210> SEQ ID NO 21
<211> LENGTH: 19
<212> TYPE: DNA
<213> ORGANISM: Artificial Sequence
<220> FEATURE:
<223> OTHER INFORMATION: Synthetic

<400> SEQUENCE: 21
agagcactgc actccttca                                               19

<210> SEQ ID NO 22
<211> LENGTH: 19
<212> TYPE: DNA
<213> ORGANISM: Artificial Sequence
<220> FEATURE:
<223> OTHER INFORMATION: Synthetic

<400> SEQUENCE: 22
agagcactgc actccttca                                               19

<210> SEQ ID NO 23
<211> LENGTH: 19
<212> TYPE: DNA
<213> ORGANISM: Artificial Sequence
<220> FEATURE:
<223> OTHER INFORMATION: Synthetic

<400> SEQUENCE: 23
agagcactgc actccttca                                               19

<210> SEQ ID NO 24
<211> LENGTH: 19
<212> TYPE: DNA
<213> ORGANISM: Artificial Sequence
<220> FEATURE:
<223> OTHER INFORMATION: Synthetic

<400> SEQUENCE: 24
agagcactgc actccttca                                               19

<210> SEQ ID NO 25
<211> LENGTH: 19
<212> TYPE: DNA
<213> ORGANISM: Artificial Sequence
<220> FEATURE:
<223> OTHER INFORMATION: Synthetic

<400> SEQUENCE: 25
agagcactgc actccttca                                               19

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
cctgcaacgg gactagttgg                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 27
atacaactgc ttgcaacagg                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
atacaactgc ttgcaacagg                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
cctgcaacgg gactagttgg                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
cgccgccccc ggacgcgacc                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
cgccgccccc ggacgcgacc                                              20

<210> SEQ ID NO 32
<211> LENGTH: 19
<212> TYPE: DNA
<213> ORGANISM: Artificial Sequence
<220> FEATURE:
<223> OTHER INFORMATION: Synthetic

<400> SEQUENCE: 32
agagcactgc actccttca                                               19

<210> SEQ ID NO 33
<211> LENGTH: 19
<212> TYPE: DNA
<213> ORGANISM: Artificial Sequence
<220> FEATURE:
<223> OTHER INFORMATION: Synthetic

<400> SEQUENCE: 33
agagcactgc actccttca                                               19

<210> SEQ ID NO 34
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 34
ccagtacaaa cctacctacg                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
ccagtacaaa cctacctacg                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
cgccgccccc ggacgcgacc                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
cgccgccccc ggacgcgacc                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
cgccgccccc ggacgcgacc                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
cgccgccccc ggacgcgacc                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
```
tccaccggcg aaagagatcc                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
tccaccggcg aaagagatcc                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
atacaactgc ttgcaacagg                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
atacaactgc ttgcaacagg                                              20

<210> SEQ ID NO 44
<211> LENGTH: 19
<212> TYPE: DNA
<213> ORGANISM: Artificial Sequence
<220> FEATURE:
<223> OTHER INFORMATION: Synthetic

<400> SEQUENCE: 44
agagcactgc actccttca                                               19

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
tcatattacg agtcagtagg                                              20

<210> SEQ ID NO 46
<211> LENGTH: 19
<212> TYPE: DNA
<213> ORGANISM: Artificial Sequence
<220> FEATURE:
<223> OTHER INFORMATION: Synthetic

<400> SEQUENCE: 46
agagcactgc actccttca                                               19

<210> SEQ ID NO 47
<211> LENGTH: 20
<212> TYPE: DNA
<213> ORGANISM: Artificial Sequence

```
<220> FEATURE:
<223> OTHER INFORMATION: Synthetic

<400> SEQUENCE: 47
tcatattacg agtcagtagg                                                   20

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
cgccgccccc ggacgcgacc                                                   20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
cgccgccccc ggacgcgacc                                                   20

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
cctgcaacgg gactagttgg                                                   20

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
cctgcaacgg gactagttgg                                                   20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
agtagtccgg gatatcagcg                                                   20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
agtagtccgg gatatcagcg                                                   20
```

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
agtagtccgg gatatcagcg                                               20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
agtagtccgg gatatcagcg                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
cctgcaacgg gactagttgg                                               20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
cctgcaacgg gactagttgg                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
atacaactgc ttgcaacagg                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
atacaactgc ttgcaacagg                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
cgccgccccc ggacgcgacc                                                    20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
cgccgccccc ggacgcgacc                                                    20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
tcatattacg agtcagtagg                                                    20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
tcatattacg agtcagtagg                                                    20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
tcatattacg agtcagtagg                                                    20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
tcatattacg agtcagtagg                                                    20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
cctgcaacgg gactagttgg                                                    20

<210> SEQ ID NO 67

```
<211> LENGTH: 20
<212> TYPE: DNA
<213> ORGANISM: Artificial Sequence
<220> FEATURE:
<223> OTHER INFORMATION: Synthetic

<400> SEQUENCE: 67
cctgcaacgg gactagttgg                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
ccagtacaaa cctacctacg                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
ccagtacaaa cctacctacg                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
agtagtccgg gatatcagcg                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
agtagtccgg gatatcagcg                                              20

<210> SEQ ID NO 72
<211> LENGTH: 19
<212> TYPE: DNA
<213> ORGANISM: Artificial Sequence
<220> FEATURE:
<223> OTHER INFORMATION: Synthetic

<400> SEQUENCE: 72
agagcactgc actccttca                                               19

<210> SEQ ID NO 73
<211> LENGTH: 19
<212> TYPE: DNA
<213> ORGANISM: Artificial Sequence
<220> FEATURE:
<223> OTHER INFORMATION: Synthetic

<400> SEQUENCE: 73
```
agagcactgc actccttca                                                    19

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74
tcatattacg agtcagtagg                                                   20

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
tcatattacg agtcagtagg                                                   20

<210> SEQ ID NO 76
<211> LENGTH: 19
<212> TYPE: DNA
<213> ORGANISM: Artificial Sequence
<220> FEATURE:
<223> OTHER INFORMATION: Synthetic

<400> SEQUENCE: 76
agagcactgc actccttca                                                    19

<210> SEQ ID NO 77
<211> LENGTH: 19
<212> TYPE: DNA
<213> ORGANISM: Artificial Sequence
<220> FEATURE:
<223> OTHER INFORMATION: Synthetic

<400> SEQUENCE: 77
agagcactgc actccttca                                                    19

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
tccaccggcg aaagagatcc                                                   20

<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
tccaccggcg aaagagatcc                                                   20

<210> SEQ ID NO 80
<211> LENGTH: 20
<212> TYPE: DNA

```
<213> ORGANISM: Artificial Sequence
<220> FEATURE:
<223> OTHER INFORMATION: Synthetic

<400> SEQUENCE: 80
atacaactgc ttgcaacagg                                                  20

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
atacaactgc ttgcaacagg                                                  20

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
cctgcaacgg gactagttgg                                                  20

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
cctgcaacgg gactagttgg                                                  20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
atacaactgc ttgcaacagg                                                  20

<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
atacaactgc ttgcaacagg                                                  20

<210> SEQ ID NO 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
atacaactgc ttgcaacagg                                                  20
```

```
<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
atacaactgc ttgcaacagg                                                    20

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
cctgcaacgg gactagttgg                                                    20

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
cctgcaacgg gactagttgg                                                    20

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
tcatattacg agtcagtagg                                                    20

<210> SEQ ID NO 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
tcatattacg agtcagtagg                                                    20

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
cgccgccccc ggacgcgacc                                                    20

<210> SEQ ID NO 93
<211> LENGTH: 20
<212> TYPE: DNA
<213> ORGANISM: Artificial Sequence
<220> FEATURE:
```

<223> OTHER INFORMATION: Synthetic

<400> SEQUENCE: 93
cgccgccccc ggacgcgacc                                              20

<210> SEQ ID NO 94
<211> LENGTH: 19
<212> TYPE: DNA
<213> ORGANISM: Artificial Sequence
<220> FEATURE:
<223> OTHER INFORMATION: Synthetic

<400> SEQUENCE: 94
agagcactgc actccttca                                               19

<210> SEQ ID NO 95
<211> LENGTH: 19
<212> TYPE: DNA
<213> ORGANISM: Artificial Sequence
<220> FEATURE:
<223> OTHER INFORMATION: Synthetic

<400> SEQUENCE: 95
agagcactgc actccttca                                               19

<210> SEQ ID NO 96
<211> LENGTH: 20
<212> TYPE: DNA
<213> ORGANISM: Artificial Sequence
<220> FEATURE:
<223> OTHER INFORMATION: Synthetic

<400> SEQUENCE: 96
agtagtccgg gatatcagcg                                              20

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
agtagtccgg gatatcagcg                                              20

<210> SEQ ID NO 98
<211> LENGTH: 20
<212> TYPE: DNA
<213> ORGANISM: Artificial Sequence
<220> FEATURE:
<223> OTHER INFORMATION: Synthetic

<400> SEQUENCE: 98
ccagtacaaa cctacctacg                                              20

<210> SEQ ID NO 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
ccagtacaaa cctacctacg                                              20

```
<210> SEQ ID NO 100
<211> LENGTH: 20
<212> TYPE: DNA
<213> ORGANISM: Artificial Sequence
<220> FEATURE:
<223> OTHER INFORMATION: Synthetic

<400> SEQUENCE: 100
cctgcaacgg gactagttgg                                              20

<210> SEQ ID NO 101
<211> LENGTH: 20
<212> TYPE: DNA
<213> ORGANISM: Artificial Sequence
<220> FEATURE:
<223> OTHER INFORMATION: Synthetic

<400> SEQUENCE: 101
cctgcaacgg gactagttgg                                              20

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
agtagtccgg gatatcagcg                                              20

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103
atacaactgc ttgcaacagg                                              20

<210> SEQ ID NO 104
<211> LENGTH: 19
<212> TYPE: DNA
<213> ORGANISM: Artificial Sequence
<220> FEATURE:
<223> OTHER INFORMATION: Synthetic

<400> SEQUENCE: 104
agagcactgc actccttca                                               19

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105
agtagtccgg gatatcagcg                                              20

<210> SEQ ID NO 106
<211> LENGTH: 20
<212> TYPE: DNA
<213> ORGANISM: Artificial Sequence
<220> FEATURE:
<223> OTHER INFORMATION: Synthetic
```

<400> SEQUENCE: 106
atacaactgc ttgcaacagg                                                     20

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
atacaactgc ttgcaacagg                                                     20

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
atacaactgc ttgcaacagg                                                     20

<210> SEQ ID NO 109
<211> LENGTH: 20
<212> TYPE: DNA
<213> ORGANISM: Artificial Sequence
<220> FEATURE:
<223> OTHER INFORMATION: Synthetic

<400> SEQUENCE: 109
cctgcaacgg gactagttgg                                                     20

<210> SEQ ID NO 110
<211> LENGTH: 20
<212> TYPE: DNA
<213> ORGANISM: Artificial Sequence
<220> FEATURE:
<223> OTHER INFORMATION: Synthetic

<400> SEQUENCE: 110
cctgcaacgg gactagttgg                                                     20

<210> SEQ ID NO 111
<211> LENGTH: 19
<212> TYPE: DNA
<213> ORGANISM: Artificial Sequence
<220> FEATURE:
<223> OTHER INFORMATION: Synthetic

<400> SEQUENCE: 111
agagcactgc actccttca                                                      19

<210> SEQ ID NO 112
<211> LENGTH: 19
<212> TYPE: DNA
<213> ORGANISM: Artificial Sequence
<220> FEATURE:
<223> OTHER INFORMATION: Synthetic

<400> SEQUENCE: 112
agagcactgc actccttca                                                      19

<210> SEQ ID NO 113
<211> LENGTH: 20

```
<212> TYPE: DNA
<213> ORGANISM: Artificial Sequence
<220> FEATURE:
<223> OTHER INFORMATION: Synthetic

<400> SEQUENCE: 113
tcatattacg agtcagtagg                                          20

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
cgccgccccc ggacgcgacc                                          20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
cgccgccccc ggacgcgacc                                          20

<210> SEQ ID NO 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
cctgcaacgg gactagttgg                                          20

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
atacaactgc ttgcaacagg                                          20

<210> SEQ ID NO 118
<211> LENGTH: 20
<212> TYPE: DNA
<213> ORGANISM: Artificial Sequence
<220> FEATURE:
<223> OTHER INFORMATION: Synthetic

<400> SEQUENCE: 118
tccaccggcg aaagagatcc                                          20

<210> SEQ ID NO 119
<211> LENGTH: 20
<212> TYPE: DNA
<213> ORGANISM: Artificial Sequence
<220> FEATURE:
<223> OTHER INFORMATION: Synthetic

<400> SEQUENCE: 119
```
atacaactgc ttgcaacagg                                        20

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
tccaccggcg aaagagatcc                                        20

<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
cctgcaacgg gactagttgg                                        20

<210> SEQ ID NO 122
<211> LENGTH: 20
<212> TYPE: DNA
<213> ORGANISM: Artificial Sequence
<220> FEATURE:
<223> OTHER INFORMATION: Synthetic

<400> SEQUENCE: 122
agtagtccgg gatatcagcg                                        20

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
atacaactgc ttgcaacagg                                        20

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
atacaactgc ttgcaacagg                                        20

<210> SEQ ID NO 125
<211> LENGTH: 20
<212> TYPE: DNA
<213> ORGANISM: Artificial Sequence
<220> FEATURE:
<223> OTHER INFORMATION: Synthetic

<400> SEQUENCE: 125
agtagtccgg gatatcagcg                                        20

<210> SEQ ID NO 126
<211> LENGTH: 20
<212> TYPE: DNA
<213> ORGANISM: Artificial Sequence

```
<220> FEATURE:
<223> OTHER INFORMATION: Synthetic

<400> SEQUENCE: 126
agtagtccgg gatatcagcg                                              20

<210> SEQ ID NO 127
<211> LENGTH: 20
<212> TYPE: DNA
<213> ORGANISM: Artificial Sequence
<220> FEATURE:
<223> OTHER INFORMATION: Synthetic

<400> SEQUENCE: 127
ccagtacaaa cctacctacg                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
ccagtacaaa cctacctacg                                              20

<210> SEQ ID NO 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
tccaccggcg aaagagatcc                                              20

<210> SEQ ID NO 130
<211> LENGTH: 20
<212> TYPE: DNA
<213> ORGANISM: Artificial Sequence
<220> FEATURE:
<223> OTHER INFORMATION: Synthetic

<400> SEQUENCE: 130
atacaactgc ttgcaacagg                                              20

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
atacaactgc ttgcaacagg                                              20

<210> SEQ ID NO 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
atacaactgc ttgcaacagg                                              20
```

<210> SEQ ID NO 133
<211> LENGTH: 20
<212> TYPE: DNA
<213> ORGANISM: Artificial Sequence
<220> FEATURE:
<223> OTHER INFORMATION: Synthetic

<400> SEQUENCE: 133
agtagtccgg gatatcagcg                                               20

<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
agtagtccgg gatatcagcg                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
agtagtccgg gatatcagcg                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
atacaactgc ttgcaacagg                                               20

<210> SEQ ID NO 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
cgccgccccc ggacgcgacc                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic

<400> SEQUENCE: 138
cgccgccccc ggacgcgacc                                               20

<210> SEQ ID NO 139
<211> LENGTH: 20
<212> TYPE: DNA
<213> ORGANISM: Artificial Sequence
<220> FEATURE:
<223> OTHER INFORMATION: Synthetic

<400> SEQUENCE: 139
agtagtccgg gatatcagcg                                              20

<210> SEQ ID NO 140
<211> LENGTH: 19
<212> TYPE: DNA
<213> ORGANISM: Artificial Sequence
<220> FEATURE:
<223> OTHER INFORMATION: Synthetic

<400> SEQUENCE: 140
agagcactgc actccttca                                               19

<210> SEQ ID NO 141
<211> LENGTH: 19
<212> TYPE: DNA
<213> ORGANISM: Artificial Sequence
<220> FEATURE:
<223> OTHER INFORMATION: Synthetic

<400> SEQUENCE: 141
agagcactgc actccttca                                               19

<210> SEQ ID NO 142
<211> LENGTH: 20
<212> TYPE: DNA
<213> ORGANISM: Artificial Sequence
<220> FEATURE:
<223> OTHER INFORMATION: Synthetic

<400> SEQUENCE: 142
agtagtccgg gatatcagcg                                              20

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
atacaactgc ttgcaacagg                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic

<400> SEQUENCE: 144
atacaactgc ttgcaacagg                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
ccagtacaaa cctacctacg                                              20

<210> SEQ ID NO 146

```
<211> LENGTH: 20
<212> TYPE: DNA
<213> ORGANISM: Artificial Sequence
<220> FEATURE:
<223> OTHER INFORMATION: Synthetic

<400> SEQUENCE: 146
cctgcaacgg gactagttgg                                                  20

<210> SEQ ID NO 147
<211> LENGTH: 20
<212> TYPE: DNA
<213> ORGANISM: Artificial Sequence
<220> FEATURE:
<223> OTHER INFORMATION: Synthetic

<400> SEQUENCE: 147
cctgcaacgg gactagttgg                                                  20

<210> SEQ ID NO 148
<211> LENGTH: 20
<212> TYPE: DNA
<213> ORGANISM: Artificial Sequence
<220> FEATURE:
<223> OTHER INFORMATION: Synthetic

<400> SEQUENCE: 148
agtagtccgg gatatcagcg                                                  20

<210> SEQ ID NO 149
<211> LENGTH: 20
<212> TYPE: DNA
<213> ORGANISM: Artificial Sequence
<220> FEATURE:
<223> OTHER INFORMATION: Synthetic

<400> SEQUENCE: 149
cctgcaacgg gactagttgg                                                  20

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
tcatattacg agtcagtagg                                                  20

<210> SEQ ID NO 151
<211> LENGTH: 20
<212> TYPE: DNA
<213> ORGANISM: Artificial Sequence
<220> FEATURE:
<223> OTHER INFORMATION: Synthetic

<400> SEQUENCE: 151
tccaccggcg aaagagatcc                                                  20

<210> SEQ ID NO 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
```
tccaccggcg aaagagatcc                                              20

<210> SEQ ID NO 153
<211> LENGTH: 20
<212> TYPE: DNA
<213> ORGANISM: Artificial Sequence
<220> FEATURE:
<223> OTHER INFORMATION: Synthetic

<400> SEQUENCE: 153
tcatattacg agtcagtagg                                              20

<210> SEQ ID NO 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
tcatattacg agtcagtagg                                              20

<210> SEQ ID NO 155
<211> LENGTH: 20
<212> TYPE: DNA
<213> ORGANISM: Artificial Sequence
<220> FEATURE:
<223> OTHER INFORMATION: Synthetic

<400> SEQUENCE: 155
ccagtacaaa cctacctacg                                              20

<210> SEQ ID NO 156
<211> LENGTH: 20
<212> TYPE: DNA
<213> ORGANISM: Artificial Sequence
<220> FEATURE:
<223> OTHER INFORMATION: Synthetic

<400> SEQUENCE: 156
ccagtacaaa cctacctacg                                              20

<210> SEQ ID NO 157
<211> LENGTH: 20
<212> TYPE: DNA
<213> ORGANISM: Artificial Sequence
<220> FEATURE:
<223> OTHER INFORMATION: Synthetic

<400> SEQUENCE: 157
ccagtacaaa cctacctacg                                              20

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
cctgcaacgg gactagttgg                                              20

<210> SEQ ID NO 159
<211> LENGTH: 20
<212> TYPE: DNA

```
<213> ORGANISM: Artificial Sequence
<220> FEATURE:
<223> OTHER INFORMATION: Synthetic

<400> SEQUENCE: 159
cctgcaacgg gactagttgg                                                   20

<210> SEQ ID NO 160
<211> LENGTH: 20
<212> TYPE: DNA
<213> ORGANISM: Artificial Sequence
<220> FEATURE:
<223> OTHER INFORMATION: Synthetic

<400> SEQUENCE: 160
cctgcaacgg gactagttgg                                                   20

<210> SEQ ID NO 161
<211> LENGTH: 19
<212> TYPE: DNA
<213> ORGANISM: Artificial Sequence
<220> FEATURE:
<223> OTHER INFORMATION: Synthetic

<400> SEQUENCE: 161
agagcactgc actccttca                                                    19

<210> SEQ ID NO 162
<211> LENGTH: 19
<212> TYPE: DNA
<213> ORGANISM: Artificial Sequence
<220> FEATURE:
<223> OTHER INFORMATION: Synthetic

<400> SEQUENCE: 162
agagcactgc actccttca                                                    19

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
tcatattacg agtcagtagg                                                   20

<210> SEQ ID NO 164
<211> LENGTH: 20
<212> TYPE: DNA
<213> ORGANISM: Artificial Sequence
<220> FEATURE:
<223> OTHER INFORMATION: Synthetic

<400> SEQUENCE: 164
tcatattacg agtcagtagg                                                   20

<210> SEQ ID NO 165
<211> LENGTH: 20
<212> TYPE: DNA
<213> ORGANISM: Artificial Sequence
<220> FEATURE:
<223> OTHER INFORMATION: Synthetic

<400> SEQUENCE: 165
tccaccggcg aaagagatcc                                                   20
```

```
<210> SEQ ID NO 166
<211> LENGTH: 20
<212> TYPE: DNA
<213> ORGANISM: Artificial Sequence
<220> FEATURE:
<223> OTHER INFORMATION: Synthetic

<400> SEQUENCE: 166
tccaccggcg aaagagatcc                                               20

<210> SEQ ID NO 167
<211> LENGTH: 20
<212> TYPE: DNA
<213> ORGANISM: Artificial Sequence
<220> FEATURE:
<223> OTHER INFORMATION: Synthetic

<400> SEQUENCE: 167
cgccgccccc ggacgcgacc                                               20

<210> SEQ ID NO 168
<211> LENGTH: 20
<212> TYPE: DNA
<213> ORGANISM: Artificial Sequence
<220> FEATURE:
<223> OTHER INFORMATION: Synthetic

<400> SEQUENCE: 168
cgccgccccc ggacgcgacc                                               20

<210> SEQ ID NO 169
<211> LENGTH: 20
<212> TYPE: DNA
<213> ORGANISM: Artificial Sequence
<220> FEATURE:
<223> OTHER INFORMATION: Synthetic

<400> SEQUENCE: 169
atacaactgc ttgcaacagg                                               20

<210> SEQ ID NO 170
<211> LENGTH: 20
<212> TYPE: DNA
<213> ORGANISM: Artificial Sequence
<220> FEATURE:
<223> OTHER INFORMATION: Synthetic

<400> SEQUENCE: 170
atacaactgc ttgcaacagg                                               20

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
ccagtacaaa cctacctacg                                               20

<210> SEQ ID NO 172
<211> LENGTH: 20
<212> TYPE: DNA
<213> ORGANISM: Artificial Sequence
<220> FEATURE:
```

<223> OTHER INFORMATION: Synthetic

<400> SEQUENCE: 172
ccagtacaaa cctacctacg                                                 20

<210> SEQ ID NO 173
<211> LENGTH: 20
<212> TYPE: DNA
<213> ORGANISM: Artificial Sequence
<220> FEATURE:
<223> OTHER INFORMATION: Synthetic

<400> SEQUENCE: 173
cctgcaacgg gactagttgg                                                 20

<210> SEQ ID NO 174
<211> LENGTH: 20
<212> TYPE: DNA
<213> ORGANISM: Artificial Sequence
<220> FEATURE:
<223> OTHER INFORMATION: Synthetic

<400> SEQUENCE: 174
tcatattacg agtcagtagg                                                 20

<210> SEQ ID NO 175
<211> LENGTH: 20
<212> TYPE: DNA
<213> ORGANISM: Artificial Sequence
<220> FEATURE:
<223> OTHER INFORMATION: Synthetic

<400> SEQUENCE: 175
tcatattacg agtcagtagg                                                 20

<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
cctgcaacgg gactagttgg                                                 20

<210> SEQ ID NO 177
<211> LENGTH: 19
<212> TYPE: DNA
<213> ORGANISM: Artificial Sequence
<220> FEATURE:
<223> OTHER INFORMATION: Synthetic

<400> SEQUENCE: 177
agagcactgc actccttca                                                  19

<210> SEQ ID NO 178
<211> LENGTH: 19
<212> TYPE: DNA
<213> ORGANISM: Artificial Sequence
<220> FEATURE:
<223> OTHER INFORMATION: Synthetic

<400> SEQUENCE: 178
agagcactgc actccttca                                                  19

```
<210> SEQ ID NO 179
<211> LENGTH: 19
<212> TYPE: DNA
<213> ORGANISM: Artificial Sequence
<220> FEATURE:
<223> OTHER INFORMATION: Synthetic

<400> SEQUENCE: 179
agagcactgc actccttca                                                  19

<210> SEQ ID NO 180
<211> LENGTH: 20
<212> TYPE: DNA
<213> ORGANISM: Artificial Sequence
<220> FEATURE:
<223> OTHER INFORMATION: Synthetic

<400> SEQUENCE: 180
atacaactgc ttgcaacagg                                                 20

<210> SEQ ID NO 181
<211> LENGTH: 20
<212> TYPE: DNA
<213> ORGANISM: Artificial Sequence
<220> FEATURE:
<223> OTHER INFORMATION: Synthetic

<400> SEQUENCE: 181
atacaactgc ttgcaacagg                                                 20

<210> SEQ ID NO 182
<211> LENGTH: 19
<212> TYPE: DNA
<213> ORGANISM: Artificial Sequence
<220> FEATURE:
<223> OTHER INFORMATION: Synthetic

<400> SEQUENCE: 182
agagcactgc actccttca                                                  19

<210> SEQ ID NO 183
<211> LENGTH: 20
<212> TYPE: DNA
<213> ORGANISM: Artificial Sequence
<220> FEATURE:
<223> OTHER INFORMATION: Synthetic

<400> SEQUENCE: 183
cctgcaacgg gactagttgg                                                 20

<210> SEQ ID NO 184
<211> LENGTH: 20
<212> TYPE: DNA
<213> ORGANISM: Artificial Sequence
<220> FEATURE:
<223> OTHER INFORMATION: Synthetic

<400> SEQUENCE: 184
cctgcaacgg gactagttgg                                                 20

<210> SEQ ID NO 185
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 185
tcatattacg agtcagtagg                                              20

<210> SEQ ID NO 186
<211> LENGTH: 20
<212> TYPE: DNA
<213> ORGANISM: Artificial Sequence
<220> FEATURE:
<223> OTHER INFORMATION: Synthetic

<400> SEQUENCE: 186
tcatattacg agtcagtagg                                              20

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
cgccgccccc ggacgcgacc                                              20

<210> SEQ ID NO 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
cgccgccccc ggacgcgacc                                              20

<210> SEQ ID NO 189
<211> LENGTH: 20
<212> TYPE: DNA
<213> ORGANISM: Artificial Sequence
<220> FEATURE:
<223> OTHER INFORMATION: Synthetic

<400> SEQUENCE: 189
tcatattacg agtcagtagg                                              20

<210> SEQ ID NO 190
<211> LENGTH: 20
<212> TYPE: DNA
<213> ORGANISM: Artificial Sequence
<220> FEATURE:
<223> OTHER INFORMATION: Synthetic

<400> SEQUENCE: 190
atacaactgc ttgcaacagg                                              20

<210> SEQ ID NO 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
atacaactgc ttgcaacagg                                              20

<210> SEQ ID NO 192
<211> LENGTH: 19
```

```
<212> TYPE: DNA
<213> ORGANISM: Artificial Sequence
<220> FEATURE:
<223> OTHER INFORMATION: Synthetic

<400> SEQUENCE: 192
agagcactgc actccttca                                                19

<210> SEQ ID NO 193
<211> LENGTH: 19
<212> TYPE: DNA
<213> ORGANISM: Artificial Sequence
<220> FEATURE:
<223> OTHER INFORMATION: Synthetic

<400> SEQUENCE: 193
agagcactgc actccttca                                                19

<210> SEQ ID NO 194
<211> LENGTH: 19
<212> TYPE: DNA
<213> ORGANISM: Artificial Sequence
<220> FEATURE:
<223> OTHER INFORMATION: Synthetic

<400> SEQUENCE: 194
agagcactgc actccttca                                                19

<210> SEQ ID NO 195
<211> LENGTH: 20
<212> TYPE: DNA
<213> ORGANISM: Artificial Sequence
<220> FEATURE:
<223> OTHER INFORMATION: Synthetic

<400> SEQUENCE: 195
ccagtacaaa cctacctacg                                               20

<210> SEQ ID NO 196
<211> LENGTH: 19
<212> TYPE: DNA
<213> ORGANISM: Artificial Sequence
<220> FEATURE:
<223> OTHER INFORMATION: Synthetic

<400> SEQUENCE: 196
agagcactgc actccttca                                                19

<210> SEQ ID NO 197
<211> LENGTH: 20
<212> TYPE: DNA
<213> ORGANISM: Artificial Sequence
<220> FEATURE:
<223> OTHER INFORMATION: Synthetic

<400> SEQUENCE: 197
atacaactgc ttgcaacagg                                               20

<210> SEQ ID NO 198
<211> LENGTH: 20
<212> TYPE: DNA
<213> ORGANISM: Artificial Sequence
<220> FEATURE:
<223> OTHER INFORMATION: Synthetic

<400> SEQUENCE: 198
```
atacaactgc ttgcaacagg                                              20

<210> SEQ ID NO 199
<211> LENGTH: 19
<212> TYPE: DNA
<213> ORGANISM: Artificial Sequence
<220> FEATURE:
<223> OTHER INFORMATION: Synthetic

<400> SEQUENCE: 199
agagcactgc actccttca                                               19

<210> SEQ ID NO 200
<211> LENGTH: 20
<212> TYPE: DNA
<213> ORGANISM: Artificial Sequence
<220> FEATURE:
<223> OTHER INFORMATION: Synthetic

<400> SEQUENCE: 200
cctgcaacgg gactagttgg                                              20

<210> SEQ ID NO 201
<211> LENGTH: 19
<212> TYPE: DNA
<213> ORGANISM: Artificial Sequence
<220> FEATURE:
<223> OTHER INFORMATION: Synthetic

<400> SEQUENCE: 201
agagcactgc actccttca                                               19

<210> SEQ ID NO 202
<211> LENGTH: 20
<212> TYPE: DNA
<213> ORGANISM: Artificial Sequence
<220> FEATURE:
<223> OTHER INFORMATION: Synthetic

<400> SEQUENCE: 202
cctgcaacgg gactagttgg                                              20

<210> SEQ ID NO 203
<211> LENGTH: 20
<212> TYPE: DNA
<213> ORGANISM: Artificial Sequence
<220> FEATURE:
<223> OTHER INFORMATION: Synthetic

<400> SEQUENCE: 203
cgccgccccc ggacgcgacc                                              20

<210> SEQ ID NO 204
<211> LENGTH: 20
<212> TYPE: DNA
<213> ORGANISM: Artificial Sequence
<220> FEATURE:
<223> OTHER INFORMATION: Synthetic

<400> SEQUENCE: 204
cctgcaacgg gactagttgg                                              20

<210> SEQ ID NO 205
<211> LENGTH: 19
<212> TYPE: DNA
<213> ORGANISM: Artificial Sequence

```
<220> FEATURE:
<223> OTHER INFORMATION: Synthetic

<400> SEQUENCE: 205
agagcactgc actccttca                                                  19

<210> SEQ ID NO 206
<211> LENGTH: 19
<212> TYPE: DNA
<213> ORGANISM: Artificial Sequence
<220> FEATURE:
<223> OTHER INFORMATION: Synthetic

<400> SEQUENCE: 206
agagcactgc actccttca                                                  19

<210> SEQ ID NO 207
<211> LENGTH: 19
<212> TYPE: DNA
<213> ORGANISM: Artificial Sequence
<220> FEATURE:
<223> OTHER INFORMATION: Synthetic

<400> SEQUENCE: 207
agagcactgc actccttca                                                  19

<210> SEQ ID NO 208
<211> LENGTH: 19
<212> TYPE: DNA
<213> ORGANISM: Artificial Sequence
<220> FEATURE:
<223> OTHER INFORMATION: Synthetic

<400> SEQUENCE: 208
agagcactgc actccttca                                                  19

<210> SEQ ID NO 209
<211> LENGTH: 20
<212> TYPE: DNA
<213> ORGANISM: Artificial Sequence
<220> FEATURE:
<223> OTHER INFORMATION: Synthetic

<400> SEQUENCE: 209
tcatattacg agtcagtagg                                                 20

<210> SEQ ID NO 210
<211> LENGTH: 20
<212> TYPE: DNA
<213> ORGANISM: Artificial Sequence
<220> FEATURE:
<223> OTHER INFORMATION: Synthetic

<400> SEQUENCE: 210
tcatattacg agtcagtagg                                                 20

<210> SEQ ID NO 211
<211> LENGTH: 20
<212> TYPE: DNA
<213> ORGANISM: Artificial Sequence
<220> FEATURE:
<223> OTHER INFORMATION: Synthetic

<400> SEQUENCE: 211
ccagtacaaa cctacctacg                                                 20
```

```
<210> SEQ ID NO 212
<211> LENGTH: 20
<212> TYPE: DNA
<213> ORGANISM: Artificial Sequence
<220> FEATURE:
<223> OTHER INFORMATION: Synthetic

<400> SEQUENCE: 212
tcatattacg agtcagtagg                                                   20

<210> SEQ ID NO 213
<211> LENGTH: 20
<212> TYPE: DNA
<213> ORGANISM: Artificial Sequence
<220> FEATURE:
<223> OTHER INFORMATION: Synthetic

<400> SEQUENCE: 213
ccagtacaaa cctacctacg                                                   20

<210> SEQ ID NO 214
<211> LENGTH: 20
<212> TYPE: DNA
<213> ORGANISM: Artificial Sequence
<220> FEATURE:
<223> OTHER INFORMATION: Synthetic

<400> SEQUENCE: 214
cctgcaacgg gactagttgg                                                   20

<210> SEQ ID NO 215
<211> LENGTH: 20
<212> TYPE: DNA
<213> ORGANISM: Artificial Sequence
<220> FEATURE:
<223> OTHER INFORMATION: Synthetic

<400> SEQUENCE: 215
cctgcaacgg gactagttgg                                                   20

<210> SEQ ID NO 216
<211> LENGTH: 20
<212> TYPE: DNA
<213> ORGANISM: Artificial Sequence
<220> FEATURE:
<223> OTHER INFORMATION: Synthetic

<400> SEQUENCE: 216
atacaactgc ttgcaacagg                                                   20

<210> SEQ ID NO 217
<211> LENGTH: 19
<212> TYPE: DNA
<213> ORGANISM: Artificial Sequence
<220> FEATURE:
<223> OTHER INFORMATION: Synthetic

<400> SEQUENCE: 217
agagcactgc actccttca                                                    19

<210> SEQ ID NO 218
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 218
tcatattacg agtcagtagg                                          20

<210> SEQ ID NO 219
<211> LENGTH: 20
<212> TYPE: DNA
<213> ORGANISM: Artificial Sequence
<220> FEATURE:
<223> OTHER INFORMATION: Synthetic

<400> SEQUENCE: 219
tcatattacg agtcagtagg                                          20

<210> SEQ ID NO 220
<211> LENGTH: 20
<212> TYPE: DNA
<213> ORGANISM: Artificial Sequence
<220> FEATURE:
<223> OTHER INFORMATION: Synthetic

<400> SEQUENCE: 220
tcatattacg agtcagtagg                                          20

<210> SEQ ID NO 221
<211> LENGTH: 20
<212> TYPE: DNA
<213> ORGANISM: Artificial Sequence
<220> FEATURE:
<223> OTHER INFORMATION: Synthetic

<400> SEQUENCE: 221
tcatattacg agtcagtagg                                          20

<210> SEQ ID NO 222
<211> LENGTH: 20
<212> TYPE: DNA
<213> ORGANISM: Artificial Sequence
<220> FEATURE:
<223> OTHER INFORMATION: Synthetic

<400> SEQUENCE: 222
cctgcaacgg gactagttgg                                          20

<210> SEQ ID NO 223
<211> LENGTH: 20
<212> TYPE: DNA
<213> ORGANISM: Artificial Sequence
<220> FEATURE:
<223> OTHER INFORMATION: Synthetic

<400> SEQUENCE: 223
atacaactgc ttgcaacagg                                          20

<210> SEQ ID NO 224
<211> LENGTH: 20
<212> TYPE: DNA
<213> ORGANISM: Artificial Sequence
<220> FEATURE:
<223> OTHER INFORMATION: Synthetic

<400> SEQUENCE: 224
atacaactgc ttgcaacagg                                          20

<210> SEQ ID NO 225
```

```
<211> LENGTH: 19
<212> TYPE: DNA
<213> ORGANISM: Artificial Sequence
<220> FEATURE:
<223> OTHER INFORMATION: Synthetic

<400> SEQUENCE: 225
agagcactgc actccttca                                                19

<210> SEQ ID NO 226
<211> LENGTH: 20
<212> TYPE: DNA
<213> ORGANISM: Artificial Sequence
<220> FEATURE:
<223> OTHER INFORMATION: Synthetic

<400> SEQUENCE: 226
tccaccggcg aaagagatcc                                               20

<210> SEQ ID NO 227
<211> LENGTH: 20
<212> TYPE: DNA
<213> ORGANISM: Artificial Sequence
<220> FEATURE:
<223> OTHER INFORMATION: Synthetic

<400> SEQUENCE: 227
atacaactgc ttgcaacagg                                               20

<210> SEQ ID NO 228
<211> LENGTH: 20
<212> TYPE: DNA
<213> ORGANISM: Artificial Sequence
<220> FEATURE:
<223> OTHER INFORMATION: Synthetic

<400> SEQUENCE: 228
atacaactgc ttgcaacagg                                               20

<210> SEQ ID NO 229
<211> LENGTH: 20
<212> TYPE: DNA
<213> ORGANISM: Artificial Sequence
<220> FEATURE:
<223> OTHER INFORMATION: Synthetic

<400> SEQUENCE: 229
atacaactgc ttgcaacagg                                               20

<210> SEQ ID NO 230
<211> LENGTH: 20
<212> TYPE: DNA
<213> ORGANISM: Artificial Sequence
<220> FEATURE:
<223> OTHER INFORMATION: Synthetic

<400> SEQUENCE: 230
tcatattacg agtcagtagg                                               20

<210> SEQ ID NO 231
<211> LENGTH: 20
<212> TYPE: DNA
<213> ORGANISM: Artificial Sequence
<220> FEATURE:
<223> OTHER INFORMATION: Synthetic

<400> SEQUENCE: 231
```

```
cctgcaacgg gactagttgg                                              20

<210> SEQ ID NO 232
<211> LENGTH: 19
<212> TYPE: DNA
<213> ORGANISM: Artificial Sequence
<220> FEATURE:
<223> OTHER INFORMATION: Synthetic

<400> SEQUENCE: 232
agagcactgc actccttca                                               19

<210> SEQ ID NO 233
<211> LENGTH: 20
<212> TYPE: DNA
<213> ORGANISM: Artificial Sequence
<220> FEATURE:
<223> OTHER INFORMATION: Synthetic

<400> SEQUENCE: 233
atacaactgc ttgcaacagg                                              20

<210> SEQ ID NO 234
<211> LENGTH: 20
<212> TYPE: DNA
<213> ORGANISM: Artificial Sequence
<220> FEATURE:
<223> OTHER INFORMATION: Synthetic

<400> SEQUENCE: 234
atacaactgc ttgcaacagg                                              20

<210> SEQ ID NO 235
<211> LENGTH: 20
<212> TYPE: DNA
<213> ORGANISM: Artificial Sequence
<220> FEATURE:
<223> OTHER INFORMATION: Synthetic

<400> SEQUENCE: 235
atacaactgc ttgcaacagg                                              20

<210> SEQ ID NO 236
<211> LENGTH: 20
<212> TYPE: DNA
<213> ORGANISM: Artificial Sequence
<220> FEATURE:
<223> OTHER INFORMATION: Synthetic

<400> SEQUENCE: 236
atacaactgc ttgcaacagg                                              20

<210> SEQ ID NO 237
<211> LENGTH: 19
<212> TYPE: DNA
<213> ORGANISM: Artificial Sequence
<220> FEATURE:
<223> OTHER INFORMATION: Synthetic

<400> SEQUENCE: 237
agagcactgc actccttca                                               19

<210> SEQ ID NO 238
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 238
atacaactgc ttgcaacagg                                                20

<210> SEQ ID NO 239
<211> LENGTH: 19
<212> TYPE: DNA
<213> ORGANISM: Artificial Sequence
<220> FEATURE:
<223> OTHER INFORMATION: Synthetic

<400> SEQUENCE: 239
agagcactgc actccttca                                                 19

<210> SEQ ID NO 240
<211> LENGTH: 19
<212> TYPE: DNA
<213> ORGANISM: Artificial Sequence
<220> FEATURE:
<223> OTHER INFORMATION: Synthetic

<400> SEQUENCE: 240
agagcactgc actccttca                                                 19

<210> SEQ ID NO 241
<211> LENGTH: 20
<212> TYPE: DNA
<213> ORGANISM: Artificial Sequence
<220> FEATURE:
<223> OTHER INFORMATION: Synthetic

<400> SEQUENCE: 241
cgccgccccc ggacgcgacc                                                20

<210> SEQ ID NO 242
<211> LENGTH: 20
<212> TYPE: DNA
<213> ORGANISM: Artificial Sequence
<220> FEATURE:
<223> OTHER INFORMATION: Synthetic

<400> SEQUENCE: 242
cgccgccccc ggacgcgacc                                                20

<210> SEQ ID NO 243
<211> LENGTH: 19
<212> TYPE: DNA
<213> ORGANISM: Artificial Sequence
<220> FEATURE:
<223> OTHER INFORMATION: Synthetic

<400> SEQUENCE: 243
agagcactgc actccttca                                                 19

<210> SEQ ID NO 244
<211> LENGTH: 19
<212> TYPE: DNA
<213> ORGANISM: Artificial Sequence
<220> FEATURE:
<223> OTHER INFORMATION: Synthetic

<400> SEQUENCE: 244
agagcactgc actccttca                                                 19
```

```
<210> SEQ ID NO 245
<211> LENGTH: 20
<212> TYPE: DNA
<213> ORGANISM: Artificial Sequence
<220> FEATURE:
<223> OTHER INFORMATION: Synthetic

<400> SEQUENCE: 245
tcatattacg agtcagtagg                                                   20

<210> SEQ ID NO 246
<211> LENGTH: 20
<212> TYPE: DNA
<213> ORGANISM: Artificial Sequence
<220> FEATURE:
<223> OTHER INFORMATION: Synthetic

<400> SEQUENCE: 246
tcatattacg agtcagtagg                                                   20

<210> SEQ ID NO 247
<211> LENGTH: 20
<212> TYPE: DNA
<213> ORGANISM: Artificial Sequence
<220> FEATURE:
<223> OTHER INFORMATION: Synthetic

<400> SEQUENCE: 247
ccagtacaaa cctacctacg                                                   20

<210> SEQ ID NO 248
<211> LENGTH: 20
<212> TYPE: DNA
<213> ORGANISM: Artificial Sequence
<220> FEATURE:
<223> OTHER INFORMATION: Synthetic

<400> SEQUENCE: 248
ccagtacaaa cctacctacg                                                   20

<210> SEQ ID NO 249
<211> LENGTH: 19
<212> TYPE: DNA
<213> ORGANISM: Artificial Sequence
<220> FEATURE:
<223> OTHER INFORMATION: Synthetic

<400> SEQUENCE: 249
agagcactgc actccttca                                                    19

<210> SEQ ID NO 250
<211> LENGTH: 19
<212> TYPE: DNA
<213> ORGANISM: Artificial Sequence
<220> FEATURE:
<223> OTHER INFORMATION: Synthetic

<400> SEQUENCE: 250
agagcactgc actccttca                                                    19

<210> SEQ ID NO 251
<211> LENGTH: 20
<212> TYPE: DNA
<213> ORGANISM: Artificial Sequence
<220> FEATURE:
```

<223> OTHER INFORMATION: Synthetic

<400> SEQUENCE: 251
cctgcaacgg gactagttgg                                               20

<210> SEQ ID NO 252
<211> LENGTH: 20
<212> TYPE: DNA
<213> ORGANISM: Artificial Sequence
<220> FEATURE:
<223> OTHER INFORMATION: Synthetic

<400> SEQUENCE: 252
cctgcaacgg gactagttgg                                               20

<210> SEQ ID NO 253
<211> LENGTH: 20
<212> TYPE: DNA
<213> ORGANISM: Artificial Sequence
<220> FEATURE:
<223> OTHER INFORMATION: Synthetic

<400> SEQUENCE: 253
cctgcaacgg gactagttgg                                               20

<210> SEQ ID NO 254
<211> LENGTH: 20
<212> TYPE: DNA
<213> ORGANISM: Artificial Sequence
<220> FEATURE:
<223> OTHER INFORMATION: Synthetic

<400> SEQUENCE: 254
cctgcaacgg gactagttgg                                               20

<210> SEQ ID NO 255
<211> LENGTH: 20
<212> TYPE: DNA
<213> ORGANISM: Artificial Sequence
<220> FEATURE:
<223> OTHER INFORMATION: Synthetic

<400> SEQUENCE: 255
tcatattacg agtcagtagg                                               20

<210> SEQ ID NO 256
<211> LENGTH: 20
<212> TYPE: DNA
<213> ORGANISM: Artificial Sequence
<220> FEATURE:
<223> OTHER INFORMATION: Synthetic

<400> SEQUENCE: 256
tcatattacg agtcagtagg                                               20

<210> SEQ ID NO 257
<211> LENGTH: 20
<212> TYPE: DNA
<213> ORGANISM: Artificial Sequence
<220> FEATURE:
<223> OTHER INFORMATION: Synthetic

<400> SEQUENCE: 257
tccaccggcg aaagagatcc                                               20

```
<210> SEQ ID NO 258
<211> LENGTH: 20
<212> TYPE: DNA
<213> ORGANISM: Artificial Sequence
<220> FEATURE:
<223> OTHER INFORMATION: Synthetic

<400> SEQUENCE: 258
tccaccggcg aaagagatcc                                            20

<210> SEQ ID NO 259
<211> LENGTH: 20
<212> TYPE: DNA
<213> ORGANISM: Artificial Sequence
<220> FEATURE:
<223> OTHER INFORMATION: Synthetic

<400> SEQUENCE: 259
agtagtccgg gatatcagcg                                            20

<210> SEQ ID NO 260
<211> LENGTH: 20
<212> TYPE: DNA
<213> ORGANISM: Artificial Sequence
<220> FEATURE:
<223> OTHER INFORMATION: Synthetic

<400> SEQUENCE: 260
agtagtccgg gatatcagcg                                            20

<210> SEQ ID NO 261
<211> LENGTH: 20
<212> TYPE: DNA
<213> ORGANISM: Artificial Sequence
<220> FEATURE:
<223> OTHER INFORMATION: Synthetic

<400> SEQUENCE: 261
ccagtacaaa cctacctacg                                            20

<210> SEQ ID NO 262
<211> LENGTH: 20
<212> TYPE: DNA
<213> ORGANISM: Artificial Sequence
<220> FEATURE:
<223> OTHER INFORMATION: Synthetic

<400> SEQUENCE: 262
ccagtacaaa cctacctacg                                            20

<210> SEQ ID NO 263
<211> LENGTH: 20
<212> TYPE: DNA
<213> ORGANISM: Artificial Sequence
<220> FEATURE:
<223> OTHER INFORMATION: Synthetic

<400> SEQUENCE: 263
cctgcaacgg gactagttgg                                            20

<210> SEQ ID NO 264
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 264
cctgcaacgg gactagttgg                                                     20

<210> SEQ ID NO 265
<211> LENGTH: 20
<212> TYPE: DNA
<213> ORGANISM: Artificial Sequence
<220> FEATURE:
<223> OTHER INFORMATION: Synthetic

<400> SEQUENCE: 265
tcatattacg agtcagtagg                                                     20

<210> SEQ ID NO 266
<211> LENGTH: 20
<212> TYPE: DNA
<213> ORGANISM: Artificial Sequence
<220> FEATURE:
<223> OTHER INFORMATION: Synthetic

<400> SEQUENCE: 266
tcatattacg agtcagtagg                                                     20

<210> SEQ ID NO 267
<211> LENGTH: 19
<212> TYPE: DNA
<213> ORGANISM: Artificial Sequence
<220> FEATURE:
<223> OTHER INFORMATION: Synthetic

<400> SEQUENCE: 267
agagcactgc actccttca                                                      19

<210> SEQ ID NO 268
<211> LENGTH: 19
<212> TYPE: DNA
<213> ORGANISM: Artificial Sequence
<220> FEATURE:
<223> OTHER INFORMATION: Synthetic

<400> SEQUENCE: 268
agagcactgc actccttca                                                      19

<210> SEQ ID NO 269
<211> LENGTH: 20
<212> TYPE: DNA
<213> ORGANISM: Artificial Sequence
<220> FEATURE:
<223> OTHER INFORMATION: Synthetic

<400> SEQUENCE: 269
cgccgccccc ggacgcgacc                                                     20

<210> SEQ ID NO 270
<211> LENGTH: 20
<212> TYPE: DNA
<213> ORGANISM: Artificial Sequence
<220> FEATURE:
<223> OTHER INFORMATION: Synthetic

<400> SEQUENCE: 270
cgccgccccc ggacgcgacc                                                     20

<210> SEQ ID NO 271
<211> LENGTH: 19
```

```
<212> TYPE: DNA
<213> ORGANISM: Artificial Sequence
<220> FEATURE:
<223> OTHER INFORMATION: Synthetic

<400> SEQUENCE: 271
agagcactgc actccttca                                              19

<210> SEQ ID NO 272
<211> LENGTH: 19
<212> TYPE: DNA
<213> ORGANISM: Artificial Sequence
<220> FEATURE:
<223> OTHER INFORMATION: Synthetic

<400> SEQUENCE: 272
agagcactgc actccttca                                              19

<210> SEQ ID NO 273
<211> LENGTH: 20
<212> TYPE: DNA
<213> ORGANISM: Artificial Sequence
<220> FEATURE:
<223> OTHER INFORMATION: Synthetic

<400> SEQUENCE: 273
agtagtccgg gatatcagcg                                             20

<210> SEQ ID NO 274
<211> LENGTH: 20
<212> TYPE: DNA
<213> ORGANISM: Artificial Sequence
<220> FEATURE:
<223> OTHER INFORMATION: Synthetic

<400> SEQUENCE: 274
agtagtccgg gatatcagcg                                             20

<210> SEQ ID NO 275
<211> LENGTH: 19
<212> TYPE: DNA
<213> ORGANISM: Artificial Sequence
<220> FEATURE:
<223> OTHER INFORMATION: Synthetic

<400> SEQUENCE: 275
agagcactgc actccttca                                              19

<210> SEQ ID NO 276
<211> LENGTH: 19
<212> TYPE: DNA
<213> ORGANISM: Artificial Sequence
<220> FEATURE:
<223> OTHER INFORMATION: Synthetic

<400> SEQUENCE: 276
agagcactgc actccttca                                              19

<210> SEQ ID NO 277
<211> LENGTH: 20
<212> TYPE: DNA
<213> ORGANISM: Artificial Sequence
<220> FEATURE:
<223> OTHER INFORMATION: Synthetic

<400> SEQUENCE: 277
```

```
atacaactgc ttgcaacagg                                               20

<210> SEQ ID NO 278
<211> LENGTH: 20
<212> TYPE: DNA
<213> ORGANISM: Artificial Sequence
<220> FEATURE:
<223> OTHER INFORMATION: Synthetic

<400> SEQUENCE: 278
atacaactgc ttgcaacagg                                               20

<210> SEQ ID NO 279
<211> LENGTH: 19
<212> TYPE: DNA
<213> ORGANISM: Artificial Sequence
<220> FEATURE:
<223> OTHER INFORMATION: Synthetic

<400> SEQUENCE: 279
agagcactgc actccttca                                                19

<210> SEQ ID NO 280
<211> LENGTH: 19
<212> TYPE: DNA
<213> ORGANISM: Artificial Sequence
<220> FEATURE:
<223> OTHER INFORMATION: Synthetic

<400> SEQUENCE: 280
agagcactgc actccttca                                                19

<210> SEQ ID NO 281
<211> LENGTH: 20
<212> TYPE: DNA
<213> ORGANISM: Artificial Sequence
<220> FEATURE:
<223> OTHER INFORMATION: Synthetic

<400> SEQUENCE: 281
tccaccggcg aaagagatcc                                               20

<210> SEQ ID NO 282
<211> LENGTH: 20
<212> TYPE: DNA
<213> ORGANISM: Artificial Sequence
<220> FEATURE:
<223> OTHER INFORMATION: Synthetic

<400> SEQUENCE: 282
tccaccggcg aaagagatcc                                               20

<210> SEQ ID NO 283
<211> LENGTH: 20
<212> TYPE: DNA
<213> ORGANISM: Artificial Sequence
<220> FEATURE:
<223> OTHER INFORMATION: Synthetic

<400> SEQUENCE: 283
agtagtccgg gatatcagcg                                               20

<210> SEQ ID NO 284
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 284
agtagtccgg gatatcagcg                                               20

<210> SEQ ID NO 285
<211> LENGTH: 20
<212> TYPE: DNA
<213> ORGANISM: Artificial Sequence
<220> FEATURE:
<223> OTHER INFORMATION: Synthetic

<400> SEQUENCE: 285
tcatattacg agtcagtagg                                               20

<210> SEQ ID NO 286
<211> LENGTH: 20
<212> TYPE: DNA
<213> ORGANISM: Artificial Sequence
<220> FEATURE:
<223> OTHER INFORMATION: Synthetic

<400> SEQUENCE: 286
tcatattacg agtcagtagg                                               20

<210> SEQ ID NO 287
<211> LENGTH: 19
<212> TYPE: DNA
<213> ORGANISM: Artificial Sequence
<220> FEATURE:
<223> OTHER INFORMATION: Synthetic

<400> SEQUENCE: 287
agagcactgc actccttca                                                19

<210> SEQ ID NO 288
<211> LENGTH: 19
<212> TYPE: DNA
<213> ORGANISM: Artificial Sequence
<220> FEATURE:
<223> OTHER INFORMATION: Synthetic

<400> SEQUENCE: 288
agagcactgc actccttca                                                19

<210> SEQ ID NO 289
<211> LENGTH: 20
<212> TYPE: DNA
<213> ORGANISM: Artificial Sequence
<220> FEATURE:
<223> OTHER INFORMATION: Synthetic

<400> SEQUENCE: 289
ccagtacaaa cctacctacg                                               20

<210> SEQ ID NO 290
<211> LENGTH: 20
<212> TYPE: DNA
<213> ORGANISM: Artificial Sequence
<220> FEATURE:
<223> OTHER INFORMATION: Synthetic

<400> SEQUENCE: 290
ccagtacaaa cctacctacg                                               20
```

```
<210> SEQ ID NO 291
<211> LENGTH: 20
<212> TYPE: DNA
<213> ORGANISM: Artificial Sequence
<220> FEATURE:
<223> OTHER INFORMATION: Synthetic

<400> SEQUENCE: 291
ccagtacaaa cctacctacg                                               20

<210> SEQ ID NO 292
<211> LENGTH: 20
<212> TYPE: DNA
<213> ORGANISM: Artificial Sequence
<220> FEATURE:
<223> OTHER INFORMATION: Synthetic

<400> SEQUENCE: 292
ccagtacaaa cctacctacg                                               20

<210> SEQ ID NO 293
<211> LENGTH: 19
<212> TYPE: DNA
<213> ORGANISM: Artificial Sequence
<220> FEATURE:
<223> OTHER INFORMATION: Synthetic

<400> SEQUENCE: 293
agagcactgc actccttca                                                19

<210> SEQ ID NO 294
<211> LENGTH: 19
<212> TYPE: DNA
<213> ORGANISM: Artificial Sequence
<220> FEATURE:
<223> OTHER INFORMATION: Synthetic

<400> SEQUENCE: 294
agagcactgc actccttca                                                19

<210> SEQ ID NO 295
<211> LENGTH: 20
<212> TYPE: DNA
<213> ORGANISM: Artificial Sequence
<220> FEATURE:
<223> OTHER INFORMATION: Synthetic

<400> SEQUENCE: 295
atacaactgc ttgcaacagg                                               20

<210> SEQ ID NO 296
<211> LENGTH: 20
<212> TYPE: DNA
<213> ORGANISM: Artificial Sequence
<220> FEATURE:
<223> OTHER INFORMATION: Synthetic

<400> SEQUENCE: 296
atacaactgc ttgcaacagg                                               20

<210> SEQ ID NO 297
<211> LENGTH: 19
<212> TYPE: DNA
<213> ORGANISM: Artificial Sequence
<220> FEATURE:
<223> OTHER INFORMATION: Synthetic
```

<400> SEQUENCE: 297
agagcactgc actccttca								19

<210> SEQ ID NO 298
<211> LENGTH: 19
<212> TYPE: DNA
<213> ORGANISM: Artificial Sequence
<220> FEATURE:
<223> OTHER INFORMATION: Synthetic

<400> SEQUENCE: 298
agagcactgc actccttca								19

<210> SEQ ID NO 299
<211> LENGTH: 20
<212> TYPE: DNA
<213> ORGANISM: Artificial Sequence
<220> FEATURE:
<223> OTHER INFORMATION: Synthetic

<400> SEQUENCE: 299
tccaccggcg aaagagatcc								20

<210> SEQ ID NO 300
<211> LENGTH: 19
<212> TYPE: DNA
<213> ORGANISM: Artificial Sequence
<220> FEATURE:
<223> OTHER INFORMATION: Synthetic

<400> SEQUENCE: 300
agagcactgc actccttca								19

<210> SEQ ID NO 301
<211> LENGTH: 19
<212> TYPE: DNA
<213> ORGANISM: Artificial Sequence
<220> FEATURE:
<223> OTHER INFORMATION: Synthetic

<400> SEQUENCE: 301
agagcactgc actccttca								19

<210> SEQ ID NO 302
<211> LENGTH: 20
<212> TYPE: DNA
<213> ORGANISM: Artificial Sequence
<220> FEATURE:
<223> OTHER INFORMATION: Synthetic

<400> SEQUENCE: 302
ccagtacaaa cctacctacg								20

<210> SEQ ID NO 303
<211> LENGTH: 20
<212> TYPE: DNA
<213> ORGANISM: Artificial Sequence
<220> FEATURE:
<223> OTHER INFORMATION: Synthetic

<400> SEQUENCE: 303
tcatattacg agtcagtagg								20

<210> SEQ ID NO 304

```
<211> LENGTH: 19
<212> TYPE: DNA
<213> ORGANISM: Artificial Sequence
<220> FEATURE:
<223> OTHER INFORMATION: Synthetic

<400> SEQUENCE: 304
agagcactgc actccttca                                                    19

<210> SEQ ID NO 305
<211> LENGTH: 20
<212> TYPE: DNA
<213> ORGANISM: Artificial Sequence
<220> FEATURE:
<223> OTHER INFORMATION: Synthetic

<400> SEQUENCE: 305
cgccgccccc ggacgcgacc                                                   20

<210> SEQ ID NO 306
<211> LENGTH: 20
<212> TYPE: DNA
<213> ORGANISM: Artificial Sequence
<220> FEATURE:
<223> OTHER INFORMATION: Synthetic

<400> SEQUENCE: 306
cgccgccccc ggacgcgacc                                                   20

<210> SEQ ID NO 307
<211> LENGTH: 20
<212> TYPE: DNA
<213> ORGANISM: Artificial Sequence
<220> FEATURE:
<223> OTHER INFORMATION: Synthetic

<400> SEQUENCE: 307
agtagtccgg gatatcagcg                                                   20

<210> SEQ ID NO 308
<211> LENGTH: 20
<212> TYPE: DNA
<213> ORGANISM: Artificial Sequence
<220> FEATURE:
<223> OTHER INFORMATION: Synthetic

<400> SEQUENCE: 308
agtagtccgg gatatcagcg                                                   20

<210> SEQ ID NO 309
<211> LENGTH: 20
<212> TYPE: DNA
<213> ORGANISM: Artificial Sequence
<220> FEATURE:
<223> OTHER INFORMATION: Synthetic

<400> SEQUENCE: 309
atacaactgc ttgcaacagg                                                   20

<210> SEQ ID NO 310
<211> LENGTH: 20
<212> TYPE: DNA
<213> ORGANISM: Artificial Sequence
<220> FEATURE:
<223> OTHER INFORMATION: Synthetic

<400> SEQUENCE: 310
```
atacaactgc ttgcaacagg                                           20

<210> SEQ ID NO 311
<211> LENGTH: 20
<212> TYPE: DNA
<213> ORGANISM: Artificial Sequence
<220> FEATURE:
<223> OTHER INFORMATION: Synthetic

<400> SEQUENCE: 311
tccaccggcg aaagagatcc                                           20

<210> SEQ ID NO 312
<211> LENGTH: 20
<212> TYPE: DNA
<213> ORGANISM: Artificial Sequence
<220> FEATURE:
<223> OTHER INFORMATION: Synthetic

<400> SEQUENCE: 312
tccaccggcg aaagagatcc                                           20

<210> SEQ ID NO 313
<211> LENGTH: 20
<212> TYPE: DNA
<213> ORGANISM: Artificial Sequence
<220> FEATURE:
<223> OTHER INFORMATION: Synthetic

<400> SEQUENCE: 313
tcatattacg agtcagtagg                                           20

<210> SEQ ID NO 314
<211> LENGTH: 20
<212> TYPE: DNA
<213> ORGANISM: Artificial Sequence
<220> FEATURE:
<223> OTHER INFORMATION: Synthetic

<400> SEQUENCE: 314
tcatattacg agtcagtagg                                           20

<210> SEQ ID NO 315
<211> LENGTH: 20
<212> TYPE: DNA
<213> ORGANISM: Artificial Sequence
<220> FEATURE:
<223> OTHER INFORMATION: Synthetic

<400> SEQUENCE: 315
tcatattacg agtcagtagg                                           20

<210> SEQ ID NO 316
<211> LENGTH: 20
<212> TYPE: DNA
<213> ORGANISM: Artificial Sequence
<220> FEATURE:
<223> OTHER INFORMATION: Synthetic

<400> SEQUENCE: 316
tcatattacg agtcagtagg                                           20

<210> SEQ ID NO 317
<211> LENGTH: 20
<212> TYPE: DNA

```
<213> ORGANISM: Artificial Sequence
<220> FEATURE:
<223> OTHER INFORMATION: Synthetic

<400> SEQUENCE: 317
cctgcaacgg gactagttgg                                                    20

<210> SEQ ID NO 318
<211> LENGTH: 20
<212> TYPE: DNA
<213> ORGANISM: Artificial Sequence
<220> FEATURE:
<223> OTHER INFORMATION: Synthetic

<400> SEQUENCE: 318
cctgcaacgg gactagttgg                                                    20

<210> SEQ ID NO 319
<211> LENGTH: 20
<212> TYPE: DNA
<213> ORGANISM: Artificial Sequence
<220> FEATURE:
<223> OTHER INFORMATION: Synthetic

<400> SEQUENCE: 319
agtagtccgg gatatcagcg                                                    20

<210> SEQ ID NO 320
<211> LENGTH: 20
<212> TYPE: DNA
<213> ORGANISM: Artificial Sequence
<220> FEATURE:
<223> OTHER INFORMATION: Synthetic

<400> SEQUENCE: 320
agtagtccgg gatatcagcg                                                    20

<210> SEQ ID NO 321
<211> LENGTH: 20
<212> TYPE: DNA
<213> ORGANISM: Artificial Sequence
<220> FEATURE:
<223> OTHER INFORMATION: Synthetic

<400> SEQUENCE: 321
atacaactgc ttgcaacagg                                                    20

<210> SEQ ID NO 322
<211> LENGTH: 20
<212> TYPE: DNA
<213> ORGANISM: Artificial Sequence
<220> FEATURE:
<223> OTHER INFORMATION: Synthetic

<400> SEQUENCE: 322
atacaactgc ttgcaacagg                                                    20

<210> SEQ ID NO 323
<211> LENGTH: 20
<212> TYPE: DNA
<213> ORGANISM: Artificial Sequence
<220> FEATURE:
<223> OTHER INFORMATION: Synthetic

<400> SEQUENCE: 323
cctgcaacgg gactagttgg                                                    20
```

<210> SEQ ID NO 324
<211> LENGTH: 20
<212> TYPE: DNA
<213> ORGANISM: Artificial Sequence
<220> FEATURE:
<223> OTHER INFORMATION: Synthetic

<400> SEQUENCE: 324
cctgcaacgg gactagttgg                                              20

<210> SEQ ID NO 325
<211> LENGTH: 20
<212> TYPE: DNA
<213> ORGANISM: Artificial Sequence
<220> FEATURE:
<223> OTHER INFORMATION: Synthetic

<400> SEQUENCE: 325
tcatattacg agtcagtagg                                              20

<210> SEQ ID NO 326
<211> LENGTH: 20
<212> TYPE: DNA
<213> ORGANISM: Artificial Sequence
<220> FEATURE:
<223> OTHER INFORMATION: Synthetic

<400> SEQUENCE: 326
tcatattacg agtcagtagg                                              20

<210> SEQ ID NO 327
<211> LENGTH: 20
<212> TYPE: DNA
<213> ORGANISM: Artificial Sequence
<220> FEATURE:
<223> OTHER INFORMATION: Synthetic

<400> SEQUENCE: 327
ccagtacaaa cctacctacg                                              20

<210> SEQ ID NO 328
<211> LENGTH: 20
<212> TYPE: DNA
<213> ORGANISM: Artificial Sequence
<220> FEATURE:
<223> OTHER INFORMATION: Synthetic

<400> SEQUENCE: 328
ccagtacaaa cctacctacg                                              20

<210> SEQ ID NO 329
<211> LENGTH: 20
<212> TYPE: DNA
<213> ORGANISM: Artificial Sequence
<220> FEATURE:
<223> OTHER INFORMATION: Synthetic

<400> SEQUENCE: 329
cctgcaacgg gactagttgg                                              20

<210> SEQ ID NO 330
<211> LENGTH: 20
<212> TYPE: DNA
<213> ORGANISM: Artificial Sequence
<220> FEATURE:

<223> OTHER INFORMATION: Synthetic

<400> SEQUENCE: 330
cctgcaacgg gactagttgg					20

<210> SEQ ID NO 331
<211> LENGTH: 20
<212> TYPE: DNA
<213> ORGANISM: Artificial Sequence
<220> FEATURE:
<223> OTHER INFORMATION: Synthetic

<400> SEQUENCE: 331
tccaccggcg aaagagatcc					20

<210> SEQ ID NO 332
<211> LENGTH: 19
<212> TYPE: DNA
<213> ORGANISM: Artificial Sequence
<220> FEATURE:
<223> OTHER INFORMATION: Synthetic

<400> SEQUENCE: 332
agagcactgc actccttca					19

<210> SEQ ID NO 333
<211> LENGTH: 20
<212> TYPE: DNA
<213> ORGANISM: Artificial Sequence
<220> FEATURE:
<223> OTHER INFORMATION: Synthetic

<400> SEQUENCE: 333
tcatattacg agtcagtagg					20

<210> SEQ ID NO 334
<211> LENGTH: 20
<212> TYPE: DNA
<213> ORGANISM: Artificial Sequence
<220> FEATURE:
<223> OTHER INFORMATION: Synthetic

<400> SEQUENCE: 334
ccagtacaaa cctacctacg					20

<210> SEQ ID NO 335
<211> LENGTH: 19
<212> TYPE: DNA
<213> ORGANISM: Artificial Sequence
<220> FEATURE:
<223> OTHER INFORMATION: Synthetic

<400> SEQUENCE: 335
agagcactgc actccttca					19

<210> SEQ ID NO 336
<211> LENGTH: 20
<212> TYPE: DNA
<213> ORGANISM: Artificial Sequence
<220> FEATURE:
<223> OTHER INFORMATION: Synthetic

<400> SEQUENCE: 336
tccaccggcg aaagagatcc					20

```
<210> SEQ ID NO 337
<211> LENGTH: 19
<212> TYPE: DNA
<213> ORGANISM: Artificial Sequence
<220> FEATURE:
<223> OTHER INFORMATION: Synthetic

<400> SEQUENCE: 337
agagcactgc actccttca                                                  19

<210> SEQ ID NO 338
<211> LENGTH: 20
<212> TYPE: DNA
<213> ORGANISM: Artificial Sequence
<220> FEATURE:
<223> OTHER INFORMATION: Synthetic

<400> SEQUENCE: 338
ccagtacaaa cctacctacg                                                 20

<210> SEQ ID NO 339
<211> LENGTH: 20
<212> TYPE: DNA
<213> ORGANISM: Artificial Sequence
<220> FEATURE:
<223> OTHER INFORMATION: Synthetic

<400> SEQUENCE: 339
cctgcaacgg gactagttgg                                                 20

<210> SEQ ID NO 340
<211> LENGTH: 20
<212> TYPE: DNA
<213> ORGANISM: Artificial Sequence
<220> FEATURE:
<223> OTHER INFORMATION: Synthetic

<400> SEQUENCE: 340
cctgcaacgg gactagttgg                                                 20

<210> SEQ ID NO 341
<211> LENGTH: 20
<212> TYPE: DNA
<213> ORGANISM: Artificial Sequence
<220> FEATURE:
<223> OTHER INFORMATION: Synthetic

<400> SEQUENCE: 341
ccagtacaaa cctacctacg                                                 20

<210> SEQ ID NO 342
<211> LENGTH: 20
<212> TYPE: DNA
<213> ORGANISM: Artificial Sequence
<220> FEATURE:
<223> OTHER INFORMATION: Synthetic

<400> SEQUENCE: 342
ccagtacaaa cctacctacg                                                 20

<210> SEQ ID NO 343
<211> LENGTH: 20
<212> TYPE: DNA
<213> ORGANISM: Artificial Sequence
<220> FEATURE:
<223> OTHER INFORMATION: Synthetic
```

<400> SEQUENCE: 343
cgccgccccc ggacgcgacc                                               20

<210> SEQ ID NO 344
<211> LENGTH: 20
<212> TYPE: DNA
<213> ORGANISM: Artificial Sequence
<220> FEATURE:
<223> OTHER INFORMATION: Synthetic

<400> SEQUENCE: 344
cgccgccccc ggacgcgacc                                               20

<210> SEQ ID NO 345
<211> LENGTH: 20
<212> TYPE: DNA
<213> ORGANISM: Artificial Sequence
<220> FEATURE:
<223> OTHER INFORMATION: Synthetic

<400> SEQUENCE: 345
cgccgccccc ggacgcgacc                                               20

<210> SEQ ID NO 346
<211> LENGTH: 20
<212> TYPE: DNA
<213> ORGANISM: Artificial Sequence
<220> FEATURE:
<223> OTHER INFORMATION: Synthetic

<400> SEQUENCE: 346
cgccgccccc ggacgcgacc                                               20

<210> SEQ ID NO 347
<211> LENGTH: 19
<212> TYPE: DNA
<213> ORGANISM: Artificial Sequence
<220> FEATURE:
<223> OTHER INFORMATION: Synthetic

<400> SEQUENCE: 347
agagcactgc actccttca                                                19

<210> SEQ ID NO 348
<211> LENGTH: 19
<212> TYPE: DNA
<213> ORGANISM: Artificial Sequence
<220> FEATURE:
<223> OTHER INFORMATION: Synthetic

<400> SEQUENCE: 348
agagcactgc actccttca                                                19

<210> SEQ ID NO 349
<211> LENGTH: 20
<212> TYPE: DNA
<213> ORGANISM: Artificial Sequence
<220> FEATURE:
<223> OTHER INFORMATION: Synthetic

<400> SEQUENCE: 349
tcatattacg agtcagtagg                                               20

<210> SEQ ID NO 350
<211> LENGTH: 20

```
<212> TYPE: DNA
<213> ORGANISM: Artificial Sequence
<220> FEATURE:
<223> OTHER INFORMATION: Synthetic

<400> SEQUENCE: 350
tcatattacg agtcagtagg                                           20

<210> SEQ ID NO 351
<211> LENGTH: 20
<212> TYPE: DNA
<213> ORGANISM: Artificial Sequence
<220> FEATURE:
<223> OTHER INFORMATION: Synthetic

<400> SEQUENCE: 351
agtagtccgg gatatcagcg                                           20

<210> SEQ ID NO 352
<211> LENGTH: 20
<212> TYPE: DNA
<213> ORGANISM: Artificial Sequence
<220> FEATURE:
<223> OTHER INFORMATION: Synthetic

<400> SEQUENCE: 352
agtagtccgg gatatcagcg                                           20

<210> SEQ ID NO 353
<211> LENGTH: 20
<212> TYPE: DNA
<213> ORGANISM: Artificial Sequence
<220> FEATURE:
<223> OTHER INFORMATION: Synthetic

<400> SEQUENCE: 353
tcatattacg agtcagtagg                                           20

<210> SEQ ID NO 354
<211> LENGTH: 20
<212> TYPE: DNA
<213> ORGANISM: Artificial Sequence
<220> FEATURE:
<223> OTHER INFORMATION: Synthetic

<400> SEQUENCE: 354
tcatattacg agtcagtagg                                           20

<210> SEQ ID NO 355
<211> LENGTH: 20
<212> TYPE: DNA
<213> ORGANISM: Artificial Sequence
<220> FEATURE:
<223> OTHER INFORMATION: Synthetic

<400> SEQUENCE: 355
ccagtacaaa cctacctacg                                           20

<210> SEQ ID NO 356
<211> LENGTH: 20
<212> TYPE: DNA
<213> ORGANISM: Artificial Sequence
<220> FEATURE:
<223> OTHER INFORMATION: Synthetic

<400> SEQUENCE: 356
```
ccagtacaaa cctacctacg                                              20

<210> SEQ ID NO 357
<211> LENGTH: 20
<212> TYPE: DNA
<213> ORGANISM: Artificial Sequence
<220> FEATURE:
<223> OTHER INFORMATION: Synthetic

<400> SEQUENCE: 357
tcatattacg agtcagtagg                                              20

<210> SEQ ID NO 358
<211> LENGTH: 20
<212> TYPE: DNA
<213> ORGANISM: Artificial Sequence
<220> FEATURE:
<223> OTHER INFORMATION: Synthetic

<400> SEQUENCE: 358
tcatattacg agtcagtagg                                              20

<210> SEQ ID NO 359
<211> LENGTH: 19
<212> TYPE: DNA
<213> ORGANISM: Artificial Sequence
<220> FEATURE:
<223> OTHER INFORMATION: Synthetic

<400> SEQUENCE: 359
agagcactgc actccttca                                               19

<210> SEQ ID NO 360
<211> LENGTH: 19
<212> TYPE: DNA
<213> ORGANISM: Artificial Sequence
<220> FEATURE:
<223> OTHER INFORMATION: Synthetic

<400> SEQUENCE: 360
agagcactgc actccttca                                               19

<210> SEQ ID NO 361
<211> LENGTH: 20
<212> TYPE: DNA
<213> ORGANISM: Artificial Sequence
<220> FEATURE:
<223> OTHER INFORMATION: Synthetic

<400> SEQUENCE: 361
cctgcaacgg gactagttgg                                              20

<210> SEQ ID NO 362
<211> LENGTH: 20
<212> TYPE: DNA
<213> ORGANISM: Artificial Sequence
<220> FEATURE:
<223> OTHER INFORMATION: Synthetic

<400> SEQUENCE: 362
cctgcaacgg gactagttgg                                              20

<210> SEQ ID NO 363
<211> LENGTH: 20
<212> TYPE: DNA
<213> ORGANISM: Artificial Sequence

```
<220> FEATURE:
<223> OTHER INFORMATION: Synthetic

<400> SEQUENCE: 363
tcatattacg agtcagtagg                                           20

<210> SEQ ID NO 364
<211> LENGTH: 20
<212> TYPE: DNA
<213> ORGANISM: Artificial Sequence
<220> FEATURE:
<223> OTHER INFORMATION: Synthetic

<400> SEQUENCE: 364
tcatattacg agtcagtagg                                           20

<210> SEQ ID NO 365
<211> LENGTH: 20
<212> TYPE: DNA
<213> ORGANISM: Artificial Sequence
<220> FEATURE:
<223> OTHER INFORMATION: Synthetic

<400> SEQUENCE: 365
agtagtccgg gatatcagcg                                           20

<210> SEQ ID NO 366
<211> LENGTH: 20
<212> TYPE: DNA
<213> ORGANISM: Artificial Sequence
<220> FEATURE:
<223> OTHER INFORMATION: Synthetic

<400> SEQUENCE: 366
agtagtccgg gatatcagcg                                           20

<210> SEQ ID NO 367
<211> LENGTH: 20
<212> TYPE: DNA
<213> ORGANISM: Artificial Sequence
<220> FEATURE:
<223> OTHER INFORMATION: Synthetic

<400> SEQUENCE: 367
ccagtacaaa cctacctacg                                           20

<210> SEQ ID NO 368
<211> LENGTH: 20
<212> TYPE: DNA
<213> ORGANISM: Artificial Sequence
<220> FEATURE:
<223> OTHER INFORMATION: Synthetic

<400> SEQUENCE: 368
ccagtacaaa cctacctacg                                           20

<210> SEQ ID NO 369
<211> LENGTH: 20
<212> TYPE: DNA
<213> ORGANISM: Artificial Sequence
<220> FEATURE:
<223> OTHER INFORMATION: Synthetic

<400> SEQUENCE: 369
cgccgccccc ggacgcgacc                                           20
```

```
<210> SEQ ID NO 370
<211> LENGTH: 20
<212> TYPE: DNA
<213> ORGANISM: Artificial Sequence
<220> FEATURE:
<223> OTHER INFORMATION: Synthetic

<400> SEQUENCE: 370
cgccgccccc ggacgcgacc                                               20

<210> SEQ ID NO 371
<211> LENGTH: 20
<212> TYPE: DNA
<213> ORGANISM: Artificial Sequence
<220> FEATURE:
<223> OTHER INFORMATION: Synthetic

<400> SEQUENCE: 371
agtagtccgg gatatcagcg                                               20

<210> SEQ ID NO 372
<211> LENGTH: 20
<212> TYPE: DNA
<213> ORGANISM: Artificial Sequence
<220> FEATURE:
<223> OTHER INFORMATION: Synthetic

<400> SEQUENCE: 372
agtagtccgg gatatcagcg                                               20

<210> SEQ ID NO 373
<211> LENGTH: 20
<212> TYPE: DNA
<213> ORGANISM: Artificial Sequence
<220> FEATURE:
<223> OTHER INFORMATION: Synthetic

<400> SEQUENCE: 373
agtagtccgg gatatcagcg                                               20

<210> SEQ ID NO 374
<211> LENGTH: 20
<212> TYPE: DNA
<213> ORGANISM: Artificial Sequence
<220> FEATURE:
<223> OTHER INFORMATION: Synthetic

<400> SEQUENCE: 374
ccagtacaaa cctacctacg                                               20

<210> SEQ ID NO 375
<211> LENGTH: 20
<212> TYPE: DNA
<213> ORGANISM: Artificial Sequence
<220> FEATURE:
<223> OTHER INFORMATION: Synthetic

<400> SEQUENCE: 375
agtagtccgg gatatcagcg                                               20

<210> SEQ ID NO 376
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 376
agtagtccgg gatatcagcg                                          20

<210> SEQ ID NO 377
<211> LENGTH: 19
<212> TYPE: DNA
<213> ORGANISM: Artificial Sequence
<220> FEATURE:
<223> OTHER INFORMATION: Synthetic

<400> SEQUENCE: 377
agagcactgc actccttca                                           19

<210> SEQ ID NO 378
<211> LENGTH: 19
<212> TYPE: DNA
<213> ORGANISM: Artificial Sequence
<220> FEATURE:
<223> OTHER INFORMATION: Synthetic

<400> SEQUENCE: 378
agagcactgc actccttca                                           19

<210> SEQ ID NO 379
<211> LENGTH: 20
<212> TYPE: DNA
<213> ORGANISM: Artificial Sequence
<220> FEATURE:
<223> OTHER INFORMATION: Synthetic

<400> SEQUENCE: 379
tcatattacg agtcagtagg                                          20

<210> SEQ ID NO 380
<211> LENGTH: 20
<212> TYPE: DNA
<213> ORGANISM: Artificial Sequence
<220> FEATURE:
<223> OTHER INFORMATION: Synthetic

<400> SEQUENCE: 380
tcatattacg agtcagtagg                                          20

<210> SEQ ID NO 381
<211> LENGTH: 19
<212> TYPE: DNA
<213> ORGANISM: Artificial Sequence
<220> FEATURE:
<223> OTHER INFORMATION: Synthetic

<400> SEQUENCE: 381
agagcactgc actccttca                                           19

<210> SEQ ID NO 382
<211> LENGTH: 20
<212> TYPE: DNA
<213> ORGANISM: Artificial Sequence
<220> FEATURE:
<223> OTHER INFORMATION: Synthetic

<400> SEQUENCE: 382
tcatattacg agtcagtagg                                          20

<210> SEQ ID NO 383
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 383
ccagtacaaa cctacctacg                                                 20

<210> SEQ ID NO 384
<211> LENGTH: 20
<212> TYPE: DNA
<213> ORGANISM: Artificial Sequence
<220> FEATURE:
<223> OTHER INFORMATION: Synthetic

<400> SEQUENCE: 384
cgccgccccc ggacgcgacc                                                 20

<210> SEQ ID NO 385
<211> LENGTH: 20
<212> TYPE: DNA
<213> ORGANISM: Artificial Sequence
<220> FEATURE:
<223> OTHER INFORMATION: Synthetic

<400> SEQUENCE: 385
tcatattacg agtcagtagg                                                 20

<210> SEQ ID NO 386
<211> LENGTH: 20
<212> TYPE: DNA
<213> ORGANISM: Artificial Sequence
<220> FEATURE:
<223> OTHER INFORMATION: Synthetic

<400> SEQUENCE: 386
tcatattacg agtcagtagg                                                 20

<210> SEQ ID NO 387
<211> LENGTH: 20
<212> TYPE: DNA
<213> ORGANISM: Artificial Sequence
<220> FEATURE:
<223> OTHER INFORMATION: Synthetic

<400> SEQUENCE: 387
tcatattacg agtcagtagg                                                 20

<210> SEQ ID NO 388
<211> LENGTH: 20
<212> TYPE: DNA
<213> ORGANISM: Artificial Sequence
<220> FEATURE:
<223> OTHER INFORMATION: Synthetic

<400> SEQUENCE: 388
ccagtacaaa cctacctacg                                                 20

<210> SEQ ID NO 389
<211> LENGTH: 20
<212> TYPE: DNA
<213> ORGANISM: Artificial Sequence
<220> FEATURE:
<223> OTHER INFORMATION: Synthetic

<400> SEQUENCE: 389
```

```
agtagtccgg gatatcagcg                                             20

<210> SEQ ID NO 390
<211> LENGTH: 20
<212> TYPE: DNA
<213> ORGANISM: Artificial Sequence
<220> FEATURE:
<223> OTHER INFORMATION: Synthetic

<400> SEQUENCE: 390
agtagtccgg gatatcagcg                                             20

<210> SEQ ID NO 391
<211> LENGTH: 20
<212> TYPE: DNA
<213> ORGANISM: Artificial Sequence
<220> FEATURE:
<223> OTHER INFORMATION: Synthetic

<400> SEQUENCE: 391
tcatattacg agtcagtagg                                             20

<210> SEQ ID NO 392
<211> LENGTH: 20
<212> TYPE: DNA
<213> ORGANISM: Artificial Sequence
<220> FEATURE:
<223> OTHER INFORMATION: Synthetic

<400> SEQUENCE: 392
tcatattacg agtcagtagg                                             20

<210> SEQ ID NO 393
<211> LENGTH: 19
<212> TYPE: DNA
<213> ORGANISM: Artificial Sequence
<220> FEATURE:
<223> OTHER INFORMATION: Synthetic

<400> SEQUENCE: 393
agagcactgc actccttca                                              19

<210> SEQ ID NO 394
<211> LENGTH: 20
<212> TYPE: DNA
<213> ORGANISM: Artificial Sequence
<220> FEATURE:
<223> OTHER INFORMATION: Synthetic

<400> SEQUENCE: 394
tccaccggcg aaagagatcc                                             20

<210> SEQ ID NO 395
<211> LENGTH: 20
<212> TYPE: DNA
<213> ORGANISM: Artificial Sequence
<220> FEATURE:
<223> OTHER INFORMATION: Synthetic

<400> SEQUENCE: 395
tccaccggcg aaagagatcc                                             20

<210> SEQ ID NO 396
<211> LENGTH: 19
<212> TYPE: DNA
```

```
<213> ORGANISM: Artificial Sequence
<220> FEATURE:
<223> OTHER INFORMATION: Synthetic

<400> SEQUENCE: 396
agagcactgc actccttca                                                19

<210> SEQ ID NO 397
<211> LENGTH: 19
<212> TYPE: DNA
<213> ORGANISM: Artificial Sequence
<220> FEATURE:
<223> OTHER INFORMATION: Synthetic

<400> SEQUENCE: 397
agagcactgc actccttca                                                19

<210> SEQ ID NO 398
<211> LENGTH: 20
<212> TYPE: DNA
<213> ORGANISM: Artificial Sequence
<220> FEATURE:
<223> OTHER INFORMATION: Synthetic

<400> SEQUENCE: 398
tccaccggcg aaagagatcc                                               20

<210> SEQ ID NO 399
<211> LENGTH: 20
<212> TYPE: DNA
<213> ORGANISM: Artificial Sequence
<220> FEATURE:
<223> OTHER INFORMATION: Synthetic

<400> SEQUENCE: 399
tcatattacg agtcagtagg                                               20

<210> SEQ ID NO 400
<211> LENGTH: 20
<212> TYPE: DNA
<213> ORGANISM: Artificial Sequence
<220> FEATURE:
<223> OTHER INFORMATION: Synthetic

<400> SEQUENCE: 400
ccagtacaaa cctacctacg                                               20

<210> SEQ ID NO 401
<211> LENGTH: 19
<212> TYPE: DNA
<213> ORGANISM: Artificial Sequence
<220> FEATURE:
<223> OTHER INFORMATION: Synthetic

<400> SEQUENCE: 401
agagcactgc actccttca                                                19

<210> SEQ ID NO 402
<211> LENGTH: 19
<212> TYPE: DNA
<213> ORGANISM: Artificial Sequence
<220> FEATURE:
<223> OTHER INFORMATION: Synthetic

<400> SEQUENCE: 402
agagcactgc actccttca                                                19
```

```
<210> SEQ ID NO 403
<211> LENGTH: 20
<212> TYPE: DNA
<213> ORGANISM: Artificial Sequence
<220> FEATURE:
<223> OTHER INFORMATION: Synthetic

<400> SEQUENCE: 403
ccagtacaaa cctacctacg                                               20

<210> SEQ ID NO 404
<211> LENGTH: 20
<212> TYPE: DNA
<213> ORGANISM: Artificial Sequence
<220> FEATURE:
<223> OTHER INFORMATION: Synthetic

<400> SEQUENCE: 404
tcatattacg agtcagtagg                                               20

<210> SEQ ID NO 405
<211> LENGTH: 20
<212> TYPE: DNA
<213> ORGANISM: Artificial Sequence
<220> FEATURE:
<223> OTHER INFORMATION: Synthetic

<400> SEQUENCE: 405
tcatattacg agtcagtagg                                               20

<210> SEQ ID NO 406
<211> LENGTH: 20
<212> TYPE: DNA
<213> ORGANISM: Artificial Sequence
<220> FEATURE:
<223> OTHER INFORMATION: Synthetic

<400> SEQUENCE: 406
cgccgccccc ggacgcgacc                                               20

<210> SEQ ID NO 407
<211> LENGTH: 20
<212> TYPE: DNA
<213> ORGANISM: Artificial Sequence
<220> FEATURE:
<223> OTHER INFORMATION: Synthetic

<400> SEQUENCE: 407
cgccgccccc ggacgcgacc                                               20

<210> SEQ ID NO 408
<211> LENGTH: 20
<212> TYPE: DNA
<213> ORGANISM: Artificial Sequence
<220> FEATURE:
<223> OTHER INFORMATION: Synthetic

<400> SEQUENCE: 408
agtagtccgg gatatcagcg                                               20

<210> SEQ ID NO 409
<211> LENGTH: 20
<212> TYPE: DNA
<213> ORGANISM: Artificial Sequence
<220> FEATURE:
```

<223> OTHER INFORMATION: Synthetic

<400> SEQUENCE: 409
agtagtccgg gatatcagcg                                              20

<210> SEQ ID NO 410
<211> LENGTH: 20
<212> TYPE: DNA
<213> ORGANISM: Artificial Sequence
<220> FEATURE:
<223> OTHER INFORMATION: Synthetic

<400> SEQUENCE: 410
tcatattacg agtcagtagg                                              20

<210> SEQ ID NO 411
<211> LENGTH: 20
<212> TYPE: DNA
<213> ORGANISM: Artificial Sequence
<220> FEATURE:
<223> OTHER INFORMATION: Synthetic

<400> SEQUENCE: 411
ccagtacaaa cctacctacg                                              20

<210> SEQ ID NO 412
<211> LENGTH: 20
<212> TYPE: DNA
<213> ORGANISM: Artificial Sequence
<220> FEATURE:
<223> OTHER INFORMATION: Synthetic

<400> SEQUENCE: 412
tcatattacg agtcagtagg                                              20

<210> SEQ ID NO 413
<211> LENGTH: 20
<212> TYPE: DNA
<213> ORGANISM: Artificial Sequence
<220> FEATURE:
<223> OTHER INFORMATION: Synthetic

<400> SEQUENCE: 413
tcatattacg agtcagtagg                                              20

<210> SEQ ID NO 414
<211> LENGTH: 19
<212> TYPE: DNA
<213> ORGANISM: Artificial Sequence
<220> FEATURE:
<223> OTHER INFORMATION: Synthetic

<400> SEQUENCE: 414
agagcactgc actccttca                                               19

<210> SEQ ID NO 415
<211> LENGTH: 19
<212> TYPE: DNA
<213> ORGANISM: Artificial Sequence
<220> FEATURE:
<223> OTHER INFORMATION: Synthetic

<400> SEQUENCE: 415
agagcactgc actccttca                                               19

```
<210> SEQ ID NO 416
<211> LENGTH: 20
<212> TYPE: DNA
<213> ORGANISM: Artificial Sequence
<220> FEATURE:
<223> OTHER INFORMATION: Synthetic

<400> SEQUENCE: 416
tccaccggcg aaagagatcc                                          20

<210> SEQ ID NO 417
<211> LENGTH: 20
<212> TYPE: DNA
<213> ORGANISM: Artificial Sequence
<220> FEATURE:
<223> OTHER INFORMATION: Synthetic

<400> SEQUENCE: 417
tcatattacg agtcagtagg                                          20

<210> SEQ ID NO 418
<211> LENGTH: 20
<212> TYPE: DNA
<213> ORGANISM: Artificial Sequence
<220> FEATURE:
<223> OTHER INFORMATION: Synthetic

<400> SEQUENCE: 418
tccaccggcg aaagagatcc                                          20

<210> SEQ ID NO 419
<211> LENGTH: 20
<212> TYPE: DNA
<213> ORGANISM: Artificial Sequence
<220> FEATURE:
<223> OTHER INFORMATION: Synthetic

<400> SEQUENCE: 419
ccagtacaaa cctacctacg                                          20

<210> SEQ ID NO 420
<211> LENGTH: 20
<212> TYPE: DNA
<213> ORGANISM: Artificial Sequence
<220> FEATURE:
<223> OTHER INFORMATION: Synthetic

<400> SEQUENCE: 420
cctgcaacgg gactagttgg                                          20

<210> SEQ ID NO 421
<211> LENGTH: 20
<212> TYPE: DNA
<213> ORGANISM: Artificial Sequence
<220> FEATURE:
<223> OTHER INFORMATION: Synthetic

<400> SEQUENCE: 421
ccagtacaaa cctacctacg                                          20

<210> SEQ ID NO 422
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 422
ccagtacaaa cctacctacg                                                  20

<210> SEQ ID NO 423
<211> LENGTH: 20
<212> TYPE: DNA
<213> ORGANISM: Artificial Sequence
<220> FEATURE:
<223> OTHER INFORMATION: Synthetic

<400> SEQUENCE: 423 cgccgcccccc ggacgcgacc                                                 20

<210> SEQ ID NO 424
<211> LENGTH: 20
<212> TYPE: DNA
<213> ORGANISM: Artificial Sequence
<220> FEATURE:
<223> OTHER INFORMATION: Synthetic

<400> SEQUENCE: 424 cgccgcccccc ggacgcgacc                                                 20

<210> SEQ ID NO 425
<211> LENGTH: 20
<212> TYPE: DNA
<213> ORGANISM: Artificial Sequence
<220> FEATURE:
<223> OTHER INFORMATION: Synthetic

<400> SEQUENCE: 425 cgccgcccccc ggacgcgacc                                                 20

<210> SEQ ID NO 426
<211> LENGTH: 20
<212> TYPE: DNA
<213> ORGANISM: Artificial Sequence
<220> FEATURE:
<223> OTHER INFORMATION: Synthetic

<400> SEQUENCE: 426 cgccgcccccc ggacgcgacc                                                 20

<210> SEQ ID NO 427
<211> LENGTH: 20
<212> TYPE: DNA
<213> ORGANISM: Artificial Sequence
<220> FEATURE:
<223> OTHER INFORMATION: Synthetic

<400> SEQUENCE: 427
cctgcaacgg gactagttgg                                                  20

<210> SEQ ID NO 428
<211> LENGTH: 20
<212> TYPE: DNA
<213> ORGANISM: Artificial Sequence
<220> FEATURE:
<223> OTHER INFORMATION: Synthetic

<400> SEQUENCE: 428
cctgcaacgg gactagttgg                                                  20

<210> SEQ ID NO 429
<211> LENGTH: 19
```

-continued

```
<212> TYPE: DNA
<213> ORGANISM: Artificial Sequence
<220> FEATURE:
<223> OTHER INFORMATION: Synthetic

<400> SEQUENCE: 429
agagcactgc actccttca                                                19

<210> SEQ ID NO 430
<211> LENGTH: 20
<212> TYPE: DNA
<213> ORGANISM: Artificial Sequence
<220> FEATURE:
<223> OTHER INFORMATION: Synthetic

<400> SEQUENCE: 430
cctgcaacgg gactagttgg                                               20

<210> SEQ ID NO 431
<211> LENGTH: 20
<212> TYPE: DNA
<213> ORGANISM: Artificial Sequence
<220> FEATURE:
<223> OTHER INFORMATION: Synthetic

<400> SEQUENCE: 431
cctgcaacgg gactagttgg                                               20

<210> SEQ ID NO 432
<211> LENGTH: 19
<212> TYPE: DNA
<213> ORGANISM: Artificial Sequence
<220> FEATURE:
<223> OTHER INFORMATION: Synthetic

<400> SEQUENCE: 432
agagcactgc actccttca                                                19

<210> SEQ ID NO 433
<211> LENGTH: 20
<212> TYPE: DNA
<213> ORGANISM: Artificial Sequence
<220> FEATURE:
<223> OTHER INFORMATION: Synthetic

<400> SEQUENCE: 433
cctgcaacgg gactagttgg                                               20

<210> SEQ ID NO 434
<211> LENGTH: 20
<212> TYPE: DNA
<213> ORGANISM: Artificial Sequence
<220> FEATURE:
<223> OTHER INFORMATION: Synthetic

<400> SEQUENCE: 434
cctgcaacgg gactagttgg                                               20

<210> SEQ ID NO 435
<211> LENGTH: 19
<212> TYPE: DNA
<213> ORGANISM: Artificial Sequence
<220> FEATURE:
<223> OTHER INFORMATION: Synthetic

<400> SEQUENCE: 435
```
agagcactgc actccttca                                     19

<210> SEQ ID NO 436
<211> LENGTH: 20
<212> TYPE: DNA
<213> ORGANISM: Artificial Sequence
<220> FEATURE:
<223> OTHER INFORMATION: Synthetic

<400> SEQUENCE: 436
ccagtacaaa cctacctacg                                    20

<210> SEQ ID NO 437
<211> LENGTH: 20
<212> TYPE: DNA
<213> ORGANISM: Artificial Sequence
<220> FEATURE:
<223> OTHER INFORMATION: Synthetic

<400> SEQUENCE: 437
tccaccggcg aaagagatcc                                    20

<210> SEQ ID NO 438
<211> LENGTH: 20
<212> TYPE: DNA
<213> ORGANISM: Artificial Sequence
<220> FEATURE:
<223> OTHER INFORMATION: Synthetic

<400> SEQUENCE: 438
tcatattacg agtcagtagg                                    20

<210> SEQ ID NO 439
<211> LENGTH: 19
<212> TYPE: DNA
<213> ORGANISM: Artificial Sequence
<220> FEATURE:
<223> OTHER INFORMATION: Synthetic

<400> SEQUENCE: 439
agagcactgc actccttca                                     19

<210> SEQ ID NO 440
<211> LENGTH: 20
<212> TYPE: DNA
<213> ORGANISM: Artificial Sequence
<220> FEATURE:
<223> OTHER INFORMATION: Synthetic

<400> SEQUENCE: 440
tccaccggcg aaagagatcc                                    20

<210> SEQ ID NO 441
<211> LENGTH: 20
<212> TYPE: DNA
<213> ORGANISM: Artificial Sequence
<220> FEATURE:
<223> OTHER INFORMATION: Synthetic

<400> SEQUENCE: 441
atacaactgc ttgcaacagg                                    20

<210> SEQ ID NO 442
<211> LENGTH: 20
<212> TYPE: DNA
<213> ORGANISM: Artificial Sequence

```
<220> FEATURE:
<223> OTHER INFORMATION: Synthetic

<400> SEQUENCE: 442
atacaactgc ttgcaacagg                                                    20

<210> SEQ ID NO 443
<211> LENGTH: 20
<212> TYPE: DNA
<213> ORGANISM: Artificial Sequence
<220> FEATURE:
<223> OTHER INFORMATION: Synthetic

<400> SEQUENCE: 443
tccaccggcg aaagagatcc                                                    20

<210> SEQ ID NO 444
<211> LENGTH: 20
<212> TYPE: DNA
<213> ORGANISM: Artificial Sequence
<220> FEATURE:
<223> OTHER INFORMATION: Synthetic

<400> SEQUENCE: 444
ccagtacaaa cctacctacg                                                    20

<210> SEQ ID NO 445
<211> LENGTH: 19
<212> TYPE: DNA
<213> ORGANISM: Artificial Sequence
<220> FEATURE:
<223> OTHER INFORMATION: Synthetic

<400> SEQUENCE: 445
agagcactgc actccttca                                                     19

<210> SEQ ID NO 446
<211> LENGTH: 19
<212> TYPE: DNA
<213> ORGANISM: Artificial Sequence
<220> FEATURE:
<223> OTHER INFORMATION: Synthetic

<400> SEQUENCE: 446
agagcactgc actccttca                                                     19

<210> SEQ ID NO 447
<211> LENGTH: 19
<212> TYPE: DNA
<213> ORGANISM: Artificial Sequence
<220> FEATURE:
<223> OTHER INFORMATION: Synthetic

<400> SEQUENCE: 447
agagcactgc actccttca                                                     19

<210> SEQ ID NO 448
<211> LENGTH: 19
<212> TYPE: DNA
<213> ORGANISM: Artificial Sequence
<220> FEATURE:
<223> OTHER INFORMATION: Synthetic

<400> SEQUENCE: 448
agagcactgc actccttca                                                     19
```

```
<210> SEQ ID NO 449
<211> LENGTH: 19
<212> TYPE: DNA
<213> ORGANISM: Artificial Sequence
<220> FEATURE:
<223> OTHER INFORMATION: Synthetic

<400> SEQUENCE: 449
agagcactgc actccttca                                                  19

<210> SEQ ID NO 450
<211> LENGTH: 19
<212> TYPE: DNA
<213> ORGANISM: Artificial Sequence
<220> FEATURE:
<223> OTHER INFORMATION: Synthetic

<400> SEQUENCE: 450
agagcactgc actccttca                                                  19

<210> SEQ ID NO 451
<211> LENGTH: 20
<212> TYPE: DNA
<213> ORGANISM: Artificial Sequence
<220> FEATURE:
<223> OTHER INFORMATION: Synthetic

<400> SEQUENCE: 451
agtagtccgg gatatcagcg                                                 20

<210> SEQ ID NO 452
<211> LENGTH: 20
<212> TYPE: DNA
<213> ORGANISM: Artificial Sequence
<220> FEATURE:
<223> OTHER INFORMATION: Synthetic

<400> SEQUENCE: 452
agtagtccgg gatatcagcg                                                 20

<210> SEQ ID NO 453
<211> LENGTH: 20
<212> TYPE: DNA
<213> ORGANISM: Artificial Sequence
<220> FEATURE:
<223> OTHER INFORMATION: Synthetic

<400> SEQUENCE: 453
tcatattacg agtcagtagg                                                 20

<210> SEQ ID NO 454
<211> LENGTH: 20
<212> TYPE: DNA
<213> ORGANISM: Artificial Sequence
<220> FEATURE:
<223> OTHER INFORMATION: Synthetic

<400> SEQUENCE: 454
tcatattacg agtcagtagg                                                 20

<210> SEQ ID NO 455
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 455
cgccgccccc ggacgcgacc                                           20

<210> SEQ ID NO 456
<211> LENGTH: 20
<212> TYPE: DNA
<213> ORGANISM: Artificial Sequence
<220> FEATURE:
<223> OTHER INFORMATION: Synthetic

<400> SEQUENCE: 456
cgccgccccc ggacgcgacc                                           20

<210> SEQ ID NO 457
<211> LENGTH: 19
<212> TYPE: DNA
<213> ORGANISM: Artificial Sequence
<220> FEATURE:
<223> OTHER INFORMATION: Synthetic

<400> SEQUENCE: 457
agagcactgc actccttca                                            19

<210> SEQ ID NO 458
<211> LENGTH: 19
<212> TYPE: DNA
<213> ORGANISM: Artificial Sequence
<220> FEATURE:
<223> OTHER INFORMATION: Synthetic

<400> SEQUENCE: 458
agagcactgc actccttca                                            19

<210> SEQ ID NO 459
<211> LENGTH: 20
<212> TYPE: DNA
<213> ORGANISM: Artificial Sequence
<220> FEATURE:
<223> OTHER INFORMATION: Synthetic

<400> SEQUENCE: 459
agtagtccgg gatatcagcg                                           20

<210> SEQ ID NO 460
<211> LENGTH: 20
<212> TYPE: DNA
<213> ORGANISM: Artificial Sequence
<220> FEATURE:
<223> OTHER INFORMATION: Synthetic

<400> SEQUENCE: 460
agtagtccgg gatatcagcg                                           20

<210> SEQ ID NO 461
<211> LENGTH: 20
<212> TYPE: DNA
<213> ORGANISM: Artificial Sequence
<220> FEATURE:
<223> OTHER INFORMATION: Synthetic

<400> SEQUENCE: 461
ccagtacaaa cctacctacg                                           20

<210> SEQ ID NO 462
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 462
ccagtacaaa cctacctacg                                               20

<210> SEQ ID NO 463
<211> LENGTH: 20
<212> TYPE: DNA
<213> ORGANISM: Artificial Sequence
<220> FEATURE:
<223> OTHER INFORMATION: Synthetic

<400> SEQUENCE: 463
atacaactgc ttgcaacagg                                               20

<210> SEQ ID NO 464
<211> LENGTH: 20
<212> TYPE: DNA
<213> ORGANISM: Artificial Sequence
<220> FEATURE:
<223> OTHER INFORMATION: Synthetic

<400> SEQUENCE: 464
atacaactgc ttgcaacagg                                               20

<210> SEQ ID NO 465
<211> LENGTH: 20
<212> TYPE: DNA
<213> ORGANISM: Artificial Sequence
<220> FEATURE:
<223> OTHER INFORMATION: Synthetic

<400> SEQUENCE: 465
cgccgccccc ggacgcgacc                                               20

<210> SEQ ID NO 466
<211> LENGTH: 20
<212> TYPE: DNA
<213> ORGANISM: Artificial Sequence
<220> FEATURE:
<223> OTHER INFORMATION: Synthetic

<400> SEQUENCE: 466
cgccgccccc ggacgcgacc                                               20

<210> SEQ ID NO 467
<211> LENGTH: 20
<212> TYPE: DNA
<213> ORGANISM: Artificial Sequence
<220> FEATURE:
<223> OTHER INFORMATION: Synthetic

<400> SEQUENCE: 467
cgccgccccc ggacgcgacc                                               20

<210> SEQ ID NO 468
<211> LENGTH: 20
<212> TYPE: DNA
<213> ORGANISM: Artificial Sequence
<220> FEATURE:
<223> OTHER INFORMATION: Synthetic

<400> SEQUENCE: 468
```
cgccgccccc ggacgcgacc                                              20

<210> SEQ ID NO 469
<211> LENGTH: 20
<212> TYPE: DNA
<213> ORGANISM: Artificial Sequence
<220> FEATURE:
<223> OTHER INFORMATION: Synthetic

<400> SEQUENCE: 469
agtagtccgg gatatcagcg                                              20

<210> SEQ ID NO 470
<211> LENGTH: 20
<212> TYPE: DNA
<213> ORGANISM: Artificial Sequence
<220> FEATURE:
<223> OTHER INFORMATION: Synthetic

<400> SEQUENCE: 470
agtagtccgg gatatcagcg                                              20

<210> SEQ ID NO 471
<211> LENGTH: 20
<212> TYPE: DNA
<213> ORGANISM: Artificial Sequence
<220> FEATURE:
<223> OTHER INFORMATION: Synthetic

<400> SEQUENCE: 471
cgccgccccc ggacgcgacc                                              20

<210> SEQ ID NO 472
<211> LENGTH: 20
<212> TYPE: DNA
<213> ORGANISM: Artificial Sequence
<220> FEATURE:
<223> OTHER INFORMATION: Synthetic

<400> SEQUENCE: 472
cgccgccccc ggacgcgacc                                              20

<210> SEQ ID NO 473
<211> LENGTH: 19
<212> TYPE: DNA
<213> ORGANISM: Artificial Sequence
<220> FEATURE:
<223> OTHER INFORMATION: Synthetic

<400> SEQUENCE: 473
agagcactgc actccttca                                               19

<210> SEQ ID NO 474
<211> LENGTH: 19
<212> TYPE: DNA
<213> ORGANISM: Artificial Sequence
<220> FEATURE:
<223> OTHER INFORMATION: Synthetic

<400> SEQUENCE: 474
agagcactgc actccttca                                               19

<210> SEQ ID NO 475
<211> LENGTH: 20
<212> TYPE: DNA

```
<213> ORGANISM: Artificial Sequence
<220> FEATURE:
<223> OTHER INFORMATION: Synthetic

<400> SEQUENCE: 475
cgccgccccc ggacgcgacc                                               20

<210> SEQ ID NO 476
<211> LENGTH: 20
<212> TYPE: DNA
<213> ORGANISM: Artificial Sequence
<220> FEATURE:
<223> OTHER INFORMATION: Synthetic

<400> SEQUENCE: 476
cgccgccccc ggacgcgacc                                               20

<210> SEQ ID NO 477
<211> LENGTH: 20
<212> TYPE: DNA
<213> ORGANISM: Artificial Sequence
<220> FEATURE:
<223> OTHER INFORMATION: Synthetic

<400> SEQUENCE: 477
cctgcaacgg gactagttgg                                               20

<210> SEQ ID NO 478
<211> LENGTH: 20
<212> TYPE: DNA
<213> ORGANISM: Artificial Sequence
<220> FEATURE:
<223> OTHER INFORMATION: Synthetic

<400> SEQUENCE: 478
cctgcaacgg gactagttgg                                               20

<210> SEQ ID NO 479
<211> LENGTH: 19
<212> TYPE: DNA
<213> ORGANISM: Artificial Sequence
<220> FEATURE:
<223> OTHER INFORMATION: Synthetic

<400> SEQUENCE: 479
agagcactgc actccttca                                                19

<210> SEQ ID NO 480
<211> LENGTH: 19
<212> TYPE: DNA
<213> ORGANISM: Artificial Sequence
<220> FEATURE:
<223> OTHER INFORMATION: Synthetic

<400> SEQUENCE: 480
agagcactgc actccttca                                                19

<210> SEQ ID NO 481
<211> LENGTH: 20
<212> TYPE: DNA
<213> ORGANISM: Artificial Sequence
<220> FEATURE:
<223> OTHER INFORMATION: Synthetic

<400> SEQUENCE: 481
cctgcaacgg gactagttgg                                               20
```

```
<210> SEQ ID NO 482
<211> LENGTH: 20
<212> TYPE: DNA
<213> ORGANISM: Artificial Sequence
<220> FEATURE:
<223> OTHER INFORMATION: Synthetic

<400> SEQUENCE: 482
cctgcaacgg gactagttgg                                           20

<210> SEQ ID NO 483
<211> LENGTH: 20
<212> TYPE: DNA
<213> ORGANISM: Artificial Sequence
<220> FEATURE:
<223> OTHER INFORMATION: Synthetic

<400> SEQUENCE: 483
cctgcaacgg gactagttgg                                           20

<210> SEQ ID NO 484
<211> LENGTH: 19
<212> TYPE: DNA
<213> ORGANISM: Artificial Sequence
<220> FEATURE:
<223> OTHER INFORMATION: Synthetic

<400> SEQUENCE: 484
agagcactgc actccttca                                            19

<210> SEQ ID NO 485
<211> LENGTH: 20
<212> TYPE: DNA
<213> ORGANISM: Artificial Sequence
<220> FEATURE:
<223> OTHER INFORMATION: Synthetic

<400> SEQUENCE: 485
cctgcaacgg gactagttgg                                           20

<210> SEQ ID NO 486
<211> LENGTH: 20
<212> TYPE: DNA
<213> ORGANISM: Artificial Sequence
<220> FEATURE:
<223> OTHER INFORMATION: Synthetic

<400> SEQUENCE: 486
cctgcaacgg gactagttgg                                           20

<210> SEQ ID NO 487
<211> LENGTH: 20
<212> TYPE: DNA
<213> ORGANISM: Artificial Sequence
<220> FEATURE:
<223> OTHER INFORMATION: Synthetic

<400> SEQUENCE: 487
tcatattacg agtcagtagg                                           20

<210> SEQ ID NO 488
<211> LENGTH: 20
<212> TYPE: DNA
<213> ORGANISM: Artificial Sequence
<220> FEATURE:
```

<223> OTHER INFORMATION: Synthetic

<400> SEQUENCE: 488
atacaactgc ttgcaacagg                                           20

<210> SEQ ID NO 489
<211> LENGTH: 20
<212> TYPE: DNA
<213> ORGANISM: Artificial Sequence
<220> FEATURE:
<223> OTHER INFORMATION: Synthetic

<400> SEQUENCE: 489
cgccgccccc ggacgcgacc                                           20

<210> SEQ ID NO 490
<211> LENGTH: 20
<212> TYPE: DNA
<213> ORGANISM: Artificial Sequence
<220> FEATURE:
<223> OTHER INFORMATION: Synthetic

<400> SEQUENCE: 490
cgccgccccc ggacgcgacc                                           20

<210> SEQ ID NO 491
<211> LENGTH: 20
<212> TYPE: DNA
<213> ORGANISM: Artificial Sequence
<220> FEATURE:
<223> OTHER INFORMATION: Synthetic

<400> SEQUENCE: 491
cgccgccccc ggacgcgacc                                           20

<210> SEQ ID NO 492
<211> LENGTH: 20
<212> TYPE: DNA
<213> ORGANISM: Artificial Sequence
<220> FEATURE:
<223> OTHER INFORMATION: Synthetic

<400> SEQUENCE: 492
cgccgccccc ggacgcgacc                                           20

<210> SEQ ID NO 493
<211> LENGTH: 20
<212> TYPE: DNA
<213> ORGANISM: Artificial Sequence
<220> FEATURE:
<223> OTHER INFORMATION: Synthetic

<400> SEQUENCE: 493
ccagtacaaa cctacctacg                                           20

<210> SEQ ID NO 494
<211> LENGTH: 20
<212> TYPE: DNA
<213> ORGANISM: Artificial Sequence
<220> FEATURE:
<223> OTHER INFORMATION: Synthetic

<400> SEQUENCE: 494
tcatattacg agtcagtagg                                           20

```
<210> SEQ ID NO 495
<211> LENGTH: 20
<212> TYPE: DNA
<213> ORGANISM: Artificial Sequence
<220> FEATURE:
<223> OTHER INFORMATION: Synthetic

<400> SEQUENCE: 495
tcatattacg agtcagtagg                                                   20

<210> SEQ ID NO 496
<211> LENGTH: 20
<212> TYPE: DNA
<213> ORGANISM: Artificial Sequence
<220> FEATURE:
<223> OTHER INFORMATION: Synthetic

<400> SEQUENCE: 496
ccagtacaaa cctacctacg                                                   20

<210> SEQ ID NO 497
<211> LENGTH: 20
<212> TYPE: DNA
<213> ORGANISM: Artificial Sequence
<220> FEATURE:
<223> OTHER INFORMATION: Synthetic

<400> SEQUENCE: 497
cgccgccccc ggacgcgacc                                                   20

<210> SEQ ID NO 498
<211> LENGTH: 20
<212> TYPE: DNA
<213> ORGANISM: Artificial Sequence
<220> FEATURE:
<223> OTHER INFORMATION: Synthetic

<400> SEQUENCE: 498
cgccgccccc ggacgcgacc                                                   20

<210> SEQ ID NO 499
<211> LENGTH: 20
<212> TYPE: DNA
<213> ORGANISM: Artificial Sequence
<220> FEATURE:
<223> OTHER INFORMATION: Synthetic

<400> SEQUENCE: 499
cctgcaacgg gactagttgg                                                   20

<210> SEQ ID NO 500
<211> LENGTH: 20
<212> TYPE: DNA
<213> ORGANISM: Artificial Sequence
<220> FEATURE:
<223> OTHER INFORMATION: Synthetic

<400> SEQUENCE: 500
cctgcaacgg gactagttgg                                                   20

<210> SEQ ID NO 501
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 501
tccaccggcg aaagagatcc                                              20

<210> SEQ ID NO 502
<211> LENGTH: 20
<212> TYPE: DNA
<213> ORGANISM: Artificial Sequence
<220> FEATURE:
<223> OTHER INFORMATION: Synthetic

<400> SEQUENCE: 502
agtagtccgg gatatcagcg                                              20

<210> SEQ ID NO 503
<211> LENGTH: 20
<212> TYPE: DNA
<213> ORGANISM: Artificial Sequence
<220> FEATURE:
<223> OTHER INFORMATION: Synthetic

<400> SEQUENCE: 503
atacaactgc ttgcaacagg                                              20

<210> SEQ ID NO 504
<211> LENGTH: 20
<212> TYPE: DNA
<213> ORGANISM: Artificial Sequence
<220> FEATURE:
<223> OTHER INFORMATION: Synthetic

<400> SEQUENCE: 504
agtagtccgg gatatcagcg                                              20

<210> SEQ ID NO 505
<211> LENGTH: 20
<212> TYPE: DNA
<213> ORGANISM: Artificial Sequence
<220> FEATURE:
<223> OTHER INFORMATION: Synthetic

<400> SEQUENCE: 505
agtagtccgg gatatcagcg                                              20

<210> SEQ ID NO 506
<211> LENGTH: 20
<212> TYPE: DNA
<213> ORGANISM: Artificial Sequence
<220> FEATURE:
<223> OTHER INFORMATION: Synthetic

<400> SEQUENCE: 506
atacaactgc ttgcaacagg                                              20

<210> SEQ ID NO 507
<211> LENGTH: 20
<212> TYPE: DNA
<213> ORGANISM: Artificial Sequence
<220> FEATURE:
<223> OTHER INFORMATION: Synthetic

<400> SEQUENCE: 507
tccaccggcg aaagagatcc                                              20

<210> SEQ ID NO 508
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 508
cctgcaacgg gactagttgg                                              20

<210> SEQ ID NO 509
<211> LENGTH: 20
<212> TYPE: DNA
<213> ORGANISM: Artificial Sequence
<220> FEATURE:
<223> OTHER INFORMATION: Synthetic

<400> SEQUENCE: 509
tccaccggcg aaagagatcc                                              20

<210> SEQ ID NO 510
<211> LENGTH: 20
<212> TYPE: DNA
<213> ORGANISM: Artificial Sequence
<220> FEATURE:
<223> OTHER INFORMATION: Synthetic

<400> SEQUENCE: 510
tccaccggcg aaagagatcc                                              20

<210> SEQ ID NO 511
<211> LENGTH: 20
<212> TYPE: DNA
<213> ORGANISM: Artificial Sequence
<220> FEATURE:
<223> OTHER INFORMATION: Synthetic

<400> SEQUENCE: 511
agtagtccgg gatatcagcg                                              20

<210> SEQ ID NO 512
<211> LENGTH: 19
<212> TYPE: DNA
<213> ORGANISM: Artificial Sequence
<220> FEATURE:
<223> OTHER INFORMATION: Synthetic

<400> SEQUENCE: 512
agagcactgc actccttca                                               19

<210> SEQ ID NO 513
<211> LENGTH: 20
<212> TYPE: DNA
<213> ORGANISM: Artificial Sequence
<220> FEATURE:
<223> OTHER INFORMATION: Synthetic

<400> SEQUENCE: 513
tccaccggcg aaagagatcc                                              20

<210> SEQ ID NO 514
<211> LENGTH: 20
<212> TYPE: DNA
<213> ORGANISM: Artificial Sequence
<220> FEATURE:
<223> OTHER INFORMATION: Synthetic

<400> SEQUENCE: 514
```
cgccgccccc ggacgcgacc                                           20

<210> SEQ ID NO 515
<211> LENGTH: 19
<212> TYPE: DNA
<213> ORGANISM: Artificial Sequence
<220> FEATURE:
<223> OTHER INFORMATION: Synthetic

<400> SEQUENCE: 515
agagcactgc actccttca                                            19

<210> SEQ ID NO 516
<211> LENGTH: 20
<212> TYPE: DNA
<213> ORGANISM: Artificial Sequence
<220> FEATURE:
<223> OTHER INFORMATION: Synthetic

<400> SEQUENCE: 516
tccaccggcg aaagagatcc                                           20

<210> SEQ ID NO 517
<211> LENGTH: 20
<212> TYPE: DNA
<213> ORGANISM: Artificial Sequence
<220> FEATURE:
<223> OTHER INFORMATION: Synthetic

<400> SEQUENCE: 517
agtagtccgg gatatcagcg                                           20

<210> SEQ ID NO 518
<211> LENGTH: 20
<212> TYPE: DNA
<213> ORGANISM: Artificial Sequence
<220> FEATURE:
<223> OTHER INFORMATION: Synthetic

<400> SEQUENCE: 518
atacaactgc ttgcaacagg                                           20

<210> SEQ ID NO 519
<211> LENGTH: 20
<212> TYPE: DNA
<213> ORGANISM: Artificial Sequence
<220> FEATURE:
<223> OTHER INFORMATION: Synthetic

<400> SEQUENCE: 519
atacaactgc ttgcaacagg                                           20

<210> SEQ ID NO 520
<211> LENGTH: 20
<212> TYPE: DNA
<213> ORGANISM: Artificial Sequence
<220> FEATURE:
<223> OTHER INFORMATION: Synthetic

<400> SEQUENCE: 520
cgccgccccc ggacgcgacc                                           20

<210> SEQ ID NO 521
<211> LENGTH: 20
<212> TYPE: DNA
<213> ORGANISM: Artificial Sequence

```
<220> FEATURE:
<223> OTHER INFORMATION: Synthetic

<400> SEQUENCE: 521
tccaccggcg aaagagatcc                                               20

<210> SEQ ID NO 522
<211> LENGTH: 20
<212> TYPE: DNA
<213> ORGANISM: Artificial Sequence
<220> FEATURE:
<223> OTHER INFORMATION: Synthetic

<400> SEQUENCE: 522
ccagtacaaa cctacctacg                                               20

<210> SEQ ID NO 523
<211> LENGTH: 20
<212> TYPE: DNA
<213> ORGANISM: Artificial Sequence
<220> FEATURE:
<223> OTHER INFORMATION: Synthetic

<400> SEQUENCE: 523
atacaactgc ttgcaacagg                                               20

<210> SEQ ID NO 524
<211> LENGTH: 20
<212> TYPE: DNA
<213> ORGANISM: Artificial Sequence
<220> FEATURE:
<223> OTHER INFORMATION: Synthetic

<400> SEQUENCE: 524
atacaactgc ttgcaacagg                                               20

<210> SEQ ID NO 525
<211> LENGTH: 19
<212> TYPE: DNA
<213> ORGANISM: Artificial Sequence
<220> FEATURE:
<223> OTHER INFORMATION: Synthetic

<400> SEQUENCE: 525
agagcactgc actccttca                                                19

<210> SEQ ID NO 526
<211> LENGTH: 20
<212> TYPE: DNA
<213> ORGANISM: Artificial Sequence
<220> FEATURE:
<223> OTHER INFORMATION: Synthetic

<400> SEQUENCE: 526
atacaactgc ttgcaacagg                                               20

<210> SEQ ID NO 527
<211> LENGTH: 20
<212> TYPE: DNA
<213> ORGANISM: Artificial Sequence
<220> FEATURE:
<223> OTHER INFORMATION: Synthetic

<400> SEQUENCE: 527
tcatattacg agtcagtagg                                               20
```

```
<210> SEQ ID NO 528
<211> LENGTH: 20
<212> TYPE: DNA
<213> ORGANISM: Artificial Sequence
<220> FEATURE:
<223> OTHER INFORMATION: Synthetic

<400> SEQUENCE: 528
tcatattacg agtcagtagg                                                   20

<210> SEQ ID NO 529
<211> LENGTH: 19
<212> TYPE: DNA
<213> ORGANISM: Artificial Sequence
<220> FEATURE:
<223> OTHER INFORMATION: Synthetic

<400> SEQUENCE: 529
agagcactgc actccttca                                                    19

<210> SEQ ID NO 530
<211> LENGTH: 20
<212> TYPE: DNA
<213> ORGANISM: Artificial Sequence
<220> FEATURE:
<223> OTHER INFORMATION: Synthetic

<400> SEQUENCE: 530
ccagtacaaa cctacctacg                                                   20

<210> SEQ ID NO 531
<211> LENGTH: 20
<212> TYPE: DNA
<213> ORGANISM: Artificial Sequence
<220> FEATURE:
<223> OTHER INFORMATION: Synthetic

<400> SEQUENCE: 531
tcatattacg agtcagtagg                                                   20

<210> SEQ ID NO 532
<211> LENGTH: 20
<212> TYPE: DNA
<213> ORGANISM: Artificial Sequence
<220> FEATURE:
<223> OTHER INFORMATION: Synthetic

<400> SEQUENCE: 532
tcatattacg agtcagtagg                                                   20

<210> SEQ ID NO 533
<211> LENGTH: 20
<212> TYPE: DNA
<213> ORGANISM: Artificial Sequence
<220> FEATURE:
<223> OTHER INFORMATION: Synthetic

<400> SEQUENCE: 533
cgccgccccc ggacgcgacc                                                   20

<210> SEQ ID NO 534
<211> LENGTH: 20
<212> TYPE: DNA
<213> ORGANISM: Artificial Sequence
<220> FEATURE:
<223> OTHER INFORMATION: Synthetic
```

<400> SEQUENCE: 534
atacaactgc ttgcaacagg                                                20

<210> SEQ ID NO 535
<211> LENGTH: 20
<212> TYPE: DNA
<213> ORGANISM: Artificial Sequence
<220> FEATURE:
<223> OTHER INFORMATION: Synthetic

<400> SEQUENCE: 535
ccagtacaaa cctacctacg                                                20

<210> SEQ ID NO 536
<211> LENGTH: 20
<212> TYPE: DNA
<213> ORGANISM: Artificial Sequence
<220> FEATURE:
<223> OTHER INFORMATION: Synthetic

<400> SEQUENCE: 536
ccagtacaaa cctacctacg                                                20

<210> SEQ ID NO 537
<211> LENGTH: 20
<212> TYPE: DNA
<213> ORGANISM: Artificial Sequence
<220> FEATURE:
<223> OTHER INFORMATION: Synthetic

<400> SEQUENCE: 537
atacaactgc ttgcaacagg                                                20

<210> SEQ ID NO 538
<211> LENGTH: 20
<212> TYPE: DNA
<213> ORGANISM: Artificial Sequence
<220> FEATURE:
<223> OTHER INFORMATION: Synthetic

<400> SEQUENCE: 538
atacaactgc ttgcaacagg                                                20

<210> SEQ ID NO 539
<211> LENGTH: 20
<212> TYPE: DNA
<213> ORGANISM: Artificial Sequence
<220> FEATURE:
<223> OTHER INFORMATION: Synthetic

<400> SEQUENCE: 539
tcatattacg agtcagtagg                                                20

<210> SEQ ID NO 540
<211> LENGTH: 20
<212> TYPE: DNA
<213> ORGANISM: Artificial Sequence
<220> FEATURE:
<223> OTHER INFORMATION: Synthetic

<400> SEQUENCE: 540
tcatattacg agtcagtagg                                                20

<210> SEQ ID NO 541

```
<211> LENGTH: 20
<212> TYPE: DNA
<213> ORGANISM: Artificial Sequence
<220> FEATURE:
<223> OTHER INFORMATION: Synthetic

<400> SEQUENCE: 541
tcatattacg agtcagtagg                                                    20

<210> SEQ ID NO 542
<211> LENGTH: 20
<212> TYPE: DNA
<213> ORGANISM: Artificial Sequence
<220> FEATURE:
<223> OTHER INFORMATION: Synthetic

<400> SEQUENCE: 542
tcatattacg agtcagtagg                                                    20

<210> SEQ ID NO 543
<211> LENGTH: 20
<212> TYPE: DNA
<213> ORGANISM: Artificial Sequence
<220> FEATURE:
<223> OTHER INFORMATION: Synthetic

<400> SEQUENCE: 543
atacaactgc ttgcaacagg                                                    20

<210> SEQ ID NO 544
<211> LENGTH: 20
<212> TYPE: DNA
<213> ORGANISM: Artificial Sequence
<220> FEATURE:
<223> OTHER INFORMATION: Synthetic

<400> SEQUENCE: 544
agtagtccgg gatatcagcg                                                    20

<210> SEQ ID NO 545
<211> LENGTH: 20
<212> TYPE: DNA
<213> ORGANISM: Artificial Sequence
<220> FEATURE:
<223> OTHER INFORMATION: Synthetic

<400> SEQUENCE: 545
cgccgccccc ggacgcgacc                                                    20

<210> SEQ ID NO 546
<211> LENGTH: 20
<212> TYPE: DNA
<213> ORGANISM: Artificial Sequence
<220> FEATURE:
<223> OTHER INFORMATION: Synthetic

<400> SEQUENCE: 546
cgccgccccc ggacgcgacc                                                    20

<210> SEQ ID NO 547
<211> LENGTH: 19
<212> TYPE: DNA
<213> ORGANISM: Artificial Sequence
<220> FEATURE:
<223> OTHER INFORMATION: Synthetic

<400> SEQUENCE: 547
```
agagcactgc actccttca                                            19

<210> SEQ ID NO 548
<211> LENGTH: 19
<212> TYPE: DNA
<213> ORGANISM: Artificial Sequence
<220> FEATURE:
<223> OTHER INFORMATION: Synthetic

<400> SEQUENCE: 548
agagcactgc actccttca                                            19

<210> SEQ ID NO 549
<211> LENGTH: 20
<212> TYPE: DNA
<213> ORGANISM: Artificial Sequence
<220> FEATURE:
<223> OTHER INFORMATION: Synthetic

<400> SEQUENCE: 549
cgccgccccc ggacgcgacc                                           20

<210> SEQ ID NO 550
<211> LENGTH: 20
<212> TYPE: DNA
<213> ORGANISM: Artificial Sequence
<220> FEATURE:
<223> OTHER INFORMATION: Synthetic

<400> SEQUENCE: 550
tcatattacg agtcagtagg                                           20

<210> SEQ ID NO 551
<211> LENGTH: 20
<212> TYPE: DNA
<213> ORGANISM: Artificial Sequence
<220> FEATURE:
<223> OTHER INFORMATION: Synthetic

<400> SEQUENCE: 551
cctgcaacgg gactagttgg                                           20

<210> SEQ ID NO 552
<211> LENGTH: 20
<212> TYPE: DNA
<213> ORGANISM: Artificial Sequence
<220> FEATURE:
<223> OTHER INFORMATION: Synthetic

<400> SEQUENCE: 552
cctgcaacgg gactagttgg                                           20

<210> SEQ ID NO 553
<211> LENGTH: 20
<212> TYPE: DNA
<213> ORGANISM: Artificial Sequence
<220> FEATURE:
<223> OTHER INFORMATION: Synthetic

<400> SEQUENCE: 553
cgccgccccc ggacgcgacc                                           20

<210> SEQ ID NO 554
<211> LENGTH: 20
<212> TYPE: DNA

```
<213> ORGANISM: Artificial Sequence
<220> FEATURE:
<223> OTHER INFORMATION: Synthetic

<400> SEQUENCE: 554
cctgcaacgg gactagttgg                                                 20

<210> SEQ ID NO 555
<211> LENGTH: 19
<212> TYPE: DNA
<213> ORGANISM: Artificial Sequence
<220> FEATURE:
<223> OTHER INFORMATION: Synthetic

<400> SEQUENCE: 555
agagcactgc actccttca                                                  19

<210> SEQ ID NO 556
<211> LENGTH: 20
<212> TYPE: DNA
<213> ORGANISM: Artificial Sequence
<220> FEATURE:
<223> OTHER INFORMATION: Synthetic

<400> SEQUENCE: 556
agtagtccgg gatatcagcg                                                 20

<210> SEQ ID NO 557
<211> LENGTH: 20
<212> TYPE: DNA
<213> ORGANISM: Artificial Sequence
<220> FEATURE:
<223> OTHER INFORMATION: Synthetic

<400> SEQUENCE: 557
cctgcaacgg gactagttgg                                                 20

<210> SEQ ID NO 558
<211> LENGTH: 20
<212> TYPE: DNA
<213> ORGANISM: Artificial Sequence
<220> FEATURE:
<223> OTHER INFORMATION: Synthetic

<400> SEQUENCE: 558
cctgcaacgg gactagttgg                                                 20

<210> SEQ ID NO 559
<211> LENGTH: 20
<212> TYPE: DNA
<213> ORGANISM: Artificial Sequence
<220> FEATURE:
<223> OTHER INFORMATION: Synthetic

<400> SEQUENCE: 559
cctgcaacgg gactagttgg                                                 20

<210> SEQ ID NO 560
<211> LENGTH: 20
<212> TYPE: DNA
<213> ORGANISM: Artificial Sequence
<220> FEATURE:
<223> OTHER INFORMATION: Synthetic

<400> SEQUENCE: 560
cctgcaacgg gactagttgg                                                 20
```

<210> SEQ ID NO 561
<211> LENGTH: 19
<212> TYPE: DNA
<213> ORGANISM: Artificial Sequence
<220> FEATURE:
<223> OTHER INFORMATION: Synthetic

<400> SEQUENCE: 561
agagcactgc actccttca                                              19

<210> SEQ ID NO 562
<211> LENGTH: 20
<212> TYPE: DNA
<213> ORGANISM: Artificial Sequence
<220> FEATURE:
<223> OTHER INFORMATION: Synthetic

<400> SEQUENCE: 562
tccaccggcg aaagagatcc                                             20

<210> SEQ ID NO 563
<211> LENGTH: 19
<212> TYPE: DNA
<213> ORGANISM: Artificial Sequence
<220> FEATURE:
<223> OTHER INFORMATION: Synthetic

<400> SEQUENCE: 563
agagcactgc actccttca                                              19

<210> SEQ ID NO 564
<211> LENGTH: 20
<212> TYPE: DNA
<213> ORGANISM: Artificial Sequence
<220> FEATURE:
<223> OTHER INFORMATION: Synthetic

<400> SEQUENCE: 564
tcatattacg agtcagtagg                                             20

<210> SEQ ID NO 565
<211> LENGTH: 19
<212> TYPE: DNA
<213> ORGANISM: Artificial Sequence
<220> FEATURE:
<223> OTHER INFORMATION: Synthetic

<400> SEQUENCE: 565
agagcactgc actccttca                                              19

<210> SEQ ID NO 566
<211> LENGTH: 19
<212> TYPE: DNA
<213> ORGANISM: Artificial Sequence
<220> FEATURE:
<223> OTHER INFORMATION: Synthetic

<400> SEQUENCE: 566
agagcactgc actccttca                                              19

<210> SEQ ID NO 567
<211> LENGTH: 20
<212> TYPE: DNA
<213> ORGANISM: Artificial Sequence
<220> FEATURE:

<223> OTHER INFORMATION: Synthetic

<400> SEQUENCE: 567
cgccgccccc ggacgcgacc                                               20

<210> SEQ ID NO 568
<211> LENGTH: 20
<212> TYPE: DNA
<213> ORGANISM: Artificial Sequence
<220> FEATURE:
<223> OTHER INFORMATION: Synthetic

<400> SEQUENCE: 568
cgccgccccc ggacgcgacc                                               20

<210> SEQ ID NO 569
<211> LENGTH: 20
<212> TYPE: DNA
<213> ORGANISM: Artificial Sequence
<220> FEATURE:
<223> OTHER INFORMATION: Synthetic

<400> SEQUENCE: 569
cctgcaacgg gactagttgg                                               20

<210> SEQ ID NO 570
<211> LENGTH: 20
<212> TYPE: DNA
<213> ORGANISM: Artificial Sequence
<220> FEATURE:
<223> OTHER INFORMATION: Synthetic

<400> SEQUENCE: 570
atacaactgc ttgcaacagg                                               20

<210> SEQ ID NO 571
<211> LENGTH: 20
<212> TYPE: DNA
<213> ORGANISM: Artificial Sequence
<220> FEATURE:
<223> OTHER INFORMATION: Synthetic

<400> SEQUENCE: 571
cctgcaacgg gactagttgg                                               20

<210> SEQ ID NO 572
<211> LENGTH: 20
<212> TYPE: DNA
<213> ORGANISM: Artificial Sequence
<220> FEATURE:
<223> OTHER INFORMATION: Synthetic

<400> SEQUENCE: 572
cctgcaacgg gactagttgg                                               20

<210> SEQ ID NO 573
<211> LENGTH: 20
<212> TYPE: DNA
<213> ORGANISM: Artificial Sequence
<220> FEATURE:
<223> OTHER INFORMATION: Synthetic

<400> SEQUENCE: 573
ccagtacaaa cctacctacg                                               20

```
<210> SEQ ID NO 574
<211> LENGTH: 20
<212> TYPE: DNA
<213> ORGANISM: Artificial Sequence
<220> FEATURE:
<223> OTHER INFORMATION: Synthetic

<400> SEQUENCE: 574
ccagtacaaa cctacctacg                                               20

<210> SEQ ID NO 575
<211> LENGTH: 20
<212> TYPE: DNA
<213> ORGANISM: Artificial Sequence
<220> FEATURE:
<223> OTHER INFORMATION: Synthetic

<400> SEQUENCE: 575
cctgcaacgg gactagttgg                                               20

<210> SEQ ID NO 576
<211> LENGTH: 20
<212> TYPE: DNA
<213> ORGANISM: Artificial Sequence
<220> FEATURE:
<223> OTHER INFORMATION: Synthetic

<400> SEQUENCE: 576
cctgcaacgg gactagttgg                                               20

<210> SEQ ID NO 577
<211> LENGTH: 19
<212> TYPE: DNA
<213> ORGANISM: Artificial Sequence
<220> FEATURE:
<223> OTHER INFORMATION: Synthetic

<400> SEQUENCE: 577
agagcactgc actccttca                                                19

<210> SEQ ID NO 578
<211> LENGTH: 20
<212> TYPE: DNA
<213> ORGANISM: Artificial Sequence
<220> FEATURE:
<223> OTHER INFORMATION: Synthetic

<400> SEQUENCE: 578
agtagtccgg gatatcagcg                                               20

<210> SEQ ID NO 579
<211> LENGTH: 20
<212> TYPE: DNA
<213> ORGANISM: Artificial Sequence
<220> FEATURE:
<223> OTHER INFORMATION: Synthetic

<400> SEQUENCE: 579
tcatattacg agtcagtagg                                               20

<210> SEQ ID NO 580
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 580
tcatattacg agtcagtagg                                              20

<210> SEQ ID NO 581
<211> LENGTH: 19
<212> TYPE: DNA
<213> ORGANISM: Artificial Sequence
<220> FEATURE:
<223> OTHER INFORMATION: Synthetic

<400> SEQUENCE: 581
agagcactgc actccttca                                               19

<210> SEQ ID NO 582
<211> LENGTH: 19
<212> TYPE: DNA
<213> ORGANISM: Artificial Sequence
<220> FEATURE:
<223> OTHER INFORMATION: Synthetic

<400> SEQUENCE: 582
agagcactgc actccttca                                               19

<210> SEQ ID NO 583
<211> LENGTH: 20
<212> TYPE: DNA
<213> ORGANISM: Artificial Sequence
<220> FEATURE:
<223> OTHER INFORMATION: Synthetic

<400> SEQUENCE: 583
agtagtccgg gatatcagcg                                              20

<210> SEQ ID NO 584
<211> LENGTH: 20
<212> TYPE: DNA
<213> ORGANISM: Artificial Sequence
<220> FEATURE:
<223> OTHER INFORMATION: Synthetic

<400> SEQUENCE: 584
cctgcaacgg gactagttgg                                              20

<210> SEQ ID NO 585
<211> LENGTH: 20
<212> TYPE: DNA
<213> ORGANISM: Artificial Sequence
<220> FEATURE:
<223> OTHER INFORMATION: Synthetic

<400> SEQUENCE: 585
tcatattacg agtcagtagg                                              20

<210> SEQ ID NO 586
<211> LENGTH: 20
<212> TYPE: DNA
<213> ORGANISM: Artificial Sequence
<220> FEATURE:
<223> OTHER INFORMATION: Synthetic

<400> SEQUENCE: 586
tcatattacg agtcagtagg                                              20

<210> SEQ ID NO 587
<211> LENGTH: 19
```

```
<212> TYPE: DNA
<213> ORGANISM: Artificial Sequence
<220> FEATURE:
<223> OTHER INFORMATION: Synthetic

<400> SEQUENCE: 587
agagcactgc actccttca                                                    19

<210> SEQ ID NO 588
<211> LENGTH: 19
<212> TYPE: DNA
<213> ORGANISM: Artificial Sequence
<220> FEATURE:
<223> OTHER INFORMATION: Synthetic

<400> SEQUENCE: 588
agagcactgc actccttca                                                    19

<210> SEQ ID NO 589
<211> LENGTH: 20
<212> TYPE: DNA
<213> ORGANISM: Artificial Sequence
<220> FEATURE:
<223> OTHER INFORMATION: Synthetic

<400> SEQUENCE: 589
tcatattacg agtcagtagg                                                   20

<210> SEQ ID NO 590
<211> LENGTH: 20
<212> TYPE: DNA
<213> ORGANISM: Artificial Sequence
<220> FEATURE:
<223> OTHER INFORMATION: Synthetic

<400> SEQUENCE: 590
tcatattacg agtcagtagg                                                   20

<210> SEQ ID NO 591
<211> LENGTH: 20
<212> TYPE: DNA
<213> ORGANISM: Artificial Sequence
<220> FEATURE:
<223> OTHER INFORMATION: Synthetic

<400> SEQUENCE: 591
tcatattacg agtcagtagg                                                   20

<210> SEQ ID NO 592
<211> LENGTH: 20
<212> TYPE: DNA
<213> ORGANISM: Artificial Sequence
<220> FEATURE:
<223> OTHER INFORMATION: Synthetic

<400> SEQUENCE: 592
ccagtacaaa cctacctacg                                                   20

<210> SEQ ID NO 593
<211> LENGTH: 19
<212> TYPE: DNA
<213> ORGANISM: Artificial Sequence
<220> FEATURE:
<223> OTHER INFORMATION: Synthetic

<400> SEQUENCE: 593
```
agagcactgc actccttca                                                        19

<210> SEQ ID NO 594
<211> LENGTH: 19
<212> TYPE: DNA
<213> ORGANISM: Artificial Sequence
<220> FEATURE:
<223> OTHER INFORMATION: Synthetic

<400> SEQUENCE: 594
agagcactgc actccttca                                                        19

<210> SEQ ID NO 595
<211> LENGTH: 20
<212> TYPE: DNA
<213> ORGANISM: Artificial Sequence
<220> FEATURE:
<223> OTHER INFORMATION: Synthetic

<400> SEQUENCE: 595
tcatattacg agtcagtagg                                                       20

<210> SEQ ID NO 596
<211> LENGTH: 20
<212> TYPE: DNA
<213> ORGANISM: Artificial Sequence
<220> FEATURE:
<223> OTHER INFORMATION: Synthetic

<400> SEQUENCE: 596
tccaccggcg aaagagatcc                                                       20

<210> SEQ ID NO 597
<211> LENGTH: 20
<212> TYPE: DNA
<213> ORGANISM: Artificial Sequence
<220> FEATURE:
<223> OTHER INFORMATION: Synthetic

<400> SEQUENCE: 597
ccagtacaaa cctacctacg                                                       20

<210> SEQ ID NO 598
<211> LENGTH: 20
<212> TYPE: DNA
<213> ORGANISM: Artificial Sequence
<220> FEATURE:
<223> OTHER INFORMATION: Synthetic

<400> SEQUENCE: 598
cgccgccccc ggacgcgacc                                                       20

<210> SEQ ID NO 599
<211> LENGTH: 19
<212> TYPE: DNA
<213> ORGANISM: Artificial Sequence
<220> FEATURE:
<223> OTHER INFORMATION: Synthetic

<400> SEQUENCE: 599
agagcactgc actccttca                                                        19

<210> SEQ ID NO 600
<211> LENGTH: 19
<212> TYPE: DNA
<213> ORGANISM: Artificial Sequence

```
<220> FEATURE:
<223> OTHER INFORMATION: Synthetic

<400> SEQUENCE: 600
agagcactgc actccttca                                                    19

<210> SEQ ID NO 601
<211> LENGTH: 20
<212> TYPE: DNA
<213> ORGANISM: Artificial Sequence
<220> FEATURE:
<223> OTHER INFORMATION: Synthetic

<400> SEQUENCE: 601
caaggaggac ggcaacatcc                                                   20

<210> SEQ ID NO 602
<211> LENGTH: 20
<212> TYPE: DNA
<213> ORGANISM: Artificial Sequence
<220> FEATURE:
<223> OTHER INFORMATION: Synthetic

<400> SEQUENCE: 602
caaggaggac ggcaacatcc                                                   20

<210> SEQ ID NO 603
<211> LENGTH: 20
<212> TYPE: DNA
<213> ORGANISM: Artificial Sequence
<220> FEATURE:
<223> OTHER INFORMATION: Synthetic

<400> SEQUENCE: 603
gccgtgccgt agctatccgg                                                   20

<210> SEQ ID NO 604
<211> LENGTH: 20
<212> TYPE: DNA
<213> ORGANISM: Artificial Sequence
<220> FEATURE:
<223> OTHER INFORMATION: Synthetic

<400> SEQUENCE: 604
gccgtgccgt agctatccgg                                                   20

<210> SEQ ID NO 605
<211> LENGTH: 20
<212> TYPE: DNA
<213> ORGANISM: Artificial Sequence
<220> FEATURE:
<223> OTHER INFORMATION: Synthetic

<400> SEQUENCE: 605
tgtactccag cttgtgcccc                                                   20

<210> SEQ ID NO 606
<211> LENGTH: 20
<212> TYPE: DNA
<213> ORGANISM: Artificial Sequence
<220> FEATURE:
<223> OTHER INFORMATION: Synthetic

<400> SEQUENCE: 606
tgtactccag cttgtgcccc                                                   20
```

```
<210> SEQ ID NO 607
<211> LENGTH: 20
<212> TYPE: DNA
<213> ORGANISM: Artificial Sequence
<220> FEATURE:
<223> OTHER INFORMATION: Synthetic

<400> SEQUENCE: 607
aaggaggacg gcaacatcct                                              20

<210> SEQ ID NO 608
<211> LENGTH: 20
<212> TYPE: DNA
<213> ORGANISM: Artificial Sequence
<220> FEATURE:
<223> OTHER INFORMATION: Synthetic

<400> SEQUENCE: 608
aaggaggacg gcaacatcct                                              20

<210> SEQ ID NO 609
<211> LENGTH: 20
<212> TYPE: DNA
<213> ORGANISM: Artificial Sequence
<220> FEATURE:
<223> OTHER INFORMATION: Synthetic

<400> SEQUENCE: 609
caaggaggac ggcaacatcc                                              20

<210> SEQ ID NO 610
<211> LENGTH: 20
<212> TYPE: DNA
<213> ORGANISM: Artificial Sequence
<220> FEATURE:
<223> OTHER INFORMATION: Synthetic

<400> SEQUENCE: 610
caaggaggac ggcaacatcc                                              20

<210> SEQ ID NO 611
<211> LENGTH: 20
<212> TYPE: DNA
<213> ORGANISM: Artificial Sequence
<220> FEATURE:
<223> OTHER INFORMATION: Synthetic

<400> SEQUENCE: 611
gccgtgccgt agctatccgg                                              20

<210> SEQ ID NO 612
<211> LENGTH: 20
<212> TYPE: DNA
<213> ORGANISM: Artificial Sequence
<220> FEATURE:
<223> OTHER INFORMATION: Synthetic

<400> SEQUENCE: 612
gccgtgccgt agctatccgg                                              20

<210> SEQ ID NO 613
<211> LENGTH: 20
<212> TYPE: DNA
<213> ORGANISM: Artificial Sequence
<220> FEATURE:
<223> OTHER INFORMATION: Synthetic
```

<400> SEQUENCE: 613
aaggaggacg gcaacatcct                                                    20

<210> SEQ ID NO 614
<211> LENGTH: 20
<212> TYPE: DNA
<213> ORGANISM: Artificial Sequence
<220> FEATURE:
<223> OTHER INFORMATION: Synthetic

<400> SEQUENCE: 614
aaggaggacg gcaacatcct                                                    20

<210> SEQ ID NO 615
<211> LENGTH: 20
<212> TYPE: DNA
<213> ORGANISM: Artificial Sequence
<220> FEATURE:
<223> OTHER INFORMATION: Synthetic

<400> SEQUENCE: 615
gtccgttcga caatttcaca                                                    20

<210> SEQ ID NO 616
<211> LENGTH: 20
<212> TYPE: DNA
<213> ORGANISM: Artificial Sequence
<220> FEATURE:
<223> OTHER INFORMATION: Synthetic

<400> SEQUENCE: 616
gtccgttcga caatttcaca                                                    20

<210> SEQ ID NO 617
<211> LENGTH: 20
<212> TYPE: DNA
<213> ORGANISM: Artificial Sequence
<220> FEATURE:
<223> OTHER INFORMATION: Synthetic

<400> SEQUENCE: 617
gtacagctaa gttaaactcg                                                    20

<210> SEQ ID NO 618
<211> LENGTH: 20
<212> TYPE: DNA
<213> ORGANISM: Artificial Sequence
<220> FEATURE:
<223> OTHER INFORMATION: Synthetic

<400> SEQUENCE: 618
gtacagctaa gttaaactcg                                                    20

<210> SEQ ID NO 619
<211> LENGTH: 20
<212> TYPE: DNA
<213> ORGANISM: Artificial Sequence
<220> FEATURE:
<223> OTHER INFORMATION: Synthetic

<400> SEQUENCE: 619
aaggaggacg gcaacatcct                                                    20

<210> SEQ ID NO 620

```
<211> LENGTH: 20
<212> TYPE: DNA
<213> ORGANISM: Artificial Sequence
<220> FEATURE:
<223> OTHER INFORMATION: Synthetic

<400> SEQUENCE: 620
aaggaggacg gcaacatcct                                                   20

<210> SEQ ID NO 621
<211> LENGTH: 20
<212> TYPE: DNA
<213> ORGANISM: Artificial Sequence
<220> FEATURE:
<223> OTHER INFORMATION: Synthetic

<400> SEQUENCE: 621
gtccgttcga caatttcaca                                                   20

<210> SEQ ID NO 622
<211> LENGTH: 20
<212> TYPE: DNA
<213> ORGANISM: Artificial Sequence
<220> FEATURE:
<223> OTHER INFORMATION: Synthetic

<400> SEQUENCE: 622
gtccgttcga caatttcaca                                                   20

<210> SEQ ID NO 623
<211> LENGTH: 20
<212> TYPE: DNA
<213> ORGANISM: Artificial Sequence
<220> FEATURE:
<223> OTHER INFORMATION: Synthetic

<400> SEQUENCE: 623
gtccgttcga caatttcaca                                                   20

<210> SEQ ID NO 624
<211> LENGTH: 20
<212> TYPE: DNA
<213> ORGANISM: Artificial Sequence
<220> FEATURE:
<223> OTHER INFORMATION: Synthetic

<400> SEQUENCE: 624
gtccgttcga caatttcaca                                                   20

<210> SEQ ID NO 625
<211> LENGTH: 20
<212> TYPE: DNA
<213> ORGANISM: Artificial Sequence
<220> FEATURE:
<223> OTHER INFORMATION: Synthetic

<400> SEQUENCE: 625
aaggaggacg gcaacatcct                                                   20

<210> SEQ ID NO 626
<211> LENGTH: 20
<212> TYPE: DNA
<213> ORGANISM: Artificial Sequence
<220> FEATURE:
<223> OTHER INFORMATION: Synthetic

<400> SEQUENCE: 626
```
aaggaggacg gcaacatcct                                              20

<210> SEQ ID NO 627
<211> LENGTH: 20
<212> TYPE: DNA
<213> ORGANISM: Artificial Sequence
<220> FEATURE:
<223> OTHER INFORMATION: Synthetic

<400> SEQUENCE: 627
gccgtgccgt agctatccgg                                              20

<210> SEQ ID NO 628
<211> LENGTH: 20
<212> TYPE: DNA
<213> ORGANISM: Artificial Sequence
<220> FEATURE:
<223> OTHER INFORMATION: Synthetic

<400> SEQUENCE: 628
gccgtgccgt agctatccgg                                              20

<210> SEQ ID NO 629
<211> LENGTH: 20
<212> TYPE: DNA
<213> ORGANISM: Artificial Sequence
<220> FEATURE:
<223> OTHER INFORMATION: Synthetic

<400> SEQUENCE: 629
ggacgctaaa ccaacggtgc                                              20

<210> SEQ ID NO 630
<211> LENGTH: 20
<212> TYPE: DNA
<213> ORGANISM: Artificial Sequence
<220> FEATURE:
<223> OTHER INFORMATION: Synthetic

<400> SEQUENCE: 630
ggacgctaaa ccaacggtgc                                              20

<210> SEQ ID NO 631
<211> LENGTH: 20
<212> TYPE: DNA
<213> ORGANISM: Artificial Sequence
<220> FEATURE:
<223> OTHER INFORMATION: Synthetic

<400> SEQUENCE: 631
gtccgttcga caatttcaca                                              20

<210> SEQ ID NO 632
<211> LENGTH: 20
<212> TYPE: DNA
<213> ORGANISM: Artificial Sequence
<220> FEATURE:
<223> OTHER INFORMATION: Synthetic

<400> SEQUENCE: 632
gtccgttcga caatttcaca                                              20

<210> SEQ ID NO 633
<211> LENGTH: 20
<212> TYPE: DNA

```
<213> ORGANISM: Artificial Sequence
<220> FEATURE:
<223> OTHER INFORMATION: Synthetic

<400> SEQUENCE: 633
ggacgctaaa ccaacggtgc                                              20

<210> SEQ ID NO 634
<211> LENGTH: 20
<212> TYPE: DNA
<213> ORGANISM: Artificial Sequence
<220> FEATURE:
<223> OTHER INFORMATION: Synthetic

<400> SEQUENCE: 634
ggacgctaaa ccaacggtgc                                              20

<210> SEQ ID NO 635
<211> LENGTH: 20
<212> TYPE: DNA
<213> ORGANISM: Artificial Sequence
<220> FEATURE:
<223> OTHER INFORMATION: Synthetic

<400> SEQUENCE: 635
aaggaggacg gcaacatcct                                              20

<210> SEQ ID NO 636
<211> LENGTH: 20
<212> TYPE: DNA
<213> ORGANISM: Artificial Sequence
<220> FEATURE:
<223> OTHER INFORMATION: Synthetic

<400> SEQUENCE: 636
aaggaggacg gcaacatcct                                              20

<210> SEQ ID NO 637
<211> LENGTH: 20
<212> TYPE: DNA
<213> ORGANISM: Artificial Sequence
<220> FEATURE:
<223> OTHER INFORMATION: Synthetic

<400> SEQUENCE: 637
caacatcctg gggcacaagc                                              20

<210> SEQ ID NO 638
<211> LENGTH: 20
<212> TYPE: DNA
<213> ORGANISM: Artificial Sequence
<220> FEATURE:
<223> OTHER INFORMATION: Synthetic

<400> SEQUENCE: 638
caacatcctg gggcacaagc                                              20

<210> SEQ ID NO 639
<211> LENGTH: 20
<212> TYPE: DNA
<213> ORGANISM: Artificial Sequence
<220> FEATURE:
<223> OTHER INFORMATION: Synthetic

<400> SEQUENCE: 639
gtccgttcga caatttcaca                                              20
```

<210> SEQ ID NO 640
<211> LENGTH: 20
<212> TYPE: DNA
<213> ORGANISM: Artificial Sequence
<220> FEATURE:
<223> OTHER INFORMATION: Synthetic

<400> SEQUENCE: 640
gtccgttcga caatttcaca                                                    20

<210> SEQ ID NO 641
<211> LENGTH: 20
<212> TYPE: DNA
<213> ORGANISM: Artificial Sequence
<220> FEATURE:
<223> OTHER INFORMATION: Synthetic

<400> SEQUENCE: 641
gccgtgccgt agctatccgg                                                    20

<210> SEQ ID NO 642
<211> LENGTH: 20
<212> TYPE: DNA
<213> ORGANISM: Artificial Sequence
<220> FEATURE:
<223> OTHER INFORMATION: Synthetic

<400> SEQUENCE: 642
gccgtgccgt agctatccgg                                                    20

<210> SEQ ID NO 643
<211> LENGTH: 20
<212> TYPE: DNA
<213> ORGANISM: Artificial Sequence
<220> FEATURE:
<223> OTHER INFORMATION: Synthetic

<400> SEQUENCE: 643
gccgtgccgt agctatccgg                                                    20

<210> SEQ ID NO 644
<211> LENGTH: 20
<212> TYPE: DNA
<213> ORGANISM: Artificial Sequence
<220> FEATURE:
<223> OTHER INFORMATION: Synthetic

<400> SEQUENCE: 644
gccgtgccgt agctatccgg                                                    20

<210> SEQ ID NO 645
<211> LENGTH: 20
<212> TYPE: DNA
<213> ORGANISM: Artificial Sequence
<220> FEATURE:
<223> OTHER INFORMATION: Synthetic

<400> SEQUENCE: 645
aaggaggacg gcaacatcct                                                    20

<210> SEQ ID NO 646
<211> LENGTH: 20
<212> TYPE: DNA
<213> ORGANISM: Artificial Sequence
<220> FEATURE:

<223> OTHER INFORMATION: Synthetic

<400> SEQUENCE: 646
aaggaggacg gcaacatcct                                                    20

<210> SEQ ID NO 647
<211> LENGTH: 20
<212> TYPE: DNA
<213> ORGANISM: Artificial Sequence
<220> FEATURE:
<223> OTHER INFORMATION: Synthetic

<400> SEQUENCE: 647
gctgcttgcg ataccaatag                                                    20

<210> SEQ ID NO 648
<211> LENGTH: 20
<212> TYPE: DNA
<213> ORGANISM: Artificial Sequence
<220> FEATURE:
<223> OTHER INFORMATION: Synthetic

<400> SEQUENCE: 648
gctgcttgcg ataccaatag                                                    20

<210> SEQ ID NO 649
<211> LENGTH: 20
<212> TYPE: DNA
<213> ORGANISM: Artificial Sequence
<220> FEATURE:
<223> OTHER INFORMATION: Synthetic

<400> SEQUENCE: 649
gccgtgccgt agctatccgg                                                    20

<210> SEQ ID NO 650
<211> LENGTH: 20
<212> TYPE: DNA
<213> ORGANISM: Artificial Sequence
<220> FEATURE:
<223> OTHER INFORMATION: Synthetic

<400> SEQUENCE: 650
gccgtgccgt agctatccgg                                                    20

<210> SEQ ID NO 651
<211> LENGTH: 20
<212> TYPE: DNA
<213> ORGANISM: Artificial Sequence
<220> FEATURE:
<223> OTHER INFORMATION: Synthetic

<400> SEQUENCE: 651
caacatcctg gggcacaagc                                                    20

<210> SEQ ID NO 652
<211> LENGTH: 20
<212> TYPE: DNA
<213> ORGANISM: Artificial Sequence
<220> FEATURE:
<223> OTHER INFORMATION: Synthetic

<400> SEQUENCE: 652
caacatcctg gggcacaagc                                                    20

```
<210> SEQ ID NO 653
<211> LENGTH: 20
<212> TYPE: DNA
<213> ORGANISM: Artificial Sequence
<220> FEATURE:
<223> OTHER INFORMATION: Synthetic

<400> SEQUENCE: 653
gccgtgccgt agctatccgg                                               20

<210> SEQ ID NO 654
<211> LENGTH: 20
<212> TYPE: DNA
<213> ORGANISM: Artificial Sequence
<220> FEATURE:
<223> OTHER INFORMATION: Synthetic

<400> SEQUENCE: 654
gccgtgccgt agctatccgg                                               20

<210> SEQ ID NO 655
<211> LENGTH: 20
<212> TYPE: DNA
<213> ORGANISM: Artificial Sequence
<220> FEATURE:
<223> OTHER INFORMATION: Synthetic

<400> SEQUENCE: 655
ggacgctaaa ccaacggtgc                                               20

<210> SEQ ID NO 656
<211> LENGTH: 20
<212> TYPE: DNA
<213> ORGANISM: Artificial Sequence
<220> FEATURE:
<223> OTHER INFORMATION: Synthetic

<400> SEQUENCE: 656
ggacgctaaa ccaacggtgc                                               20

<210> SEQ ID NO 657
<211> LENGTH: 20
<212> TYPE: DNA
<213> ORGANISM: Artificial Sequence
<220> FEATURE:
<223> OTHER INFORMATION: Synthetic

<400> SEQUENCE: 657
aggaggacgg caacatcctg                                               20

<210> SEQ ID NO 658
<211> LENGTH: 20
<212> TYPE: DNA
<213> ORGANISM: Artificial Sequence
<220> FEATURE:
<223> OTHER INFORMATION: Synthetic

<400> SEQUENCE: 658
aggaggacgg caacatcctg                                               20

<210> SEQ ID NO 659
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 659
gctgcttgcg ataccaatag                                                   20

<210> SEQ ID NO 660
<211> LENGTH: 20
<212> TYPE: DNA
<213> ORGANISM: Artificial Sequence
<220> FEATURE:
<223> OTHER INFORMATION: Synthetic

<400> SEQUENCE: 660
gctgcttgcg ataccaatag                                                   20

<210> SEQ ID NO 661
<211> LENGTH: 20
<212> TYPE: DNA
<213> ORGANISM: Artificial Sequence
<220> FEATURE:
<223> OTHER INFORMATION: Synthetic

<400> SEQUENCE: 661
gccgtgccgt agctatccgg                                                   20

<210> SEQ ID NO 662
<211> LENGTH: 20
<212> TYPE: DNA
<213> ORGANISM: Artificial Sequence
<220> FEATURE:
<223> OTHER INFORMATION: Synthetic

<400> SEQUENCE: 662
gccgtgccgt agctatccgg                                                   20

<210> SEQ ID NO 663
<211> LENGTH: 20
<212> TYPE: DNA
<213> ORGANISM: Artificial Sequence
<220> FEATURE:
<223> OTHER INFORMATION: Synthetic

<400> SEQUENCE: 663
tgtactccag cttgtgcccc                                                   20

<210> SEQ ID NO 664
<211> LENGTH: 20
<212> TYPE: DNA
<213> ORGANISM: Artificial Sequence
<220> FEATURE:
<223> OTHER INFORMATION: Synthetic

<400> SEQUENCE: 664
tgtactccag cttgtgcccc                                                   20

<210> SEQ ID NO 665
<211> LENGTH: 20
<212> TYPE: DNA
<213> ORGANISM: Artificial Sequence
<220> FEATURE:
<223> OTHER INFORMATION: Synthetic

<400> SEQUENCE: 665
tgtactccag cttgtgcccc                                                   20

<210> SEQ ID NO 666
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 666
tgtactccag cttgtgcccc                                            20

<210> SEQ ID NO 667
<211> LENGTH: 20
<212> TYPE: DNA
<213> ORGANISM: Artificial Sequence
<220> FEATURE:
<223> OTHER INFORMATION: Synthetic

<400> SEQUENCE: 667
gtccgttcga caatttcaca                                            20

<210> SEQ ID NO 668
<211> LENGTH: 20
<212> TYPE: DNA
<213> ORGANISM: Artificial Sequence
<220> FEATURE:
<223> OTHER INFORMATION: Synthetic

<400> SEQUENCE: 668
gtccgttcga caatttcaca                                            20

<210> SEQ ID NO 669
<211> LENGTH: 20
<212> TYPE: DNA
<213> ORGANISM: Artificial Sequence
<220> FEATURE:
<223> OTHER INFORMATION: Synthetic

<400> SEQUENCE: 669
ggacgctaaa ccaacggtgc                                            20

<210> SEQ ID NO 670
<211> LENGTH: 20
<212> TYPE: DNA
<213> ORGANISM: Artificial Sequence
<220> FEATURE:
<223> OTHER INFORMATION: Synthetic

<400> SEQUENCE: 670
ggacgctaaa ccaacggtgc                                            20

<210> SEQ ID NO 671
<211> LENGTH: 20
<212> TYPE: DNA
<213> ORGANISM: Artificial Sequence
<220> FEATURE:
<223> OTHER INFORMATION: Synthetic

<400> SEQUENCE: 671
caaggaggac ggcaacatcc                                            20

<210> SEQ ID NO 672
<211> LENGTH: 20
<212> TYPE: DNA
<213> ORGANISM: Artificial Sequence
<220> FEATURE:
<223> OTHER INFORMATION: Synthetic

<400> SEQUENCE: 672
```
caaggaggac ggcaacatcc                                              20

<210> SEQ ID NO 673
<211> LENGTH: 20
<212> TYPE: DNA
<213> ORGANISM: Artificial Sequence
<220> FEATURE:
<223> OTHER INFORMATION: Synthetic

<400> SEQUENCE: 673
gtccgttcga caatttcaca                                              20

<210> SEQ ID NO 674
<211> LENGTH: 20
<212> TYPE: DNA
<213> ORGANISM: Artificial Sequence
<220> FEATURE:
<223> OTHER INFORMATION: Synthetic

<400> SEQUENCE: 674
gtccgttcga caatttcaca                                              20

<210> SEQ ID NO 675
<211> LENGTH: 20
<212> TYPE: DNA
<213> ORGANISM: Artificial Sequence
<220> FEATURE:
<223> OTHER INFORMATION: Synthetic

<400> SEQUENCE: 675
tgtactccag cttgtgcccc                                              20

<210> SEQ ID NO 676
<211> LENGTH: 20
<212> TYPE: DNA
<213> ORGANISM: Artificial Sequence
<220> FEATURE:
<223> OTHER INFORMATION: Synthetic

<400> SEQUENCE: 676
tgtactccag cttgtgcccc                                              20

<210> SEQ ID NO 677
<211> LENGTH: 20
<212> TYPE: DNA
<213> ORGANISM: Artificial Sequence
<220> FEATURE:
<223> OTHER INFORMATION: Synthetic

<400> SEQUENCE: 677
gctgcttgcg ataccaatag                                              20

<210> SEQ ID NO 678
<211> LENGTH: 20
<212> TYPE: DNA
<213> ORGANISM: Artificial Sequence
<220> FEATURE:
<223> OTHER INFORMATION: Synthetic

<400> SEQUENCE: 678
gctgcttgcg ataccaatag                                              20

<210> SEQ ID NO 679
<211> LENGTH: 20
<212> TYPE: DNA
<213> ORGANISM: Artificial Sequence

```
<220> FEATURE:
<223> OTHER INFORMATION: Synthetic

<400> SEQUENCE: 679
tgtactccag cttgtgcccc                                          20

<210> SEQ ID NO 680
<211> LENGTH: 20
<212> TYPE: DNA
<213> ORGANISM: Artificial Sequence
<220> FEATURE:
<223> OTHER INFORMATION: Synthetic

<400> SEQUENCE: 680
tgtactccag cttgtgcccc                                          20

<210> SEQ ID NO 681
<211> LENGTH: 20
<212> TYPE: DNA
<213> ORGANISM: Artificial Sequence
<220> FEATURE:
<223> OTHER INFORMATION: Synthetic

<400> SEQUENCE: 681
tgtactccag cttgtgcccc                                          20

<210> SEQ ID NO 682
<211> LENGTH: 20
<212> TYPE: DNA
<213> ORGANISM: Artificial Sequence
<220> FEATURE:
<223> OTHER INFORMATION: Synthetic

<400> SEQUENCE: 682
tgtactccag cttgtgcccc                                          20

<210> SEQ ID NO 683
<211> LENGTH: 20
<212> TYPE: DNA
<213> ORGANISM: Artificial Sequence
<220> FEATURE:
<223> OTHER INFORMATION: Synthetic

<400> SEQUENCE: 683
ggacgctaaa ccaacggtgc                                          20

<210> SEQ ID NO 684
<211> LENGTH: 20
<212> TYPE: DNA
<213> ORGANISM: Artificial Sequence
<220> FEATURE:
<223> OTHER INFORMATION: Synthetic

<400> SEQUENCE: 684
ggacgctaaa ccaacggtgc                                          20

<210> SEQ ID NO 685
<211> LENGTH: 20
<212> TYPE: DNA
<213> ORGANISM: Artificial Sequence
<220> FEATURE:
<223> OTHER INFORMATION: Synthetic

<400> SEQUENCE: 685
gtacagctaa gttaaactcg                                          20
```

<210> SEQ ID NO 686
<211> LENGTH: 20
<212> TYPE: DNA
<213> ORGANISM: Artificial Sequence
<220> FEATURE:
<223> OTHER INFORMATION: Synthetic

<400> SEQUENCE: 686
gtacagctaa gttaaactcg                                               20

<210> SEQ ID NO 687
<211> LENGTH: 20
<212> TYPE: DNA
<213> ORGANISM: Artificial Sequence
<220> FEATURE:
<223> OTHER INFORMATION: Synthetic

<400> SEQUENCE: 687
gtccgttcga caatttcaca                                               20

<210> SEQ ID NO 688
<211> LENGTH: 20
<212> TYPE: DNA
<213> ORGANISM: Artificial Sequence
<220> FEATURE:
<223> OTHER INFORMATION: Synthetic

<400> SEQUENCE: 688
gtccgttcga caatttcaca                                               20

<210> SEQ ID NO 689
<211> LENGTH: 20
<212> TYPE: DNA
<213> ORGANISM: Artificial Sequence
<220> FEATURE:
<223> OTHER INFORMATION: Synthetic

<400> SEQUENCE: 689
gccgtgccgt agctatccgg                                               20

<210> SEQ ID NO 690
<211> LENGTH: 20
<212> TYPE: DNA
<213> ORGANISM: Artificial Sequence
<220> FEATURE:
<223> OTHER INFORMATION: Synthetic

<400> SEQUENCE: 690
gccgtgccgt agctatccgg                                               20

<210> SEQ ID NO 691
<211> LENGTH: 20
<212> TYPE: DNA
<213> ORGANISM: Artificial Sequence
<220> FEATURE:
<223> OTHER INFORMATION: Synthetic

<400> SEQUENCE: 691
gccgtgccgt agctatccgg                                               20

<210> SEQ ID NO 692
<211> LENGTH: 20
<212> TYPE: DNA
<213> ORGANISM: Artificial Sequence
<220> FEATURE:
<223> OTHER INFORMATION: Synthetic

<400> SEQUENCE: 692
gccgtgccgt agctatccgg                                                   20

<210> SEQ ID NO 693
<211> LENGTH: 20
<212> TYPE: DNA
<213> ORGANISM: Artificial Sequence
<220> FEATURE:
<223> OTHER INFORMATION: Synthetic

<400> SEQUENCE: 693
caaggaggac ggcaacatcc                                                   20

<210> SEQ ID NO 694
<211> LENGTH: 20
<212> TYPE: DNA
<213> ORGANISM: Artificial Sequence
<220> FEATURE:
<223> OTHER INFORMATION: Synthetic

<400> SEQUENCE: 694
caaggaggac ggcaacatcc                                                   20

<210> SEQ ID NO 695
<211> LENGTH: 20
<212> TYPE: DNA
<213> ORGANISM: Artificial Sequence
<220> FEATURE:
<223> OTHER INFORMATION: Synthetic

<400> SEQUENCE: 695
gccgtgccgt agctatccgg                                                   20

<210> SEQ ID NO 696
<211> LENGTH: 20
<212> TYPE: DNA
<213> ORGANISM: Artificial Sequence
<220> FEATURE:
<223> OTHER INFORMATION: Synthetic

<400> SEQUENCE: 696
gccgtgccgt agctatccgg                                                   20

<210> SEQ ID NO 697
<211> LENGTH: 20
<212> TYPE: DNA
<213> ORGANISM: Artificial Sequence
<220> FEATURE:
<223> OTHER INFORMATION: Synthetic

<400> SEQUENCE: 697
gtccgttcga caatttcaca                                                   20

<210> SEQ ID NO 698
<211> LENGTH: 20
<212> TYPE: DNA
<213> ORGANISM: Artificial Sequence
<220> FEATURE:
<223> OTHER INFORMATION: Synthetic

<400> SEQUENCE: 698
gtccgttcga caatttcaca                                                   20

<210> SEQ ID NO 699

```
<211> LENGTH: 20
<212> TYPE: DNA
<213> ORGANISM: Artificial Sequence
<220> FEATURE:
<223> OTHER INFORMATION: Synthetic

<400> SEQUENCE: 699
ggacgctaaa ccaacggtgc                                              20

<210> SEQ ID NO 700
<211> LENGTH: 20
<212> TYPE: DNA
<213> ORGANISM: Artificial Sequence
<220> FEATURE:
<223> OTHER INFORMATION: Synthetic

<400> SEQUENCE: 700
ggacgctaaa ccaacggtgc                                              20

<210> SEQ ID NO 701
<211> LENGTH: 20
<212> TYPE: DNA
<213> ORGANISM: Artificial Sequence
<220> FEATURE:
<223> OTHER INFORMATION: Synthetic

<400> SEQUENCE: 701
gtccgttcga caatttcaca                                              20

<210> SEQ ID NO 702
<211> LENGTH: 20
<212> TYPE: DNA
<213> ORGANISM: Artificial Sequence
<220> FEATURE:
<223> OTHER INFORMATION: Synthetic

<400> SEQUENCE: 702
gtccgttcga caatttcaca                                              20

<210> SEQ ID NO 703
<211> LENGTH: 20
<212> TYPE: DNA
<213> ORGANISM: Artificial Sequence
<220> FEATURE:
<223> OTHER INFORMATION: Synthetic

<400> SEQUENCE: 703
gtccgttcga caatttcaca                                              20

<210> SEQ ID NO 704
<211> LENGTH: 20
<212> TYPE: DNA
<213> ORGANISM: Artificial Sequence
<220> FEATURE:
<223> OTHER INFORMATION: Synthetic

<400> SEQUENCE: 704
gtccgttcga caatttcaca                                              20

<210> SEQ ID NO 705
<211> LENGTH: 20
<212> TYPE: DNA
<213> ORGANISM: Artificial Sequence
<220> FEATURE:
<223> OTHER INFORMATION: Synthetic

<400> SEQUENCE: 705
```

```
gtacagctaa gttaaactcg                                          20

<210> SEQ ID NO 706
<211> LENGTH: 20
<212> TYPE: DNA
<213> ORGANISM: Artificial Sequence
<220> FEATURE:
<223> OTHER INFORMATION: Synthetic

<400> SEQUENCE: 706
gtacagctaa gttaaactcg                                          20

<210> SEQ ID NO 707
<211> LENGTH: 20
<212> TYPE: DNA
<213> ORGANISM: Artificial Sequence
<220> FEATURE:
<223> OTHER INFORMATION: Synthetic

<400> SEQUENCE: 707
gtccgttcga caatttcaca                                          20

<210> SEQ ID NO 708
<211> LENGTH: 20
<212> TYPE: DNA
<213> ORGANISM: Artificial Sequence
<220> FEATURE:
<223> OTHER INFORMATION: Synthetic

<400> SEQUENCE: 708
gtccgttcga caatttcaca                                          20

<210> SEQ ID NO 709
<211> LENGTH: 20
<212> TYPE: DNA
<213> ORGANISM: Artificial Sequence
<220> FEATURE:
<223> OTHER INFORMATION: Synthetic

<400> SEQUENCE: 709
gtccgttcga caatttcaca                                          20

<210> SEQ ID NO 710
<211> LENGTH: 20
<212> TYPE: DNA
<213> ORGANISM: Artificial Sequence
<220> FEATURE:
<223> OTHER INFORMATION: Synthetic

<400> SEQUENCE: 710
gtccgttcga caatttcaca                                          20

<210> SEQ ID NO 711
<211> LENGTH: 20
<212> TYPE: DNA
<213> ORGANISM: Artificial Sequence
<220> FEATURE:
<223> OTHER INFORMATION: Synthetic

<400> SEQUENCE: 711
caaggaggac ggcaacatcc                                          20

<210> SEQ ID NO 712
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 712
caaggaggac ggcaacatcc                                                    20

<210> SEQ ID NO 713
<211> LENGTH: 20
<212> TYPE: DNA
<213> ORGANISM: Artificial Sequence
<220> FEATURE:
<223> OTHER INFORMATION: Synthetic

<400> SEQUENCE: 713
caaggaggac ggcaacatcc                                                    20

<210> SEQ ID NO 714
<211> LENGTH: 20
<212> TYPE: DNA
<213> ORGANISM: Artificial Sequence
<220> FEATURE:
<223> OTHER INFORMATION: Synthetic

<400> SEQUENCE: 714
caaggaggac ggcaacatcc                                                    20

<210> SEQ ID NO 715
<211> LENGTH: 20
<212> TYPE: DNA
<213> ORGANISM: Artificial Sequence
<220> FEATURE:
<223> OTHER INFORMATION: Synthetic

<400> SEQUENCE: 715
caaggaggac ggcaacatcc                                                    20

<210> SEQ ID NO 716
<211> LENGTH: 20
<212> TYPE: DNA
<213> ORGANISM: Artificial Sequence
<220> FEATURE:
<223> OTHER INFORMATION: Synthetic

<400> SEQUENCE: 716
caaggaggac ggcaacatcc                                                    20

<210> SEQ ID NO 717
<211> LENGTH: 20
<212> TYPE: DNA
<213> ORGANISM: Artificial Sequence
<220> FEATURE:
<223> OTHER INFORMATION: Synthetic

<400> SEQUENCE: 717
caacatcctg gggcacaagc                                                    20

<210> SEQ ID NO 718
<211> LENGTH: 20
<212> TYPE: DNA
<213> ORGANISM: Artificial Sequence
<220> FEATURE:
<223> OTHER INFORMATION: Synthetic

<400> SEQUENCE: 718
caacatcctg gggcacaagc                                                    20
```

<210> SEQ ID NO 719
<211> LENGTH: 20
<212> TYPE: DNA
<213> ORGANISM: Artificial Sequence
<220> FEATURE:
<223> OTHER INFORMATION: Synthetic

<400> SEQUENCE: 719
tgtactccag cttgtgcccc                                              20

<210> SEQ ID NO 720
<211> LENGTH: 20
<212> TYPE: DNA
<213> ORGANISM: Artificial Sequence
<220> FEATURE:
<223> OTHER INFORMATION: Synthetic

<400> SEQUENCE: 720
tgtactccag cttgtgcccc                                              20

<210> SEQ ID NO 721
<211> LENGTH: 20
<212> TYPE: DNA
<213> ORGANISM: Artificial Sequence
<220> FEATURE:
<223> OTHER INFORMATION: Synthetic

<400> SEQUENCE: 721
gtccgttcga caatttcaca                                              20

<210> SEQ ID NO 722
<211> LENGTH: 20
<212> TYPE: DNA
<213> ORGANISM: Artificial Sequence
<220> FEATURE:
<223> OTHER INFORMATION: Synthetic

<400> SEQUENCE: 722
gtccgttcga caatttcaca                                              20

<210> SEQ ID NO 723
<211> LENGTH: 20
<212> TYPE: DNA
<213> ORGANISM: Artificial Sequence
<220> FEATURE:
<223> OTHER INFORMATION: Synthetic

<400> SEQUENCE: 723
gtccgttcga caatttcaca                                              20

<210> SEQ ID NO 724
<211> LENGTH: 20
<212> TYPE: DNA
<213> ORGANISM: Artificial Sequence
<220> FEATURE:
<223> OTHER INFORMATION: Synthetic

<400> SEQUENCE: 724
gtccgttcga caatttcaca                                              20

<210> SEQ ID NO 725
<211> LENGTH: 20
<212> TYPE: DNA
<213> ORGANISM: Artificial Sequence
<220> FEATURE:

-continued

<223> OTHER INFORMATION: Synthetic

<400> SEQUENCE: 725
gctgcttgcg ataccaatag                                                    20

<210> SEQ ID NO 726
<211> LENGTH: 20
<212> TYPE: DNA
<213> ORGANISM: Artificial Sequence
<220> FEATURE:
<223> OTHER INFORMATION: Synthetic

<400> SEQUENCE: 726
gccgtgccgt agctatccgg                                                    20

<210> SEQ ID NO 727
<211> LENGTH: 20
<212> TYPE: DNA
<213> ORGANISM: Artificial Sequence
<220> FEATURE:
<223> OTHER INFORMATION: Synthetic

<400> SEQUENCE: 727
aaggaggacg gcaacatcct                                                    20

<210> SEQ ID NO 728
<211> LENGTH: 20
<212> TYPE: DNA
<213> ORGANISM: Artificial Sequence
<220> FEATURE:
<223> OTHER INFORMATION: Synthetic

<400> SEQUENCE: 728
aaggaggacg gcaacatcct                                                    20

<210> SEQ ID NO 729
<211> LENGTH: 20
<212> TYPE: DNA
<213> ORGANISM: Artificial Sequence
<220> FEATURE:
<223> OTHER INFORMATION: Synthetic

<400> SEQUENCE: 729
caaggaggac ggcaacatcc                                                    20

<210> SEQ ID NO 730
<211> LENGTH: 20
<212> TYPE: DNA
<213> ORGANISM: Artificial Sequence
<220> FEATURE:
<223> OTHER INFORMATION: Synthetic

<400> SEQUENCE: 730
caaggaggac ggcaacatcc                                                    20

<210> SEQ ID NO 731
<211> LENGTH: 20
<212> TYPE: DNA
<213> ORGANISM: Artificial Sequence
<220> FEATURE:
<223> OTHER INFORMATION: Synthetic

<400> SEQUENCE: 731
ggacgctaaa ccaacggtgc                                                    20

-continued

```
<210> SEQ ID NO 732
<211> LENGTH: 20
<212> TYPE: DNA
<213> ORGANISM: Artificial Sequence
<220> FEATURE:
<223> OTHER INFORMATION: Synthetic

<400> SEQUENCE: 732
ggacgctaaa ccaacggtgc                                                 20

<210> SEQ ID NO 733
<211> LENGTH: 20
<212> TYPE: DNA
<213> ORGANISM: Artificial Sequence
<220> FEATURE:
<223> OTHER INFORMATION: Synthetic

<400> SEQUENCE: 733
gctgcttgcg ataccaatag                                                 20

<210> SEQ ID NO 734
<211> LENGTH: 20
<212> TYPE: DNA
<213> ORGANISM: Artificial Sequence
<220> FEATURE:
<223> OTHER INFORMATION: Synthetic

<400> SEQUENCE: 734
gctgcttgcg ataccaatag                                                 20

<210> SEQ ID NO 735
<211> LENGTH: 20
<212> TYPE: DNA
<213> ORGANISM: Artificial Sequence
<220> FEATURE:
<223> OTHER INFORMATION: Synthetic

<400> SEQUENCE: 735
gtacagctaa gttaaactcg                                                 20

<210> SEQ ID NO 736
<211> LENGTH: 20
<212> TYPE: DNA
<213> ORGANISM: Artificial Sequence
<220> FEATURE:
<223> OTHER INFORMATION: Synthetic

<400> SEQUENCE: 736
gtacagctaa gttaaactcg                                                 20

<210> SEQ ID NO 737
<211> LENGTH: 20
<212> TYPE: DNA
<213> ORGANISM: Artificial Sequence
<220> FEATURE:
<223> OTHER INFORMATION: Synthetic

<400> SEQUENCE: 737
tgtactccag cttgtgcccc                                                 20

<210> SEQ ID NO 738
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 738
tgtactccag cttgtgcccc                                              20

<210> SEQ ID NO 739
<211> LENGTH: 20
<212> TYPE: DNA
<213> ORGANISM: Artificial Sequence
<220> FEATURE:
<223> OTHER INFORMATION: Synthetic

<400> SEQUENCE: 739
tgtactccag cttgtgcccc                                              20

<210> SEQ ID NO 740
<211> LENGTH: 20
<212> TYPE: DNA
<213> ORGANISM: Artificial Sequence
<220> FEATURE:
<223> OTHER INFORMATION: Synthetic

<400> SEQUENCE: 740
tgtactccag cttgtgcccc                                              20

<210> SEQ ID NO 741
<211> LENGTH: 20
<212> TYPE: DNA
<213> ORGANISM: Artificial Sequence
<220> FEATURE:
<223> OTHER INFORMATION: Synthetic

<400> SEQUENCE: 741
tgtactccag cttgtgcccc                                              20

<210> SEQ ID NO 742
<211> LENGTH: 20
<212> TYPE: DNA
<213> ORGANISM: Artificial Sequence
<220> FEATURE:
<223> OTHER INFORMATION: Synthetic

<400> SEQUENCE: 742
tgtactccag cttgtgcccc                                              20

<210> SEQ ID NO 743
<211> LENGTH: 20
<212> TYPE: DNA
<213> ORGANISM: Artificial Sequence
<220> FEATURE:
<223> OTHER INFORMATION: Synthetic

<400> SEQUENCE: 743
tgtactccag cttgtgcccc                                              20

<210> SEQ ID NO 744
<211> LENGTH: 20
<212> TYPE: DNA
<213> ORGANISM: Artificial Sequence
<220> FEATURE:
<223> OTHER INFORMATION: Synthetic

<400> SEQUENCE: 744
tgtactccag cttgtgcccc                                              20

<210> SEQ ID NO 745
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 745
gccgtgccgt agctatccgg                                              20

<210> SEQ ID NO 746
<211> LENGTH: 20
<212> TYPE: DNA
<213> ORGANISM: Artificial Sequence
<220> FEATURE:
<223> OTHER INFORMATION: Synthetic

<400> SEQUENCE: 746
gccgtgccgt agctatccgg                                              20

<210> SEQ ID NO 747
<211> LENGTH: 20
<212> TYPE: DNA
<213> ORGANISM: Artificial Sequence
<220> FEATURE:
<223> OTHER INFORMATION: Synthetic

<400> SEQUENCE: 747
aaggaggacg gcaacatcct                                              20

<210> SEQ ID NO 748
<211> LENGTH: 20
<212> TYPE: DNA
<213> ORGANISM: Artificial Sequence
<220> FEATURE:
<223> OTHER INFORMATION: Synthetic

<400> SEQUENCE: 748
aaggaggacg gcaacatcct                                              20

<210> SEQ ID NO 749
<211> LENGTH: 20
<212> TYPE: DNA
<213> ORGANISM: Artificial Sequence
<220> FEATURE:
<223> OTHER INFORMATION: Synthetic

<400> SEQUENCE: 749
caaggaggac ggcaacatcc                                              20

<210> SEQ ID NO 750
<211> LENGTH: 20
<212> TYPE: DNA
<213> ORGANISM: Artificial Sequence
<220> FEATURE:
<223> OTHER INFORMATION: Synthetic

<400> SEQUENCE: 750
caaggaggac ggcaacatcc                                              20

<210> SEQ ID NO 751
<211> LENGTH: 20
<212> TYPE: DNA
<213> ORGANISM: Artificial Sequence
<220> FEATURE:
<223> OTHER INFORMATION: Synthetic

<400> SEQUENCE: 751
```
tgtactccag cttgtgcccc                                                     20

<210> SEQ ID NO 752
<211> LENGTH: 20
<212> TYPE: DNA
<213> ORGANISM: Artificial Sequence
<220> FEATURE:
<223> OTHER INFORMATION: Synthetic

<400> SEQUENCE: 752
tgtactccag cttgtgcccc                                                     20

<210> SEQ ID NO 753
<211> LENGTH: 20
<212> TYPE: DNA
<213> ORGANISM: Artificial Sequence
<220> FEATURE:
<223> OTHER INFORMATION: Synthetic

<400> SEQUENCE: 753
gtccgttcga caatttcaca                                                     20

<210> SEQ ID NO 754
<211> LENGTH: 20
<212> TYPE: DNA
<213> ORGANISM: Artificial Sequence
<220> FEATURE:
<223> OTHER INFORMATION: Synthetic

<400> SEQUENCE: 754
gtccgttcga caatttcaca                                                     20

<210> SEQ ID NO 755
<211> LENGTH: 20
<212> TYPE: DNA
<213> ORGANISM: Artificial Sequence
<220> FEATURE:
<223> OTHER INFORMATION: Synthetic

<400> SEQUENCE: 755
gctgcttgcg ataccaatag                                                     20

<210> SEQ ID NO 756
<211> LENGTH: 20
<212> TYPE: DNA
<213> ORGANISM: Artificial Sequence
<220> FEATURE:
<223> OTHER INFORMATION: Synthetic

<400> SEQUENCE: 756
gctgcttgcg ataccaatag                                                     20

<210> SEQ ID NO 757
<211> LENGTH: 20
<212> TYPE: DNA
<213> ORGANISM: Artificial Sequence
<220> FEATURE:
<223> OTHER INFORMATION: Synthetic

<400> SEQUENCE: 757
aggaggacgg caacatcctg                                                     20

<210> SEQ ID NO 758
<211> LENGTH: 20
<212> TYPE: DNA
<213> ORGANISM: Artificial Sequence

```
<220> FEATURE:
<223> OTHER INFORMATION: Synthetic

<400> SEQUENCE: 758
aggaggacgg caacatcctg                                          20

<210> SEQ ID NO 759
<211> LENGTH: 20
<212> TYPE: DNA
<213> ORGANISM: Artificial Sequence
<220> FEATURE:
<223> OTHER INFORMATION: Synthetic

<400> SEQUENCE: 759
caaggaggac ggcaacatcc                                          20

<210> SEQ ID NO 760
<211> LENGTH: 20
<212> TYPE: DNA
<213> ORGANISM: Artificial Sequence
<220> FEATURE:
<223> OTHER INFORMATION: Synthetic

<400> SEQUENCE: 760
caaggaggac ggcaacatcc                                          20

<210> SEQ ID NO 761
<211> LENGTH: 20
<212> TYPE: DNA
<213> ORGANISM: Artificial Sequence
<220> FEATURE:
<223> OTHER INFORMATION: Synthetic

<400> SEQUENCE: 761
gtccgttcga caatttcaca                                          20

<210> SEQ ID NO 762
<211> LENGTH: 20
<212> TYPE: DNA
<213> ORGANISM: Artificial Sequence
<220> FEATURE:
<223> OTHER INFORMATION: Synthetic

<400> SEQUENCE: 762
gtccgttcga caatttcaca                                          20

<210> SEQ ID NO 763
<211> LENGTH: 20
<212> TYPE: DNA
<213> ORGANISM: Artificial Sequence
<220> FEATURE:
<223> OTHER INFORMATION: Synthetic

<400> SEQUENCE: 763
aggaggacgg caacatcctg                                          20

<210> SEQ ID NO 764
<211> LENGTH: 20
<212> TYPE: DNA
<213> ORGANISM: Artificial Sequence
<220> FEATURE:
<223> OTHER INFORMATION: Synthetic

<400> SEQUENCE: 764
aggaggacgg caacatcctg                                          20
```

```
<210> SEQ ID NO 765
<211> LENGTH: 20
<212> TYPE: DNA
<213> ORGANISM: Artificial Sequence
<220> FEATURE:
<223> OTHER INFORMATION: Synthetic

<400> SEQUENCE: 765
gccgtgccgt agctatccgg                                            20

<210> SEQ ID NO 766
<211> LENGTH: 20
<212> TYPE: DNA
<213> ORGANISM: Artificial Sequence
<220> FEATURE:
<223> OTHER INFORMATION: Synthetic

<400> SEQUENCE: 766
gccgtgccgt agctatccgg                                            20

<210> SEQ ID NO 767
<211> LENGTH: 20
<212> TYPE: DNA
<213> ORGANISM: Artificial Sequence
<220> FEATURE:
<223> OTHER INFORMATION: Synthetic

<400> SEQUENCE: 767
ggacgctaaa ccaacggtgc                                            20

<210> SEQ ID NO 768
<211> LENGTH: 20
<212> TYPE: DNA
<213> ORGANISM: Artificial Sequence
<220> FEATURE:
<223> OTHER INFORMATION: Synthetic

<400> SEQUENCE: 768
ggacgctaaa ccaacggtgc                                            20

<210> SEQ ID NO 769
<211> LENGTH: 20
<212> TYPE: DNA
<213> ORGANISM: Artificial Sequence
<220> FEATURE:
<223> OTHER INFORMATION: Synthetic

<400> SEQUENCE: 769
aaggaggacg gcaacatcct                                            20

<210> SEQ ID NO 770
<211> LENGTH: 20
<212> TYPE: DNA
<213> ORGANISM: Artificial Sequence
<220> FEATURE:
<223> OTHER INFORMATION: Synthetic

<400> SEQUENCE: 770
aaggaggacg gcaacatcct                                            20

<210> SEQ ID NO 771
<211> LENGTH: 20
<212> TYPE: DNA
<213> ORGANISM: Artificial Sequence
<220> FEATURE:
<223> OTHER INFORMATION: Synthetic
```

<400> SEQUENCE: 771
tgtactccag cttgtgcccc                                              20

<210> SEQ ID NO 772
<211> LENGTH: 20
<212> TYPE: DNA
<213> ORGANISM: Artificial Sequence
<220> FEATURE:
<223> OTHER INFORMATION: Synthetic

<400> SEQUENCE: 772
tgtactccag cttgtgcccc                                              20

<210> SEQ ID NO 773
<211> LENGTH: 20
<212> TYPE: DNA
<213> ORGANISM: Artificial Sequence
<220> FEATURE:
<223> OTHER INFORMATION: Synthetic

<400> SEQUENCE: 773
gtacagctaa gttaaactcg                                              20

<210> SEQ ID NO 774
<211> LENGTH: 20
<212> TYPE: DNA
<213> ORGANISM: Artificial Sequence
<220> FEATURE:
<223> OTHER INFORMATION: Synthetic

<400> SEQUENCE: 774
gtacagctaa gttaaactcg                                              20

<210> SEQ ID NO 775
<211> LENGTH: 20
<212> TYPE: DNA
<213> ORGANISM: Artificial Sequence
<220> FEATURE:
<223> OTHER INFORMATION: Synthetic

<400> SEQUENCE: 775
ggacgctaaa ccaacggtgc                                              20

<210> SEQ ID NO 776
<211> LENGTH: 20
<212> TYPE: DNA
<213> ORGANISM: Artificial Sequence
<220> FEATURE:
<223> OTHER INFORMATION: Synthetic

<400> SEQUENCE: 776
ggacgctaaa ccaacggtgc                                              20

<210> SEQ ID NO 777
<211> LENGTH: 20
<212> TYPE: DNA
<213> ORGANISM: Artificial Sequence
<220> FEATURE:
<223> OTHER INFORMATION: Synthetic

<400> SEQUENCE: 777
gccgtgccgt agctatccgg                                              20

<210> SEQ ID NO 778

```
<211> LENGTH: 20
<212> TYPE: DNA
<213> ORGANISM: Artificial Sequence
<220> FEATURE:
<223> OTHER INFORMATION: Synthetic

<400> SEQUENCE: 778
gccgtgccgt agctatccgg                                              20

<210> SEQ ID NO 779
<211> LENGTH: 20
<212> TYPE: DNA
<213> ORGANISM: Artificial Sequence
<220> FEATURE:
<223> OTHER INFORMATION: Synthetic

<400> SEQUENCE: 779
aggaggacgg caacatcctg                                              20

<210> SEQ ID NO 780
<211> LENGTH: 20
<212> TYPE: DNA
<213> ORGANISM: Artificial Sequence
<220> FEATURE:
<223> OTHER INFORMATION: Synthetic

<400> SEQUENCE: 780
aggaggacgg caacatcctg                                              20

<210> SEQ ID NO 781
<211> LENGTH: 20
<212> TYPE: DNA
<213> ORGANISM: Artificial Sequence
<220> FEATURE:
<223> OTHER INFORMATION: Synthetic

<400> SEQUENCE: 781
gtacagctaa gttaaactcg                                              20

<210> SEQ ID NO 782
<211> LENGTH: 20
<212> TYPE: DNA
<213> ORGANISM: Artificial Sequence
<220> FEATURE:
<223> OTHER INFORMATION: Synthetic

<400> SEQUENCE: 782
gtacagctaa gttaaactcg                                              20

<210> SEQ ID NO 783
<211> LENGTH: 20
<212> TYPE: DNA
<213> ORGANISM: Artificial Sequence
<220> FEATURE:
<223> OTHER INFORMATION: Synthetic

<400> SEQUENCE: 783
tgtactccag cttgtgcccc                                              20

<210> SEQ ID NO 784
<211> LENGTH: 20
<212> TYPE: DNA
<213> ORGANISM: Artificial Sequence
<220> FEATURE:
<223> OTHER INFORMATION: Synthetic

<400> SEQUENCE: 784
```
tgtactccag cttgtgcccc                                          20

<210> SEQ ID NO 785
<211> LENGTH: 20
<212> TYPE: DNA
<213> ORGANISM: Artificial Sequence
<220> FEATURE:
<223> OTHER INFORMATION: Synthetic

<400> SEQUENCE: 785
gccgtgccgt agctatccgg                                          20

<210> SEQ ID NO 786
<211> LENGTH: 20
<212> TYPE: DNA
<213> ORGANISM: Artificial Sequence
<220> FEATURE:
<223> OTHER INFORMATION: Synthetic

<400> SEQUENCE: 786
gccgtgccgt agctatccgg                                          20

<210> SEQ ID NO 787
<211> LENGTH: 20
<212> TYPE: DNA
<213> ORGANISM: Artificial Sequence
<220> FEATURE:
<223> OTHER INFORMATION: Synthetic

<400> SEQUENCE: 787
aggaggacgg caacatcctg                                          20

<210> SEQ ID NO 788
<211> LENGTH: 20
<212> TYPE: DNA
<213> ORGANISM: Artificial Sequence
<220> FEATURE:
<223> OTHER INFORMATION: Synthetic

<400> SEQUENCE: 788
aggaggacgg caacatcctg                                          20

<210> SEQ ID NO 789
<211> LENGTH: 20
<212> TYPE: DNA
<213> ORGANISM: Artificial Sequence
<220> FEATURE:
<223> OTHER INFORMATION: Synthetic

<400> SEQUENCE: 789
caacatcctg gggcacaagc                                          20

<210> SEQ ID NO 790
<211> LENGTH: 20
<212> TYPE: DNA
<213> ORGANISM: Artificial Sequence
<220> FEATURE:
<223> OTHER INFORMATION: Synthetic

<400> SEQUENCE: 790
caacatcctg gggcacaagc                                          20

<210> SEQ ID NO 791
<211> LENGTH: 20
<212> TYPE: DNA

```
<213> ORGANISM: Artificial Sequence
<220> FEATURE:
<223> OTHER INFORMATION: Synthetic

<400> SEQUENCE: 791
gtccgttcga caatttcaca                                               20

<210> SEQ ID NO 792
<211> LENGTH: 20
<212> TYPE: DNA
<213> ORGANISM: Artificial Sequence
<220> FEATURE:
<223> OTHER INFORMATION: Synthetic

<400> SEQUENCE: 792
gtccgttcga caatttcaca                                               20

<210> SEQ ID NO 793
<211> LENGTH: 20
<212> TYPE: DNA
<213> ORGANISM: Artificial Sequence
<220> FEATURE:
<223> OTHER INFORMATION: Synthetic

<400> SEQUENCE: 793
gccgtgccgt agctatccgg                                               20

<210> SEQ ID NO 794
<211> LENGTH: 20
<212> TYPE: DNA
<213> ORGANISM: Artificial Sequence
<220> FEATURE:
<223> OTHER INFORMATION: Synthetic

<400> SEQUENCE: 794
gccgtgccgt agctatccgg                                               20

<210> SEQ ID NO 795
<211> LENGTH: 20
<212> TYPE: DNA
<213> ORGANISM: Artificial Sequence
<220> FEATURE:
<223> OTHER INFORMATION: Synthetic

<400> SEQUENCE: 795
aaggaggacg gcaacatcct                                               20

<210> SEQ ID NO 796
<211> LENGTH: 20
<212> TYPE: DNA
<213> ORGANISM: Artificial Sequence
<220> FEATURE:
<223> OTHER INFORMATION: Synthetic

<400> SEQUENCE: 796
aaggaggacg gcaacatcct                                               20

<210> SEQ ID NO 797
<211> LENGTH: 20
<212> TYPE: DNA
<213> ORGANISM: Artificial Sequence
<220> FEATURE:
<223> OTHER INFORMATION: Synthetic

<400> SEQUENCE: 797
ggacgctaaa ccaacggtgc                                               20
```

<210> SEQ ID NO 798
<211> LENGTH: 20
<212> TYPE: DNA
<213> ORGANISM: Artificial Sequence
<220> FEATURE:
<223> OTHER INFORMATION: Synthetic

<400> SEQUENCE: 798
ggacgctaaa ccaacggtgc                                               20

<210> SEQ ID NO 799
<211> LENGTH: 20
<212> TYPE: DNA
<213> ORGANISM: Artificial Sequence
<220> FEATURE:
<223> OTHER INFORMATION: Synthetic

<400> SEQUENCE: 799
ggacgctaaa ccaacggtgc                                               20

<210> SEQ ID NO 800
<211> LENGTH: 20
<212> TYPE: DNA
<213> ORGANISM: Artificial Sequence
<220> FEATURE:
<223> OTHER INFORMATION: Synthetic

<400> SEQUENCE: 800
ggacgctaaa ccaacggtgc                                               20

<210> SEQ ID NO 801
<211> LENGTH: 20
<212> TYPE: DNA
<213> ORGANISM: Artificial Sequence
<220> FEATURE:
<223> OTHER INFORMATION: Synthetic

<400> SEQUENCE: 801
ggacgctaaa ccaacggtgc                                               20

<210> SEQ ID NO 802
<211> LENGTH: 20
<212> TYPE: DNA
<213> ORGANISM: Artificial Sequence
<220> FEATURE:
<223> OTHER INFORMATION: Synthetic

<400> SEQUENCE: 802
ggacgctaaa ccaacggtgc                                               20

<210> SEQ ID NO 803
<211> LENGTH: 20
<212> TYPE: DNA
<213> ORGANISM: Artificial Sequence
<220> FEATURE:
<223> OTHER INFORMATION: Synthetic

<400> SEQUENCE: 803
gctgcttgcg ataccaatag                                               20

<210> SEQ ID NO 804
<211> LENGTH: 20
<212> TYPE: DNA
<213> ORGANISM: Artificial Sequence
<220> FEATURE:

<223> OTHER INFORMATION: Synthetic

<400> SEQUENCE: 804
tgtactccag cttgtgcccc                                                   20

<210> SEQ ID NO 805
<211> LENGTH: 20
<212> TYPE: DNA
<213> ORGANISM: Artificial Sequence
<220> FEATURE:
<223> OTHER INFORMATION: Synthetic

<400> SEQUENCE: 805
tgtactccag cttgtgcccc                                                   20

<210> SEQ ID NO 806
<211> LENGTH: 20
<212> TYPE: DNA
<213> ORGANISM: Artificial Sequence
<220> FEATURE:
<223> OTHER INFORMATION: Synthetic

<400> SEQUENCE: 806
tgtactccag cttgtgcccc                                                   20

<210> SEQ ID NO 807
<211> LENGTH: 20
<212> TYPE: DNA
<213> ORGANISM: Artificial Sequence
<220> FEATURE:
<223> OTHER INFORMATION: Synthetic

<400> SEQUENCE: 807
gccgtgccgt agctatccgg                                                   20

<210> SEQ ID NO 808
<211> LENGTH: 20
<212> TYPE: DNA
<213> ORGANISM: Artificial Sequence
<220> FEATURE:
<223> OTHER INFORMATION: Synthetic

<400> SEQUENCE: 808
gccgtgccgt agctatccgg                                                   20

<210> SEQ ID NO 809
<211> LENGTH: 20
<212> TYPE: DNA
<213> ORGANISM: Artificial Sequence
<220> FEATURE:
<223> OTHER INFORMATION: Synthetic

<400> SEQUENCE: 809
tgtactccag cttgtgcccc                                                   20

<210> SEQ ID NO 810
<211> LENGTH: 20
<212> TYPE: DNA
<213> ORGANISM: Artificial Sequence
<220> FEATURE:
<223> OTHER INFORMATION: Synthetic

<400> SEQUENCE: 810
tgtactccag cttgtgcccc                                                   20

```
<210> SEQ ID NO 811
<211> LENGTH: 20
<212> TYPE: DNA
<213> ORGANISM: Artificial Sequence
<220> FEATURE:
<223> OTHER INFORMATION: Synthetic

<400> SEQUENCE: 811
aaggaggacg gcaacatcct                                                   20

<210> SEQ ID NO 812
<211> LENGTH: 20
<212> TYPE: DNA
<213> ORGANISM: Artificial Sequence
<220> FEATURE:
<223> OTHER INFORMATION: Synthetic

<400> SEQUENCE: 812
aaggaggacg gcaacatcct                                                   20

<210> SEQ ID NO 813
<211> LENGTH: 20
<212> TYPE: DNA
<213> ORGANISM: Artificial Sequence
<220> FEATURE:
<223> OTHER INFORMATION: Synthetic

<400> SEQUENCE: 813
caaggaggac ggcaacatcc                                                   20

<210> SEQ ID NO 814
<211> LENGTH: 20
<212> TYPE: DNA
<213> ORGANISM: Artificial Sequence
<220> FEATURE:
<223> OTHER INFORMATION: Synthetic

<400> SEQUENCE: 814
caaggaggac ggcaacatcc                                                   20

<210> SEQ ID NO 815
<211> LENGTH: 20
<212> TYPE: DNA
<213> ORGANISM: Artificial Sequence
<220> FEATURE:
<223> OTHER INFORMATION: Synthetic

<400> SEQUENCE: 815
gccgtgccgt agctatccgg                                                   20

<210> SEQ ID NO 816
<211> LENGTH: 20
<212> TYPE: DNA
<213> ORGANISM: Artificial Sequence
<220> FEATURE:
<223> OTHER INFORMATION: Synthetic

<400> SEQUENCE: 816
gtccgttcga caatttcaca                                                   20

<210> SEQ ID NO 817
<211> LENGTH: 20
<212> TYPE: DNA
<213> ORGANISM: Artificial Sequence
<220> FEATURE:
<223> OTHER INFORMATION: Synthetic
```

<400> SEQUENCE: 817
gccgtgccgt agctatccgg								20

<210> SEQ ID NO 818
<211> LENGTH: 20
<212> TYPE: DNA
<213> ORGANISM: Artificial Sequence
<220> FEATURE:
<223> OTHER INFORMATION: Synthetic

<400> SEQUENCE: 818
gtccgttcga caatttcaca								20

<210> SEQ ID NO 819
<211> LENGTH: 20
<212> TYPE: DNA
<213> ORGANISM: Artificial Sequence
<220> FEATURE:
<223> OTHER INFORMATION: Synthetic

<400> SEQUENCE: 819
gccgtgccgt agctatccgg								20

<210> SEQ ID NO 820
<211> LENGTH: 20
<212> TYPE: DNA
<213> ORGANISM: Artificial Sequence
<220> FEATURE:
<223> OTHER INFORMATION: Synthetic

<400> SEQUENCE: 820
gtccgttcga caatttcaca								20

<210> SEQ ID NO 821
<211> LENGTH: 20
<212> TYPE: DNA
<213> ORGANISM: Artificial Sequence
<220> FEATURE:
<223> OTHER INFORMATION: Synthetic

<400> SEQUENCE: 821
gtccgttcga caatttcaca								20

<210> SEQ ID NO 822
<211> LENGTH: 20
<212> TYPE: DNA
<213> ORGANISM: Artificial Sequence
<220> FEATURE:
<223> OTHER INFORMATION: Synthetic

<400> SEQUENCE: 822
gtccgttcga caatttcaca								20

<210> SEQ ID NO 823
<211> LENGTH: 20
<212> TYPE: DNA
<213> ORGANISM: Artificial Sequence
<220> FEATURE:
<223> OTHER INFORMATION: Synthetic

<400> SEQUENCE: 823
gctgcttgcg ataccaatag								20

<210> SEQ ID NO 824
<211> LENGTH: 20

```
<212> TYPE: DNA
<213> ORGANISM: Artificial Sequence
<220> FEATURE:
<223> OTHER INFORMATION: Synthetic

<400> SEQUENCE: 824
gctgcttgcg ataccaatag                                                 20

<210> SEQ ID NO 825
<211> LENGTH: 20
<212> TYPE: DNA
<213> ORGANISM: Artificial Sequence
<220> FEATURE:
<223> OTHER INFORMATION: Synthetic

<400> SEQUENCE: 825
caaggaggac ggcaacatcc                                                 20

<210> SEQ ID NO 826
<211> LENGTH: 20
<212> TYPE: DNA
<213> ORGANISM: Artificial Sequence
<220> FEATURE:
<223> OTHER INFORMATION: Synthetic

<400> SEQUENCE: 826
caaggaggac ggcaacatcc                                                 20

<210> SEQ ID NO 827
<211> LENGTH: 20
<212> TYPE: DNA
<213> ORGANISM: Artificial Sequence
<220> FEATURE:
<223> OTHER INFORMATION: Synthetic

<400> SEQUENCE: 827
caaggaggac ggcaacatcc                                                 20

<210> SEQ ID NO 828
<211> LENGTH: 20
<212> TYPE: DNA
<213> ORGANISM: Artificial Sequence
<220> FEATURE:
<223> OTHER INFORMATION: Synthetic

<400> SEQUENCE: 828
caaggaggac ggcaacatcc                                                 20

<210> SEQ ID NO 829
<211> LENGTH: 20
<212> TYPE: DNA
<213> ORGANISM: Artificial Sequence
<220> FEATURE:
<223> OTHER INFORMATION: Synthetic

<400> SEQUENCE: 829
gtccgttcga caatttcaca                                                 20

<210> SEQ ID NO 830
<211> LENGTH: 20
<212> TYPE: DNA
<213> ORGANISM: Artificial Sequence
<220> FEATURE:
<223> OTHER INFORMATION: Synthetic

<400> SEQUENCE: 830
```
gtccgttcga caatttcaca                                               20

<210> SEQ ID NO 831
<211> LENGTH: 20
<212> TYPE: DNA
<213> ORGANISM: Artificial Sequence
<220> FEATURE:
<223> OTHER INFORMATION: Synthetic

<400> SEQUENCE: 831
ggacgctaaa ccaacggtgc                                               20

<210> SEQ ID NO 832
<211> LENGTH: 20
<212> TYPE: DNA
<213> ORGANISM: Artificial Sequence
<220> FEATURE:
<223> OTHER INFORMATION: Synthetic

<400> SEQUENCE: 832
ggacgctaaa ccaacggtgc                                               20

<210> SEQ ID NO 833
<211> LENGTH: 20
<212> TYPE: DNA
<213> ORGANISM: Artificial Sequence
<220> FEATURE:
<223> OTHER INFORMATION: Synthetic

<400> SEQUENCE: 833
ggacgctaaa ccaacggtgc                                               20

<210> SEQ ID NO 834
<211> LENGTH: 20
<212> TYPE: DNA
<213> ORGANISM: Artificial Sequence
<220> FEATURE:
<223> OTHER INFORMATION: Synthetic

<400> SEQUENCE: 834
ggacgctaaa ccaacggtgc                                               20

<210> SEQ ID NO 835
<211> LENGTH: 20
<212> TYPE: DNA
<213> ORGANISM: Artificial Sequence
<220> FEATURE:
<223> OTHER INFORMATION: Synthetic

<400> SEQUENCE: 835
caaggaggac ggcaacatcc                                               20

<210> SEQ ID NO 836
<211> LENGTH: 20
<212> TYPE: DNA
<213> ORGANISM: Artificial Sequence
<220> FEATURE:
<223> OTHER INFORMATION: Synthetic

<400> SEQUENCE: 836
caaggaggac ggcaacatcc                                               20

<210> SEQ ID NO 837
<211> LENGTH: 20
<212> TYPE: DNA
<213> ORGANISM: Artificial Sequence

```
<220> FEATURE:
<223> OTHER INFORMATION: Synthetic

<400> SEQUENCE: 837
caacatcctg gggcacaagc                                                    20

<210> SEQ ID NO 838
<211> LENGTH: 20
<212> TYPE: DNA
<213> ORGANISM: Artificial Sequence
<220> FEATURE:
<223> OTHER INFORMATION: Synthetic

<400> SEQUENCE: 838
caacatcctg gggcacaagc                                                    20

<210> SEQ ID NO 839
<211> LENGTH: 20
<212> TYPE: DNA
<213> ORGANISM: Artificial Sequence
<220> FEATURE:
<223> OTHER INFORMATION: Synthetic

<400> SEQUENCE: 839
tgtactccag cttgtgcccc                                                    20

<210> SEQ ID NO 840
<211> LENGTH: 20
<212> TYPE: DNA
<213> ORGANISM: Artificial Sequence
<220> FEATURE:
<223> OTHER INFORMATION: Synthetic

<400> SEQUENCE: 840
tgtactccag cttgtgcccc                                                    20

<210> SEQ ID NO 841
<211> LENGTH: 20
<212> TYPE: DNA
<213> ORGANISM: Artificial Sequence
<220> FEATURE:
<223> OTHER INFORMATION: Synthetic

<400> SEQUENCE: 841
aggaggacgg caacatcctg                                                    20

<210> SEQ ID NO 842
<211> LENGTH: 20
<212> TYPE: DNA
<213> ORGANISM: Artificial Sequence
<220> FEATURE:
<223> OTHER INFORMATION: Synthetic

<400> SEQUENCE: 842
aggaggacgg caacatcctg                                                    20

<210> SEQ ID NO 843
<211> LENGTH: 20
<212> TYPE: DNA
<213> ORGANISM: Artificial Sequence
<220> FEATURE:
<223> OTHER INFORMATION: Synthetic

<400> SEQUENCE: 843
aaggaggacg gcaacatcct                                                    20
```

```
<210> SEQ ID NO 844
<211> LENGTH: 20
<212> TYPE: DNA
<213> ORGANISM: Artificial Sequence
<220> FEATURE:
<223> OTHER INFORMATION: Synthetic

<400> SEQUENCE: 844
aaggaggacg gcaacatcct                                              20

<210> SEQ ID NO 845
<211> LENGTH: 20
<212> TYPE: DNA
<213> ORGANISM: Artificial Sequence
<220> FEATURE:
<223> OTHER INFORMATION: Synthetic

<400> SEQUENCE: 845
gccgtgccgt agctatccgg                                              20

<210> SEQ ID NO 846
<211> LENGTH: 20
<212> TYPE: DNA
<213> ORGANISM: Artificial Sequence
<220> FEATURE:
<223> OTHER INFORMATION: Synthetic

<400> SEQUENCE: 846
gccgtgccgt agctatccgg                                              20

<210> SEQ ID NO 847
<211> LENGTH: 20
<212> TYPE: DNA
<213> ORGANISM: Artificial Sequence
<220> FEATURE:
<223> OTHER INFORMATION: Synthetic

<400> SEQUENCE: 847
caaggaggac ggcaacatcc                                              20

<210> SEQ ID NO 848
<211> LENGTH: 20
<212> TYPE: DNA
<213> ORGANISM: Artificial Sequence
<220> FEATURE:
<223> OTHER INFORMATION: Synthetic

<400> SEQUENCE: 848
caaggaggac ggcaacatcc                                              20

<210> SEQ ID NO 849
<211> LENGTH: 20
<212> TYPE: DNA
<213> ORGANISM: Artificial Sequence
<220> FEATURE:
<223> OTHER INFORMATION: Synthetic

<400> SEQUENCE: 849
gtacagctaa gttaaactcg                                              20

<210> SEQ ID NO 850
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 850
caaggaggac ggcaacatcc                                              20

<210> SEQ ID NO 851
<211> LENGTH: 20
<212> TYPE: DNA
<213> ORGANISM: Artificial Sequence
<220> FEATURE:
<223> OTHER INFORMATION: Synthetic

<400> SEQUENCE: 851
gtccgttcga caatttcaca                                              20

<210> SEQ ID NO 852
<211> LENGTH: 20
<212> TYPE: DNA
<213> ORGANISM: Artificial Sequence
<220> FEATURE:
<223> OTHER INFORMATION: Synthetic

<400> SEQUENCE: 852
gtccgttcga caatttcaca                                              20

<210> SEQ ID NO 853
<211> LENGTH: 20
<212> TYPE: DNA
<213> ORGANISM: Artificial Sequence
<220> FEATURE:
<223> OTHER INFORMATION: Synthetic

<400> SEQUENCE: 853
gccgtgccgt agctatccgg                                              20

<210> SEQ ID NO 854
<211> LENGTH: 20
<212> TYPE: DNA
<213> ORGANISM: Artificial Sequence
<220> FEATURE:
<223> OTHER INFORMATION: Synthetic

<400> SEQUENCE: 854
gccgtgccgt agctatccgg                                              20

<210> SEQ ID NO 855
<211> LENGTH: 20
<212> TYPE: DNA
<213> ORGANISM: Artificial Sequence
<220> FEATURE:
<223> OTHER INFORMATION: Synthetic

<400> SEQUENCE: 855
gtccgttcga caatttcaca                                              20

<210> SEQ ID NO 856
<211> LENGTH: 20
<212> TYPE: DNA
<213> ORGANISM: Artificial Sequence
<220> FEATURE:
<223> OTHER INFORMATION: Synthetic

<400> SEQUENCE: 856
gtccgttcga caatttcaca                                              20

<210> SEQ ID NO 857
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 857
gtccgttcga caatttcaca                                               20

<210> SEQ ID NO 858
<211> LENGTH: 20
<212> TYPE: DNA
<213> ORGANISM: Artificial Sequence
<220> FEATURE:
<223> OTHER INFORMATION: Synthetic

<400> SEQUENCE: 858
tgtactccag cttgtgcccc                                               20

<210> SEQ ID NO 859
<211> LENGTH: 20
<212> TYPE: DNA
<213> ORGANISM: Artificial Sequence
<220> FEATURE:
<223> OTHER INFORMATION: Synthetic

<400> SEQUENCE: 859
gtccgttcga caatttcaca                                               20

<210> SEQ ID NO 860
<211> LENGTH: 20
<212> TYPE: DNA
<213> ORGANISM: Artificial Sequence
<220> FEATURE:
<223> OTHER INFORMATION: Synthetic

<400> SEQUENCE: 860
caaggaggac ggcaacatcc                                               20

<210> SEQ ID NO 861
<211> LENGTH: 20
<212> TYPE: DNA
<213> ORGANISM: Artificial Sequence
<220> FEATURE:
<223> OTHER INFORMATION: Synthetic

<400> SEQUENCE: 861
gtccgttcga caatttcaca                                               20

<210> SEQ ID NO 862
<211> LENGTH: 20
<212> TYPE: DNA
<213> ORGANISM: Artificial Sequence
<220> FEATURE:
<223> OTHER INFORMATION: Synthetic

<400> SEQUENCE: 862
gtccgttcga caatttcaca                                               20

<210> SEQ ID NO 863
<211> LENGTH: 20
<212> TYPE: DNA
<213> ORGANISM: Artificial Sequence
<220> FEATURE:
<223> OTHER INFORMATION: Synthetic

<400> SEQUENCE: 863
```
gtccgttcga caatttcaca                                           20

<210> SEQ ID NO 864
<211> LENGTH: 20
<212> TYPE: DNA
<213> ORGANISM: Artificial Sequence
<220> FEATURE:
<223> OTHER INFORMATION: Synthetic

<400> SEQUENCE: 864
aaggaggacg gcaacatcct                                           20

<210> SEQ ID NO 865
<211> LENGTH: 20
<212> TYPE: DNA
<213> ORGANISM: Artificial Sequence
<220> FEATURE:
<223> OTHER INFORMATION: Synthetic

<400> SEQUENCE: 865
caaggaggac ggcaacatcc                                           20

<210> SEQ ID NO 866
<211> LENGTH: 20
<212> TYPE: DNA
<213> ORGANISM: Artificial Sequence
<220> FEATURE:
<223> OTHER INFORMATION: Synthetic

<400> SEQUENCE: 866
gtccgttcga caatttcaca                                           20

<210> SEQ ID NO 867
<211> LENGTH: 20
<212> TYPE: DNA
<213> ORGANISM: Artificial Sequence
<220> FEATURE:
<223> OTHER INFORMATION: Synthetic

<400> SEQUENCE: 867
gtccgttcga caatttcaca                                           20

<210> SEQ ID NO 868
<211> LENGTH: 20
<212> TYPE: DNA
<213> ORGANISM: Artificial Sequence
<220> FEATURE:
<223> OTHER INFORMATION: Synthetic

<400> SEQUENCE: 868
caacatcctg gggcacaagc                                           20

<210> SEQ ID NO 869
<211> LENGTH: 20
<212> TYPE: DNA
<213> ORGANISM: Artificial Sequence
<220> FEATURE:
<223> OTHER INFORMATION: Synthetic

<400> SEQUENCE: 869
ggacgctaaa ccaacggtgc                                           20

<210> SEQ ID NO 870
<211> LENGTH: 20
<212> TYPE: DNA

```
<213> ORGANISM: Artificial Sequence
<220> FEATURE:
<223> OTHER INFORMATION: Synthetic

<400> SEQUENCE: 870
aggaggacgg caacatcctg                                              20

<210> SEQ ID NO 871
<211> LENGTH: 20
<212> TYPE: DNA
<213> ORGANISM: Artificial Sequence
<220> FEATURE:
<223> OTHER INFORMATION: Synthetic

<400> SEQUENCE: 871
ggacgctaaa ccaacggtgc                                              20

<210> SEQ ID NO 872
<211> LENGTH: 20
<212> TYPE: DNA
<213> ORGANISM: Artificial Sequence
<220> FEATURE:
<223> OTHER INFORMATION: Synthetic

<400> SEQUENCE: 872
aggaggacgg caacatcctg                                              20

<210> SEQ ID NO 873
<211> LENGTH: 20
<212> TYPE: DNA
<213> ORGANISM: Artificial Sequence
<220> FEATURE:
<223> OTHER INFORMATION: Synthetic

<400> SEQUENCE: 873
tgtactccag cttgtgcccc                                              20

<210> SEQ ID NO 874
<211> LENGTH: 20
<212> TYPE: DNA
<213> ORGANISM: Artificial Sequence
<220> FEATURE:
<223> OTHER INFORMATION: Synthetic

<400> SEQUENCE: 874
aaggaggacg gcaacatcct                                              20

<210> SEQ ID NO 875
<211> LENGTH: 20
<212> TYPE: DNA
<213> ORGANISM: Artificial Sequence
<220> FEATURE:
<223> OTHER INFORMATION: Synthetic

<400> SEQUENCE: 875
tgtactccag cttgtgcccc                                              20

<210> SEQ ID NO 876
<211> LENGTH: 20
<212> TYPE: DNA
<213> ORGANISM: Artificial Sequence
<220> FEATURE:
<223> OTHER INFORMATION: Synthetic

<400> SEQUENCE: 876
aaggaggacg gcaacatcct                                              20
```

```
<210> SEQ ID NO 877
<211> LENGTH: 20
<212> TYPE: DNA
<213> ORGANISM: Artificial Sequence
<220> FEATURE:
<223> OTHER INFORMATION: Synthetic

<400> SEQUENCE: 877
aaggaggacg gcaacatcct                                              20

<210> SEQ ID NO 878
<211> LENGTH: 20
<212> TYPE: DNA
<213> ORGANISM: Artificial Sequence
<220> FEATURE:
<223> OTHER INFORMATION: Synthetic

<400> SEQUENCE: 878
caacatcctg gggcacaagc                                              20

<210> SEQ ID NO 879
<211> LENGTH: 20
<212> TYPE: DNA
<213> ORGANISM: Artificial Sequence
<220> FEATURE:
<223> OTHER INFORMATION: Synthetic

<400> SEQUENCE: 879
caacatcctg gggcacaagc                                              20

<210> SEQ ID NO 880
<211> LENGTH: 20
<212> TYPE: DNA
<213> ORGANISM: Artificial Sequence
<220> FEATURE:
<223> OTHER INFORMATION: Synthetic

<400> SEQUENCE: 880
gccgtgccgt agctatccgg                                              20

<210> SEQ ID NO 881
<211> LENGTH: 20
<212> TYPE: DNA
<213> ORGANISM: Artificial Sequence
<220> FEATURE:
<223> OTHER INFORMATION: Synthetic

<400> SEQUENCE: 881
caaggaggac ggcaacatcc                                              20

<210> SEQ ID NO 882
<211> LENGTH: 20
<212> TYPE: DNA
<213> ORGANISM: Artificial Sequence
<220> FEATURE:
<223> OTHER INFORMATION: Synthetic

<400> SEQUENCE: 882
caaggaggac ggcaacatcc                                              20

<210> SEQ ID NO 883
<211> LENGTH: 20
<212> TYPE: DNA
<213> ORGANISM: Artificial Sequence
<220> FEATURE:
```

<223> OTHER INFORMATION: Synthetic

<400> SEQUENCE: 883
aggaggacgg caacatcctg                                              20

<210> SEQ ID NO 884
<211> LENGTH: 20
<212> TYPE: DNA
<213> ORGANISM: Artificial Sequence
<220> FEATURE:
<223> OTHER INFORMATION: Synthetic

<400> SEQUENCE: 884
aggaggacgg caacatcctg                                              20

<210> SEQ ID NO 885
<211> LENGTH: 20
<212> TYPE: DNA
<213> ORGANISM: Artificial Sequence
<220> FEATURE:
<223> OTHER INFORMATION: Synthetic

<400> SEQUENCE: 885
gtacagctaa gttaaactcg                                              20

<210> SEQ ID NO 886
<211> LENGTH: 20
<212> TYPE: DNA
<213> ORGANISM: Artificial Sequence
<220> FEATURE:
<223> OTHER INFORMATION: Synthetic

<400> SEQUENCE: 886
gtacagctaa gttaaactcg                                              20

<210> SEQ ID NO 887
<211> LENGTH: 20
<212> TYPE: DNA
<213> ORGANISM: Artificial Sequence
<220> FEATURE:
<223> OTHER INFORMATION: Synthetic

<400> SEQUENCE: 887
caacatcctg gggcacaagc                                              20

<210> SEQ ID NO 888
<211> LENGTH: 20
<212> TYPE: DNA
<213> ORGANISM: Artificial Sequence
<220> FEATURE:
<223> OTHER INFORMATION: Synthetic

<400> SEQUENCE: 888
caacatcctg gggcacaagc                                              20

<210> SEQ ID NO 889
<211> LENGTH: 20
<212> TYPE: DNA
<213> ORGANISM: Artificial Sequence
<220> FEATURE:
<223> OTHER INFORMATION: Synthetic

<400> SEQUENCE: 889
caacatcctg gggcacaagc                                              20

```
<210> SEQ ID NO 890
<211> LENGTH: 20
<212> TYPE: DNA
<213> ORGANISM: Artificial Sequence
<220> FEATURE:
<223> OTHER INFORMATION: Synthetic

<400> SEQUENCE: 890
caacatcctg gggcacaagc                                                 20

<210> SEQ ID NO 891
<211> LENGTH: 20
<212> TYPE: DNA
<213> ORGANISM: Artificial Sequence
<220> FEATURE:
<223> OTHER INFORMATION: Synthetic

<400> SEQUENCE: 891
aggaggacgg caacatcctg                                                 20

<210> SEQ ID NO 892
<211> LENGTH: 20
<212> TYPE: DNA
<213> ORGANISM: Artificial Sequence
<220> FEATURE:
<223> OTHER INFORMATION: Synthetic

<400> SEQUENCE: 892
aggaggacgg caacatcctg                                                 20

<210> SEQ ID NO 893
<211> LENGTH: 20
<212> TYPE: DNA
<213> ORGANISM: Artificial Sequence
<220> FEATURE:
<223> OTHER INFORMATION: Synthetic

<400> SEQUENCE: 893
gctgcttgcg ataccaatag                                                 20

<210> SEQ ID NO 894
<211> LENGTH: 20
<212> TYPE: DNA
<213> ORGANISM: Artificial Sequence
<220> FEATURE:
<223> OTHER INFORMATION: Synthetic

<400> SEQUENCE: 894
aaggaggacg gcaacatcct                                                 20

<210> SEQ ID NO 895
<211> LENGTH: 20
<212> TYPE: DNA
<213> ORGANISM: Artificial Sequence
<220> FEATURE:
<223> OTHER INFORMATION: Synthetic

<400> SEQUENCE: 895
caaggaggac ggcaacatcc                                                 20

<210> SEQ ID NO 896
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 896
tgtactccag cttgtgcccc                                              20

<210> SEQ ID NO 897
<211> LENGTH: 20
<212> TYPE: DNA
<213> ORGANISM: Artificial Sequence
<220> FEATURE:
<223> OTHER INFORMATION: Synthetic

<400> SEQUENCE: 897
aaggaggacg gcaacatcct                                              20

<210> SEQ ID NO 898
<211> LENGTH: 20
<212> TYPE: DNA
<213> ORGANISM: Artificial Sequence
<220> FEATURE:
<223> OTHER INFORMATION: Synthetic

<400> SEQUENCE: 898
caacatcctg gggcacaagc                                              20

<210> SEQ ID NO 899
<211> LENGTH: 20
<212> TYPE: DNA
<213> ORGANISM: Artificial Sequence
<220> FEATURE:
<223> OTHER INFORMATION: Synthetic

<400> SEQUENCE: 899
caacatcctg gggcacaagc                                              20

<210> SEQ ID NO 900
<211> LENGTH: 20
<212> TYPE: DNA
<213> ORGANISM: Artificial Sequence
<220> FEATURE:
<223> OTHER INFORMATION: Synthetic

<400> SEQUENCE: 900
gccgtgccgt agctatccgg                                              20

<210> SEQ ID NO 901
<211> LENGTH: 20
<212> TYPE: DNA
<213> ORGANISM: Artificial Sequence
<220> FEATURE:
<223> OTHER INFORMATION: Synthetic

<400> SEQUENCE: 901
aggaggacgg caacatcctg                                              20

<210> SEQ ID NO 902
<211> LENGTH: 20
<212> TYPE: DNA
<213> ORGANISM: Artificial Sequence
<220> FEATURE:
<223> OTHER INFORMATION: Synthetic

<400> SEQUENCE: 902
aggaggacgg caacatcctg                                              20

<210> SEQ ID NO 903
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 903
gtacagctaa gttaaactcg                                               20

<210> SEQ ID NO 904
<211> LENGTH: 20
<212> TYPE: DNA
<213> ORGANISM: Artificial Sequence
<220> FEATURE:
<223> OTHER INFORMATION: Synthetic

<400> SEQUENCE: 904
gtacagctaa gttaaactcg                                               20

<210> SEQ ID NO 905
<211> LENGTH: 20
<212> TYPE: DNA
<213> ORGANISM: Artificial Sequence
<220> FEATURE:
<223> OTHER INFORMATION: Synthetic

<400> SEQUENCE: 905
ggacgctaaa ccaacggtgc                                               20

<210> SEQ ID NO 906
<211> LENGTH: 20
<212> TYPE: DNA
<213> ORGANISM: Artificial Sequence
<220> FEATURE:
<223> OTHER INFORMATION: Synthetic

<400> SEQUENCE: 906
ggacgctaaa ccaacggtgc                                               20

<210> SEQ ID NO 907
<211> LENGTH: 20
<212> TYPE: DNA
<213> ORGANISM: Artificial Sequence
<220> FEATURE:
<223> OTHER INFORMATION: Synthetic

<400> SEQUENCE: 907
ggacgctaaa ccaacggtgc                                               20

<210> SEQ ID NO 908
<211> LENGTH: 20
<212> TYPE: DNA
<213> ORGANISM: Artificial Sequence
<220> FEATURE:
<223> OTHER INFORMATION: Synthetic

<400> SEQUENCE: 908
ggacgctaaa ccaacggtgc                                               20

<210> SEQ ID NO 909
<211> LENGTH: 20
<212> TYPE: DNA
<213> ORGANISM: Artificial Sequence
<220> FEATURE:
<223> OTHER INFORMATION: Synthetic

<400> SEQUENCE: 909
```
aggaggacgg caacatcctg                                              20

<210> SEQ ID NO 910
<211> LENGTH: 20
<212> TYPE: DNA
<213> ORGANISM: Artificial Sequence
<220> FEATURE:
<223> OTHER INFORMATION: Synthetic

<400> SEQUENCE: 910
aggaggacgg caacatcctg                                              20

<210> SEQ ID NO 911
<211> LENGTH: 20
<212> TYPE: DNA
<213> ORGANISM: Artificial Sequence
<220> FEATURE:
<223> OTHER INFORMATION: Synthetic

<400> SEQUENCE: 911
caacatcctg gggcacaagc                                              20

<210> SEQ ID NO 912
<211> LENGTH: 20
<212> TYPE: DNA
<213> ORGANISM: Artificial Sequence
<220> FEATURE:
<223> OTHER INFORMATION: Synthetic

<400> SEQUENCE: 912
caacatcctg gggcacaagc                                              20

<210> SEQ ID NO 913
<211> LENGTH: 20
<212> TYPE: DNA
<213> ORGANISM: Artificial Sequence
<220> FEATURE:
<223> OTHER INFORMATION: Synthetic

<400> SEQUENCE: 913
aaggaggacg gcaacatcct                                              20

<210> SEQ ID NO 914
<211> LENGTH: 20
<212> TYPE: DNA
<213> ORGANISM: Artificial Sequence
<220> FEATURE:
<223> OTHER INFORMATION: Synthetic

<400> SEQUENCE: 914
tgtactccag cttgtgcccc                                              20

<210> SEQ ID NO 915
<211> LENGTH: 20
<212> TYPE: DNA
<213> ORGANISM: Artificial Sequence
<220> FEATURE:
<223> OTHER INFORMATION: Synthetic

<400> SEQUENCE: 915
tgtactccag cttgtgcccc                                              20

<210> SEQ ID NO 916
<211> LENGTH: 20
<212> TYPE: DNA
<213> ORGANISM: Artificial Sequence
<220> FEATURE:
<223> OTHER INFORMATION: Synthetic

<400> SEQUENCE: 916
aaggaggacg gcaacatcct           20

<210> SEQ ID NO 917
<211> LENGTH: 20
<212> TYPE: DNA
<213> ORGANISM: Artificial Sequence
<220> FEATURE:
<223> OTHER INFORMATION: Synthetic

<400> SEQUENCE: 917
caaggaggac ggcaacatcc           20

<210> SEQ ID NO 918
<211> LENGTH: 20
<212> TYPE: DNA
<213> ORGANISM: Artificial Sequence
<220> FEATURE:
<223> OTHER INFORMATION: Synthetic

<400> SEQUENCE: 918
caaggaggac ggcaacatcc           20

<210> SEQ ID NO 919
<211> LENGTH: 20
<212> TYPE: DNA
<213> ORGANISM: Artificial Sequence
<220> FEATURE:
<223> OTHER INFORMATION: Synthetic

<400> SEQUENCE: 919
gctgcttgcg ataccaatag           20

<210> SEQ ID NO 920
<211> LENGTH: 20
<212> TYPE: DNA
<213> ORGANISM: Artificial Sequence
<220> FEATURE:
<223> OTHER INFORMATION: Synthetic

<400> SEQUENCE: 920
gctgcttgcg ataccaatag           20

<210> SEQ ID NO 921
<211> LENGTH: 20
<212> TYPE: DNA
<213> ORGANISM: Artificial Sequence
<220> FEATURE:
<223> OTHER INFORMATION: Synthetic

<400> SEQUENCE: 921
caacatcctg gggcacaagc           20

<210> SEQ ID NO 922
<211> LENGTH: 20
<212> TYPE: DNA
<213> ORGANISM: Artificial Sequence
<220> FEATURE:
<223> OTHER INFORMATION: Synthetic

<400> SEQUENCE: 922
ggacgctaaa ccaacggtgc           20

<210> SEQ ID NO 923
<211> LENGTH: 20
<212> TYPE: DNA
<213> ORGANISM: Artificial Sequence
<220> FEATURE:
<223> OTHER INFORMATION: Synthetic

<400> SEQUENCE: 923
caacatcctg gggcacaagc                                               20

<210> SEQ ID NO 924
<211> LENGTH: 20
<212> TYPE: DNA
<213> ORGANISM: Artificial Sequence
<220> FEATURE:
<223> OTHER INFORMATION: Synthetic

<400> SEQUENCE: 924
caacatcctg gggcacaagc                                               20

<210> SEQ ID NO 925
<211> LENGTH: 20
<212> TYPE: DNA
<213> ORGANISM: Artificial Sequence
<220> FEATURE:
<223> OTHER INFORMATION: Synthetic

<400> SEQUENCE: 925
caacatcctg gggcacaagc                                               20

<210> SEQ ID NO 926
<211> LENGTH: 20
<212> TYPE: DNA
<213> ORGANISM: Artificial Sequence
<220> FEATURE:
<223> OTHER INFORMATION: Synthetic

<400> SEQUENCE: 926
caacatcctg gggcacaagc                                               20

<210> SEQ ID NO 927
<211> LENGTH: 20
<212> TYPE: DNA
<213> ORGANISM: Artificial Sequence
<220> FEATURE:
<223> OTHER INFORMATION: Synthetic

<400> SEQUENCE: 927
ggacgctaaa ccaacggtgc                                               20

<210> SEQ ID NO 928
<211> LENGTH: 20
<212> TYPE: DNA
<213> ORGANISM: Artificial Sequence
<220> FEATURE:
<223> OTHER INFORMATION: Synthetic

<400> SEQUENCE: 928
ggacgctaaa ccaacggtgc                                               20

<210> SEQ ID NO 929
<211> LENGTH: 20
<212> TYPE: DNA
<213> ORGANISM: Artificial Sequence
<220> FEATURE:
<223> OTHER INFORMATION: Synthetic

<400> SEQUENCE: 929
ggacgctaaa ccaacggtgc                                               20

<210> SEQ ID NO 930
<211> LENGTH: 20
<212> TYPE: DNA
<213> ORGANISM: Artificial Sequence
<220> FEATURE:
<223> OTHER INFORMATION: Synthetic

<400> SEQUENCE: 930
ggacgctaaa ccaacggtgc                                               20

<210> SEQ ID NO 931
<211> LENGTH: 20
<212> TYPE: DNA
<213> ORGANISM: Artificial Sequence
<220> FEATURE:
<223> OTHER INFORMATION: Synthetic

<400> SEQUENCE: 931
aggaggacgg caacatcctg                                               20

<210> SEQ ID NO 932
<211> LENGTH: 20
<212> TYPE: DNA
<213> ORGANISM: Artificial Sequence
<220> FEATURE:
<223> OTHER INFORMATION: Synthetic

<400> SEQUENCE: 932
aggaggacgg caacatcctg                                               20

<210> SEQ ID NO 933
<211> LENGTH: 20
<212> TYPE: DNA
<213> ORGANISM: Artificial Sequence
<220> FEATURE:
<223> OTHER INFORMATION: Synthetic

<400> SEQUENCE: 933
gccgtgccgt agctatccgg                                               20

<210> SEQ ID NO 934
<211> LENGTH: 20
<212> TYPE: DNA
<213> ORGANISM: Artificial Sequence
<220> FEATURE:
<223> OTHER INFORMATION: Synthetic

<400> SEQUENCE: 934
gccgtgccgt agctatccgg                                               20

<210> SEQ ID NO 935
<211> LENGTH: 20
<212> TYPE: DNA
<213> ORGANISM: Artificial Sequence
<220> FEATURE:
<223> OTHER INFORMATION: Synthetic

<400> SEQUENCE: 935
gctgcttgcg ataccaatag                                               20

<210> SEQ ID NO 936

```
<211> LENGTH: 20
<212> TYPE: DNA
<213> ORGANISM: Artificial Sequence
<220> FEATURE:
<223> OTHER INFORMATION: Synthetic

<400> SEQUENCE: 936
gctgcttgcg ataccaatag                                          20

<210> SEQ ID NO 937
<211> LENGTH: 20
<212> TYPE: DNA
<213> ORGANISM: Artificial Sequence
<220> FEATURE:
<223> OTHER INFORMATION: Synthetic

<400> SEQUENCE: 937
gctgcttgcg ataccaatag                                          20

<210> SEQ ID NO 938
<211> LENGTH: 20
<212> TYPE: DNA
<213> ORGANISM: Artificial Sequence
<220> FEATURE:
<223> OTHER INFORMATION: Synthetic

<400> SEQUENCE: 938
aggaggacgg caacatcctg                                          20

<210> SEQ ID NO 939
<211> LENGTH: 20
<212> TYPE: DNA
<213> ORGANISM: Artificial Sequence
<220> FEATURE:
<223> OTHER INFORMATION: Synthetic

<400> SEQUENCE: 939
aaggaggacg gcaacatcct                                          20

<210> SEQ ID NO 940
<211> LENGTH: 20
<212> TYPE: DNA
<213> ORGANISM: Artificial Sequence
<220> FEATURE:
<223> OTHER INFORMATION: Synthetic

<400> SEQUENCE: 940
aggaggacgg caacatcctg                                          20

<210> SEQ ID NO 941
<211> LENGTH: 20
<212> TYPE: DNA
<213> ORGANISM: Artificial Sequence
<220> FEATURE:
<223> OTHER INFORMATION: Synthetic

<400> SEQUENCE: 941
caacatcctg gggcacaagc                                          20

<210> SEQ ID NO 942
<211> LENGTH: 20
<212> TYPE: DNA
<213> ORGANISM: Artificial Sequence
<220> FEATURE:
<223> OTHER INFORMATION: Synthetic

<400> SEQUENCE: 942
```
caacatcctg gggcacaagc 20

<210> SEQ ID NO 943
<211> LENGTH: 20
<212> TYPE: DNA
<213> ORGANISM: Artificial Sequence
<220> FEATURE:
<223> OTHER INFORMATION: Synthetic

<400> SEQUENCE: 943
gtacagctaa gttaaactcg 20

<210> SEQ ID NO 944
<211> LENGTH: 20
<212> TYPE: DNA
<213> ORGANISM: Artificial Sequence
<220> FEATURE:
<223> OTHER INFORMATION: Synthetic

<400> SEQUENCE: 944
aaggaggacg gcaacatcct 20

<210> SEQ ID NO 945
<211> LENGTH: 20
<212> TYPE: DNA
<213> ORGANISM: Artificial Sequence
<220> FEATURE:
<223> OTHER INFORMATION: Synthetic

<400> SEQUENCE: 945
aaggaggacg gcaacatcct 20

<210> SEQ ID NO 946
<211> LENGTH: 19
<212> TYPE: DNA
<213> ORGANISM: Artificial Sequence
<220> FEATURE:
<223> OTHER INFORMATION: Synthetic

<400> SEQUENCE: 946
agagcactgc actccttca 19

<210> SEQ ID NO 947
<211> LENGTH: 19
<212> TYPE: DNA
<213> ORGANISM: Artificial Sequence
<220> FEATURE:
<223> OTHER INFORMATION: Synthetic

<400> SEQUENCE: 947
agagcactgc actccttca 19

<210> SEQ ID NO 948
<211> LENGTH: 20
<212> TYPE: DNA
<213> ORGANISM: Artificial Sequence
<220> FEATURE:
<223> OTHER INFORMATION: Synthetic

<400> SEQUENCE: 948
agtagtccgg gatatcagcg 20

<210> SEQ ID NO 949
<211> LENGTH: 20
<212> TYPE: DNA

```
<213> ORGANISM: Artificial Sequence
<220> FEATURE:
<223> OTHER INFORMATION: Synthetic

<400> SEQUENCE: 949
atacaactgc ttgcaacagg                                              20

<210> SEQ ID NO 950
<211> LENGTH: 20
<212> TYPE: DNA
<213> ORGANISM: Artificial Sequence
<220> FEATURE:
<223> OTHER INFORMATION: Synthetic

<400> SEQUENCE: 950
tccaccggcg aaagagatcc                                              20

<210> SEQ ID NO 951
<211> LENGTH: 20
<212> TYPE: DNA
<213> ORGANISM: Artificial Sequence
<220> FEATURE:
<223> OTHER INFORMATION: Synthetic

<400> SEQUENCE: 951
cgccgccccc ggacgcgacc                                              20

<210> SEQ ID NO 952
<211> LENGTH: 19
<212> TYPE: DNA
<213> ORGANISM: Artificial Sequence
<220> FEATURE:
<223> OTHER INFORMATION: Synthetic

<400> SEQUENCE: 952
agagcactgc actccttca                                               19

<210> SEQ ID NO 953
<211> LENGTH: 20
<212> TYPE: DNA
<213> ORGANISM: Artificial Sequence
<220> FEATURE:
<223> OTHER INFORMATION: Synthetic

<400> SEQUENCE: 953
tcatattacg agtcagtagg                                              20

<210> SEQ ID NO 954
<211> LENGTH: 20
<212> TYPE: DNA
<213> ORGANISM: Artificial Sequence
<220> FEATURE:
<223> OTHER INFORMATION: Synthetic

<400> SEQUENCE: 954
ccagtacaaa cctacctacg                                              20

<210> SEQ ID NO 955
<211> LENGTH: 19
<212> TYPE: DNA
<213> ORGANISM: Artificial Sequence
<220> FEATURE:
<223> OTHER INFORMATION: Synthetic

<400> SEQUENCE: 955
agagcactgc actccttca                                               19
```

<210> SEQ ID NO 956
<211> LENGTH: 19
<212> TYPE: DNA
<213> ORGANISM: Artificial Sequence
<220> FEATURE:
<223> OTHER INFORMATION: Synthetic

<400> SEQUENCE: 956
agagcactgc actccttca                                                  19

<210> SEQ ID NO 957
<211> LENGTH: 19
<212> TYPE: DNA
<213> ORGANISM: Artificial Sequence
<220> FEATURE:
<223> OTHER INFORMATION: Synthetic

<400> SEQUENCE: 957
agagcactgc actccttca                                                  19

<210> SEQ ID NO 958
<211> LENGTH: 20
<212> TYPE: DNA
<213> ORGANISM: Artificial Sequence
<220> FEATURE:
<223> OTHER INFORMATION: Synthetic

<400> SEQUENCE: 958
atacaactgc ttgcaacagg                                                 20

<210> SEQ ID NO 959
<211> LENGTH: 20
<212> TYPE: DNA
<213> ORGANISM: Artificial Sequence
<220> FEATURE:
<223> OTHER INFORMATION: Synthetic

<400> SEQUENCE: 959
cctgcaacgg gactagttgg                                                 20

<210> SEQ ID NO 960
<211> LENGTH: 20
<212> TYPE: DNA
<213> ORGANISM: Artificial Sequence
<220> FEATURE:
<223> OTHER INFORMATION: Synthetic

<400> SEQUENCE: 960
cgccgccccc ggacgcgacc                                                 20

<210> SEQ ID NO 961
<211> LENGTH: 19
<212> TYPE: DNA
<213> ORGANISM: Artificial Sequence
<220> FEATURE:
<223> OTHER INFORMATION: Synthetic

<400> SEQUENCE: 961
agagcactgc actccttca                                                  19

<210> SEQ ID NO 962
<211> LENGTH: 20
<212> TYPE: DNA
<213> ORGANISM: Artificial Sequence
<220> FEATURE:

<223> OTHER INFORMATION: Synthetic

<400> SEQUENCE: 962
ccagtacaaa cctacctacg                                                   20

<210> SEQ ID NO 963
<211> LENGTH: 20
<212> TYPE: DNA
<213> ORGANISM: Artificial Sequence
<220> FEATURE:
<223> OTHER INFORMATION: Synthetic

<400> SEQUENCE: 963
cgccgccccc ggacgcgacc                                                   20

<210> SEQ ID NO 964
<211> LENGTH: 20
<212> TYPE: DNA
<213> ORGANISM: Artificial Sequence
<220> FEATURE:
<223> OTHER INFORMATION: Synthetic

<400> SEQUENCE: 964
cgccgccccc ggacgcgacc                                                   20

<210> SEQ ID NO 965
<211> LENGTH: 20
<212> TYPE: DNA
<213> ORGANISM: Artificial Sequence
<220> FEATURE:
<223> OTHER INFORMATION: Synthetic

<400> SEQUENCE: 965
tccaccggcg aaagagatcc                                                   20

<210> SEQ ID NO 966
<211> LENGTH: 20
<212> TYPE: DNA
<213> ORGANISM: Artificial Sequence
<220> FEATURE:
<223> OTHER INFORMATION: Synthetic

<400> SEQUENCE: 966
atacaactgc ttgcaacagg                                                   20

<210> SEQ ID NO 967
<211> LENGTH: 19
<212> TYPE: DNA
<213> ORGANISM: Artificial Sequence
<220> FEATURE:
<223> OTHER INFORMATION: Synthetic

<400> SEQUENCE: 967
agagcactgc actccttca                                                    19

<210> SEQ ID NO 968
<211> LENGTH: 20
<212> TYPE: DNA
<213> ORGANISM: Artificial Sequence
<220> FEATURE:
<223> OTHER INFORMATION: Synthetic

<400> SEQUENCE: 968
tcatattacg agtcagtagg                                                   20

```
<210> SEQ ID NO 969
<211> LENGTH: 20
<212> TYPE: DNA
<213> ORGANISM: Artificial Sequence
<220> FEATURE:
<223> OTHER INFORMATION: Synthetic

<400> SEQUENCE: 969
cgccgccccc ggacgcgacc                                              20

<210> SEQ ID NO 970
<211> LENGTH: 20
<212> TYPE: DNA
<213> ORGANISM: Artificial Sequence
<220> FEATURE:
<223> OTHER INFORMATION: Synthetic

<400> SEQUENCE: 970
cctgcaacgg gactagttgg                                              20

<210> SEQ ID NO 971
<211> LENGTH: 20
<212> TYPE: DNA
<213> ORGANISM: Artificial Sequence
<220> FEATURE:
<223> OTHER INFORMATION: Synthetic

<400> SEQUENCE: 971
agtagtccgg gatatcagcg                                              20

<210> SEQ ID NO 972
<211> LENGTH: 20
<212> TYPE: DNA
<213> ORGANISM: Artificial Sequence
<220> FEATURE:
<223> OTHER INFORMATION: Synthetic

<400> SEQUENCE: 972
agtagtccgg gatatcagcg                                              20

<210> SEQ ID NO 973
<211> LENGTH: 20
<212> TYPE: DNA
<213> ORGANISM: Artificial Sequence
<220> FEATURE:
<223> OTHER INFORMATION: Synthetic

<400> SEQUENCE: 973
cctgcaacgg gactagttgg                                              20

<210> SEQ ID NO 974
<211> LENGTH: 20
<212> TYPE: DNA
<213> ORGANISM: Artificial Sequence
<220> FEATURE:
<223> OTHER INFORMATION: Synthetic

<400> SEQUENCE: 974
atacaactgc ttgcaacagg                                              20

<210> SEQ ID NO 975
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 975
cgccgccccc ggacgcgacc                                               20

<210> SEQ ID NO 976
<211> LENGTH: 20
<212> TYPE: DNA
<213> ORGANISM: Artificial Sequence
<220> FEATURE:
<223> OTHER INFORMATION: Synthetic

<400> SEQUENCE: 976
tcatattacg agtcagtagg                                               20

<210> SEQ ID NO 977
<211> LENGTH: 20
<212> TYPE: DNA
<213> ORGANISM: Artificial Sequence
<220> FEATURE:
<223> OTHER INFORMATION: Synthetic

<400> SEQUENCE: 977
tcatattacg agtcagtagg                                               20

<210> SEQ ID NO 978
<211> LENGTH: 20
<212> TYPE: DNA
<213> ORGANISM: Artificial Sequence
<220> FEATURE:
<223> OTHER INFORMATION: Synthetic

<400> SEQUENCE: 978
cctgcaacgg gactagttgg                                               20

<210> SEQ ID NO 979
<211> LENGTH: 20
<212> TYPE: DNA
<213> ORGANISM: Artificial Sequence
<220> FEATURE:
<223> OTHER INFORMATION: Synthetic

<400> SEQUENCE: 979
ccagtacaaa cctacctacg                                               20

<210> SEQ ID NO 980
<211> LENGTH: 20
<212> TYPE: DNA
<213> ORGANISM: Artificial Sequence
<220> FEATURE:
<223> OTHER INFORMATION: Synthetic

<400> SEQUENCE: 980
agtagtccgg gatatcagcg                                               20

<210> SEQ ID NO 981
<211> LENGTH: 19
<212> TYPE: DNA
<213> ORGANISM: Artificial Sequence
<220> FEATURE:
<223> OTHER INFORMATION: Synthetic

<400> SEQUENCE: 981
agagcactgc actccttca                                                19

<210> SEQ ID NO 982
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 982
tcatattacg agtcagtagg                                               20

<210> SEQ ID NO 983
<211> LENGTH: 19
<212> TYPE: DNA
<213> ORGANISM: Artificial Sequence
<220> FEATURE:
<223> OTHER INFORMATION: Synthetic

<400> SEQUENCE: 983
agagcactgc actccttca                                                19

<210> SEQ ID NO 984
<211> LENGTH: 20
<212> TYPE: DNA
<213> ORGANISM: Artificial Sequence
<220> FEATURE:
<223> OTHER INFORMATION: Synthetic

<400> SEQUENCE: 984
tccaccggcg aaagagatcc                                               20

<210> SEQ ID NO 985
<211> LENGTH: 20
<212> TYPE: DNA
<213> ORGANISM: Artificial Sequence
<220> FEATURE:
<223> OTHER INFORMATION: Synthetic

<400> SEQUENCE: 985
atacaactgc ttgcaacagg                                               20

<210> SEQ ID NO 986
<211> LENGTH: 20
<212> TYPE: DNA
<213> ORGANISM: Artificial Sequence
<220> FEATURE:
<223> OTHER INFORMATION: Synthetic

<400> SEQUENCE: 986
cctgcaacgg gactagttgg                                               20

<210> SEQ ID NO 987
<211> LENGTH: 20
<212> TYPE: DNA
<213> ORGANISM: Artificial Sequence
<220> FEATURE:
<223> OTHER INFORMATION: Synthetic

<400> SEQUENCE: 987
atacaactgc ttgcaacagg                                               20

<210> SEQ ID NO 988
<211> LENGTH: 20
<212> TYPE: DNA
<213> ORGANISM: Artificial Sequence
<220> FEATURE:
<223> OTHER INFORMATION: Synthetic

<400> SEQUENCE: 988
```

-continued atacaactgc ttgcaacagg					20

<210> SEQ ID NO 989
<211> LENGTH: 20
<212> TYPE: DNA
<213> ORGANISM: Artificial Sequence
<220> FEATURE:
<223> OTHER INFORMATION: Synthetic

<400> SEQUENCE: 989
cctgcaacgg gactagttgg					20

<210> SEQ ID NO 990
<211> LENGTH: 20
<212> TYPE: DNA
<213> ORGANISM: Artificial Sequence
<220> FEATURE:
<223> OTHER INFORMATION: Synthetic

<400> SEQUENCE: 990
tcatattacg agtcagtagg					20

<210> SEQ ID NO 991
<211> LENGTH: 20
<212> TYPE: DNA
<213> ORGANISM: Artificial Sequence
<220> FEATURE:
<223> OTHER INFORMATION: Synthetic

<400> SEQUENCE: 991
cgccgccccc ggacgcgacc					20

<210> SEQ ID NO 992
<211> LENGTH: 19
<212> TYPE: DNA
<213> ORGANISM: Artificial Sequence
<220> FEATURE:
<223> OTHER INFORMATION: Synthetic

<400> SEQUENCE: 992
agagcactgc actccttca					19

<210> SEQ ID NO 993
<211> LENGTH: 20
<212> TYPE: DNA
<213> ORGANISM: Artificial Sequence
<220> FEATURE:
<223> OTHER INFORMATION: Synthetic

<400> SEQUENCE: 993
agtagtccgg gatatcagcg					20

<210> SEQ ID NO 994
<211> LENGTH: 20
<212> TYPE: DNA
<213> ORGANISM: Artificial Sequence
<220> FEATURE:
<223> OTHER INFORMATION: Synthetic

<400> SEQUENCE: 994
ccagtacaaa cctacctacg					20

<210> SEQ ID NO 995
<211> LENGTH: 20
<212> TYPE: DNA
<213> ORGANISM: Artificial Sequence

```
<220> FEATURE:
<223> OTHER INFORMATION: Synthetic

<400> SEQUENCE: 995
cctgcaacgg gactagttgg                                          20

<210> SEQ ID NO 996
<211> LENGTH: 19
<212> TYPE: DNA
<213> ORGANISM: Artificial Sequence
<220> FEATURE:
<223> OTHER INFORMATION: Synthetic

<400> SEQUENCE: 996
agagcactgc actccttca                                           19

<210> SEQ ID NO 997
<211> LENGTH: 20
<212> TYPE: DNA
<213> ORGANISM: Artificial Sequence
<220> FEATURE:
<223> OTHER INFORMATION: Synthetic

<400> SEQUENCE: 997
agtagtccgg gatatcagcg                                          20

<210> SEQ ID NO 998
<211> LENGTH: 20
<212> TYPE: DNA
<213> ORGANISM: Artificial Sequence
<220> FEATURE:
<223> OTHER INFORMATION: Synthetic

<400> SEQUENCE: 998
atacaactgc ttgcaacagg                                          20

<210> SEQ ID NO 999
<211> LENGTH: 20
<212> TYPE: DNA
<213> ORGANISM: Artificial Sequence
<220> FEATURE:
<223> OTHER INFORMATION: Synthetic

<400> SEQUENCE: 999
atacaactgc ttgcaacagg                                          20

<210> SEQ ID NO 1000
<211> LENGTH: 20
<212> TYPE: DNA
<213> ORGANISM: Artificial Sequence
<220> FEATURE:
<223> OTHER INFORMATION: Synthetic

<400> SEQUENCE: 1000
cctgcaacgg gactagttgg                                          20

<210> SEQ ID NO 1001
<211> LENGTH: 20
<212> TYPE: DNA
<213> ORGANISM: Artificial Sequence
<220> FEATURE:
<223> OTHER INFORMATION: Synthetic

<400> SEQUENCE: 1001
tcatattacg agtcagtagg                                          20
```

```
<210> SEQ ID NO 1002
<211> LENGTH: 20
<212> TYPE: DNA
<213> ORGANISM: Artificial Sequence
<220> FEATURE:
<223> OTHER INFORMATION: Synthetic

<400> SEQUENCE: 1002
cgccgccccc ggacgcgacc                                              20

<210> SEQ ID NO 1003
<211> LENGTH: 20
<212> TYPE: DNA
<213> ORGANISM: Artificial Sequence
<220> FEATURE:
<223> OTHER INFORMATION: Synthetic

<400> SEQUENCE: 1003
atacaactgc ttgcaacagg                                              20

<210> SEQ ID NO 1004
<211> LENGTH: 20
<212> TYPE: DNA
<213> ORGANISM: Artificial Sequence
<220> FEATURE:
<223> OTHER INFORMATION: Synthetic

<400> SEQUENCE: 1004
tccaccggcg aaagagatcc                                              20

<210> SEQ ID NO 1005
<211> LENGTH: 20
<212> TYPE: DNA
<213> ORGANISM: Artificial Sequence
<220> FEATURE:
<223> OTHER INFORMATION: Synthetic

<400> SEQUENCE: 1005
agtagtccgg gatatcagcg                                              20

<210> SEQ ID NO 1006
<211> LENGTH: 20
<212> TYPE: DNA
<213> ORGANISM: Artificial Sequence
<220> FEATURE:
<223> OTHER INFORMATION: Synthetic

<400> SEQUENCE: 1006
atacaactgc ttgcaacagg                                              20

<210> SEQ ID NO 1007
<211> LENGTH: 20
<212> TYPE: DNA
<213> ORGANISM: Artificial Sequence
<220> FEATURE:
<223> OTHER INFORMATION: Synthetic

<400> SEQUENCE: 1007
agtagtccgg gatatcagcg                                              20

<210> SEQ ID NO 1008
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 1008
ccagtacaaa cctacctacg                                              20

<210> SEQ ID NO 1009
<211> LENGTH: 20
<212> TYPE: DNA
<213> ORGANISM: Artificial Sequence
<220> FEATURE:
<223> OTHER INFORMATION: Synthetic

<400> SEQUENCE: 1009
atacaactgc ttgcaacagg                                              20

<210> SEQ ID NO 1010
<211> LENGTH: 20
<212> TYPE: DNA
<213> ORGANISM: Artificial Sequence
<220> FEATURE:
<223> OTHER INFORMATION: Synthetic

<400> SEQUENCE: 1010
atacaactgc ttgcaacagg                                              20

<210> SEQ ID NO 1011
<211> LENGTH: 20
<212> TYPE: DNA
<213> ORGANISM: Artificial Sequence
<220> FEATURE:
<223> OTHER INFORMATION: Synthetic

<400> SEQUENCE: 1011
agtagtccgg gatatcagcg                                              20

<210> SEQ ID NO 1012
<211> LENGTH: 20
<212> TYPE: DNA
<213> ORGANISM: Artificial Sequence
<220> FEATURE:
<223> OTHER INFORMATION: Synthetic

<400> SEQUENCE: 1012
atacaactgc ttgcaacagg                                              20

<210> SEQ ID NO 1013
<211> LENGTH: 20
<212> TYPE: DNA
<213> ORGANISM: Artificial Sequence
<220> FEATURE:
<223> OTHER INFORMATION: Synthetic

<400> SEQUENCE: 1013
cgccgccccc ggacgcgacc                                              20

<210> SEQ ID NO 1014
<211> LENGTH: 19
<212> TYPE: DNA
<213> ORGANISM: Artificial Sequence
<220> FEATURE:
<223> OTHER INFORMATION: Synthetic

<400> SEQUENCE: 1014
agagcactgc actccttca                                               19

<210> SEQ ID NO 1015
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 1015
agtagtccgg gatatcagcg                                              20

<210> SEQ ID NO 1016
<211> LENGTH: 20
<212> TYPE: DNA
<213> ORGANISM: Artificial Sequence
<220> FEATURE:
<223> OTHER INFORMATION: Synthetic

<400> SEQUENCE: 1016
atacaactgc ttgcaacagg                                              20

<210> SEQ ID NO 1017
<211> LENGTH: 20
<212> TYPE: DNA
<213> ORGANISM: Artificial Sequence
<220> FEATURE:
<223> OTHER INFORMATION: Synthetic

<400> SEQUENCE: 1017
cctgcaacgg gactagttgg                                              20

<210> SEQ ID NO 1018
<211> LENGTH: 20
<212> TYPE: DNA
<213> ORGANISM: Artificial Sequence
<220> FEATURE:
<223> OTHER INFORMATION: Synthetic

<400> SEQUENCE: 1018
agtagtccgg gatatcagcg                                              20

<210> SEQ ID NO 1019
<211> LENGTH: 20
<212> TYPE: DNA
<213> ORGANISM: Artificial Sequence
<220> FEATURE:
<223> OTHER INFORMATION: Synthetic

<400> SEQUENCE: 1019
tcatattacg agtcagtagg                                              20

<210> SEQ ID NO 1020
<211> LENGTH: 20
<212> TYPE: DNA
<213> ORGANISM: Artificial Sequence
<220> FEATURE:
<223> OTHER INFORMATION: Synthetic

<400> SEQUENCE: 1020
tccaccggcg aaagagatcc                                              20

<210> SEQ ID NO 1021
<211> LENGTH: 20
<212> TYPE: DNA
<213> ORGANISM: Artificial Sequence
<220> FEATURE:
<223> OTHER INFORMATION: Synthetic

<400> SEQUENCE: 1021
```
tcatattacg agtcagtagg					20

<210> SEQ ID NO 1022
<211> LENGTH: 20
<212> TYPE: DNA
<213> ORGANISM: Artificial Sequence
<220> FEATURE:
<223> OTHER INFORMATION: Synthetic

<400> SEQUENCE: 1022
ccagtacaaa cctacctacg					20

<210> SEQ ID NO 1023
<211> LENGTH: 20
<212> TYPE: DNA
<213> ORGANISM: Artificial Sequence
<220> FEATURE:
<223> OTHER INFORMATION: Synthetic

<400> SEQUENCE: 1023
cctgcaacgg gactagttgg					20

<210> SEQ ID NO 1024
<211> LENGTH: 20
<212> TYPE: DNA
<213> ORGANISM: Artificial Sequence
<220> FEATURE:
<223> OTHER INFORMATION: Synthetic

<400> SEQUENCE: 1024
cctgcaacgg gactagttgg					20

<210> SEQ ID NO 1025
<211> LENGTH: 19
<212> TYPE: DNA
<213> ORGANISM: Artificial Sequence
<220> FEATURE:
<223> OTHER INFORMATION: Synthetic

<400> SEQUENCE: 1025
agagcactgc actccttca					19

<210> SEQ ID NO 1026
<211> LENGTH: 20
<212> TYPE: DNA
<213> ORGANISM: Artificial Sequence
<220> FEATURE:
<223> OTHER INFORMATION: Synthetic

<400> SEQUENCE: 1026
tcatattacg agtcagtagg					20

<210> SEQ ID NO 1027
<211> LENGTH: 20
<212> TYPE: DNA
<213> ORGANISM: Artificial Sequence
<220> FEATURE:
<223> OTHER INFORMATION: Synthetic

<400> SEQUENCE: 1027
tccaccggcg aaagagatcc					20

<210> SEQ ID NO 1028
<211> LENGTH: 20
<212> TYPE: DNA

```
<213> ORGANISM: Artificial Sequence
<220> FEATURE:
<223> OTHER INFORMATION: Synthetic

<400> SEQUENCE: 1028
cgccgccccc ggacgcgacc                                           20

<210> SEQ ID NO 1029
<211> LENGTH: 20
<212> TYPE: DNA
<213> ORGANISM: Artificial Sequence
<220> FEATURE:
<223> OTHER INFORMATION: Synthetic

<400> SEQUENCE: 1029
atacaactgc ttgcaacagg                                           20

<210> SEQ ID NO 1030
<211> LENGTH: 20
<212> TYPE: DNA
<213> ORGANISM: Artificial Sequence
<220> FEATURE:
<223> OTHER INFORMATION: Synthetic

<400> SEQUENCE: 1030
ccagtacaaa cctacctacg                                           20

<210> SEQ ID NO 1031
<211> LENGTH: 20
<212> TYPE: DNA
<213> ORGANISM: Artificial Sequence
<220> FEATURE:
<223> OTHER INFORMATION: Synthetic

<400> SEQUENCE: 1031
tcatattacg agtcagtagg                                           20

<210> SEQ ID NO 1032
<211> LENGTH: 20
<212> TYPE: DNA
<213> ORGANISM: Artificial Sequence
<220> FEATURE:
<223> OTHER INFORMATION: Synthetic

<400> SEQUENCE: 1032
cctgcaacgg gactagttgg                                           20

<210> SEQ ID NO 1033
<211> LENGTH: 19
<212> TYPE: DNA
<213> ORGANISM: Artificial Sequence
<220> FEATURE:
<223> OTHER INFORMATION: Synthetic

<400> SEQUENCE: 1033
agagcactgc actccttca                                            19

<210> SEQ ID NO 1034
<211> LENGTH: 20
<212> TYPE: DNA
<213> ORGANISM: Artificial Sequence
<220> FEATURE:
<223> OTHER INFORMATION: Synthetic

<400> SEQUENCE: 1034
atacaactgc ttgcaacagg                                           20
```

<210> SEQ ID NO 1035
<211> LENGTH: 19
<212> TYPE: DNA
<213> ORGANISM: Artificial Sequence
<220> FEATURE:
<223> OTHER INFORMATION: Synthetic

<400> SEQUENCE: 1035
agagcactgc actccttca                                                19

<210> SEQ ID NO 1036
<211> LENGTH: 20
<212> TYPE: DNA
<213> ORGANISM: Artificial Sequence
<220> FEATURE:
<223> OTHER INFORMATION: Synthetic

<400> SEQUENCE: 1036
cctgcaacgg gactagttgg                                               20

<210> SEQ ID NO 1037
<211> LENGTH: 20
<212> TYPE: DNA
<213> ORGANISM: Artificial Sequence
<220> FEATURE:
<223> OTHER INFORMATION: Synthetic

<400> SEQUENCE: 1037
tcatattacg agtcagtagg                                               20

<210> SEQ ID NO 1038
<211> LENGTH: 20
<212> TYPE: DNA
<213> ORGANISM: Artificial Sequence
<220> FEATURE:
<223> OTHER INFORMATION: Synthetic

<400> SEQUENCE: 1038
cgccgccccc ggacgcgacc                                               20

<210> SEQ ID NO 1039
<211> LENGTH: 20
<212> TYPE: DNA
<213> ORGANISM: Artificial Sequence
<220> FEATURE:
<223> OTHER INFORMATION: Synthetic

<400> SEQUENCE: 1039
atacaactgc ttgcaacagg                                               20

<210> SEQ ID NO 1040
<211> LENGTH: 19
<212> TYPE: DNA
<213> ORGANISM: Artificial Sequence
<220> FEATURE:
<223> OTHER INFORMATION: Synthetic

<400> SEQUENCE: 1040
agagcactgc actccttca                                                19

<210> SEQ ID NO 1041
<211> LENGTH: 19
<212> TYPE: DNA
<213> ORGANISM: Artificial Sequence
<220> FEATURE:

```
<223> OTHER INFORMATION: Synthetic

<400> SEQUENCE: 1041
agagcactgc actccttca                                               19

<210> SEQ ID NO 1042
<211> LENGTH: 19
<212> TYPE: DNA
<213> ORGANISM: Artificial Sequence
<220> FEATURE:
<223> OTHER INFORMATION: Synthetic

<400> SEQUENCE: 1042
agagcactgc actccttca                                               19

<210> SEQ ID NO 1043
<211> LENGTH: 20
<212> TYPE: DNA
<213> ORGANISM: Artificial Sequence
<220> FEATURE:
<223> OTHER INFORMATION: Synthetic

<400> SEQUENCE: 1043
atacaactgc ttgcaacagg                                              20

<210> SEQ ID NO 1044
<211> LENGTH: 20
<212> TYPE: DNA
<213> ORGANISM: Artificial Sequence
<220> FEATURE:
<223> OTHER INFORMATION: Synthetic

<400> SEQUENCE: 1044
cctgcaacgg gactagttgg                                              20

<210> SEQ ID NO 1045
<211> LENGTH: 20
<212> TYPE: DNA
<213> ORGANISM: Artificial Sequence
<220> FEATURE:
<223> OTHER INFORMATION: Synthetic

<400> SEQUENCE: 1045
cctgcaacgg gactagttgg                                              20

<210> SEQ ID NO 1046
<211> LENGTH: 20
<212> TYPE: DNA
<213> ORGANISM: Artificial Sequence
<220> FEATURE:
<223> OTHER INFORMATION: Synthetic

<400> SEQUENCE: 1046
cctgcaacgg gactagttgg                                              20

<210> SEQ ID NO 1047
<211> LENGTH: 19
<212> TYPE: DNA
<213> ORGANISM: Artificial Sequence
<220> FEATURE:
<223> OTHER INFORMATION: Synthetic

<400> SEQUENCE: 1047
agagcactgc actccttca                                               19
```

```
<210> SEQ ID NO 1048
<211> LENGTH: 19
<212> TYPE: DNA
<213> ORGANISM: Artificial Sequence
<220> FEATURE:
<223> OTHER INFORMATION: Synthetic

<400> SEQUENCE: 1048
agagcactgc actccttca                                                19

<210> SEQ ID NO 1049
<211> LENGTH: 20
<212> TYPE: DNA
<213> ORGANISM: Artificial Sequence
<220> FEATURE:
<223> OTHER INFORMATION: Synthetic

<400> SEQUENCE: 1049
tcatattacg agtcagtagg                                               20

<210> SEQ ID NO 1050
<211> LENGTH: 20
<212> TYPE: DNA
<213> ORGANISM: Artificial Sequence
<220> FEATURE:
<223> OTHER INFORMATION: Synthetic

<400> SEQUENCE: 1050
ccagtacaaa cctacctacg                                               20

<210> SEQ ID NO 1051
<211> LENGTH: 20
<212> TYPE: DNA
<213> ORGANISM: Artificial Sequence
<220> FEATURE:
<223> OTHER INFORMATION: Synthetic

<400> SEQUENCE: 1051
cctgcaacgg gactagttgg                                               20

<210> SEQ ID NO 1052
<211> LENGTH: 19
<212> TYPE: DNA
<213> ORGANISM: Artificial Sequence
<220> FEATURE:
<223> OTHER INFORMATION: Synthetic

<400> SEQUENCE: 1052
agagcactgc actccttca                                                19

<210> SEQ ID NO 1053
<211> LENGTH: 20
<212> TYPE: DNA
<213> ORGANISM: Artificial Sequence
<220> FEATURE:
<223> OTHER INFORMATION: Synthetic

<400> SEQUENCE: 1053
tcatattacg agtcagtagg                                               20

<210> SEQ ID NO 1054
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 1054
tcatattacg agtcagtagg                                               20

<210> SEQ ID NO 1055
<211> LENGTH: 20
<212> TYPE: DNA
<213> ORGANISM: Artificial Sequence
<220> FEATURE:
<223> OTHER INFORMATION: Synthetic

<400> SEQUENCE: 1055
atacaactgc ttgcaacagg                                               20

<210> SEQ ID NO 1056
<211> LENGTH: 19
<212> TYPE: DNA
<213> ORGANISM: Artificial Sequence
<220> FEATURE:
<223> OTHER INFORMATION: Synthetic

<400> SEQUENCE: 1056
agagcactgc actccttca                                                19

<210> SEQ ID NO 1057
<211> LENGTH: 20
<212> TYPE: DNA
<213> ORGANISM: Artificial Sequence
<220> FEATURE:
<223> OTHER INFORMATION: Synthetic

<400> SEQUENCE: 1057
atacaactgc ttgcaacagg                                               20

<210> SEQ ID NO 1058
<211> LENGTH: 20
<212> TYPE: DNA
<213> ORGANISM: Artificial Sequence
<220> FEATURE:
<223> OTHER INFORMATION: Synthetic

<400> SEQUENCE: 1058
atacaactgc ttgcaacagg                                               20

<210> SEQ ID NO 1059
<211> LENGTH: 20
<212> TYPE: DNA
<213> ORGANISM: Artificial Sequence
<220> FEATURE:
<223> OTHER INFORMATION: Synthetic

<400> SEQUENCE: 1059
cctgcaacgg gactagttgg                                               20

<210> SEQ ID NO 1060
<211> LENGTH: 20
<212> TYPE: DNA
<213> ORGANISM: Artificial Sequence
<220> FEATURE:
<223> OTHER INFORMATION: Synthetic

<400> SEQUENCE: 1060
atacaactgc ttgcaacagg                                               20

<210> SEQ ID NO 1061
<211> LENGTH: 20
```

<212> TYPE: DNA
<213> ORGANISM: Artificial Sequence
<220> FEATURE:
<223> OTHER INFORMATION: Synthetic

<400> SEQUENCE: 1061
atacaactgc ttgcaacagg                                              20

<210> SEQ ID NO 1062
<211> LENGTH: 20
<212> TYPE: DNA
<213> ORGANISM: Artificial Sequence
<220> FEATURE:
<223> OTHER INFORMATION: Synthetic

<400> SEQUENCE: 1062
atacaactgc ttgcaacagg                                              20

<210> SEQ ID NO 1063
<211> LENGTH: 19
<212> TYPE: DNA
<213> ORGANISM: Artificial Sequence
<220> FEATURE:
<223> OTHER INFORMATION: Synthetic

<400> SEQUENCE: 1063
agagcactgc actccttca                                               19

<210> SEQ ID NO 1064
<211> LENGTH: 20
<212> TYPE: DNA
<213> ORGANISM: Artificial Sequence
<220> FEATURE:
<223> OTHER INFORMATION: Synthetic

<400> SEQUENCE: 1064
cgccgccccc ggacgcgacc                                              20

<210> SEQ ID NO 1065
<211> LENGTH: 19
<212> TYPE: DNA
<213> ORGANISM: Artificial Sequence
<220> FEATURE:
<223> OTHER INFORMATION: Synthetic

<400> SEQUENCE: 1065
agagcactgc actccttca                                               19

<210> SEQ ID NO 1066
<211> LENGTH: 20
<212> TYPE: DNA
<213> ORGANISM: Artificial Sequence
<220> FEATURE:
<223> OTHER INFORMATION: Synthetic

<400> SEQUENCE: 1066
tcatattacg agtcagtagg                                              20

<210> SEQ ID NO 1067
<211> LENGTH: 20
<212> TYPE: DNA
<213> ORGANISM: Artificial Sequence
<220> FEATURE:
<223> OTHER INFORMATION: Synthetic

<400> SEQUENCE: 1067

```
ccagtacaaa cctacctacg                                               20

<210> SEQ ID NO 1068
<211> LENGTH: 19
<212> TYPE: DNA
<213> ORGANISM: Artificial Sequence
<220> FEATURE:
<223> OTHER INFORMATION: Synthetic

<400> SEQUENCE: 1068
agagcactgc actccttca                                                19

<210> SEQ ID NO 1069
<211> LENGTH: 20
<212> TYPE: DNA
<213> ORGANISM: Artificial Sequence
<220> FEATURE:
<223> OTHER INFORMATION: Synthetic

<400> SEQUENCE: 1069
cctgcaacgg gactagttgg                                               20

<210> SEQ ID NO 1070
<211> LENGTH: 20
<212> TYPE: DNA
<213> ORGANISM: Artificial Sequence
<220> FEATURE:
<223> OTHER INFORMATION: Synthetic

<400> SEQUENCE: 1070
cctgcaacgg gactagttgg                                               20

<210> SEQ ID NO 1071
<211> LENGTH: 20
<212> TYPE: DNA
<213> ORGANISM: Artificial Sequence
<220> FEATURE:
<223> OTHER INFORMATION: Synthetic

<400> SEQUENCE: 1071
tcatattacg agtcagtagg                                               20

<210> SEQ ID NO 1072
<211> LENGTH: 20
<212> TYPE: DNA
<213> ORGANISM: Artificial Sequence
<220> FEATURE:
<223> OTHER INFORMATION: Synthetic

<400> SEQUENCE: 1072
tccaccggcg aaagagatcc                                               20

<210> SEQ ID NO 1073
<211> LENGTH: 20
<212> TYPE: DNA
<213> ORGANISM: Artificial Sequence
<220> FEATURE:
<223> OTHER INFORMATION: Synthetic

<400> SEQUENCE: 1073
agtagtccgg gatatcagcg                                               20

<210> SEQ ID NO 1074
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 1074
ccagtacaaa cctacctacg                                              20

<210> SEQ ID NO 1075
<211> LENGTH: 20
<212> TYPE: DNA
<213> ORGANISM: Artificial Sequence
<220> FEATURE:
<223> OTHER INFORMATION: Synthetic

<400> SEQUENCE: 1075
cctgcaacgg gactagttgg                                              20

<210> SEQ ID NO 1076
<211> LENGTH: 20
<212> TYPE: DNA
<213> ORGANISM: Artificial Sequence
<220> FEATURE:
<223> OTHER INFORMATION: Synthetic

<400> SEQUENCE: 1076
tcatattacg agtcagtagg                                              20

<210> SEQ ID NO 1077
<211> LENGTH: 19
<212> TYPE: DNA
<213> ORGANISM: Artificial Sequence
<220> FEATURE:
<223> OTHER INFORMATION: Synthetic

<400> SEQUENCE: 1077
agagcactgc actccttca                                               19

<210> SEQ ID NO 1078
<211> LENGTH: 20
<212> TYPE: DNA
<213> ORGANISM: Artificial Sequence
<220> FEATURE:
<223> OTHER INFORMATION: Synthetic

<400> SEQUENCE: 1078
cgccgccccc ggacgcgacc                                              20

<210> SEQ ID NO 1079
<211> LENGTH: 19
<212> TYPE: DNA
<213> ORGANISM: Artificial Sequence
<220> FEATURE:
<223> OTHER INFORMATION: Synthetic

<400> SEQUENCE: 1079
agagcactgc actccttca                                               19

<210> SEQ ID NO 1080
<211> LENGTH: 20
<212> TYPE: DNA
<213> ORGANISM: Artificial Sequence
<220> FEATURE:
<223> OTHER INFORMATION: Synthetic

<400> SEQUENCE: 1080
agtagtccgg gatatcagcg                                              20
```

-continued

```
<210> SEQ ID NO 1081
<211> LENGTH: 19
<212> TYPE: DNA
<213> ORGANISM: Artificial Sequence
<220> FEATURE:
<223> OTHER INFORMATION: Synthetic

<400> SEQUENCE: 1081
agagcactgc actccttca                                              19

<210> SEQ ID NO 1082
<211> LENGTH: 20
<212> TYPE: DNA
<213> ORGANISM: Artificial Sequence
<220> FEATURE:
<223> OTHER INFORMATION: Synthetic

<400> SEQUENCE: 1082
atacaactgc ttgcaacagg                                             20

<210> SEQ ID NO 1083
<211> LENGTH: 19
<212> TYPE: DNA
<213> ORGANISM: Artificial Sequence
<220> FEATURE:
<223> OTHER INFORMATION: Synthetic

<400> SEQUENCE: 1083
agagcactgc actccttca                                              19

<210> SEQ ID NO 1084
<211> LENGTH: 20
<212> TYPE: DNA
<213> ORGANISM: Artificial Sequence
<220> FEATURE:
<223> OTHER INFORMATION: Synthetic

<400> SEQUENCE: 1084
tccaccggcg aaagagatcc                                             20

<210> SEQ ID NO 1085
<211> LENGTH: 20
<212> TYPE: DNA
<213> ORGANISM: Artificial Sequence
<220> FEATURE:
<223> OTHER INFORMATION: Synthetic

<400> SEQUENCE: 1085
agtagtccgg gatatcagcg                                             20

<210> SEQ ID NO 1086
<211> LENGTH: 20
<212> TYPE: DNA
<213> ORGANISM: Artificial Sequence
<220> FEATURE:
<223> OTHER INFORMATION: Synthetic

<400> SEQUENCE: 1086
tcatattacg agtcagtagg                                             20

<210> SEQ ID NO 1087
<211> LENGTH: 19
<212> TYPE: DNA
<213> ORGANISM: Artificial Sequence
<220> FEATURE:
<223> OTHER INFORMATION: Synthetic
```

```
<400> SEQUENCE: 1087
agagcactgc actccttca                                                19

<210> SEQ ID NO 1088
<211> LENGTH: 20
<212> TYPE: DNA
<213> ORGANISM: Artificial Sequence
<220> FEATURE:
<223> OTHER INFORMATION: Synthetic

<400> SEQUENCE: 1088
ccagtacaaa cctacctacg                                               20

<210> SEQ ID NO 1089
<211> LENGTH: 20
<212> TYPE: DNA
<213> ORGANISM: Artificial Sequence
<220> FEATURE:
<223> OTHER INFORMATION: Synthetic

<400> SEQUENCE: 1089
ccagtacaaa cctacctacg                                               20

<210> SEQ ID NO 1090
<211> LENGTH: 19
<212> TYPE: DNA
<213> ORGANISM: Artificial Sequence
<220> FEATURE:
<223> OTHER INFORMATION: Synthetic

<400> SEQUENCE: 1090
agagcactgc actccttca                                                19

<210> SEQ ID NO 1091
<211> LENGTH: 20
<212> TYPE: DNA
<213> ORGANISM: Artificial Sequence
<220> FEATURE:
<223> OTHER INFORMATION: Synthetic

<400> SEQUENCE: 1091
atacaactgc ttgcaacagg                                               20

<210> SEQ ID NO 1092
<211> LENGTH: 19
<212> TYPE: DNA
<213> ORGANISM: Artificial Sequence
<220> FEATURE:
<223> OTHER INFORMATION: Synthetic

<400> SEQUENCE: 1092
agagcactgc actccttca                                                19

<210> SEQ ID NO 1093
<211> LENGTH: 19
<212> TYPE: DNA
<213> ORGANISM: Artificial Sequence
<220> FEATURE:
<223> OTHER INFORMATION: Synthetic

<400> SEQUENCE: 1093
agagcactgc actccttca                                                19

<210> SEQ ID NO 1094
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 1094
cgccgccccc ggacgcgacc                                               20

<210> SEQ ID NO 1095
<211> LENGTH: 20
<212> TYPE: DNA
<213> ORGANISM: Artificial Sequence
<220> FEATURE:
<223> OTHER INFORMATION: Synthetic

<400> SEQUENCE: 1095
agtagtccgg gatatcagcg                                               20

<210> SEQ ID NO 1096
<211> LENGTH: 20
<212> TYPE: DNA
<213> ORGANISM: Artificial Sequence
<220> FEATURE:
<223> OTHER INFORMATION: Synthetic

<400> SEQUENCE: 1096
atacaactgc ttgcaacagg                                               20

<210> SEQ ID NO 1097
<211> LENGTH: 20
<212> TYPE: DNA
<213> ORGANISM: Artificial Sequence
<220> FEATURE:
<223> OTHER INFORMATION: Synthetic

<400> SEQUENCE: 1097
tccaccggcg aaagagatcc                                               20

<210> SEQ ID NO 1098
<211> LENGTH: 20
<212> TYPE: DNA
<213> ORGANISM: Artificial Sequence
<220> FEATURE:
<223> OTHER INFORMATION: Synthetic

<400> SEQUENCE: 1098
tcatattacg agtcagtagg                                               20

<210> SEQ ID NO 1099
<211> LENGTH: 20
<212> TYPE: DNA
<213> ORGANISM: Artificial Sequence
<220> FEATURE:
<223> OTHER INFORMATION: Synthetic

<400> SEQUENCE: 1099
tcatattacg agtcagtagg                                               20

<210> SEQ ID NO 1100
<211> LENGTH: 20
<212> TYPE: DNA
<213> ORGANISM: Artificial Sequence
<220> FEATURE:
<223> OTHER INFORMATION: Synthetic

<400> SEQUENCE: 1100
```
cctgcaacgg gactagttgg                                    20

<210> SEQ ID NO 1101
<211> LENGTH: 20
<212> TYPE: DNA
<213> ORGANISM: Artificial Sequence
<220> FEATURE:
<223> OTHER INFORMATION: Synthetic

<400> SEQUENCE: 1101
agtagtccgg gatatcagcg                                    20

<210> SEQ ID NO 1102
<211> LENGTH: 20
<212> TYPE: DNA
<213> ORGANISM: Artificial Sequence
<220> FEATURE:
<223> OTHER INFORMATION: Synthetic

<400> SEQUENCE: 1102
atacaactgc ttgcaacagg                                    20

<210> SEQ ID NO 1103
<211> LENGTH: 20
<212> TYPE: DNA
<213> ORGANISM: Artificial Sequence
<220> FEATURE:
<223> OTHER INFORMATION: Synthetic

<400> SEQUENCE: 1103
cctgcaacgg gactagttgg                                    20

<210> SEQ ID NO 1104
<211> LENGTH: 20
<212> TYPE: DNA
<213> ORGANISM: Artificial Sequence
<220> FEATURE:
<223> OTHER INFORMATION: Synthetic

<400> SEQUENCE: 1104
tcatattacg agtcagtagg                                    20

<210> SEQ ID NO 1105
<211> LENGTH: 20
<212> TYPE: DNA
<213> ORGANISM: Artificial Sequence
<220> FEATURE:
<223> OTHER INFORMATION: Synthetic

<400> SEQUENCE: 1105
ccagtacaaa cctacctacg                                    20

<210> SEQ ID NO 1106
<211> LENGTH: 20
<212> TYPE: DNA
<213> ORGANISM: Artificial Sequence
<220> FEATURE:
<223> OTHER INFORMATION: Synthetic

<400> SEQUENCE: 1106
cctgcaacgg gactagttgg                                    20

<210> SEQ ID NO 1107
<211> LENGTH: 20
<212> TYPE: DNA

```
<213> ORGANISM: Artificial Sequence
<220> FEATURE:
<223> OTHER INFORMATION: Synthetic

<400> SEQUENCE: 1107
tccaccggcg aaagagatcc                                                   20

<210> SEQ ID NO 1108
<211> LENGTH: 19
<212> TYPE: DNA
<213> ORGANISM: Artificial Sequence
<220> FEATURE:
<223> OTHER INFORMATION: Synthetic

<400> SEQUENCE: 1108
agagcactgc actccttca                                                    19

<210> SEQ ID NO 1109
<211> LENGTH: 20
<212> TYPE: DNA
<213> ORGANISM: Artificial Sequence
<220> FEATURE:
<223> OTHER INFORMATION: Synthetic

<400> SEQUENCE: 1109
ccagtacaaa cctacctacg                                                   20

<210> SEQ ID NO 1110
<211> LENGTH: 20
<212> TYPE: DNA
<213> ORGANISM: Artificial Sequence
<220> FEATURE:
<223> OTHER INFORMATION: Synthetic

<400> SEQUENCE: 1110
cctgcaacgg gactagttgg                                                   20

<210> SEQ ID NO 1111
<211> LENGTH: 20
<212> TYPE: DNA
<213> ORGANISM: Artificial Sequence
<220> FEATURE:
<223> OTHER INFORMATION: Synthetic

<400> SEQUENCE: 1111
ccagtacaaa cctacctacg                                                   20

<210> SEQ ID NO 1112
<211> LENGTH: 20
<212> TYPE: DNA
<213> ORGANISM: Artificial Sequence
<220> FEATURE:
<223> OTHER INFORMATION: Synthetic

<400> SEQUENCE: 1112
cgccgccccc ggacgcgacc                                                   20

<210> SEQ ID NO 1113
<211> LENGTH: 20
<212> TYPE: DNA
<213> ORGANISM: Artificial Sequence
<220> FEATURE:
<223> OTHER INFORMATION: Synthetic

<400> SEQUENCE: 1113
cgccgccccc ggacgcgacc                                                   20
```

```
<210> SEQ ID NO 1114
<211> LENGTH: 19
<212> TYPE: DNA
<213> ORGANISM: Artificial Sequence
<220> FEATURE:
<223> OTHER INFORMATION: Synthetic

<400> SEQUENCE: 1114
agagcactgc actccttca                                               19

<210> SEQ ID NO 1115
<211> LENGTH: 20
<212> TYPE: DNA
<213> ORGANISM: Artificial Sequence
<220> FEATURE:
<223> OTHER INFORMATION: Synthetic

<400> SEQUENCE: 1115
tcatattacg agtcagtagg                                              20

<210> SEQ ID NO 1116
<211> LENGTH: 20
<212> TYPE: DNA
<213> ORGANISM: Artificial Sequence
<220> FEATURE:
<223> OTHER INFORMATION: Synthetic

<400> SEQUENCE: 1116
agtagtccgg gatatcagcg                                              20

<210> SEQ ID NO 1117
<211> LENGTH: 20
<212> TYPE: DNA
<213> ORGANISM: Artificial Sequence
<220> FEATURE:
<223> OTHER INFORMATION: Synthetic

<400> SEQUENCE: 1117
tcatattacg agtcagtagg                                              20

<210> SEQ ID NO 1118
<211> LENGTH: 20
<212> TYPE: DNA
<213> ORGANISM: Artificial Sequence
<220> FEATURE:
<223> OTHER INFORMATION: Synthetic

<400> SEQUENCE: 1118
ccagtacaaa cctacctacg                                              20

<210> SEQ ID NO 1119
<211> LENGTH: 20
<212> TYPE: DNA
<213> ORGANISM: Artificial Sequence
<220> FEATURE:
<223> OTHER INFORMATION: Synthetic

<400> SEQUENCE: 1119
tcatattacg agtcagtagg                                              20

<210> SEQ ID NO 1120
<211> LENGTH: 19
<212> TYPE: DNA
<213> ORGANISM: Artificial Sequence
<220> FEATURE:
```

<223> OTHER INFORMATION: Synthetic

<400> SEQUENCE: 1120
agagcactgc actccttca                    19

<210> SEQ ID NO 1121
<211> LENGTH: 20
<212> TYPE: DNA
<213> ORGANISM: Artificial Sequence
<220> FEATURE:
<223> OTHER INFORMATION: Synthetic

<400> SEQUENCE: 1121
cctgcaacgg gactagttgg                    20

<210> SEQ ID NO 1122
<211> LENGTH: 20
<212> TYPE: DNA
<213> ORGANISM: Artificial Sequence
<220> FEATURE:
<223> OTHER INFORMATION: Synthetic

<400> SEQUENCE: 1122
tcatattacg agtcagtagg                    20

<210> SEQ ID NO 1123
<211> LENGTH: 20
<212> TYPE: DNA
<213> ORGANISM: Artificial Sequence
<220> FEATURE:
<223> OTHER INFORMATION: Synthetic

<400> SEQUENCE: 1123
agtagtccgg gatatcagcg                    20

<210> SEQ ID NO 1124
<211> LENGTH: 20
<212> TYPE: DNA
<213> ORGANISM: Artificial Sequence
<220> FEATURE:
<223> OTHER INFORMATION: Synthetic

<400> SEQUENCE: 1124
ccagtacaaa cctacctacg                    20

<210> SEQ ID NO 1125
<211> LENGTH: 20
<212> TYPE: DNA
<213> ORGANISM: Artificial Sequence
<220> FEATURE:
<223> OTHER INFORMATION: Synthetic

<400> SEQUENCE: 1125
cgccgccccc ggacgcgacc                    20

<210> SEQ ID NO 1126
<211> LENGTH: 20
<212> TYPE: DNA
<213> ORGANISM: Artificial Sequence
<220> FEATURE:
<223> OTHER INFORMATION: Synthetic

<400> SEQUENCE: 1126
agtagtccgg gatatcagcg                    20

```
<210> SEQ ID NO 1127
<211> LENGTH: 20
<212> TYPE: DNA
<213> ORGANISM: Artificial Sequence
<220> FEATURE:
<223> OTHER INFORMATION: Synthetic

<400> SEQUENCE: 1127
ccagtacaaa cctacctacg                                        20

<210> SEQ ID NO 1128
<211> LENGTH: 20
<212> TYPE: DNA
<213> ORGANISM: Artificial Sequence
<220> FEATURE:
<223> OTHER INFORMATION: Synthetic

<400> SEQUENCE: 1128
agtagtccgg gatatcagcg                                        20

<210> SEQ ID NO 1129
<211> LENGTH: 19
<212> TYPE: DNA
<213> ORGANISM: Artificial Sequence
<220> FEATURE:
<223> OTHER INFORMATION: Synthetic

<400> SEQUENCE: 1129
agagcactgc actccttca                                         19

<210> SEQ ID NO 1130
<211> LENGTH: 20
<212> TYPE: DNA
<213> ORGANISM: Artificial Sequence
<220> FEATURE:
<223> OTHER INFORMATION: Synthetic

<400> SEQUENCE: 1130
tcatattacg agtcagtagg                                        20

<210> SEQ ID NO 1131
<211> LENGTH: 20
<212> TYPE: DNA
<213> ORGANISM: Artificial Sequence
<220> FEATURE:
<223> OTHER INFORMATION: Synthetic

<400> SEQUENCE: 1131
cgccgccccc ggacgcgacc                                        20

<210> SEQ ID NO 1132
<211> LENGTH: 20
<212> TYPE: DNA
<213> ORGANISM: Artificial Sequence
<220> FEATURE:
<223> OTHER INFORMATION: Synthetic

<400> SEQUENCE: 1132
tcatattacg agtcagtagg                                        20

<210> SEQ ID NO 1133
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 1133
agtagtccgg gatatcagcg                                              20

<210> SEQ ID NO 1134
<211> LENGTH: 20
<212> TYPE: DNA
<213> ORGANISM: Artificial Sequence
<220> FEATURE:
<223> OTHER INFORMATION: Synthetic

<400> SEQUENCE: 1134
tcatattacg agtcagtagg                                              20

<210> SEQ ID NO 1135
<211> LENGTH: 20
<212> TYPE: DNA
<213> ORGANISM: Artificial Sequence
<220> FEATURE:
<223> OTHER INFORMATION: Synthetic

<400> SEQUENCE: 1135
tccaccggcg aaagagatcc                                              20

<210> SEQ ID NO 1136
<211> LENGTH: 19
<212> TYPE: DNA
<213> ORGANISM: Artificial Sequence
<220> FEATURE:
<223> OTHER INFORMATION: Synthetic

<400> SEQUENCE: 1136
agagcactgc actccttca                                               19

<210> SEQ ID NO 1137
<211> LENGTH: 19
<212> TYPE: DNA
<213> ORGANISM: Artificial Sequence
<220> FEATURE:
<223> OTHER INFORMATION: Synthetic

<400> SEQUENCE: 1137
agagcactgc actccttca                                               19

<210> SEQ ID NO 1138
<211> LENGTH: 20
<212> TYPE: DNA
<213> ORGANISM: Artificial Sequence
<220> FEATURE:
<223> OTHER INFORMATION: Synthetic

<400> SEQUENCE: 1138
tcatattacg agtcagtagg                                              20

<210> SEQ ID NO 1139
<211> LENGTH: 20
<212> TYPE: DNA
<213> ORGANISM: Artificial Sequence
<220> FEATURE:
<223> OTHER INFORMATION: Synthetic

<400> SEQUENCE: 1139
cgccgccccc ggacgcgacc                                              20

<210> SEQ ID NO 1140
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 1140
agtagtccgg gatatcagcg                                                  20

<210> SEQ ID NO 1141
<211> LENGTH: 20
<212> TYPE: DNA
<213> ORGANISM: Artificial Sequence
<220> FEATURE:
<223> OTHER INFORMATION: Synthetic

<400> SEQUENCE: 1141
ccagtacaaa cctacctacg                                                  20

<210> SEQ ID NO 1142
<211> LENGTH: 20
<212> TYPE: DNA
<213> ORGANISM: Artificial Sequence
<220> FEATURE:
<223> OTHER INFORMATION: Synthetic

<400> SEQUENCE: 1142
tcatattacg agtcagtagg                                                  20

<210> SEQ ID NO 1143
<211> LENGTH: 20
<212> TYPE: DNA
<213> ORGANISM: Artificial Sequence
<220> FEATURE:
<223> OTHER INFORMATION: Synthetic

<400> SEQUENCE: 1143
cctgcaacgg gactagttgg                                                  20

<210> SEQ ID NO 1144
<211> LENGTH: 20
<212> TYPE: DNA
<213> ORGANISM: Artificial Sequence
<220> FEATURE:
<223> OTHER INFORMATION: Synthetic

<400> SEQUENCE: 1144
ccagtacaaa cctacctacg                                                  20

<210> SEQ ID NO 1145
<211> LENGTH: 20
<212> TYPE: DNA
<213> ORGANISM: Artificial Sequence
<220> FEATURE:
<223> OTHER INFORMATION: Synthetic

<400> SEQUENCE: 1145
cgccgccccc ggacgcgacc                                                  20

<210> SEQ ID NO 1146
<211> LENGTH: 20
<212> TYPE: DNA
<213> ORGANISM: Artificial Sequence
<220> FEATURE:
<223> OTHER INFORMATION: Synthetic

<400> SEQUENCE: 1146
```
cgccgccccc ggacgcgacc                                          20

<210> SEQ ID NO 1147
<211> LENGTH: 20
<212> TYPE: DNA
<213> ORGANISM: Artificial Sequence
<220> FEATURE:
<223> OTHER INFORMATION: Synthetic

<400> SEQUENCE: 1147
cctgcaacgg gactagttgg                                          20

<210> SEQ ID NO 1148
<211> LENGTH: 20
<212> TYPE: DNA
<213> ORGANISM: Artificial Sequence
<220> FEATURE:
<223> OTHER INFORMATION: Synthetic

<400> SEQUENCE: 1148
cctgcaacgg gactagttgg                                          20

<210> SEQ ID NO 1149
<211> LENGTH: 20
<212> TYPE: DNA
<213> ORGANISM: Artificial Sequence
<220> FEATURE:
<223> OTHER INFORMATION: Synthetic

<400> SEQUENCE: 1149
cctgcaacgg gactagttgg                                          20

<210> SEQ ID NO 1150
<211> LENGTH: 19
<212> TYPE: DNA
<213> ORGANISM: Artificial Sequence
<220> FEATURE:
<223> OTHER INFORMATION: Synthetic

<400> SEQUENCE: 1150
agagcactgc actccttca                                           19

<210> SEQ ID NO 1151
<211> LENGTH: 20
<212> TYPE: DNA
<213> ORGANISM: Artificial Sequence
<220> FEATURE:
<223> OTHER INFORMATION: Synthetic

<400> SEQUENCE: 1151
tccaccggcg aaagagatcc                                          20

<210> SEQ ID NO 1152
<211> LENGTH: 20
<212> TYPE: DNA
<213> ORGANISM: Artificial Sequence
<220> FEATURE:
<223> OTHER INFORMATION: Synthetic

<400> SEQUENCE: 1152
atacaactgc ttgcaacagg                                          20

<210> SEQ ID NO 1153
<211> LENGTH: 19
<212> TYPE: DNA
<213> ORGANISM: Artificial Sequence

```
<220> FEATURE:
<223> OTHER INFORMATION: Synthetic

<400> SEQUENCE: 1153
agagcactgc actccttca                                                19

<210> SEQ ID NO 1154
<211> LENGTH: 19
<212> TYPE: DNA
<213> ORGANISM: Artificial Sequence
<220> FEATURE:
<223> OTHER INFORMATION: Synthetic

<400> SEQUENCE: 1154
agagcactgc actccttca                                                19

<210> SEQ ID NO 1155
<211> LENGTH: 19
<212> TYPE: DNA
<213> ORGANISM: Artificial Sequence
<220> FEATURE:
<223> OTHER INFORMATION: Synthetic

<400> SEQUENCE: 1155
agagcactgc actccttca                                                19

<210> SEQ ID NO 1156
<211> LENGTH: 20
<212> TYPE: DNA
<213> ORGANISM: Artificial Sequence
<220> FEATURE:
<223> OTHER INFORMATION: Synthetic

<400> SEQUENCE: 1156
agtagtccgg gatatcagcg                                               20

<210> SEQ ID NO 1157
<211> LENGTH: 20
<212> TYPE: DNA
<213> ORGANISM: Artificial Sequence
<220> FEATURE:
<223> OTHER INFORMATION: Synthetic

<400> SEQUENCE: 1157
tcatattacg agtcagtagg                                               20

<210> SEQ ID NO 1158
<211> LENGTH: 20
<212> TYPE: DNA
<213> ORGANISM: Artificial Sequence
<220> FEATURE:
<223> OTHER INFORMATION: Synthetic

<400> SEQUENCE: 1158
cgccgccccc ggacgcgacc                                               20

<210> SEQ ID NO 1159
<211> LENGTH: 19
<212> TYPE: DNA
<213> ORGANISM: Artificial Sequence
<220> FEATURE:
<223> OTHER INFORMATION: Synthetic

<400> SEQUENCE: 1159
agagcactgc actccttca                                                19
```

```
<210> SEQ ID NO 1160
<211> LENGTH: 20
<212> TYPE: DNA
<213> ORGANISM: Artificial Sequence
<220> FEATURE:
<223> OTHER INFORMATION: Synthetic

<400> SEQUENCE: 1160
agtagtccgg gatatcagcg                                              20

<210> SEQ ID NO 1161
<211> LENGTH: 20
<212> TYPE: DNA
<213> ORGANISM: Artificial Sequence
<220> FEATURE:
<223> OTHER INFORMATION: Synthetic

<400> SEQUENCE: 1161
ccagtacaaa cctacctacg                                              20

<210> SEQ ID NO 1162
<211> LENGTH: 20
<212> TYPE: DNA
<213> ORGANISM: Artificial Sequence
<220> FEATURE:
<223> OTHER INFORMATION: Synthetic

<400> SEQUENCE: 1162
atacaactgc ttgcaacagg                                              20

<210> SEQ ID NO 1163
<211> LENGTH: 20
<212> TYPE: DNA
<213> ORGANISM: Artificial Sequence
<220> FEATURE:
<223> OTHER INFORMATION: Synthetic

<400> SEQUENCE: 1163
cgccgccccc ggacgcgacc                                              20

<210> SEQ ID NO 1164
<211> LENGTH: 20
<212> TYPE: DNA
<213> ORGANISM: Artificial Sequence
<220> FEATURE:
<223> OTHER INFORMATION: Synthetic

<400> SEQUENCE: 1164
cgccgccccc ggacgcgacc                                              20

<210> SEQ ID NO 1165
<211> LENGTH: 20
<212> TYPE: DNA
<213> ORGANISM: Artificial Sequence
<220> FEATURE:
<223> OTHER INFORMATION: Synthetic

<400> SEQUENCE: 1165
agtagtccgg gatatcagcg                                              20

<210> SEQ ID NO 1166
<211> LENGTH: 20
<212> TYPE: DNA
<213> ORGANISM: Artificial Sequence
<220> FEATURE:
<223> OTHER INFORMATION: Synthetic
```

<400> SEQUENCE: 1166
cgccgccccc ggacgcgacc                                          20

<210> SEQ ID NO 1167
<211> LENGTH: 19
<212> TYPE: DNA
<213> ORGANISM: Artificial Sequence
<220> FEATURE:
<223> OTHER INFORMATION: Synthetic

<400> SEQUENCE: 1167
agagcactgc actccttca                                           19

<210> SEQ ID NO 1168
<211> LENGTH: 20
<212> TYPE: DNA
<213> ORGANISM: Artificial Sequence
<220> FEATURE:
<223> OTHER INFORMATION: Synthetic

<400> SEQUENCE: 1168
cgccgccccc ggacgcgacc                                          20

<210> SEQ ID NO 1169
<211> LENGTH: 20
<212> TYPE: DNA
<213> ORGANISM: Artificial Sequence
<220> FEATURE:
<223> OTHER INFORMATION: Synthetic

<400> SEQUENCE: 1169
cctgcaacgg gactagttgg                                          20

<210> SEQ ID NO 1170
<211> LENGTH: 19
<212> TYPE: DNA
<213> ORGANISM: Artificial Sequence
<220> FEATURE:
<223> OTHER INFORMATION: Synthetic

<400> SEQUENCE: 1170
agagcactgc actccttca                                           19

<210> SEQ ID NO 1171
<211> LENGTH: 20
<212> TYPE: DNA
<213> ORGANISM: Artificial Sequence
<220> FEATURE:
<223> OTHER INFORMATION: Synthetic

<400> SEQUENCE: 1171
cctgcaacgg gactagttgg                                          20

<210> SEQ ID NO 1172
<211> LENGTH: 19
<212> TYPE: DNA
<213> ORGANISM: Artificial Sequence
<220> FEATURE:
<223> OTHER INFORMATION: Synthetic

<400> SEQUENCE: 1172
agagcactgc actccttca                                           19

<210> SEQ ID NO 1173

```
<211> LENGTH: 20
<212> TYPE: DNA
<213> ORGANISM: Artificial Sequence
<220> FEATURE:
<223> OTHER INFORMATION: Synthetic

<400> SEQUENCE: 1173
cctgcaacgg gactagttgg                                                   20

<210> SEQ ID NO 1174
<211> LENGTH: 20
<212> TYPE: DNA
<213> ORGANISM: Artificial Sequence
<220> FEATURE:
<223> OTHER INFORMATION: Synthetic

<400> SEQUENCE: 1174
atacaactgc ttgcaacagg                                                   20

<210> SEQ ID NO 1175
<211> LENGTH: 20
<212> TYPE: DNA
<213> ORGANISM: Artificial Sequence
<220> FEATURE:
<223> OTHER INFORMATION: Synthetic

<400> SEQUENCE: 1175
cgccgccccc ggacgcgacc                                                   20

<210> SEQ ID NO 1176
<211> LENGTH: 20
<212> TYPE: DNA
<213> ORGANISM: Artificial Sequence
<220> FEATURE:
<223> OTHER INFORMATION: Synthetic

<400> SEQUENCE: 1176
cgccgccccc ggacgcgacc                                                   20

<210> SEQ ID NO 1177
<211> LENGTH: 20
<212> TYPE: DNA
<213> ORGANISM: Artificial Sequence
<220> FEATURE:
<223> OTHER INFORMATION: Synthetic

<400> SEQUENCE: 1177
tcatattacg agtcagtagg                                                   20

<210> SEQ ID NO 1178
<211> LENGTH: 20
<212> TYPE: DNA
<213> ORGANISM: Artificial Sequence
<220> FEATURE:
<223> OTHER INFORMATION: Synthetic

<400> SEQUENCE: 1178
ccagtacaaa cctacctacg                                                   20

<210> SEQ ID NO 1179
<211> LENGTH: 20
<212> TYPE: DNA
<213> ORGANISM: Artificial Sequence
<220> FEATURE:
<223> OTHER INFORMATION: Synthetic

<400> SEQUENCE: 1179
```
cgccgccccc ggacgcgacc                                              20

<210> SEQ ID NO 1180
<211> LENGTH: 20
<212> TYPE: DNA
<213> ORGANISM: Artificial Sequence
<220> FEATURE:
<223> OTHER INFORMATION: Synthetic

<400> SEQUENCE: 1180
cctgcaacgg gactagttgg                                              20

<210> SEQ ID NO 1181
<211> LENGTH: 20
<212> TYPE: DNA
<213> ORGANISM: Artificial Sequence
<220> FEATURE:
<223> OTHER INFORMATION: Synthetic

<400> SEQUENCE: 1181
agtagtccgg gatatcagcg                                              20

<210> SEQ ID NO 1182
<211> LENGTH: 20
<212> TYPE: DNA
<213> ORGANISM: Artificial Sequence
<220> FEATURE:
<223> OTHER INFORMATION: Synthetic

<400> SEQUENCE: 1182
agtagtccgg gatatcagcg                                              20

<210> SEQ ID NO 1183
<211> LENGTH: 20
<212> TYPE: DNA
<213> ORGANISM: Artificial Sequence
<220> FEATURE:
<223> OTHER INFORMATION: Synthetic

<400> SEQUENCE: 1183
atacaactgc ttgcaacagg                                              20

<210> SEQ ID NO 1184
<211> LENGTH: 20
<212> TYPE: DNA
<213> ORGANISM: Artificial Sequence
<220> FEATURE:
<223> OTHER INFORMATION: Synthetic

<400> SEQUENCE: 1184
cctgcaacgg gactagttgg                                              20

<210> SEQ ID NO 1185
<211> LENGTH: 20
<212> TYPE: DNA
<213> ORGANISM: Artificial Sequence
<220> FEATURE:
<223> OTHER INFORMATION: Synthetic

<400> SEQUENCE: 1185
tccaccggcg aaagagatcc                                              20

<210> SEQ ID NO 1186
<211> LENGTH: 20
<212> TYPE: DNA

```
<213> ORGANISM: Artificial Sequence
<220> FEATURE:
<223> OTHER INFORMATION: Synthetic

<400> SEQUENCE: 1186
cgccgccccc ggacgcgacc                                              20

<210> SEQ ID NO 1187
<211> LENGTH: 19
<212> TYPE: DNA
<213> ORGANISM: Artificial Sequence
<220> FEATURE:
<223> OTHER INFORMATION: Synthetic

<400> SEQUENCE: 1187
agagcactgc actccttca                                               19

<210> SEQ ID NO 1188
<211> LENGTH: 20
<212> TYPE: DNA
<213> ORGANISM: Artificial Sequence
<220> FEATURE:
<223> OTHER INFORMATION: Synthetic

<400> SEQUENCE: 1188
tccaccggcg aaagagatcc                                              20

<210> SEQ ID NO 1189
<211> LENGTH: 20
<212> TYPE: DNA
<213> ORGANISM: Artificial Sequence
<220> FEATURE:
<223> OTHER INFORMATION: Synthetic

<400> SEQUENCE: 1189
atacaactgc ttgcaacagg                                              20

<210> SEQ ID NO 1190
<211> LENGTH: 20
<212> TYPE: DNA
<213> ORGANISM: Artificial Sequence
<220> FEATURE:
<223> OTHER INFORMATION: Synthetic

<400> SEQUENCE: 1190
cgccgccccc ggacgcgacc                                              20

<210> SEQ ID NO 1191
<211> LENGTH: 20
<212> TYPE: DNA
<213> ORGANISM: Artificial Sequence
<220> FEATURE:
<223> OTHER INFORMATION: Synthetic

<400> SEQUENCE: 1191
atacaactgc ttgcaacagg                                              20

<210> SEQ ID NO 1192
<211> LENGTH: 20
<212> TYPE: DNA
<213> ORGANISM: Artificial Sequence
<220> FEATURE:
<223> OTHER INFORMATION: Synthetic

<400> SEQUENCE: 1192
atacaactgc ttgcaacagg                                              20
```

<210> SEQ ID NO 1193
<211> LENGTH: 20
<212> TYPE: DNA
<213> ORGANISM: Artificial Sequence
<220> FEATURE:
<223> OTHER INFORMATION: Synthetic

<400> SEQUENCE: 1193
tcatattacg agtcagtagg                                          20

<210> SEQ ID NO 1194
<211> LENGTH: 20
<212> TYPE: DNA
<213> ORGANISM: Artificial Sequence
<220> FEATURE:
<223> OTHER INFORMATION: Synthetic

<400> SEQUENCE: 1194
ccagtacaaa cctacctacg                                          20

<210> SEQ ID NO 1195
<211> LENGTH: 20
<212> TYPE: DNA
<213> ORGANISM: Artificial Sequence
<220> FEATURE:
<223> OTHER INFORMATION: Synthetic

<400> SEQUENCE: 1195
tcatattacg agtcagtagg                                          20

<210> SEQ ID NO 1196
<211> LENGTH: 20
<212> TYPE: DNA
<213> ORGANISM: Artificial Sequence
<220> FEATURE:
<223> OTHER INFORMATION: Synthetic

<400> SEQUENCE: 1196
atacaactgc ttgcaacagg                                          20

<210> SEQ ID NO 1197
<211> LENGTH: 20
<212> TYPE: DNA
<213> ORGANISM: Artificial Sequence
<220> FEATURE:
<223> OTHER INFORMATION: Synthetic

<400> SEQUENCE: 1197
ccagtacaaa cctacctacg                                          20

<210> SEQ ID NO 1198
<211> LENGTH: 20
<212> TYPE: DNA
<213> ORGANISM: Artificial Sequence
<220> FEATURE:
<223> OTHER INFORMATION: Synthetic

<400> SEQUENCE: 1198
atacaactgc ttgcaacagg                                          20

<210> SEQ ID NO 1199
<211> LENGTH: 20
<212> TYPE: DNA
<213> ORGANISM: Artificial Sequence
<220> FEATURE:

<223> OTHER INFORMATION: Synthetic

<400> SEQUENCE: 1199
tcatattacg agtcagtagg                                          20

<210> SEQ ID NO 1200
<211> LENGTH: 20
<212> TYPE: DNA
<213> ORGANISM: Artificial Sequence
<220> FEATURE:
<223> OTHER INFORMATION: Synthetic

<400> SEQUENCE: 1200
tcatattacg agtcagtagg                                          20

<210> SEQ ID NO 1201
<211> LENGTH: 20
<212> TYPE: DNA
<213> ORGANISM: Artificial Sequence
<220> FEATURE:
<223> OTHER INFORMATION: Synthetic

<400> SEQUENCE: 1201
agtagtccgg gatatcagcg                                          20

<210> SEQ ID NO 1202
<211> LENGTH: 20
<212> TYPE: DNA
<213> ORGANISM: Artificial Sequence
<220> FEATURE:
<223> OTHER INFORMATION: Synthetic

<400> SEQUENCE: 1202
cgccgccccc ggacgcgacc                                          20

<210> SEQ ID NO 1203
<211> LENGTH: 19
<212> TYPE: DNA
<213> ORGANISM: Artificial Sequence
<220> FEATURE:
<223> OTHER INFORMATION: Synthetic

<400> SEQUENCE: 1203
agagcactgc actccttca                                           19

<210> SEQ ID NO 1204
<211> LENGTH: 20
<212> TYPE: DNA
<213> ORGANISM: Artificial Sequence
<220> FEATURE:
<223> OTHER INFORMATION: Synthetic

<400> SEQUENCE: 1204
tcatattacg agtcagtagg                                          20

<210> SEQ ID NO 1205
<211> LENGTH: 20
<212> TYPE: DNA
<213> ORGANISM: Artificial Sequence
<220> FEATURE:
<223> OTHER INFORMATION: Synthetic

<400> SEQUENCE: 1205
cctgcaacgg gactagttgg                                          20

```
<210> SEQ ID NO 1206
<211> LENGTH: 20
<212> TYPE: DNA
<213> ORGANISM: Artificial Sequence
<220> FEATURE:
<223> OTHER INFORMATION: Synthetic

<400> SEQUENCE: 1206
cctgcaacgg gactagttgg                                          20

<210> SEQ ID NO 1207
<211> LENGTH: 20
<212> TYPE: DNA
<213> ORGANISM: Artificial Sequence
<220> FEATURE:
<223> OTHER INFORMATION: Synthetic

<400> SEQUENCE: 1207
agtagtccgg gatatcagcg                                          20

<210> SEQ ID NO 1208
<211> LENGTH: 20
<212> TYPE: DNA
<213> ORGANISM: Artificial Sequence
<220> FEATURE:
<223> OTHER INFORMATION: Synthetic

<400> SEQUENCE: 1208
cctgcaacgg gactagttgg                                          20

<210> SEQ ID NO 1209
<211> LENGTH: 20
<212> TYPE: DNA
<213> ORGANISM: Artificial Sequence
<220> FEATURE:
<223> OTHER INFORMATION: Synthetic

<400> SEQUENCE: 1209
cctgcaacgg gactagttgg                                          20

<210> SEQ ID NO 1210
<211> LENGTH: 19
<212> TYPE: DNA
<213> ORGANISM: Artificial Sequence
<220> FEATURE:
<223> OTHER INFORMATION: Synthetic

<400> SEQUENCE: 1210
agagcactgc actccttca                                           19

<210> SEQ ID NO 1211
<211> LENGTH: 20
<212> TYPE: DNA
<213> ORGANISM: Artificial Sequence
<220> FEATURE:
<223> OTHER INFORMATION: Synthetic

<400> SEQUENCE: 1211
tcatattacg agtcagtagg                                          20

<210> SEQ ID NO 1212
<211> LENGTH: 19
<212> TYPE: DNA
<213> ORGANISM: Artificial Sequence
<220> FEATURE:
<223> OTHER INFORMATION: Synthetic
```

```
<400> SEQUENCE: 1212
agagcactgc actccttca                                               19

<210> SEQ ID NO 1213
<211> LENGTH: 20
<212> TYPE: DNA
<213> ORGANISM: Artificial Sequence
<220> FEATURE:
<223> OTHER INFORMATION: Synthetic

<400> SEQUENCE: 1213
cgccgccccc ggacgcgacc                                              20

<210> SEQ ID NO 1214
<211> LENGTH: 20
<212> TYPE: DNA
<213> ORGANISM: Artificial Sequence
<220> FEATURE:
<223> OTHER INFORMATION: Synthetic

<400> SEQUENCE: 1214
atacaactgc ttgcaacagg                                              20

<210> SEQ ID NO 1215
<211> LENGTH: 20
<212> TYPE: DNA
<213> ORGANISM: Artificial Sequence
<220> FEATURE:
<223> OTHER INFORMATION: Synthetic

<400> SEQUENCE: 1215
cctgcaacgg gactagttgg                                              20

<210> SEQ ID NO 1216
<211> LENGTH: 20
<212> TYPE: DNA
<213> ORGANISM: Artificial Sequence
<220> FEATURE:
<223> OTHER INFORMATION: Synthetic

<400> SEQUENCE: 1216
ccagtacaaa cctacctacg                                              20

<210> SEQ ID NO 1217
<211> LENGTH: 20
<212> TYPE: DNA
<213> ORGANISM: Artificial Sequence
<220> FEATURE:
<223> OTHER INFORMATION: Synthetic

<400> SEQUENCE: 1217
cctgcaacgg gactagttgg                                              20

<210> SEQ ID NO 1218
<211> LENGTH: 20
<212> TYPE: DNA
<213> ORGANISM: Artificial Sequence
<220> FEATURE:
<223> OTHER INFORMATION: Synthetic

<400> SEQUENCE: 1218
agtagtccgg gatatcagcg                                              20

<210> SEQ ID NO 1219
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 1219
tcatattacg agtcagtagg                                            20

<210> SEQ ID NO 1220
<211> LENGTH: 19
<212> TYPE: DNA
<213> ORGANISM: Artificial Sequence
<220> FEATURE:
<223> OTHER INFORMATION: Synthetic

<400> SEQUENCE: 1220
agagcactgc actccttca                                             19

<210> SEQ ID NO 1221
<211> LENGTH: 20
<212> TYPE: DNA
<213> ORGANISM: Artificial Sequence
<220> FEATURE:
<223> OTHER INFORMATION: Synthetic

<400> SEQUENCE: 1221
cctgcaacgg gactagttgg                                            20

<210> SEQ ID NO 1222
<211> LENGTH: 20
<212> TYPE: DNA
<213> ORGANISM: Artificial Sequence
<220> FEATURE:
<223> OTHER INFORMATION: Synthetic

<400> SEQUENCE: 1222
tcatattacg agtcagtagg                                            20

<210> SEQ ID NO 1223
<211> LENGTH: 19
<212> TYPE: DNA
<213> ORGANISM: Artificial Sequence
<220> FEATURE:
<223> OTHER INFORMATION: Synthetic

<400> SEQUENCE: 1223
agagcactgc actccttca                                             19

<210> SEQ ID NO 1224
<211> LENGTH: 20
<212> TYPE: DNA
<213> ORGANISM: Artificial Sequence
<220> FEATURE:
<223> OTHER INFORMATION: Synthetic

<400> SEQUENCE: 1224
tcatattacg agtcagtagg                                            20

<210> SEQ ID NO 1225
<211> LENGTH: 19
<212> TYPE: DNA
<213> ORGANISM: Artificial Sequence
<220> FEATURE:
<223> OTHER INFORMATION: Synthetic

<400> SEQUENCE: 1225
```

```
agagcactgc actccttca                                        19

<210> SEQ ID NO 1226
<211> LENGTH: 20
<212> TYPE: DNA
<213> ORGANISM: Artificial Sequence
<220> FEATURE:
<223> OTHER INFORMATION: Synthetic

<400> SEQUENCE: 1226
cgccgccccc ggacgcgacc                                       20

<210> SEQ ID NO 1227
<211> LENGTH: 19
<212> TYPE: DNA
<213> ORGANISM: Artificial Sequence
<220> FEATURE:
<223> OTHER INFORMATION: Synthetic

<400> SEQUENCE: 1227
agagcactgc actccttca                                        19

<210> SEQ ID NO 1228
<211> LENGTH: 12
<212> TYPE: DNA
<213> ORGANISM: Artificial Sequence
<220> FEATURE:
<223> OTHER INFORMATION: Synthetic

<400> SEQUENCE: 1228
ctatatatga cc                                               12

<210> SEQ ID NO 1229
<211> LENGTH: 20
<212> TYPE: DNA
<213> ORGANISM: Artificial Sequence
<220> FEATURE:
<223> OTHER INFORMATION: Synthetic

<400> SEQUENCE: 1229
caaggaggac ggcaacatcc                                       20

<210> SEQ ID NO 1230
<211> LENGTH: 12
<212> TYPE: DNA
<213> ORGANISM: Artificial Sequence
<220> FEATURE:
<223> OTHER INFORMATION: Synthetic

<400> SEQUENCE: 1230
gacatgcgta gc                                               12

<210> SEQ ID NO 1231
<211> LENGTH: 20
<212> TYPE: DNA
<213> ORGANISM: Artificial Sequence
<220> FEATURE:
<223> OTHER INFORMATION: Synthetic

<400> SEQUENCE: 1231
gccgtgccgt agctatccgg                                       20

<210> SEQ ID NO 1232
<211> LENGTH: 12
<212> TYPE: DNA
<213> ORGANISM: Artificial Sequence
```

```
<220> FEATURE:
<223> OTHER INFORMATION: Synthetic

<400> SEQUENCE: 1232
agctctgaca ca                                                              12

<210> SEQ ID NO 1233
<211> LENGTH: 20
<212> TYPE: DNA
<213> ORGANISM: Artificial Sequence
<220> FEATURE:
<223> OTHER INFORMATION: Synthetic

<400> SEQUENCE: 1233
tgtactccag cttgtgcccc                                                      20

<210> SEQ ID NO 1234
<211> LENGTH: 12
<212> TYPE: DNA
<213> ORGANISM: Artificial Sequence
<220> FEATURE:
<223> OTHER INFORMATION: Synthetic

<400> SEQUENCE: 1234
tccaaagaga ca                                                              12

<210> SEQ ID NO 1235
<211> LENGTH: 20
<212> TYPE: DNA
<213> ORGANISM: Artificial Sequence
<220> FEATURE:
<223> OTHER INFORMATION: Synthetic

<400> SEQUENCE: 1235
aaggaggacg gcaacatcct                                                      20

<210> SEQ ID NO 1236
<211> LENGTH: 12
<212> TYPE: DNA
<213> ORGANISM: Artificial Sequence
<220> FEATURE:
<223> OTHER INFORMATION: Synthetic

<400> SEQUENCE: 1236
ctatatatga cc                                                              12

<210> SEQ ID NO 1237
<211> LENGTH: 20
<212> TYPE: DNA
<213> ORGANISM: Artificial Sequence
<220> FEATURE:
<223> OTHER INFORMATION: Synthetic

<400> SEQUENCE: 1237
caaggaggac ggcaacatcc                                                      20

<210> SEQ ID NO 1238
<211> LENGTH: 12
<212> TYPE: DNA
<213> ORGANISM: Artificial Sequence
<220> FEATURE:
<223> OTHER INFORMATION: Synthetic

<400> SEQUENCE: 1238
agatgataac gg                                                              12
```

```
<210> SEQ ID NO 1239
<211> LENGTH: 20
<212> TYPE: DNA
<213> ORGANISM: Artificial Sequence
<220> FEATURE:
<223> OTHER INFORMATION: Synthetic

<400> SEQUENCE: 1239
gccgtgccgt agctatccgg                                                 20

<210> SEQ ID NO 1240

<400> SEQUENCE: 1240

000

<210> SEQ ID NO 1241
<211> LENGTH: 12
<212> TYPE: DNA
<213> ORGANISM: Artificial Sequence
<220> FEATURE:
<223> OTHER INFORMATION: Synthetic

<400> SEQUENCE: 1241
tccaaagaga ca                                                         12

<210> SEQ ID NO 1242
<211> LENGTH: 20
<212> TYPE: DNA
<213> ORGANISM: Artificial Sequence
<220> FEATURE:
<223> OTHER INFORMATION: Synthetic

<400> SEQUENCE: 1242
aaggaggacg gcaacatcct                                                 20

<210> SEQ ID NO 1243
<211> LENGTH: 12
<212> TYPE: DNA
<213> ORGANISM: Artificial Sequence
<220> FEATURE:
<223> OTHER INFORMATION: Synthetic

<400> SEQUENCE: 1243
agatgggttc cg                                                         12

<210> SEQ ID NO 1244
<211> LENGTH: 20
<212> TYPE: DNA
<213> ORGANISM: Artificial Sequence
<220> FEATURE:
<223> OTHER INFORMATION: Synthetic

<400> SEQUENCE: 1244
gtccgttcga caatttcaca                                                 20

<210> SEQ ID NO 1245
<211> LENGTH: 12
<212> TYPE: DNA
<213> ORGANISM: Artificial Sequence
<220> FEATURE:
<223> OTHER INFORMATION: Synthetic

<400> SEQUENCE: 1245
agcacggaga ca                                                         12
```

```
<210> SEQ ID NO 1246
<211> LENGTH: 20
<212> TYPE: DNA
<213> ORGANISM: Artificial Sequence
<220> FEATURE:
<223> OTHER INFORMATION: Synthetic

<400> SEQUENCE: 1246
gtacagctaa gttaaactcg                                               20

<210> SEQ ID NO 1247
<211> LENGTH: 12
<212> TYPE: DNA
<213> ORGANISM: Artificial Sequence
<220> FEATURE:
<223> OTHER INFORMATION: Synthetic

<400> SEQUENCE: 1247
gaatccgctc gc                                                       12

<210> SEQ ID NO 1248
<211> LENGTH: 20
<212> TYPE: DNA
<213> ORGANISM: Artificial Sequence
<220> FEATURE:
<223> OTHER INFORMATION: Synthetic

<400> SEQUENCE: 1248
aaggaggacg gcaacatcct                                               20

<210> SEQ ID NO 1249
<211> LENGTH: 12
<212> TYPE: DNA
<213> ORGANISM: Artificial Sequence
<220> FEATURE:
<223> OTHER INFORMATION: Synthetic

<400> SEQUENCE: 1249
gacaagtaca ct                                                       12

<210> SEQ ID NO 1250
<211> LENGTH: 20
<212> TYPE: DNA
<213> ORGANISM: Artificial Sequence
<220> FEATURE:
<223> OTHER INFORMATION: Synthetic

<400> SEQUENCE: 1250
gtccgttcga caatttcaca                                               20

<210> SEQ ID NO 1251
<211> LENGTH: 12
<212> TYPE: DNA
<213> ORGANISM: Artificial Sequence
<220> FEATURE:
<223> OTHER INFORMATION: Synthetic

<400> SEQUENCE: 1251
ctcaatttac ag                                                       12

<210> SEQ ID NO 1252
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 1252
gtccgttcga caatttcaca                                          20

<210> SEQ ID NO 1253
<211> LENGTH: 12
<212> TYPE: DNA
<213> ORGANISM: Artificial Sequence
<220> FEATURE:
<223> OTHER INFORMATION: Synthetic

<400> SEQUENCE: 1253
ctagtgtcca ca                                                  12

<210> SEQ ID NO 1254
<211> LENGTH: 20
<212> TYPE: DNA
<213> ORGANISM: Artificial Sequence
<220> FEATURE:
<223> OTHER INFORMATION: Synthetic

<400> SEQUENCE: 1254
aaggaggacg gcaacatcct                                          20

<210> SEQ ID NO 1255
<211> LENGTH: 12
<212> TYPE: DNA
<213> ORGANISM: Artificial Sequence
<220> FEATURE:
<223> OTHER INFORMATION: Synthetic

<400> SEQUENCE: 1255
gacaacgaga ac                                                  12

<210> SEQ ID NO 1256
<211> LENGTH: 20
<212> TYPE: DNA
<213> ORGANISM: Artificial Sequence
<220> FEATURE:
<223> OTHER INFORMATION: Synthetic

<400> SEQUENCE: 1256
gccgtgccgt agctatccgg                                          20

<210> SEQ ID NO 1257
<211> LENGTH: 12
<212> TYPE: DNA
<213> ORGANISM: Artificial Sequence
<220> FEATURE:
<223> OTHER INFORMATION: Synthetic

<400> SEQUENCE: 1257
agagacttca ca                                                  12

<210> SEQ ID NO 1258
<211> LENGTH: 20
<212> TYPE: DNA
<213> ORGANISM: Artificial Sequence
<220> FEATURE:
<223> OTHER INFORMATION: Synthetic

<400> SEQUENCE: 1258
ggacgctaaa ccaacggtgc                                          20

<210> SEQ ID NO 1259
```

```
<211> LENGTH: 12
<212> TYPE: DNA
<213> ORGANISM: Artificial Sequence
<220> FEATURE:
<223> OTHER INFORMATION: Synthetic

<400> SEQUENCE: 1259
agatgggttc cg                                                              12

<210> SEQ ID NO 1260
<211> LENGTH: 20
<212> TYPE: DNA
<213> ORGANISM: Artificial Sequence
<220> FEATURE:
<223> OTHER INFORMATION: Synthetic

<400> SEQUENCE: 1260
gtccgttcga caatttcaca                                                      20

<210> SEQ ID NO 1261
<211> LENGTH: 12
<212> TYPE: DNA
<213> ORGANISM: Artificial Sequence
<220> FEATURE:
<223> OTHER INFORMATION: Synthetic

<400> SEQUENCE: 1261
gacaggctac ct                                                              12

<210> SEQ ID NO 1262
<211> LENGTH: 20
<212> TYPE: DNA
<213> ORGANISM: Artificial Sequence
<220> FEATURE:
<223> OTHER INFORMATION: Synthetic

<400> SEQUENCE: 1262
ggacgctaaa ccaacggtgc                                                      20

<210> SEQ ID NO 1263
<211> LENGTH: 12
<212> TYPE: DNA
<213> ORGANISM: Artificial Sequence
<220> FEATURE:
<223> OTHER INFORMATION: Synthetic

<400> SEQUENCE: 1263
gaatgaacca cg                                                              12

<210> SEQ ID NO 1264
<211> LENGTH: 20
<212> TYPE: DNA
<213> ORGANISM: Artificial Sequence
<220> FEATURE:
<223> OTHER INFORMATION: Synthetic

<400> SEQUENCE: 1264
aaggaggacg gcaacatcct                                                      20

<210> SEQ ID NO 1265
<211> LENGTH: 12
<212> TYPE: DNA
<213> ORGANISM: Artificial Sequence
<220> FEATURE:
<223> OTHER INFORMATION: Synthetic

<400> SEQUENCE: 1265
```

```
gaacgcgaaa gc                                                        12

<210> SEQ ID NO 1266
<211> LENGTH: 20
<212> TYPE: DNA
<213> ORGANISM: Artificial Sequence
<220> FEATURE:
<223> OTHER INFORMATION: Synthetic

<400> SEQUENCE: 1266
caacatcctg gggcacaagc                                                20

<210> SEQ ID NO 1267
<211> LENGTH: 12
<212> TYPE: DNA
<213> ORGANISM: Artificial Sequence
<220> FEATURE:
<223> OTHER INFORMATION: Synthetic

<400> SEQUENCE: 1267
gacaagtaca ct                                                        12

<210> SEQ ID NO 1268
<211> LENGTH: 20
<212> TYPE: DNA
<213> ORGANISM: Artificial Sequence
<220> FEATURE:
<223> OTHER INFORMATION: Synthetic

<400> SEQUENCE: 1268
gtccgttcga caatttcaca                                                20

<210> SEQ ID NO 1269
<211> LENGTH: 12
<212> TYPE: DNA
<213> ORGANISM: Artificial Sequence
<220> FEATURE:
<223> OTHER INFORMATION: Synthetic

<400> SEQUENCE: 1269
ctcactgaca ct                                                        12

<210> SEQ ID NO 1270
<211> LENGTH: 20
<212> TYPE: DNA
<213> ORGANISM: Artificial Sequence
<220> FEATURE:
<223> OTHER INFORMATION: Synthetic

<400> SEQUENCE: 1270
gccgtgccgt agctatccgg                                                20

<210> SEQ ID NO 1271
<211> LENGTH: 12
<212> TYPE: DNA
<213> ORGANISM: Artificial Sequence
<220> FEATURE:
<223> OTHER INFORMATION: Synthetic

<400> SEQUENCE: 1271
gacatgcgta gc                                                        12

<210> SEQ ID NO 1272
<211> LENGTH: 20
<212> TYPE: DNA
```

<213> ORGANISM: Artificial Sequence
<220> FEATURE:
<223> OTHER INFORMATION: Synthetic

<400> SEQUENCE: 1272
gccgtgccgt agctatccgg                                               20

<210> SEQ ID NO 1273
<211> LENGTH: 12
<212> TYPE: DNA
<213> ORGANISM: Artificial Sequence
<220> FEATURE:
<223> OTHER INFORMATION: Synthetic

<400> SEQUENCE: 1273
tccaaagaga ca                                                       12

<210> SEQ ID NO 1274
<211> LENGTH: 20
<212> TYPE: DNA
<213> ORGANISM: Artificial Sequence
<220> FEATURE:
<223> OTHER INFORMATION: Synthetic

<400> SEQUENCE: 1274
aaggaggacg gcaacatcct                                               20

<210> SEQ ID NO 1275
<211> LENGTH: 12
<212> TYPE: DNA
<213> ORGANISM: Artificial Sequence
<220> FEATURE:
<223> OTHER INFORMATION: Synthetic

<400> SEQUENCE: 1275
agcagcccta gc                                                       12

<210> SEQ ID NO 1276
<211> LENGTH: 20
<212> TYPE: DNA
<213> ORGANISM: Artificial Sequence
<220> FEATURE:
<223> OTHER INFORMATION: Synthetic

<400> SEQUENCE: 1276
gctgcttgcg ataccaatag                                               20

<210> SEQ ID NO 1277
<211> LENGTH: 12
<212> TYPE: DNA
<213> ORGANISM: Artificial Sequence
<220> FEATURE:
<223> OTHER INFORMATION: Synthetic

<400> SEQUENCE: 1277
ctcactgaca ct                                                       12

<210> SEQ ID NO 1278
<211> LENGTH: 20
<212> TYPE: DNA
<213> ORGANISM: Artificial Sequence
<220> FEATURE:
<223> OTHER INFORMATION: Synthetic

<400> SEQUENCE: 1278
gccgtgccgt agctatccgg                                               20

```
<210> SEQ ID NO 1279
<211> LENGTH: 12
<212> TYPE: DNA
<213> ORGANISM: Artificial Sequence
<220> FEATURE:
<223> OTHER INFORMATION: Synthetic

<400> SEQUENCE: 1279
agagcagaaa gg                                                          12

<210> SEQ ID NO 1280
<211> LENGTH: 20
<212> TYPE: DNA
<213> ORGANISM: Artificial Sequence
<220> FEATURE:
<223> OTHER INFORMATION: Synthetic

<400> SEQUENCE: 1280
caacatcctg gggcacaagc                                                  20

<210> SEQ ID NO 1281
<211> LENGTH: 12
<212> TYPE: DNA
<213> ORGANISM: Artificial Sequence
<220> FEATURE:
<223> OTHER INFORMATION: Synthetic

<400> SEQUENCE: 1281
agatgataac gg                                                          12

<210> SEQ ID NO 1282
<211> LENGTH: 20
<212> TYPE: DNA
<213> ORGANISM: Artificial Sequence
<220> FEATURE:
<223> OTHER INFORMATION: Synthetic

<400> SEQUENCE: 1282
gccgtgccgt agctatccgg                                                  20

<210> SEQ ID NO 1283
<211> LENGTH: 12
<212> TYPE: DNA
<213> ORGANISM: Artificial Sequence
<220> FEATURE:
<223> OTHER INFORMATION: Synthetic

<400> SEQUENCE: 1283
tccagagcac ct                                                          12

<210> SEQ ID NO 1284
<211> LENGTH: 20
<212> TYPE: DNA
<213> ORGANISM: Artificial Sequence
<220> FEATURE:
<223> OTHER INFORMATION: Synthetic

<400> SEQUENCE: 1284
ggacgctaaa ccaacggtgc                                                  20

<210> SEQ ID NO 1285
<211> LENGTH: 12
<212> TYPE: DNA
<213> ORGANISM: Artificial Sequence
<220> FEATURE:
```

<223> OTHER INFORMATION: Synthetic

<400> SEQUENCE: 1285
agcgaccttt ca                                                            12

<210> SEQ ID NO 1286
<211> LENGTH: 20
<212> TYPE: DNA
<213> ORGANISM: Artificial Sequence
<220> FEATURE:
<223> OTHER INFORMATION: Synthetic

<400> SEQUENCE: 1286
aggaggacgg caacatcctg                                                    20

<210> SEQ ID NO 1287
<211> LENGTH: 12
<212> TYPE: DNA
<213> ORGANISM: Artificial Sequence
<220> FEATURE:
<223> OTHER INFORMATION: Synthetic

<400> SEQUENCE: 1287
agcagtgtac ct                                                            12

<210> SEQ ID NO 1288
<211> LENGTH: 20
<212> TYPE: DNA
<213> ORGANISM: Artificial Sequence
<220> FEATURE:
<223> OTHER INFORMATION: Synthetic

<400> SEQUENCE: 1288
gctgcttgcg ataccaatag                                                    20

<210> SEQ ID NO 1289
<211> LENGTH: 12
<212> TYPE: DNA
<213> ORGANISM: Artificial Sequence
<220> FEATURE:
<223> OTHER INFORMATION: Synthetic

<400> SEQUENCE: 1289
agatgataac gg                                                            12

<210> SEQ ID NO 1290
<211> LENGTH: 20
<212> TYPE: DNA
<213> ORGANISM: Artificial Sequence
<220> FEATURE:
<223> OTHER INFORMATION: Synthetic

<400> SEQUENCE: 1290
gccgtgccgt agctatccgg                                                    20

<210> SEQ ID NO 1291
<211> LENGTH: 12
<212> TYPE: DNA
<213> ORGANISM: Artificial Sequence
<220> FEATURE:
<223> OTHER INFORMATION: Synthetic

<400> SEQUENCE: 1291
agctagccta gg                                                            12

```
<210> SEQ ID NO 1292
<211> LENGTH: 20
<212> TYPE: DNA
<213> ORGANISM: Artificial Sequence
<220> FEATURE:
<223> OTHER INFORMATION: Synthetic

<400> SEQUENCE: 1292
tgtactccag cttgtgcccc                                              20

<210> SEQ ID NO 1293
<211> LENGTH: 12
<212> TYPE: DNA
<213> ORGANISM: Artificial Sequence
<220> FEATURE:
<223> OTHER INFORMATION: Synthetic

<400> SEQUENCE: 1293
agctagccta gg                                                      12

<210> SEQ ID NO 1294
<211> LENGTH: 20
<212> TYPE: DNA
<213> ORGANISM: Artificial Sequence
<220> FEATURE:
<223> OTHER INFORMATION: Synthetic

<400> SEQUENCE: 1294
tgtactccag cttgtgcccc                                              20

<210> SEQ ID NO 1295
<211> LENGTH: 12
<212> TYPE: DNA
<213> ORGANISM: Artificial Sequence
<220> FEATURE:
<223> OTHER INFORMATION: Synthetic

<400> SEQUENCE: 1295
agatgggttc cg                                                      12

<210> SEQ ID NO 1296
<211> LENGTH: 20
<212> TYPE: DNA
<213> ORGANISM: Artificial Sequence
<220> FEATURE:
<223> OTHER INFORMATION: Synthetic

<400> SEQUENCE: 1296
gtccgttcga caatttcaca                                              20

<210> SEQ ID NO 1297
<211> LENGTH: 12
<212> TYPE: DNA
<213> ORGANISM: Artificial Sequence
<220> FEATURE:
<223> OTHER INFORMATION: Synthetic

<400> SEQUENCE: 1297
agatcgacca cc                                                      12

<210> SEQ ID NO 1298
<211> LENGTH: 20
<212> TYPE: DNA
<213> ORGANISM: Artificial Sequence
<220> FEATURE:
<223> OTHER INFORMATION: Synthetic
```

<400> SEQUENCE: 1298
ggacgctaaa ccaacggtgc                                               20

<210> SEQ ID NO 1299
<211> LENGTH: 12
<212> TYPE: DNA
<213> ORGANISM: Artificial Sequence
<220> FEATURE:
<223> OTHER INFORMATION: Synthetic

<400> SEQUENCE: 1299
ctatatatga cc                                                       12

<210> SEQ ID NO 1300
<211> LENGTH: 20
<212> TYPE: DNA
<213> ORGANISM: Artificial Sequence
<220> FEATURE:
<223> OTHER INFORMATION: Synthetic

<400> SEQUENCE: 1300
caaggaggac ggcaacatcc                                               20

<210> SEQ ID NO 1301
<211> LENGTH: 12
<212> TYPE: DNA
<213> ORGANISM: Artificial Sequence
<220> FEATURE:
<223> OTHER INFORMATION: Synthetic

<400> SEQUENCE: 1301
ctcaatttac ag                                                       12

<210> SEQ ID NO 1302
<211> LENGTH: 20
<212> TYPE: DNA
<213> ORGANISM: Artificial Sequence
<220> FEATURE:
<223> OTHER INFORMATION: Synthetic

<400> SEQUENCE: 1302
gtccgttcga caatttcaca                                               20

<210> SEQ ID NO 1303
<211> LENGTH: 12
<212> TYPE: DNA
<213> ORGANISM: Artificial Sequence
<220> FEATURE:
<223> OTHER INFORMATION: Synthetic

<400> SEQUENCE: 1303
agcgccgtca tt                                                       12

<210> SEQ ID NO 1304
<211> LENGTH: 20
<212> TYPE: DNA
<213> ORGANISM: Artificial Sequence
<220> FEATURE:
<223> OTHER INFORMATION: Synthetic

<400> SEQUENCE: 1304
tgtactccag cttgtgcccc                                               20

<210> SEQ ID NO 1305
<211> LENGTH: 12

<212> TYPE: DNA
<213> ORGANISM: Artificial Sequence
<220> FEATURE:
<223> OTHER INFORMATION: Synthetic

<400> SEQUENCE: 1305
gaagtgggca ac                                                       12

<210> SEQ ID NO 1306
<211> LENGTH: 20
<212> TYPE: DNA
<213> ORGANISM: Artificial Sequence
<220> FEATURE:
<223> OTHER INFORMATION: Synthetic

<400> SEQUENCE: 1306
gctgcttgcg ataccaatag                                               20

<210> SEQ ID NO 1307
<211> LENGTH: 12
<212> TYPE: DNA
<213> ORGANISM: Artificial Sequence
<220> FEATURE:
<223> OTHER INFORMATION: Synthetic

<400> SEQUENCE: 1307
gaactagcca ct                                                       12

<210> SEQ ID NO 1308
<211> LENGTH: 20
<212> TYPE: DNA
<213> ORGANISM: Artificial Sequence
<220> FEATURE:
<223> OTHER INFORMATION: Synthetic

<400> SEQUENCE: 1308
tgtactccag cttgtgcccc                                               20

<210> SEQ ID NO 1309
<211> LENGTH: 12
<212> TYPE: DNA
<213> ORGANISM: Artificial Sequence
<220> FEATURE:
<223> OTHER INFORMATION: Synthetic

<400> SEQUENCE: 1309
agctagccta gg                                                       12

<210> SEQ ID NO 1310
<211> LENGTH: 20
<212> TYPE: DNA
<213> ORGANISM: Artificial Sequence
<220> FEATURE:
<223> OTHER INFORMATION: Synthetic

<400> SEQUENCE: 1310
tgtactccag cttgtgcccc                                               20

<210> SEQ ID NO 1311
<211> LENGTH: 12
<212> TYPE: DNA
<213> ORGANISM: Artificial Sequence
<220> FEATURE:
<223> OTHER INFORMATION: Synthetic

<400> SEQUENCE: 1311

```
agatcgacca cc                                                        12

<210> SEQ ID NO 1312
<211> LENGTH: 20
<212> TYPE: DNA
<213> ORGANISM: Artificial Sequence
<220> FEATURE:
<223> OTHER INFORMATION: Synthetic

<400> SEQUENCE: 1312
ggacgctaaa ccaacggtgc                                                20

<210> SEQ ID NO 1313
<211> LENGTH: 12
<212> TYPE: DNA
<213> ORGANISM: Artificial Sequence
<220> FEATURE:
<223> OTHER INFORMATION: Synthetic

<400> SEQUENCE: 1313
agcacggaga ca                                                        12

<210> SEQ ID NO 1314
<211> LENGTH: 20
<212> TYPE: DNA
<213> ORGANISM: Artificial Sequence
<220> FEATURE:
<223> OTHER INFORMATION: Synthetic

<400> SEQUENCE: 1314
gtacagctaa gttaaactcg                                                20

<210> SEQ ID NO 1315
<211> LENGTH: 12
<212> TYPE: DNA
<213> ORGANISM: Artificial Sequence
<220> FEATURE:
<223> OTHER INFORMATION: Synthetic

<400> SEQUENCE: 1315
gacaagtaca ct                                                        12

<210> SEQ ID NO 1316
<211> LENGTH: 20
<212> TYPE: DNA
<213> ORGANISM: Artificial Sequence
<220> FEATURE:
<223> OTHER INFORMATION: Synthetic

<400> SEQUENCE: 1316
gtccgttcga caatttcaca                                                20

<210> SEQ ID NO 1317
<211> LENGTH: 12
<212> TYPE: DNA
<213> ORGANISM: Artificial Sequence
<220> FEATURE:
<223> OTHER INFORMATION: Synthetic

<400> SEQUENCE: 1317
agatgataac gg                                                        12

<210> SEQ ID NO 1318
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 1318
gccgtgccgt agctatccgg                                               20

<210> SEQ ID NO 1319
<211> LENGTH: 12
<212> TYPE: DNA
<213> ORGANISM: Artificial Sequence
<220> FEATURE:
<223> OTHER INFORMATION: Synthetic

<400> SEQUENCE: 1319
agatgataac gg                                                       12

<210> SEQ ID NO 1320
<211> LENGTH: 20
<212> TYPE: DNA
<213> ORGANISM: Artificial Sequence
<220> FEATURE:
<223> OTHER INFORMATION: Synthetic

<400> SEQUENCE: 1320
gccgtgccgt agctatccgg                                               20

<210> SEQ ID NO 1321
<211> LENGTH: 12
<212> TYPE: DNA
<213> ORGANISM: Artificial Sequence
<220> FEATURE:
<223> OTHER INFORMATION: Synthetic

<400> SEQUENCE: 1321
ctatatatga cc                                                       12

<210> SEQ ID NO 1322
<211> LENGTH: 20
<212> TYPE: DNA
<213> ORGANISM: Artificial Sequence
<220> FEATURE:
<223> OTHER INFORMATION: Synthetic

<400> SEQUENCE: 1322
caaggaggac ggcaacatcc                                               20

<210> SEQ ID NO 1323
<211> LENGTH: 12
<212> TYPE: DNA
<213> ORGANISM: Artificial Sequence
<220> FEATURE:
<223> OTHER INFORMATION: Synthetic

<400> SEQUENCE: 1323
ctcactgaca ct                                                       12

<210> SEQ ID NO 1324
<211> LENGTH: 20
<212> TYPE: DNA
<213> ORGANISM: Artificial Sequence
<220> FEATURE:
<223> OTHER INFORMATION: Synthetic

<400> SEQUENCE: 1324
gccgtgccgt agctatccgg                                               20
```

<210> SEQ ID NO 1325
<211> LENGTH: 12
<212> TYPE: DNA
<213> ORGANISM: Artificial Sequence
<220> FEATURE:
<223> OTHER INFORMATION: Synthetic

<400> SEQUENCE: 1325
ctcaatttac ag                                                         12

<210> SEQ ID NO 1326
<211> LENGTH: 20
<212> TYPE: DNA
<213> ORGANISM: Artificial Sequence
<220> FEATURE:
<223> OTHER INFORMATION: Synthetic

<400> SEQUENCE: 1326
gtccgttcga caatttcaca                                                 20

<210> SEQ ID NO 1327
<211> LENGTH: 12
<212> TYPE: DNA
<213> ORGANISM: Artificial Sequence
<220> FEATURE:
<223> OTHER INFORMATION: Synthetic

<400> SEQUENCE: 1327
gacaggctac ct                                                         12

<210> SEQ ID NO 1328
<211> LENGTH: 20
<212> TYPE: DNA
<213> ORGANISM: Artificial Sequence
<220> FEATURE:
<223> OTHER INFORMATION: Synthetic

<400> SEQUENCE: 1328
ggacgctaaa ccaacggtgc                                                 20

<210> SEQ ID NO 1329
<211> LENGTH: 12
<212> TYPE: DNA
<213> ORGANISM: Artificial Sequence
<220> FEATURE:
<223> OTHER INFORMATION: Synthetic

<400> SEQUENCE: 1329
agatgggttc cg                                                         12

<210> SEQ ID NO 1330
<211> LENGTH: 20
<212> TYPE: DNA
<213> ORGANISM: Artificial Sequence
<220> FEATURE:
<223> OTHER INFORMATION: Synthetic

<400> SEQUENCE: 1330
gtccgttcga caatttcaca                                                 20

<210> SEQ ID NO 1331
<211> LENGTH: 12
<212> TYPE: DNA
<213> ORGANISM: Artificial Sequence
<220> FEATURE:
<223> OTHER INFORMATION: Synthetic

```
<400> SEQUENCE: 1331
gacaagtaca ct                                                          12

<210> SEQ ID NO 1332
<211> LENGTH: 20
<212> TYPE: DNA
<213> ORGANISM: Artificial Sequence
<220> FEATURE:
<223> OTHER INFORMATION: Synthetic

<400> SEQUENCE: 1332
gtccgttcga caatttcaca                                                  20

<210> SEQ ID NO 1333
<211> LENGTH: 12
<212> TYPE: DNA
<213> ORGANISM: Artificial Sequence
<220> FEATURE:
<223> OTHER INFORMATION: Synthetic

<400> SEQUENCE: 1333
agcacggaga ca                                                          12

<210> SEQ ID NO 1334
<211> LENGTH: 20
<212> TYPE: DNA
<213> ORGANISM: Artificial Sequence
<220> FEATURE:
<223> OTHER INFORMATION: Synthetic

<400> SEQUENCE: 1334
gtacagctaa gttaaactcg                                                  20

<210> SEQ ID NO 1335
<211> LENGTH: 12
<212> TYPE: DNA
<213> ORGANISM: Artificial Sequence
<220> FEATURE:
<223> OTHER INFORMATION: Synthetic

<400> SEQUENCE: 1335
agatgggttc cg                                                          12

<210> SEQ ID NO 1336
<211> LENGTH: 20
<212> TYPE: DNA
<213> ORGANISM: Artificial Sequence
<220> FEATURE:
<223> OTHER INFORMATION: Synthetic

<400> SEQUENCE: 1336
gtccgttcga caatttcaca                                                  20

<210> SEQ ID NO 1337
<211> LENGTH: 12
<212> TYPE: DNA
<213> ORGANISM: Artificial Sequence
<220> FEATURE:
<223> OTHER INFORMATION: Synthetic

<400> SEQUENCE: 1337
agatgggttc cg                                                          12

<210> SEQ ID NO 1338
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 1338
gtccgttcga caatttcaca                                               20

<210> SEQ ID NO 1339
<211> LENGTH: 12
<212> TYPE: DNA
<213> ORGANISM: Artificial Sequence
<220> FEATURE:
<223> OTHER INFORMATION: Synthetic

<400> SEQUENCE: 1339
gaactcagga ca                                                       12

<210> SEQ ID NO 1340
<211> LENGTH: 20
<212> TYPE: DNA
<213> ORGANISM: Artificial Sequence
<220> FEATURE:
<223> OTHER INFORMATION: Synthetic

<400> SEQUENCE: 1340
caaggaggac ggcaacatcc                                               20

<210> SEQ ID NO 1341
<211> LENGTH: 12
<212> TYPE: DNA
<213> ORGANISM: Artificial Sequence
<220> FEATURE:
<223> OTHER INFORMATION: Synthetic

<400> SEQUENCE: 1341
ctatatatga cc                                                       12

<210> SEQ ID NO 1342
<211> LENGTH: 20
<212> TYPE: DNA
<213> ORGANISM: Artificial Sequence
<220> FEATURE:
<223> OTHER INFORMATION: Synthetic

<400> SEQUENCE: 1342
caaggaggac ggcaacatcc                                               20

<210> SEQ ID NO 1343
<211> LENGTH: 12
<212> TYPE: DNA
<213> ORGANISM: Artificial Sequence
<220> FEATURE:
<223> OTHER INFORMATION: Synthetic

<400> SEQUENCE: 1343
gaactcagga ca                                                       12

<210> SEQ ID NO 1344
<211> LENGTH: 20
<212> TYPE: DNA
<213> ORGANISM: Artificial Sequence
<220> FEATURE:
<223> OTHER INFORMATION: Synthetic

<400> SEQUENCE: 1344
```
caaggaggac ggcaacatcc                                              20

<210> SEQ ID NO 1345
<211> LENGTH: 12
<212> TYPE: DNA
<213> ORGANISM: Artificial Sequence
<220> FEATURE:
<223> OTHER INFORMATION: Synthetic

<400> SEQUENCE: 1345
agattcatga cg                                                      12

<210> SEQ ID NO 1346
<211> LENGTH: 20
<212> TYPE: DNA
<213> ORGANISM: Artificial Sequence
<220> FEATURE:
<223> OTHER INFORMATION: Synthetic

<400> SEQUENCE: 1346
caacatcctg gggcacaagc                                              20

<210> SEQ ID NO 1347
<211> LENGTH: 12
<212> TYPE: DNA
<213> ORGANISM: Artificial Sequence
<220> FEATURE:
<223> OTHER INFORMATION: Synthetic

<400> SEQUENCE: 1347
agcgccgtca tt                                                      12

<210> SEQ ID NO 1348
<211> LENGTH: 20
<212> TYPE: DNA
<213> ORGANISM: Artificial Sequence
<220> FEATURE:
<223> OTHER INFORMATION: Synthetic

<400> SEQUENCE: 1348
tgtactccag cttgtgcccc                                              20

<210> SEQ ID NO 1349
<211> LENGTH: 12
<212> TYPE: DNA
<213> ORGANISM: Artificial Sequence
<220> FEATURE:
<223> OTHER INFORMATION: Synthetic

<400> SEQUENCE: 1349
agcaacttca ct                                                      12

<210> SEQ ID NO 1350
<211> LENGTH: 20
<212> TYPE: DNA
<213> ORGANISM: Artificial Sequence
<220> FEATURE:
<223> OTHER INFORMATION: Synthetic

<400> SEQUENCE: 1350
gtccgttcga caatttcaca                                              20

<210> SEQ ID NO 1351
<211> LENGTH: 12
<212> TYPE: DNA

```
<213> ORGANISM: Artificial Sequence
<220> FEATURE:
<223> OTHER INFORMATION: Synthetic

<400> SEQUENCE: 1351
agatgggttc cg                                                         12

<210> SEQ ID NO 1352
<211> LENGTH: 20
<212> TYPE: DNA
<213> ORGANISM: Artificial Sequence
<220> FEATURE:
<223> OTHER INFORMATION: Synthetic

<400> SEQUENCE: 1352
gtccgttcga caatttcaca                                                 20

<210> SEQ ID NO 1353
<211> LENGTH: 12
<212> TYPE: DNA
<213> ORGANISM: Artificial Sequence
<220> FEATURE:
<223> OTHER INFORMATION: Synthetic

<400> SEQUENCE: 1353
agagctgcta cg                                                         12

<210> SEQ ID NO 1354
<211> LENGTH: 20
<212> TYPE: DNA
<213> ORGANISM: Artificial Sequence
<220> FEATURE:
<223> OTHER INFORMATION: Synthetic

<400> SEQUENCE: 1354
gccgtgccgt agctatccgg                                                 20

<210> SEQ ID NO 1355
<211> LENGTH: 12
<212> TYPE: DNA
<213> ORGANISM: Artificial Sequence
<220> FEATURE:
<223> OTHER INFORMATION: Synthetic

<400> SEQUENCE: 1355
tccaaagaga ca                                                         12

<210> SEQ ID NO 1356
<211> LENGTH: 20
<212> TYPE: DNA
<213> ORGANISM: Artificial Sequence
<220> FEATURE:
<223> OTHER INFORMATION: Synthetic

<400> SEQUENCE: 1356
aaggaggacg gcaacatcct                                                 20

<210> SEQ ID NO 1357
<211> LENGTH: 12
<212> TYPE: DNA
<213> ORGANISM: Artificial Sequence
<220> FEATURE:
<223> OTHER INFORMATION: Synthetic

<400> SEQUENCE: 1357
agccaccagt at                                                         12
```

```
<210> SEQ ID NO 1358
<211> LENGTH: 20
<212> TYPE: DNA
<213> ORGANISM: Artificial Sequence
<220> FEATURE:
<223> OTHER INFORMATION: Synthetic

<400> SEQUENCE: 1358
caaggaggac ggcaacatcc                                                 20

<210> SEQ ID NO 1359
<211> LENGTH: 12
<212> TYPE: DNA
<213> ORGANISM: Artificial Sequence
<220> FEATURE:
<223> OTHER INFORMATION: Synthetic

<400> SEQUENCE: 1359
tccagagcac ct                                                         12

<210> SEQ ID NO 1360
<211> LENGTH: 20
<212> TYPE: DNA
<213> ORGANISM: Artificial Sequence
<220> FEATURE:
<223> OTHER INFORMATION: Synthetic

<400> SEQUENCE: 1360
ggacgctaaa ccaacggtgc                                                 20

<210> SEQ ID NO 1361
<211> LENGTH: 12
<212> TYPE: DNA
<213> ORGANISM: Artificial Sequence
<220> FEATURE:
<223> OTHER INFORMATION: Synthetic

<400> SEQUENCE: 1361
agcagtgtac ct                                                         12

<210> SEQ ID NO 1362
<211> LENGTH: 20
<212> TYPE: DNA
<213> ORGANISM: Artificial Sequence
<220> FEATURE:
<223> OTHER INFORMATION: Synthetic

<400> SEQUENCE: 1362
gctgcttgcg ataccaatag                                                 20

<210> SEQ ID NO 1363
<211> LENGTH: 12
<212> TYPE: DNA
<213> ORGANISM: Artificial Sequence
<220> FEATURE:
<223> OTHER INFORMATION: Synthetic

<400> SEQUENCE: 1363
gaattagtga cc                                                         12

<210> SEQ ID NO 1364
<211> LENGTH: 20
<212> TYPE: DNA
<213> ORGANISM: Artificial Sequence
<220> FEATURE:
```

<223> OTHER INFORMATION: Synthetic

<400> SEQUENCE: 1364
gtacagctaa gttaaactcg                                               20

<210> SEQ ID NO 1365
<211> LENGTH: 12
<212> TYPE: DNA
<213> ORGANISM: Artificial Sequence
<220> FEATURE:
<223> OTHER INFORMATION: Synthetic

<400> SEQUENCE: 1365
agcgccgtca tt                                                       12

<210> SEQ ID NO 1366
<211> LENGTH: 20
<212> TYPE: DNA
<213> ORGANISM: Artificial Sequence
<220> FEATURE:
<223> OTHER INFORMATION: Synthetic

<400> SEQUENCE: 1366
tgtactccag cttgtgcccc                                               20

<210> SEQ ID NO 1367
<211> LENGTH: 12
<212> TYPE: DNA
<213> ORGANISM: Artificial Sequence
<220> FEATURE:
<223> OTHER INFORMATION: Synthetic

<400> SEQUENCE: 1367
agctagccta gg                                                       12

<210> SEQ ID NO 1368
<211> LENGTH: 20
<212> TYPE: DNA
<213> ORGANISM: Artificial Sequence
<220> FEATURE:
<223> OTHER INFORMATION: Synthetic

<400> SEQUENCE: 1368
tgtactccag cttgtgcccc                                               20

<210> SEQ ID NO 1369
<211> LENGTH: 12
<212> TYPE: DNA
<213> ORGANISM: Artificial Sequence
<220> FEATURE:
<223> OTHER INFORMATION: Synthetic

<400> SEQUENCE: 1369
agctctgaca ca                                                       12

<210> SEQ ID NO 1370
<211> LENGTH: 20
<212> TYPE: DNA
<213> ORGANISM: Artificial Sequence
<220> FEATURE:
<223> OTHER INFORMATION: Synthetic

<400> SEQUENCE: 1370
tgtactccag cttgtgcccc                                               20

-continued

```
<210> SEQ ID NO 1371
<211> LENGTH: 12
<212> TYPE: DNA
<213> ORGANISM: Artificial Sequence
<220> FEATURE:
<223> OTHER INFORMATION: Synthetic

<400> SEQUENCE: 1371
catgatccca ca                                                          12

<210> SEQ ID NO 1372
<211> LENGTH: 20
<212> TYPE: DNA
<213> ORGANISM: Artificial Sequence
<220> FEATURE:
<223> OTHER INFORMATION: Synthetic

<400> SEQUENCE: 1372
tgtactccag cttgtgcccc                                                  20

<210> SEQ ID NO 1373
<211> LENGTH: 12
<212> TYPE: DNA
<213> ORGANISM: Artificial Sequence
<220> FEATURE:
<223> OTHER INFORMATION: Synthetic

<400> SEQUENCE: 1373
ctcactgaca ct                                                          12

<210> SEQ ID NO 1374
<211> LENGTH: 20
<212> TYPE: DNA
<213> ORGANISM: Artificial Sequence
<220> FEATURE:
<223> OTHER INFORMATION: Synthetic

<400> SEQUENCE: 1374
gccgtgccgt agctatccgg                                                  20

<210> SEQ ID NO 1375
<211> LENGTH: 12
<212> TYPE: DNA
<213> ORGANISM: Artificial Sequence
<220> FEATURE:
<223> OTHER INFORMATION: Synthetic

<400> SEQUENCE: 1375
gaatgaacca cg                                                          12

<210> SEQ ID NO 1376
<211> LENGTH: 20
<212> TYPE: DNA
<213> ORGANISM: Artificial Sequence
<220> FEATURE:
<223> OTHER INFORMATION: Synthetic

<400> SEQUENCE: 1376
aaggaggacg gcaacatcct                                                  20

<210> SEQ ID NO 1377
<211> LENGTH: 12
<212> TYPE: DNA
<213> ORGANISM: Artificial Sequence
<220> FEATURE:
<223> OTHER INFORMATION: Synthetic
```

```
<400> SEQUENCE: 1377
ctatatatga cc                                                    12

<210> SEQ ID NO 1378
<211> LENGTH: 20
<212> TYPE: DNA
<213> ORGANISM: Artificial Sequence
<220> FEATURE:
<223> OTHER INFORMATION: Synthetic

<400> SEQUENCE: 1378
caaggaggac ggcaacatcc                                            20

<210> SEQ ID NO 1379
<211> LENGTH: 12
<212> TYPE: DNA
<213> ORGANISM: Artificial Sequence
<220> FEATURE:
<223> OTHER INFORMATION: Synthetic

<400> SEQUENCE: 1379
gaactagcca ct                                                    12

<210> SEQ ID NO 1380
<211> LENGTH: 20
<212> TYPE: DNA
<213> ORGANISM: Artificial Sequence
<220> FEATURE:
<223> OTHER INFORMATION: Synthetic

<400> SEQUENCE: 1380
tgtactccag cttgtgcccc                                            20

<210> SEQ ID NO 1381
<211> LENGTH: 12
<212> TYPE: DNA
<213> ORGANISM: Artificial Sequence
<220> FEATURE:
<223> OTHER INFORMATION: Synthetic

<400> SEQUENCE: 1381
gacaagtaca ct                                                    12

<210> SEQ ID NO 1382
<211> LENGTH: 20
<212> TYPE: DNA
<213> ORGANISM: Artificial Sequence
<220> FEATURE:
<223> OTHER INFORMATION: Synthetic

<400> SEQUENCE: 1382
gtccgttcga caatttcaca                                            20

<210> SEQ ID NO 1383
<211> LENGTH: 12
<212> TYPE: DNA
<213> ORGANISM: Artificial Sequence
<220> FEATURE:
<223> OTHER INFORMATION: Synthetic

<400> SEQUENCE: 1383
agcagcccta gc                                                    12

<210> SEQ ID NO 1384
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 1384
gctgcttgcg ataccaatag                                          20

<210> SEQ ID NO 1385
<211> LENGTH: 12
<212> TYPE: DNA
<213> ORGANISM: Artificial Sequence
<220> FEATURE:
<223> OTHER INFORMATION: Synthetic

<400> SEQUENCE: 1385
agcgacctta ca                                                  12

<210> SEQ ID NO 1386
<211> LENGTH: 20
<212> TYPE: DNA
<213> ORGANISM: Artificial Sequence
<220> FEATURE:
<223> OTHER INFORMATION: Synthetic

<400> SEQUENCE: 1386
aggaggacgg caacatcctg                                          20

<210> SEQ ID NO 1387
<211> LENGTH: 12
<212> TYPE: DNA
<213> ORGANISM: Artificial Sequence
<220> FEATURE:
<223> OTHER INFORMATION: Synthetic

<400> SEQUENCE: 1387
gaactcagga ca                                                  12

<210> SEQ ID NO 1388
<211> LENGTH: 20
<212> TYPE: DNA
<213> ORGANISM: Artificial Sequence
<220> FEATURE:
<223> OTHER INFORMATION: Synthetic

<400> SEQUENCE: 1388
caaggaggac ggcaacatcc                                          20

<210> SEQ ID NO 1389
<211> LENGTH: 12
<212> TYPE: DNA
<213> ORGANISM: Artificial Sequence
<220> FEATURE:
<223> OTHER INFORMATION: Synthetic

<400> SEQUENCE: 1389
gacaagtaca ct                                                  12

<210> SEQ ID NO 1390
<211> LENGTH: 20
<212> TYPE: DNA
<213> ORGANISM: Artificial Sequence
<220> FEATURE:
<223> OTHER INFORMATION: Synthetic

<400> SEQUENCE: 1390
```
gtccgttcga caatttcaca                                          20

<210> SEQ ID NO 1391
<211> LENGTH: 12
<212> TYPE: DNA
<213> ORGANISM: Artificial Sequence
<220> FEATURE:
<223> OTHER INFORMATION: Synthetic

<400> SEQUENCE: 1391
agcgacctta ca                                                  12

<210> SEQ ID NO 1392
<211> LENGTH: 20
<212> TYPE: DNA
<213> ORGANISM: Artificial Sequence
<220> FEATURE:
<223> OTHER INFORMATION: Synthetic

<400> SEQUENCE: 1392
aggaggacgg caacatcctg                                          20

<210> SEQ ID NO 1393
<211> LENGTH: 12
<212> TYPE: DNA
<213> ORGANISM: Artificial Sequence
<220> FEATURE:
<223> OTHER INFORMATION: Synthetic

<400> SEQUENCE: 1393
gacatgcgta gc                                                  12

<210> SEQ ID NO 1394
<211> LENGTH: 20
<212> TYPE: DNA
<213> ORGANISM: Artificial Sequence
<220> FEATURE:
<223> OTHER INFORMATION: Synthetic

<400> SEQUENCE: 1394
gccgtgccgt agctatccgg                                          20

<210> SEQ ID NO 1395
<211> LENGTH: 12
<212> TYPE: DNA
<213> ORGANISM: Artificial Sequence
<220> FEATURE:
<223> OTHER INFORMATION: Synthetic

<400> SEQUENCE: 1395
agatcgacca cc                                                  12

<210> SEQ ID NO 1396
<211> LENGTH: 20
<212> TYPE: DNA
<213> ORGANISM: Artificial Sequence
<220> FEATURE:
<223> OTHER INFORMATION: Synthetic

<400> SEQUENCE: 1396
ggacgctaaa ccaacggtgc                                          20

<210> SEQ ID NO 1397
<211> LENGTH: 12
<212> TYPE: DNA
<213> ORGANISM: Artificial Sequence

```
<220> FEATURE:
<223> OTHER INFORMATION: Synthetic

<400> SEQUENCE: 1397
gaatgaacca cg                                                          12

<210> SEQ ID NO 1398
<211> LENGTH: 20
<212> TYPE: DNA
<213> ORGANISM: Artificial Sequence
<220> FEATURE:
<223> OTHER INFORMATION: Synthetic

<400> SEQUENCE: 1398
aaggaggacg gcaacatcct                                                  20

<210> SEQ ID NO 1399
<211> LENGTH: 12
<212> TYPE: DNA
<213> ORGANISM: Artificial Sequence
<220> FEATURE:
<223> OTHER INFORMATION: Synthetic

<400> SEQUENCE: 1399
agctctgaca ca                                                          12

<210> SEQ ID NO 1400
<211> LENGTH: 20
<212> TYPE: DNA
<213> ORGANISM: Artificial Sequence
<220> FEATURE:
<223> OTHER INFORMATION: Synthetic

<400> SEQUENCE: 1400
tgtactccag cttgtgcccc                                                  20

<210> SEQ ID NO 1401
<211> LENGTH: 12
<212> TYPE: DNA
<213> ORGANISM: Artificial Sequence
<220> FEATURE:
<223> OTHER INFORMATION: Synthetic

<400> SEQUENCE: 1401
tccatcaata cg                                                          12

<210> SEQ ID NO 1402
<211> LENGTH: 20
<212> TYPE: DNA
<213> ORGANISM: Artificial Sequence
<220> FEATURE:
<223> OTHER INFORMATION: Synthetic

<400> SEQUENCE: 1402
gtacagctaa gttaaactcg                                                  20

<210> SEQ ID NO 1403
<211> LENGTH: 12
<212> TYPE: DNA
<213> ORGANISM: Artificial Sequence
<220> FEATURE:
<223> OTHER INFORMATION: Synthetic

<400> SEQUENCE: 1403
gacaggctac ct                                                          12
```

<210> SEQ ID NO 1404
<211> LENGTH: 20
<212> TYPE: DNA
<213> ORGANISM: Artificial Sequence
<220> FEATURE:
<223> OTHER INFORMATION: Synthetic

<400> SEQUENCE: 1404
ggacgctaaa ccaacggtgc                                               20

<210> SEQ ID NO 1405
<211> LENGTH: 12
<212> TYPE: DNA
<213> ORGANISM: Artificial Sequence
<220> FEATURE:
<223> OTHER INFORMATION: Synthetic

<400> SEQUENCE: 1405
ctcactgaca ct                                                       12

<210> SEQ ID NO 1406
<211> LENGTH: 20
<212> TYPE: DNA
<213> ORGANISM: Artificial Sequence
<220> FEATURE:
<223> OTHER INFORMATION: Synthetic

<400> SEQUENCE: 1406
gccgtgccgt agctatccgg                                               20

<210> SEQ ID NO 1407
<211> LENGTH: 12
<212> TYPE: DNA
<213> ORGANISM: Artificial Sequence
<220> FEATURE:
<223> OTHER INFORMATION: Synthetic

<400> SEQUENCE: 1407
agcgacctta ca                                                       12

<210> SEQ ID NO 1408
<211> LENGTH: 20
<212> TYPE: DNA
<213> ORGANISM: Artificial Sequence
<220> FEATURE:
<223> OTHER INFORMATION: Synthetic

<400> SEQUENCE: 1408
aggaggacgg caacatcctg                                               20

<210> SEQ ID NO 1409
<211> LENGTH: 12
<212> TYPE: DNA
<213> ORGANISM: Artificial Sequence
<220> FEATURE:
<223> OTHER INFORMATION: Synthetic

<400> SEQUENCE: 1409
ctagatgtta gc                                                       12

<210> SEQ ID NO 1410
<211> LENGTH: 20
<212> TYPE: DNA
<213> ORGANISM: Artificial Sequence
<220> FEATURE:
<223> OTHER INFORMATION: Synthetic -continued

```
<400> SEQUENCE: 1410
gtacagctaa gttaaactcg                                              20

<210> SEQ ID NO 1411
<211> LENGTH: 12
<212> TYPE: DNA
<213> ORGANISM: Artificial Sequence
<220> FEATURE:
<223> OTHER INFORMATION: Synthetic

<400> SEQUENCE: 1411
agcgccgtca tt                                                      12

<210> SEQ ID NO 1412
<211> LENGTH: 20
<212> TYPE: DNA
<213> ORGANISM: Artificial Sequence
<220> FEATURE:
<223> OTHER INFORMATION: Synthetic

<400> SEQUENCE: 1412
tgtactccag cttgtgcccc                                              20

<210> SEQ ID NO 1413
<211> LENGTH: 12
<212> TYPE: DNA
<213> ORGANISM: Artificial Sequence
<220> FEATURE:
<223> OTHER INFORMATION: Synthetic

<400> SEQUENCE: 1413
gacaacgaga ac                                                      12

<210> SEQ ID NO 1414
<211> LENGTH: 20
<212> TYPE: DNA
<213> ORGANISM: Artificial Sequence
<220> FEATURE:
<223> OTHER INFORMATION: Synthetic

<400> SEQUENCE: 1414
gccgtgccgt agctatccgg                                              20

<210> SEQ ID NO 1415
<211> LENGTH: 12
<212> TYPE: DNA
<213> ORGANISM: Artificial Sequence
<220> FEATURE:
<223> OTHER INFORMATION: Synthetic

<400> SEQUENCE: 1415
gaatggacag cg                                                      12

<210> SEQ ID NO 1416
<211> LENGTH: 20
<212> TYPE: DNA
<213> ORGANISM: Artificial Sequence
<220> FEATURE:
<223> OTHER INFORMATION: Synthetic

<400> SEQUENCE: 1416
aggaggacgg caacatcctg                                              20

<210> SEQ ID NO 1417
```

```
<211> LENGTH: 12
<212> TYPE: DNA
<213> ORGANISM: Artificial Sequence
<220> FEATURE:
<223> OTHER INFORMATION: Synthetic

<400> SEQUENCE: 1417
gaacgcgaaa gc                                                          12

<210> SEQ ID NO 1418
<211> LENGTH: 20
<212> TYPE: DNA
<213> ORGANISM: Artificial Sequence
<220> FEATURE:
<223> OTHER INFORMATION: Synthetic

<400> SEQUENCE: 1418
caacatcctg gggcacaagc                                                  20

<210> SEQ ID NO 1419
<211> LENGTH: 12
<212> TYPE: DNA
<213> ORGANISM: Artificial Sequence
<220> FEATURE:
<223> OTHER INFORMATION: Synthetic

<400> SEQUENCE: 1419
gacaagtaca ct                                                          12

<210> SEQ ID NO 1420
<211> LENGTH: 20
<212> TYPE: DNA
<213> ORGANISM: Artificial Sequence
<220> FEATURE:
<223> OTHER INFORMATION: Synthetic

<400> SEQUENCE: 1420
gtccgttcga caatttcaca                                                  20

<210> SEQ ID NO 1421
<211> LENGTH: 12
<212> TYPE: DNA
<213> ORGANISM: Artificial Sequence
<220> FEATURE:
<223> OTHER INFORMATION: Synthetic

<400> SEQUENCE: 1421
ctcactgaca ct                                                          12

<210> SEQ ID NO 1422
<211> LENGTH: 20
<212> TYPE: DNA
<213> ORGANISM: Artificial Sequence
<220> FEATURE:
<223> OTHER INFORMATION: Synthetic

<400> SEQUENCE: 1422
gccgtgccgt agctatccgg                                                  20

<210> SEQ ID NO 1423
<211> LENGTH: 12
<212> TYPE: DNA
<213> ORGANISM: Artificial Sequence
<220> FEATURE:
<223> OTHER INFORMATION: Synthetic

<400> SEQUENCE: 1423
```

```
tccaaagaga ca                                                           12

<210> SEQ ID NO 1424
<211> LENGTH: 20
<212> TYPE: DNA
<213> ORGANISM: Artificial Sequence
<220> FEATURE:
<223> OTHER INFORMATION: Synthetic

<400> SEQUENCE: 1424
aaggaggacg gcaacatcct                                                   20

<210> SEQ ID NO 1425
<211> LENGTH: 12
<212> TYPE: DNA
<213> ORGANISM: Artificial Sequence
<220> FEATURE:
<223> OTHER INFORMATION: Synthetic

<400> SEQUENCE: 1425
tccagagcac ct                                                           12

<210> SEQ ID NO 1426
<211> LENGTH: 20
<212> TYPE: DNA
<213> ORGANISM: Artificial Sequence
<220> FEATURE:
<223> OTHER INFORMATION: Synthetic

<400> SEQUENCE: 1426
ggacgctaaa ccaacggtgc                                                   20

<210> SEQ ID NO 1427
<211> LENGTH: 12
<212> TYPE: DNA
<213> ORGANISM: Artificial Sequence
<220> FEATURE:
<223> OTHER INFORMATION: Synthetic

<400> SEQUENCE: 1427
agagacttca ca                                                           12

<210> SEQ ID NO 1428
<211> LENGTH: 20
<212> TYPE: DNA
<213> ORGANISM: Artificial Sequence
<220> FEATURE:
<223> OTHER INFORMATION: Synthetic

<400> SEQUENCE: 1428
ggacgctaaa ccaacggtgc                                                   20

<210> SEQ ID NO 1429
<211> LENGTH: 12
<212> TYPE: DNA
<213> ORGANISM: Artificial Sequence
<220> FEATURE:
<223> OTHER INFORMATION: Synthetic

<400> SEQUENCE: 1429
tccagagcac ct                                                           12

<210> SEQ ID NO 1430
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 1430
ggacgctaaa ccaacggtgc                                                 20

<210> SEQ ID NO 1431
<211> LENGTH: 12
<212> TYPE: DNA
<213> ORGANISM: Artificial Sequence
<220> FEATURE:
<223> OTHER INFORMATION: Synthetic

<400> SEQUENCE: 1431
gaagtgggca ac                                                         12

<210> SEQ ID NO 1432
<211> LENGTH: 20
<212> TYPE: DNA
<213> ORGANISM: Artificial Sequence
<220> FEATURE:
<223> OTHER INFORMATION: Synthetic

<400> SEQUENCE: 1432
tgtactccag cttgtgcccc                                                 20

<210> SEQ ID NO 1433
<211> LENGTH: 12
<212> TYPE: DNA
<213> ORGANISM: Artificial Sequence
<220> FEATURE:
<223> OTHER INFORMATION: Synthetic

<400> SEQUENCE: 1433
agctctgaca ca                                                         12

<210> SEQ ID NO 1434
<211> LENGTH: 20
<212> TYPE: DNA
<213> ORGANISM: Artificial Sequence
<220> FEATURE:
<223> OTHER INFORMATION: Synthetic

<400> SEQUENCE: 1434
tgtactccag cttgtgcccc                                                 20

<210> SEQ ID NO 1435
<211> LENGTH: 12
<212> TYPE: DNA
<213> ORGANISM: Artificial Sequence
<220> FEATURE:
<223> OTHER INFORMATION: Synthetic

<400> SEQUENCE: 1435
ctcactgaca ct                                                         12

<210> SEQ ID NO 1436
<211> LENGTH: 20
<212> TYPE: DNA
<213> ORGANISM: Artificial Sequence
<220> FEATURE:
<223> OTHER INFORMATION: Synthetic

<400> SEQUENCE: 1436
gccgtgccgt agctatccgg                                                 20
```

<210> SEQ ID NO 1437
<211> LENGTH: 12
<212> TYPE: DNA
<213> ORGANISM: Artificial Sequence
<220> FEATURE:
<223> OTHER INFORMATION: Synthetic

<400> SEQUENCE: 1437
agctagccta gg                                                         12

<210> SEQ ID NO 1438
<211> LENGTH: 20
<212> TYPE: DNA
<213> ORGANISM: Artificial Sequence
<220> FEATURE:
<223> OTHER INFORMATION: Synthetic

<400> SEQUENCE: 1438
tgtactccag cttgtgcccc                                                 20

<210> SEQ ID NO 1439
<211> LENGTH: 12
<212> TYPE: DNA
<213> ORGANISM: Artificial Sequence
<220> FEATURE:
<223> OTHER INFORMATION: Synthetic

<400> SEQUENCE: 1439
ctagtgtcca ca                                                         12

<210> SEQ ID NO 1440
<211> LENGTH: 20
<212> TYPE: DNA
<213> ORGANISM: Artificial Sequence
<220> FEATURE:
<223> OTHER INFORMATION: Synthetic

<400> SEQUENCE: 1440
aaggaggacg gcaacatcct                                                 20

<210> SEQ ID NO 1441
<211> LENGTH: 12
<212> TYPE: DNA
<213> ORGANISM: Artificial Sequence
<220> FEATURE:
<223> OTHER INFORMATION: Synthetic

<400> SEQUENCE: 1441
agccagtcaa tc                                                         12

<210> SEQ ID NO 1442
<211> LENGTH: 20
<212> TYPE: DNA
<213> ORGANISM: Artificial Sequence
<220> FEATURE:
<223> OTHER INFORMATION: Synthetic

<400> SEQUENCE: 1442
caaggaggac ggcaacatcc                                                 20

<210> SEQ ID NO 1443
<211> LENGTH: 12
<212> TYPE: DNA
<213> ORGANISM: Artificial Sequence
<220> FEATURE:

<223> OTHER INFORMATION: Synthetic

<400> SEQUENCE: 1443
gacatgcgta gc                                                          12

<210> SEQ ID NO 1444
<211> LENGTH: 20
<212> TYPE: DNA
<213> ORGANISM: Artificial Sequence
<220> FEATURE:
<223> OTHER INFORMATION: Synthetic

<400> SEQUENCE: 1444
gtccgttcga caatttcaca                                                  20

<210> SEQ ID NO 1445
<211> LENGTH: 12
<212> TYPE: DNA
<213> ORGANISM: Artificial Sequence
<220> FEATURE:
<223> OTHER INFORMATION: Synthetic

<400> SEQUENCE: 1445
agatgataac gg                                                          12

<210> SEQ ID NO 1446
<211> LENGTH: 12
<212> TYPE: DNA
<213> ORGANISM: Artificial Sequence
<220> FEATURE:
<223> OTHER INFORMATION: Synthetic

<400> SEQUENCE: 1446
agcaacttca ct                                                          12

<210> SEQ ID NO 1447
<211> LENGTH: 20
<212> TYPE: DNA
<213> ORGANISM: Artificial Sequence
<220> FEATURE:
<223> OTHER INFORMATION: Synthetic

<400> SEQUENCE: 1447
gccgtgccgt agctatccgg                                                  20

<210> SEQ ID NO 1448
<211> LENGTH: 20
<212> TYPE: DNA
<213> ORGANISM: Artificial Sequence
<220> FEATURE:
<223> OTHER INFORMATION: Synthetic

<400> SEQUENCE: 1448
gtccgttcga caatttcaca                                                  20

<210> SEQ ID NO 1449
<211> LENGTH: 12
<212> TYPE: DNA
<213> ORGANISM: Artificial Sequence
<220> FEATURE:
<223> OTHER INFORMATION: Synthetic

<400> SEQUENCE: 1449
agcaacttca ct                                                          12

```
<210> SEQ ID NO 1450
<211> LENGTH: 20
<212> TYPE: DNA
<213> ORGANISM: Artificial Sequence
<220> FEATURE:
<223> OTHER INFORMATION: Synthetic

<400> SEQUENCE: 1450
gtccgttcga caatttcaca                                               20

<210> SEQ ID NO 1451
<211> LENGTH: 12
<212> TYPE: DNA
<213> ORGANISM: Artificial Sequence
<220> FEATURE:
<223> OTHER INFORMATION: Synthetic

<400> SEQUENCE: 1451
agcagcccta gc                                                       12

<210> SEQ ID NO 1452
<211> LENGTH: 20
<212> TYPE: DNA
<213> ORGANISM: Artificial Sequence
<220> FEATURE:
<223> OTHER INFORMATION: Synthetic

<400> SEQUENCE: 1452
gctgcttgcg ataccaatag                                               20

<210> SEQ ID NO 1453
<211> LENGTH: 12
<212> TYPE: DNA
<213> ORGANISM: Artificial Sequence
<220> FEATURE:
<223> OTHER INFORMATION: Synthetic

<400> SEQUENCE: 1453
gaactcagga ca                                                       12

<210> SEQ ID NO 1454
<211> LENGTH: 20
<212> TYPE: DNA
<213> ORGANISM: Artificial Sequence
<220> FEATURE:
<223> OTHER INFORMATION: Synthetic

<400> SEQUENCE: 1454
caaggaggac ggcaacatcc                                               20

<210> SEQ ID NO 1455
<211> LENGTH: 12
<212> TYPE: DNA
<213> ORGANISM: Artificial Sequence
<220> FEATURE:
<223> OTHER INFORMATION: Synthetic

<400> SEQUENCE: 1455
ctatatatga cc                                                       12

<210> SEQ ID NO 1456
<211> LENGTH: 20
<212> TYPE: DNA
<213> ORGANISM: Artificial Sequence
<220> FEATURE:
<223> OTHER INFORMATION: Synthetic
```

<400> SEQUENCE: 1456
caaggaggac ggcaacatcc                                                    20

<210> SEQ ID NO 1457
<211> LENGTH: 12
<212> TYPE: DNA
<213> ORGANISM: Artificial Sequence
<220> FEATURE:
<223> OTHER INFORMATION: Synthetic

<400> SEQUENCE: 1457
ctcaatttac ag                                                            12

<210> SEQ ID NO 1458
<211> LENGTH: 20
<212> TYPE: DNA
<213> ORGANISM: Artificial Sequence
<220> FEATURE:
<223> OTHER INFORMATION: Synthetic

<400> SEQUENCE: 1458
gtccgttcga caatttcaca                                                    20

<210> SEQ ID NO 1459
<211> LENGTH: 12
<212> TYPE: DNA
<213> ORGANISM: Artificial Sequence
<220> FEATURE:
<223> OTHER INFORMATION: Synthetic

<400> SEQUENCE: 1459
tccagagcac ct                                                            12

<210> SEQ ID NO 1460
<211> LENGTH: 20
<212> TYPE: DNA
<213> ORGANISM: Artificial Sequence
<220> FEATURE:
<223> OTHER INFORMATION: Synthetic

<400> SEQUENCE: 1460
ggacgctaaa ccaacggtgc                                                    20

<210> SEQ ID NO 1461
<211> LENGTH: 12
<212> TYPE: DNA
<213> ORGANISM: Artificial Sequence
<220> FEATURE:
<223> OTHER INFORMATION: Synthetic

<400> SEQUENCE: 1461
agagacttca ca                                                            12

<210> SEQ ID NO 1462
<211> LENGTH: 20
<212> TYPE: DNA
<213> ORGANISM: Artificial Sequence
<220> FEATURE:
<223> OTHER INFORMATION: Synthetic

<400> SEQUENCE: 1462
ggacgctaaa ccaacggtgc                                                    20

<210> SEQ ID NO 1463
<211> LENGTH: 12

```
<212> TYPE: DNA
<213> ORGANISM: Artificial Sequence
<220> FEATURE:
<223> OTHER INFORMATION: Synthetic

<400> SEQUENCE: 1463
agccaccagt at                                                           12

<210> SEQ ID NO 1464
<211> LENGTH: 20
<212> TYPE: DNA
<213> ORGANISM: Artificial Sequence
<220> FEATURE:
<223> OTHER INFORMATION: Synthetic

<400> SEQUENCE: 1464
caaggaggac ggcaacatcc                                                   20

<210> SEQ ID NO 1465
<211> LENGTH: 12
<212> TYPE: DNA
<213> ORGANISM: Artificial Sequence
<220> FEATURE:
<223> OTHER INFORMATION: Synthetic

<400> SEQUENCE: 1465
gaacgcgaaa gc                                                           12

<210> SEQ ID NO 1466
<211> LENGTH: 20
<212> TYPE: DNA
<213> ORGANISM: Artificial Sequence
<220> FEATURE:
<223> OTHER INFORMATION: Synthetic

<400> SEQUENCE: 1466
caacatcctg gggcacaagc                                                   20

<210> SEQ ID NO 1467
<211> LENGTH: 12
<212> TYPE: DNA
<213> ORGANISM: Artificial Sequence
<220> FEATURE:
<223> OTHER INFORMATION: Synthetic

<400> SEQUENCE: 1467
agctagccta gg                                                           12

<210> SEQ ID NO 1468
<211> LENGTH: 20
<212> TYPE: DNA
<213> ORGANISM: Artificial Sequence
<220> FEATURE:
<223> OTHER INFORMATION: Synthetic

<400> SEQUENCE: 1468
tgtactccag cttgtgcccc                                                   20

<210> SEQ ID NO 1469
<211> LENGTH: 12
<212> TYPE: DNA
<213> ORGANISM: Artificial Sequence
<220> FEATURE:
<223> OTHER INFORMATION: Synthetic

<400> SEQUENCE: 1469
```
agcgacctta ca                                               12

<210> SEQ ID NO 1470
<211> LENGTH: 20
<212> TYPE: DNA
<213> ORGANISM: Artificial Sequence
<220> FEATURE:
<223> OTHER INFORMATION: Synthetic

<400> SEQUENCE: 1470
aggaggacgg caacatcctg                                       20

<210> SEQ ID NO 1471
<211> LENGTH: 12
<212> TYPE: DNA
<213> ORGANISM: Artificial Sequence
<220> FEATURE:
<223> OTHER INFORMATION: Synthetic

<400> SEQUENCE: 1471
gaatccgctc gc                                               12

<210> SEQ ID NO 1472
<211> LENGTH: 20
<212> TYPE: DNA
<213> ORGANISM: Artificial Sequence
<220> FEATURE:
<223> OTHER INFORMATION: Synthetic

<400> SEQUENCE: 1472
aaggaggacg gcaacatcct                                       20

<210> SEQ ID NO 1473
<211> LENGTH: 12
<212> TYPE: DNA
<213> ORGANISM: Artificial Sequence
<220> FEATURE:
<223> OTHER INFORMATION: Synthetic

<400> SEQUENCE: 1473
agatgataac gg                                               12

<210> SEQ ID NO 1474
<211> LENGTH: 20
<212> TYPE: DNA
<213> ORGANISM: Artificial Sequence
<220> FEATURE:
<223> OTHER INFORMATION: Synthetic

<400> SEQUENCE: 1474
gccgtgccgt agctatccgg                                       20

<210> SEQ ID NO 1475
<211> LENGTH: 12
<212> TYPE: DNA
<213> ORGANISM: Artificial Sequence
<220> FEATURE:
<223> OTHER INFORMATION: Synthetic

<400> SEQUENCE: 1475
agccaccagt at                                               12

<210> SEQ ID NO 1476
<211> LENGTH: 20
<212> TYPE: DNA
<213> ORGANISM: Artificial Sequence

```
<220> FEATURE:
<223> OTHER INFORMATION: Synthetic

<400> SEQUENCE: 1476
caaggaggac ggcaacatcc                                              20

<210> SEQ ID NO 1477
<211> LENGTH: 12
<212> TYPE: DNA
<213> ORGANISM: Artificial Sequence
<220> FEATURE:
<223> OTHER INFORMATION: Synthetic

<400> SEQUENCE: 1477
tccatcaata cg                                                      12

<210> SEQ ID NO 1478
<211> LENGTH: 20
<212> TYPE: DNA
<213> ORGANISM: Artificial Sequence
<220> FEATURE:
<223> OTHER INFORMATION: Synthetic

<400> SEQUENCE: 1478
caaggaggac ggcaacatcc                                              20

<210> SEQ ID NO 1479
<211> LENGTH: 12
<212> TYPE: DNA
<213> ORGANISM: Artificial Sequence
<220> FEATURE:
<223> OTHER INFORMATION: Synthetic

<400> SEQUENCE: 1479
agatgggttc cg                                                      12

<210> SEQ ID NO 1480
<211> LENGTH: 20
<212> TYPE: DNA
<213> ORGANISM: Artificial Sequence
<220> FEATURE:
<223> OTHER INFORMATION: Synthetic

<400> SEQUENCE: 1480
gtccgttcga caatttcaca                                              20

<210> SEQ ID NO 1481
<211> LENGTH: 12
<212> TYPE: DNA
<213> ORGANISM: Artificial Sequence
<220> FEATURE:
<223> OTHER INFORMATION: Synthetic

<400> SEQUENCE: 1481
ctcactgaca ct                                                      12

<210> SEQ ID NO 1482
<211> LENGTH: 20
<212> TYPE: DNA
<213> ORGANISM: Artificial Sequence
<220> FEATURE:
<223> OTHER INFORMATION: Synthetic

<400> SEQUENCE: 1482
gccgtgccgt agctatccgg                                              20
```

```
<210> SEQ ID NO 1483
<211> LENGTH: 12
<212> TYPE: DNA
<213> ORGANISM: Artificial Sequence
<220> FEATURE:
<223> OTHER INFORMATION: Synthetic

<400> SEQUENCE: 1483
agatgggttc cg                                                        12

<210> SEQ ID NO 1484
<211> LENGTH: 20
<212> TYPE: DNA
<213> ORGANISM: Artificial Sequence
<220> FEATURE:
<223> OTHER INFORMATION: Synthetic

<400> SEQUENCE: 1484
gtccgttcga caatttcaca                                                20

<210> SEQ ID NO 1485
<211> LENGTH: 12
<212> TYPE: DNA
<213> ORGANISM: Artificial Sequence
<220> FEATURE:
<223> OTHER INFORMATION: Synthetic

<400> SEQUENCE: 1485
agcaacttca ct                                                        12

<210> SEQ ID NO 1486
<211> LENGTH: 12
<212> TYPE: DNA
<213> ORGANISM: Artificial Sequence
<220> FEATURE:
<223> OTHER INFORMATION: Synthetic

<400> SEQUENCE: 1486
agctagccta gg                                                        12

<210> SEQ ID NO 1487
<211> LENGTH: 20
<212> TYPE: DNA
<213> ORGANISM: Artificial Sequence
<220> FEATURE:
<223> OTHER INFORMATION: Synthetic

<400> SEQUENCE: 1487
gtccgttcga caatttcaca                                                20

<210> SEQ ID NO 1488
<211> LENGTH: 20
<212> TYPE: DNA
<213> ORGANISM: Artificial Sequence
<220> FEATURE:
<223> OTHER INFORMATION: Synthetic

<400> SEQUENCE: 1488
caaggaggac ggcaacatcc                                                20

<210> SEQ ID NO 1489
<211> LENGTH: 12
<212> TYPE: DNA
<213> ORGANISM: Artificial Sequence
<220> FEATURE:
<223> OTHER INFORMATION: Synthetic
```

```
<400> SEQUENCE: 1489
gacaagtaca ct                                                         12

<210> SEQ ID NO 1490
<211> LENGTH: 20
<212> TYPE: DNA
<213> ORGANISM: Artificial Sequence
<220> FEATURE:
<223> OTHER INFORMATION: Synthetic

<400> SEQUENCE: 1490
gtccgttcga caatttcaca                                                 20

<210> SEQ ID NO 1491
<211> LENGTH: 12
<212> TYPE: DNA
<213> ORGANISM: Artificial Sequence
<220> FEATURE:
<223> OTHER INFORMATION: Synthetic

<400> SEQUENCE: 1491
agatgggttc cg                                                         12

<210> SEQ ID NO 1492
<211> LENGTH: 20
<212> TYPE: DNA
<213> ORGANISM: Artificial Sequence
<220> FEATURE:
<223> OTHER INFORMATION: Synthetic

<400> SEQUENCE: 1492
aaggaggacg gcaacatcct                                                 20

<210> SEQ ID NO 1493
<211> LENGTH: 12
<212> TYPE: DNA
<213> ORGANISM: Artificial Sequence
<220> FEATURE:
<223> OTHER INFORMATION: Synthetic

<400> SEQUENCE: 1493
agccagtcaa tc                                                         12

<210> SEQ ID NO 1494
<211> LENGTH: 20
<212> TYPE: DNA
<213> ORGANISM: Artificial Sequence
<220> FEATURE:
<223> OTHER INFORMATION: Synthetic

<400> SEQUENCE: 1494
gtccgttcga caatttcaca                                                 20

<210> SEQ ID NO 1495
<211> LENGTH: 12
<212> TYPE: DNA
<213> ORGANISM: Artificial Sequence
<220> FEATURE:
<223> OTHER INFORMATION: Synthetic

<400> SEQUENCE: 1495
agcaacttca ct                                                         12

<210> SEQ ID NO 1496
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 1496
caacatcctg gggcacaagc                                                   20

<210> SEQ ID NO 1497
<211> LENGTH: 12
<212> TYPE: DNA
<213> ORGANISM: Artificial Sequence
<220> FEATURE:
<223> OTHER INFORMATION: Synthetic

<400> SEQUENCE: 1497
gacaggctac ct                                                           12

<210> SEQ ID NO 1498
<211> LENGTH: 12
<212> TYPE: DNA
<213> ORGANISM: Artificial Sequence
<220> FEATURE:
<223> OTHER INFORMATION: Synthetic

<400> SEQUENCE: 1498
gaatggacag cg                                                           12

<210> SEQ ID NO 1499
<211> LENGTH: 20
<212> TYPE: DNA
<213> ORGANISM: Artificial Sequence
<220> FEATURE:
<223> OTHER INFORMATION: Synthetic

<400> SEQUENCE: 1499
ggacgctaaa ccaacggtgc                                                   20

<210> SEQ ID NO 1500
<211> LENGTH: 20
<212> TYPE: DNA
<213> ORGANISM: Artificial Sequence
<220> FEATURE:
<223> OTHER INFORMATION: Synthetic

<400> SEQUENCE: 1500
aggaggacgg caacatcctg                                                   20

<210> SEQ ID NO 1501
<211> LENGTH: 12
<212> TYPE: DNA
<213> ORGANISM: Artificial Sequence
<220> FEATURE:
<223> OTHER INFORMATION: Synthetic

<400> SEQUENCE: 1501
agcgccgtca tt                                                           12

<210> SEQ ID NO 1502
<211> LENGTH: 20
<212> TYPE: DNA
<213> ORGANISM: Artificial Sequence
<220> FEATURE:
<223> OTHER INFORMATION: Synthetic

<400> SEQUENCE: 1502
```
aaggaggacg gcaacatcct                                              20

<210> SEQ ID NO 1503
<211> LENGTH: 12
<212> TYPE: DNA
<213> ORGANISM: Artificial Sequence
<220> FEATURE:
<223> OTHER INFORMATION: Synthetic

<400> SEQUENCE: 1503
agcgccgtca tt                                                      12

<210> SEQ ID NO 1504
<211> LENGTH: 20
<212> TYPE: DNA
<213> ORGANISM: Artificial Sequence
<220> FEATURE:
<223> OTHER INFORMATION: Synthetic

<400> SEQUENCE: 1504
aaggaggacg gcaacatcct                                              20

<210> SEQ ID NO 1505
<211> LENGTH: 12
<212> TYPE: DNA
<213> ORGANISM: Artificial Sequence
<220> FEATURE:
<223> OTHER INFORMATION: Synthetic

<400> SEQUENCE: 1505
gaatgaacca cg                                                      12

<210> SEQ ID NO 1506
<211> LENGTH: 12
<212> TYPE: DNA
<213> ORGANISM: Artificial Sequence
<220> FEATURE:
<223> OTHER INFORMATION: Synthetic

<400> SEQUENCE: 1506
gaacgcgaaa gc                                                      12

<210> SEQ ID NO 1507
<211> LENGTH: 20
<212> TYPE: DNA
<213> ORGANISM: Artificial Sequence
<220> FEATURE:
<223> OTHER INFORMATION: Synthetic

<400> SEQUENCE: 1507
caacatcctg gggcacaagc                                              20

<210> SEQ ID NO 1508
<211> LENGTH: 20
<212> TYPE: DNA
<213> ORGANISM: Artificial Sequence
<220> FEATURE:
<223> OTHER INFORMATION: Synthetic

<400> SEQUENCE: 1508
gccgtgccgt agctatccgg                                              20

<210> SEQ ID NO 1509
<211> LENGTH: 12
<212> TYPE: DNA

```
<213> ORGANISM: Artificial Sequence
<220> FEATURE:
<223> OTHER INFORMATION: Synthetic

<400> SEQUENCE: 1509
agccagtcaa tc                                                          12

<210> SEQ ID NO 1510
<211> LENGTH: 20
<212> TYPE: DNA
<213> ORGANISM: Artificial Sequence
<220> FEATURE:
<223> OTHER INFORMATION: Synthetic

<400> SEQUENCE: 1510
caaggaggac ggcaacatcc                                                  20

<210> SEQ ID NO 1511
<211> LENGTH: 12
<212> TYPE: DNA
<213> ORGANISM: Artificial Sequence
<220> FEATURE:
<223> OTHER INFORMATION: Synthetic

<400> SEQUENCE: 1511
agcggtataa ct                                                          12

<210> SEQ ID NO 1512
<211> LENGTH: 20
<212> TYPE: DNA
<213> ORGANISM: Artificial Sequence
<220> FEATURE:
<223> OTHER INFORMATION: Synthetic

<400> SEQUENCE: 1512
aggaggacgg caacatcctg                                                  20

<210> SEQ ID NO 1513
<211> LENGTH: 12
<212> TYPE: DNA
<213> ORGANISM: Artificial Sequence
<220> FEATURE:
<223> OTHER INFORMATION: Synthetic

<400> SEQUENCE: 1513
tccatcaata cg                                                          12

<210> SEQ ID NO 1514
<211> LENGTH: 20
<212> TYPE: DNA
<213> ORGANISM: Artificial Sequence
<220> FEATURE:
<223> OTHER INFORMATION: Synthetic

<400> SEQUENCE: 1514
gtacagctaa gttaaactcg                                                  20

<210> SEQ ID NO 1515
<211> LENGTH: 12
<212> TYPE: DNA
<213> ORGANISM: Artificial Sequence
<220> FEATURE:
<223> OTHER INFORMATION: Synthetic

<400> SEQUENCE: 1515
agctttctga ct                                                          12
```

<210> SEQ ID NO 1516
<211> LENGTH: 20
<212> TYPE: DNA
<213> ORGANISM: Artificial Sequence
<220> FEATURE:
<223> OTHER INFORMATION: Synthetic

<400> SEQUENCE: 1516
caacatcctg gggcacaagc                                               20

<210> SEQ ID NO 1517
<211> LENGTH: 12
<212> TYPE: DNA
<213> ORGANISM: Artificial Sequence
<220> FEATURE:
<223> OTHER INFORMATION: Synthetic

<400> SEQUENCE: 1517
gaacgcgaaa gc                                                       12

<210> SEQ ID NO 1518
<211> LENGTH: 20
<212> TYPE: DNA
<213> ORGANISM: Artificial Sequence
<220> FEATURE:
<223> OTHER INFORMATION: Synthetic

<400> SEQUENCE: 1518
caacatcctg gggcacaagc                                               20

<210> SEQ ID NO 1519
<211> LENGTH: 12
<212> TYPE: DNA
<213> ORGANISM: Artificial Sequence
<220> FEATURE:
<223> OTHER INFORMATION: Synthetic

<400> SEQUENCE: 1519
agcggtataa ct                                                       12

<210> SEQ ID NO 1520
<211> LENGTH: 20
<212> TYPE: DNA
<213> ORGANISM: Artificial Sequence
<220> FEATURE:
<223> OTHER INFORMATION: Synthetic

<400> SEQUENCE: 1520
aggaggacgg caacatcctg                                               20

<210> SEQ ID NO 1521
<211> LENGTH: 12
<212> TYPE: DNA
<213> ORGANISM: Artificial Sequence
<220> FEATURE:
<223> OTHER INFORMATION: Synthetic

<400> SEQUENCE: 1521
agagctgcta cg                                                       12

<210> SEQ ID NO 1522
<211> LENGTH: 20
<212> TYPE: DNA
<213> ORGANISM: Artificial Sequence
<220> FEATURE:

<223> OTHER INFORMATION: Synthetic

<400> SEQUENCE: 1522
aaggaggacg gcaacatcct                                               20

<210> SEQ ID NO 1523
<211> LENGTH: 12
<212> TYPE: DNA
<213> ORGANISM: Artificial Sequence
<220> FEATURE:
<223> OTHER INFORMATION: Synthetic

<400> SEQUENCE: 1523
agccagtcaa tc                                                       12

<210> SEQ ID NO 1524
<211> LENGTH: 20
<212> TYPE: DNA
<213> ORGANISM: Artificial Sequence
<220> FEATURE:
<223> OTHER INFORMATION: Synthetic

<400> SEQUENCE: 1524
tgtactccag cttgtgcccc                                               20

<210> SEQ ID NO 1525
<211> LENGTH: 12
<212> TYPE: DNA
<213> ORGANISM: Artificial Sequence
<220> FEATURE:
<223> OTHER INFORMATION: Synthetic

<400> SEQUENCE: 1525
gaatgaacca cg                                                       12

<210> SEQ ID NO 1526
<211> LENGTH: 12
<212> TYPE: DNA
<213> ORGANISM: Artificial Sequence
<220> FEATURE:
<223> OTHER INFORMATION: Synthetic

<400> SEQUENCE: 1526
gaacgcgaaa gc                                                       12

<210> SEQ ID NO 1527
<211> LENGTH: 20
<212> TYPE: DNA
<213> ORGANISM: Artificial Sequence
<220> FEATURE:
<223> OTHER INFORMATION: Synthetic

<400> SEQUENCE: 1527
caacatcctg gggcacaagc                                               20

<210> SEQ ID NO 1528
<211> LENGTH: 20
<212> TYPE: DNA
<213> ORGANISM: Artificial Sequence
<220> FEATURE:
<223> OTHER INFORMATION: Synthetic

<400> SEQUENCE: 1528
gccgtgccgt agctatccgg                                               20

```
<210> SEQ ID NO 1529
<211> LENGTH: 12
<212> TYPE: DNA
<213> ORGANISM: Artificial Sequence
<220> FEATURE:
<223> OTHER INFORMATION: Synthetic

<400> SEQUENCE: 1529
agcggtataa ct                                                              12

<210> SEQ ID NO 1530
<211> LENGTH: 20
<212> TYPE: DNA
<213> ORGANISM: Artificial Sequence
<220> FEATURE:
<223> OTHER INFORMATION: Synthetic

<400> SEQUENCE: 1530
aggaggacgg caacatcctg                                                      20

<210> SEQ ID NO 1531
<211> LENGTH: 12
<212> TYPE: DNA
<213> ORGANISM: Artificial Sequence
<220> FEATURE:
<223> OTHER INFORMATION: Synthetic

<400> SEQUENCE: 1531
tccatcaata cg                                                              12

<210> SEQ ID NO 1532
<211> LENGTH: 20
<212> TYPE: DNA
<213> ORGANISM: Artificial Sequence
<220> FEATURE:
<223> OTHER INFORMATION: Synthetic

<400> SEQUENCE: 1532
gtacagctaa gttaaactcg                                                      20

<210> SEQ ID NO 1533
<211> LENGTH: 12
<212> TYPE: DNA
<213> ORGANISM: Artificial Sequence
<220> FEATURE:
<223> OTHER INFORMATION: Synthetic

<400> SEQUENCE: 1533
gacaggctac ct                                                              12

<210> SEQ ID NO 1534
<211> LENGTH: 20
<212> TYPE: DNA
<213> ORGANISM: Artificial Sequence
<220> FEATURE:
<223> OTHER INFORMATION: Synthetic

<400> SEQUENCE: 1534
ggacgctaaa ccaacggtgc                                                      20

<210> SEQ ID NO 1535
<211> LENGTH: 12
<212> TYPE: DNA
<213> ORGANISM: Artificial Sequence
<220> FEATURE:
<223> OTHER INFORMATION: Synthetic
```

```
<400> SEQUENCE: 1535
agagacttca ca                                                              12

<210> SEQ ID NO 1536
<211> LENGTH: 20
<212> TYPE: DNA
<213> ORGANISM: Artificial Sequence
<220> FEATURE:
<223> OTHER INFORMATION: Synthetic

<400> SEQUENCE: 1536
ggacgctaaa ccaacggtgc                                                      20

<210> SEQ ID NO 1537
<211> LENGTH: 12
<212> TYPE: DNA
<213> ORGANISM: Artificial Sequence
<220> FEATURE:
<223> OTHER INFORMATION: Synthetic

<400> SEQUENCE: 1537
gatatcgtga cc                                                              12

<210> SEQ ID NO 1538
<211> LENGTH: 20
<212> TYPE: DNA
<213> ORGANISM: Artificial Sequence
<220> FEATURE:
<223> OTHER INFORMATION: Synthetic

<400> SEQUENCE: 1538
aggaggacgg caacatcctg                                                      20

<210> SEQ ID NO 1539
<211> LENGTH: 12
<212> TYPE: DNA
<213> ORGANISM: Artificial Sequence
<220> FEATURE:
<223> OTHER INFORMATION: Synthetic

<400> SEQUENCE: 1539
caacgcccaa gg                                                              12

<210> SEQ ID NO 1540
<211> LENGTH: 20
<212> TYPE: DNA
<213> ORGANISM: Artificial Sequence
<220> FEATURE:
<223> OTHER INFORMATION: Synthetic

<400> SEQUENCE: 1540
caacatcctg gggcacaagc                                                      20

<210> SEQ ID NO 1541
<211> LENGTH: 12
<212> TYPE: DNA
<213> ORGANISM: Artificial Sequence
<220> FEATURE:
<223> OTHER INFORMATION: Synthetic

<400> SEQUENCE: 1541
taggaagtta gg                                                              12

<210> SEQ ID NO 1542
<211> LENGTH: 12
```

<212> TYPE: DNA
<213> ORGANISM: Artificial Sequence
<220> FEATURE:
<223> OTHER INFORMATION: Synthetic

<400> SEQUENCE: 1542
ttcgccgaaa gc                                                          12

<210> SEQ ID NO 1543
<211> LENGTH: 20
<212> TYPE: DNA
<213> ORGANISM: Artificial Sequence
<220> FEATURE:
<223> OTHER INFORMATION: Synthetic

<400> SEQUENCE: 1543
tgtactccag cttgtgcccc                                                  20

<210> SEQ ID NO 1544
<211> LENGTH: 20
<212> TYPE: DNA
<213> ORGANISM: Artificial Sequence
<220> FEATURE:
<223> OTHER INFORMATION: Synthetic

<400> SEQUENCE: 1544
aaggaggacg gcaacatcct                                                  20

<210> SEQ ID NO 1545
<211> LENGTH: 12
<212> TYPE: DNA
<213> ORGANISM: Artificial Sequence
<220> FEATURE:
<223> OTHER INFORMATION: Synthetic

<400> SEQUENCE: 1545
aggctattaa tg                                                          12

<210> SEQ ID NO 1546
<211> LENGTH: 20
<212> TYPE: DNA
<213> ORGANISM: Artificial Sequence
<220> FEATURE:
<223> OTHER INFORMATION: Synthetic

<400> SEQUENCE: 1546
caaggaggac ggcaacatcc                                                  20

<210> SEQ ID NO 1547
<211> LENGTH: 12
<212> TYPE: DNA
<213> ORGANISM: Artificial Sequence
<220> FEATURE:
<223> OTHER INFORMATION: Synthetic

<400> SEQUENCE: 1547
atcagtggca gc                                                          12

<210> SEQ ID NO 1548
<211> LENGTH: 20
<212> TYPE: DNA
<213> ORGANISM: Artificial Sequence
<220> FEATURE:
<223> OTHER INFORMATION: Synthetic

<400> SEQUENCE: 1548

```
gctgcttgcg ataccaatag                                              20

<210> SEQ ID NO 1549
<211> LENGTH: 12
<212> TYPE: DNA
<213> ORGANISM: Artificial Sequence
<220> FEATURE:
<223> OTHER INFORMATION: Synthetic

<400> SEQUENCE: 1549
tgttaatgca gg                                                      12

<210> SEQ ID NO 1550
<211> LENGTH: 20
<212> TYPE: DNA
<213> ORGANISM: Artificial Sequence
<220> FEATURE:
<223> OTHER INFORMATION: Synthetic

<400> SEQUENCE: 1550
ggacgctaaa ccaacggtgc                                              20

<210> SEQ ID NO 1551
<211> LENGTH: 12
<212> TYPE: DNA
<213> ORGANISM: Artificial Sequence
<220> FEATURE:
<223> OTHER INFORMATION: Synthetic

<400> SEQUENCE: 1551
tctatttgac gg                                                      12

<210> SEQ ID NO 1552
<211> LENGTH: 20
<212> TYPE: DNA
<213> ORGANISM: Artificial Sequence
<220> FEATURE:
<223> OTHER INFORMATION: Synthetic

<400> SEQUENCE: 1552
caacatcctg gggcacaagc                                              20

<210> SEQ ID NO 1553
<211> LENGTH: 12
<212> TYPE: DNA
<213> ORGANISM: Artificial Sequence
<220> FEATURE:
<223> OTHER INFORMATION: Synthetic

<400> SEQUENCE: 1553
ccgtaacgaa ca                                                      12

<210> SEQ ID NO 1554
<211> LENGTH: 20
<212> TYPE: DNA
<213> ORGANISM: Artificial Sequence
<220> FEATURE:
<223> OTHER INFORMATION: Synthetic

<400> SEQUENCE: 1554
caacatcctg gggcacaagc                                              20

<210> SEQ ID NO 1555
<211> LENGTH: 12
<212> TYPE: DNA
<213> ORGANISM: Artificial Sequence
```

```
<220> FEATURE:
<223> OTHER INFORMATION: Synthetic

<400> SEQUENCE: 1555
agtttgcagc ca                                                           12

<210> SEQ ID NO 1556
<211> LENGTH: 20
<212> TYPE: DNA
<213> ORGANISM: Artificial Sequence
<220> FEATURE:
<223> OTHER INFORMATION: Synthetic

<400> SEQUENCE: 1556
ggacgctaaa ccaacggtgc                                                   20

<210> SEQ ID NO 1557
<211> LENGTH: 12
<212> TYPE: DNA
<213> ORGANISM: Artificial Sequence
<220> FEATURE:
<223> OTHER INFORMATION: Synthetic

<400> SEQUENCE: 1557
tcgaaatgac ac                                                           12

<210> SEQ ID NO 1558
<211> LENGTH: 20
<212> TYPE: DNA
<213> ORGANISM: Artificial Sequence
<220> FEATURE:
<223> OTHER INFORMATION: Synthetic

<400> SEQUENCE: 1558
ggacgctaaa ccaacggtgc                                                   20

<210> SEQ ID NO 1559
<211> LENGTH: 12
<212> TYPE: DNA
<213> ORGANISM: Artificial Sequence
<220> FEATURE:
<223> OTHER INFORMATION: Synthetic

<400> SEQUENCE: 1559
tcagtgaata cg                                                           12

<210> SEQ ID NO 1560
<211> LENGTH: 20
<212> TYPE: DNA
<213> ORGANISM: Artificial Sequence
<220> FEATURE:
<223> OTHER INFORMATION: Synthetic

<400> SEQUENCE: 1560
aggaggacgg caacatcctg                                                   20

<210> SEQ ID NO 1561
<211> LENGTH: 12
<212> TYPE: DNA
<213> ORGANISM: Artificial Sequence
<220> FEATURE:
<223> OTHER INFORMATION: Synthetic

<400> SEQUENCE: 1561
cgcaaaagga tt                                                           12
```

```
<210> SEQ ID NO 1562
<211> LENGTH: 20
<212> TYPE: DNA
<213> ORGANISM: Artificial Sequence
<220> FEATURE:
<223> OTHER INFORMATION: Synthetic

<400> SEQUENCE: 1562
gccgtgccgt agctatccgg                                                    20

<210> SEQ ID NO 1563
<211> LENGTH: 12
<212> TYPE: DNA
<213> ORGANISM: Artificial Sequence
<220> FEATURE:
<223> OTHER INFORMATION: Synthetic

<400> SEQUENCE: 1563
atcagtggca gc                                                            12

<210> SEQ ID NO 1564
<211> LENGTH: 20
<212> TYPE: DNA
<213> ORGANISM: Artificial Sequence
<220> FEATURE:
<223> OTHER INFORMATION: Synthetic

<400> SEQUENCE: 1564
gctgcttgcg ataccaatag                                                    20

<210> SEQ ID NO 1565
<211> LENGTH: 12
<212> TYPE: DNA
<213> ORGANISM: Artificial Sequence
<220> FEATURE:
<223> OTHER INFORMATION: Synthetic

<400> SEQUENCE: 1565
aacgatggga ct                                                            12

<210> SEQ ID NO 1566
<211> LENGTH: 12
<212> TYPE: DNA
<213> ORGANISM: Artificial Sequence
<220> FEATURE:
<223> OTHER INFORMATION: Synthetic

<400> SEQUENCE: 1566
tcattcagag cg                                                            12

<210> SEQ ID NO 1567
<211> LENGTH: 20
<212> TYPE: DNA
<213> ORGANISM: Artificial Sequence
<220> FEATURE:
<223> OTHER INFORMATION: Synthetic

<400> SEQUENCE: 1567
aaggaggacg gcaacatcct                                                    20

<210> SEQ ID NO 1568
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 1568
aggaggacgg caacatcctg                                          20

<210> SEQ ID NO 1569
<211> LENGTH: 12
<212> TYPE: DNA
<213> ORGANISM: Artificial Sequence
<220> FEATURE:
<223> OTHER INFORMATION: Synthetic

<400> SEQUENCE: 1569
tcttcacaac cg                                                  12

<210> SEQ ID NO 1570
<211> LENGTH: 20
<212> TYPE: DNA
<213> ORGANISM: Artificial Sequence
<220> FEATURE:
<223> OTHER INFORMATION: Synthetic

<400> SEQUENCE: 1570
caacatcctg gggcacaagc                                          20

<210> SEQ ID NO 1571
<211> LENGTH: 12
<212> TYPE: DNA
<213> ORGANISM: Artificial Sequence
<220> FEATURE:
<223> OTHER INFORMATION: Synthetic

<400> SEQUENCE: 1571
cgtgtgatga ta                                                  12

<210> SEQ ID NO 1572
<211> LENGTH: 12
<212> TYPE: DNA
<213> ORGANISM: Artificial Sequence
<220> FEATURE:
<223> OTHER INFORMATION: Synthetic

<400> SEQUENCE: 1572
attgctattc gg                                                  12

<210> SEQ ID NO 1573
<211> LENGTH: 20
<212> TYPE: DNA
<213> ORGANISM: Artificial Sequence
<220> FEATURE:
<223> OTHER INFORMATION: Synthetic

<400> SEQUENCE: 1573
aaggaggacg gcaacatcct                                          20

<210> SEQ ID NO 1574
<211> LENGTH: 7963
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1736)..(1755)
<223> OTHER INFORMATION: n is a, c, g, or t
<220> FEATURE:
<221> NAME/KEY: misc_feature
<222> LOCATION: (3516)..(3527)
```

<223> OTHER INFORMATION: n is a, c, g, or t

<400> SEQUENCE: 1574

```
gggtctctct ggttagacca gatctgagcc tgggagctct ctggctaact agggaaccca      60
ctgcttaagc ctcaataaag cttgccttga gtgcttcaag tagtgtgtgc ccgtctgttg     120
tgtgactctg gtaactagag atccctcaga ccctttagt cagtgtggaa aatctctagc     180
agtggcgccc gaacagggac ttgaaagcga aagggaaacc agaggagctc tctcgacgca     240
ggactcggct tgctgaagcg cgcacggcaa gaggcgaggg gcggcgactg gtgagtacgc     300
caaaaatttt gactagcgga ggctagaagg agagagatgg gtgcgagagc gtcagtatta     360
agcgggggag aattagatcg cgatgggaaa aaattcggtt aaggccaggg ggaaagaaaa     420
aatataaatt aaaacatata gtatgggcaa gcagggagct agaacgattc gcagttaatc     480
ctggcctgtt agaaacatca gaaggctgta gacaaatact gggacagcta caaccatccc     540
ttcagacagg atcagaagaa cttagatcat tatataatac agtagcaacc ctctattgtg     600
tgcatcaaag gatagagata aaagacacca aggaagcttt agacaagata gaggaagagc     660
aaaacaaaag taagaccacc gcacagcaag cggccgctga tcttcagacc tggaggagga     720
gatatgaggg acaattggag aagtgaatta tataaatata agtagtaaa aattgaacca     780
ttaggagtag cacccaccaa ggcaaagaga agagtggtgc agagagaaaa aagagcagtg     840
ggaataggag ctttgttcct tgggttcttg ggagcagcag gaagcactat gggcgcagcg     900
tcaatgacgc tgacggtaca ggccagacaa ttattgtctg gtatagtgca gcagcagaac     960
aatttgctga gggctattga ggcgaacag catctgttgc aactcacagt ctggggcatc    1020
aagcagctcc aggcaagaat cctggctgtg gaaagatacc taaaggatca acagctcctg    1080
gggatttggg gttgctctgg aaaactcatt tgcaccactg ctgtgccttg gaatgctagt    1140
tggagtaata aatctctgga acagatttgg aatcacacga cctggatgga gtgggacaga    1200
gaaattaaca attacacaag cttaatacac tccttaattg aagaatcgca aaaccagcaa    1260
gaaaagaatg aacaagaatt attggaatta gataaatggg caagtttgtg gaattggttt    1320
aacataacaa attggctgtg gtatataaaa ttattcataa tgatagtagg aggcttggta    1380
ggtttaagaa tagtttttgc tgtactttct atagtgaata gagttaggca gggatattca    1440
ccattatcgt ttcagaccca cctcccaacc ccgaggggac ccagagaggg cctatttccc    1500
atgattcctt catatttgca tatacgatac aaggctgtta gagagataat tagaattaat    1560
ttgactgtaa acacaaagat attagtacaa aatacgtgac gtagaaagta ataatttctt    1620
gggtagtttg cagttttaaa attatgtttt aaaatggact atcatatgct taccgtaact    1680
tgaaagtatt tcgatttctt ggctttatat atcttgtgga aaggacgaaa caccgnnnnn    1740
nnnnnnnnnn nnnnngtttc agagctatgc tggaaacagc atagcaagtt gaaataaggc    1800
tagtccgtta tcaacttgaa aaagtggcac cgagtcggtg cttttttgga tcctgcaaag    1860
atggataaag ttttaaacag agaggaatct ttgcagctaa tggaccttct aggtcttgaa    1920
aggagtggga attggctccg gtgcccgtca gtgggcagag cgcacatcgc ccacagtccc    1980
cgagaagttg gggggagggg tcggcaattg atccggtgcc tagagaaggt ggcgcggggt    2040
aaactgggaa agtgatgtcg tgtactggct ccgcctttt cccgagggtg ggggagaacc    2100
gtatataagt gcagtagtcg ccgtgaacgt tctttttcgc aacgggtttg ccgccagaac    2160
acaggtaagt gccgtgtgtg gttcccgcgg gcctggcctc tttacgggtt atggcccttg    2220
cgtgccttga attacttcca ctggctgcag tacgtgattc ttgatcccga gcttcgggtt    2280
```

```
ggaagtgggt gggagagttc gaggccttgc gcttaaggag ccccttcgcc tcgtgcttga   2340
gttgaggcct ggcctgggcg ctggggccgc cgcgtgcgaa tctggtggca ccttcgcgcc   2400
tgtctcgctg ctttcgataa gtctctagcc atttaaaatt tttgatgacc tgctgcgacg   2460
cttttttcct ggcaagatag tcttgtaaat gcgggccaag atctgcacac tggtatttcg   2520 gttttttgggg ccgcgggcgg cgacggggcc cgtgcgtccc agcgcacatg ttcggcgagg   2580
cggggcctgc gagcgcggcc accgagaatc ggacgggggt agtctcaagc tggccggcct   2640
gctctggtgc ctggcctcgc gccgccgtgt atcgccccgc cctgggcggc aaggctggcc   2700
cggtcggcac cagttgcgtg agcggaaaga tggccgcttc ccggccctgc tgcagggagc   2760
tcaaaatgga ggacgcggcg ctcgggagag cgggcgggtg agtcacccac acaaaggaaa   2820
agggcctttc cgtcctcagc cgtcgcttca tgtgactcca cggagtaccg ggcgccgtcc   2880
aggcacctcg attagttctc gagcttttgg agtacgtcgt ctttaggttg gggggagggg   2940
ttttatgcga tggagtttcc ccacactgag tgggtggaga ctgaagttag gccagcttgg   3000
cacttgatgt aattctcctt ggaatttgcc ctttttgagt ttggatcttg gttcattctc   3060
aagcctcaga cagtggttca aagtttttt cttccatttc aggtgtcgtg atgtacaatg   3120
gccaagttga ccagtgccgt tccggtgctc accgcgcgcg acgtcgccgg agcggtcgag   3180
ttctggaccg accggctcgg gttctcccgg gacttcgtgg aggacgactt cgccggtgtg   3240
gtccgggacg acgtgaccct gttcatcagc gcggtccagg accaggtggt gccggacaac   3300
accctggcct gggtgtgggt gcgcggcctg gacgagctgt acgccgagtg gtcggaggtc   3360
gtgtccacga acttccggga cgcctccggg ccggccatga ccgagatcgg cgagcagccg   3420
tgggggcggg agttcgccct gcgcgacccg gccggcaact gcgtgcactt cgtggccgag   3480
gagcaggact gagctagctg ttcaatcaac attccnnnnn nnnnnnnact ggctattcat   3540
tcgccctttg ggtaagcaca cgtcgaattc gatatcaagc ttatcggtaa tcaacctctg   3600
gattacaaaa tttgtgaaag attgactggt attcttaact atgttgctcc ttttacgcta   3660
tgtggatacg ctgctttaat gcctttgtat catgctattg cttcccgtat ggctttcatt   3720
ttctcctcct tgtataaatc ctggttgctg tctctttatg aggagttgtg gcccgttgtc   3780
aggcaacgtg gcgtggtgtg cactgtgttt gctgacgcaa ccccccactgg ttggggcatt   3840 gccaccacct gtcagctcct ttccgggact ttcgctttcc cctcccctat gccacggcg   3900 gaactcatcg ccgcctgcct tgcccgctgc tggacagggg ctcggctgtt gggcactgac   3960
aattccgtgg tgttgtcggg gaaatcatcg tcctttcctt ggctgctcgc ctgtgttgcc   4020
acctggattc tgcgcgggac gtccttctgc tacgtccctt cggccctcaa tccagcggac   4080
cttccttccc gcggcctgct gccggctctg cggcctcttc cgcgtcttcg ccttcgccct   4140
cagacgagtc ggatctcccct ttgggccgcc tccccgcgtc gactttaaga ccaatgactt   4200
acaaggcagc tgtagatctt agccactttt taaaagaaaa ggggggactg aagggctaa    4260 ttcactccca acgaagacaa gatctgcttt ttgcttgtac tgggtctctc tggttagacc   4320
agatctgagc ctgggagctc tctggctaac tagggaaccc actgcttaag cctcaataaa   4380
gcttgccttg agtgcttcaa gtagtgtgtg cccgtctgtt gtgtgactct ggtaactaga   4440
gatccctcag accctttag tcagtgtgga aaatctctag cagtacgtat agtagttcat   4500
gtcatcttat tattcagtat ttataacttg caaagaaatg aatatcagag agtgagagga   4560
acttgtttat tgcagcttat aatggttaca aataaagcaa tagcatcaca aatttcacaa   4620
```

```
ataaagcatt tttttcactg cattctagtt gtggtttgtc caaactcatc aatgtatctt    4680
atcatgtctg gctctagcta tcccgcccct aactccgccc atcccgcccc taactccgcc    4740
cagttccgcc cattctccgc cccatggctg actaattttt tttatttatg cagaggccga    4800
ggccgcctcg gcctctgagc tattccagaa gtagtgagga ggcttttttg gaggcctagg    4860
gacgtaccca attcgcccta tagtgagtcg tattacgcgc gctcactggc cgtcgtttta    4920
caacgtcgtg actgggaaaa ccctggcgtt acccaactta atcgccttgc agcacatccc    4980
cctttcgcca gctggcgtaa tagcgaagag gcccgcaccg atcgcccttc ccaacagttg    5040
cgcagcctga atggcgaatg ggacgcgccc tgtagcggcg cattaagcgc ggcgggtgtg    5100
gtggttacgc gcagcgtgac cgctacactt gccagcgccc tagcgcccgc tcctttcgct    5160
ttcttccctt cctttctcgc cacgttcgcc ggctttcccc gtcaagctct aaatcggggg    5220 ctcccttttag ggttccgatt tagtgcttta cggcacctcg accccaaaaa acttgattag    5280
ggtgatggtt cacgtagtgg gccatcgccc tgatagacgg ttttcgccc tttgacgttg    5340 gagtccacgt tctttaatag tggactcttg ttccaaactg gaacaacact caaccctatc    5400
tcggtctatt cttttgattt ataagggatt ttgccgattt cggcctattg gttaaaaaat    5460
gagctgattt aacaaaaatt taacgcgaat tttaacaaaa tattaacgct tacaatttag    5520
gtggcacttt tcggggaaat gtgcgcggaa cccctatttg tttatttttc taaatacatt    5580
caaatatgta tccgctcatg agacaataac cctgataaat gcttcaataa tattgaaaaa    5640
ggaagagtat gagtattcaa catttccgtg tcgcccttat tcccttttt gcggcatttt    5700 gccttcctgt ttttgctcac ccagaaacgc tggtgaaagt aaaagatgct gaagatcagt    5760
tgggtgcacg agtgggttac atcgaactgg atctcaacag cggtaagatc cttgagagtt    5820
ttcgccccga agaacgtttt ccaatgatga gcacttttaa agttctgcta tgtggcgcgg    5880
tattatcccg tattgacgcc gggcaagagc aactcggtcg ccgcatacac tattctcaga    5940
atgacttggt tgagtactca ccagtcacag aaaagcatct tacggatggc atgacagtaa    6000
gagaattatg cagtgctgcc ataaccatga gtgataacac tgcggccaac ttacttctga    6060
caacgatcgg aggaccgaag gagctaaccg cttttttgca caacatgggg gatcatgtaa    6120
ctcgccttga tcgttgggaa ccggagctga atgaagccat accaaacgac gagcgtgaca    6180
ccacgatgcc tgtagcaatg gcaacaacgt tgcgcaaact attaactggc gaactactta    6240
ctctagcttc ccggcaacaa ttaatagact ggatggaggc ggataaagtt gcaggaccac    6300
ttctgcgctc ggcccttccg gctggctggt ttattgctga taaatctgga gccggtgagc    6360
gtgggtctcg cggtatcatt gcagcactgg ggccagatgg taagccctcc cgtatcgtag    6420
ttatctacac gacggggagt caggcaacta tggatgaacg aaatagacag atcgctgaga    6480
taggtgcctc actgattaag cattggtaac tgtcagacca agtttactca tatatacttt    6540
agattgattt aaaacttcat ttttaattta aaaggatcta ggtgaagatc ctttttgata    6600
atctcatgac caaaatccct taacgtgagt tttcgttcca ctgagcgtca gaccccgtag    6660
aaaagatcaa aggatcttct tgagatcctt ttttctgcg cgtaatctgc tgcttgcaaa    6720
caaaaaaacc accgctacca gcggtggttt gtttgccgga tcaagagcta ccaactcttt    6780
ttccgaaggt aactggcttc agcagagcgc agataccaaa tactgttctt ctagtgtagc    6840
cgtagttagg ccaccacttc aagaactctg tagcaccgcc tacatacctc gctctgctaa    6900
tcctgttacc agtggctgct gccagtggcg ataagtcgtg tcttaccggg ttggactcaa    6960
gacgatagtt accggataag gcgcagcggt cgggctgaac ggggggttcg tgcacacagc    7020
```

-continued

```
ccagcttgga gcgaacgacc tacaccgaac tgagatacct acagcgtgag ctatgagaaa      7080
gcgccacgct tcccgaaggg agaaaggcgg acaggtatcc ggtaagcggc agggtcggaa      7140
caggagagcg cacgagggag cttccagggg gaaacgcctg gtatctttat agtcctgtcg      7200
ggtttcgcca cctctgactt gagcgtcgat ttttgtgatg ctcgtcaggg gggcggagcc      7260
tatggaaaaa cgccagcaac gcggccttttt tacggttcct ggccttttgc tggccttttg    7320
ctcacatgtt ctttcctgcg ttatcccctg attctgtgga taaccgtatt accgcctttg     7380
agtgagctga taccgctcgc cgcagccgaa cgaccgagcg cagcgagtca gtgagcgagg     7440
aagcggaaga gcgcccaata cgcaaaccgc ctctccccgc gcgttggccg attcattaat     7500
gcagctggca cgacaggttt cccgactgga aagcgggcag tgagcgcaac gcaattaatg     7560
tgagttagct cactcattag gcacccagg ctttacactt tatgcttccg gctcgtatgt      7620
tgtgtggaat tgtgagcgga taacaatttc acacaggaaa cagctatgac catgattacg    7680
ccaagcgcgc aattaaccct cactaaaggg aacaaaagct ggagctgcaa gcttaatgta    7740
gtcttatgca atactcttgt agtcttgcaa catggtaacg atgagttagc aacatgcctt    7800
acaaggagag aaaaagcacc gtgcatgccg attggtggaa gtaaggtggt acgatcgtgc    7860
cttattagga aggcaacaga cgggtctgac atggattgga cgaaccactg aattgccgca    7920
ttgcagagat attgtattta agtgcctagc tcgatacata aac                       7963
```